(12) United States Patent
Yuan et al.

(10) Patent No.: US 9,340,582 B2
(45) Date of Patent: May 17, 2016

(54) BIOCONJUGATES OF SYNTHETIC APELIN POLYPEPTIDES

(71) Applicants: Jun Yuan, Boston, MA (US); Frederic Zecri, Brookline, MA (US); Philipp Grosche, Inzlingen (DE); Hongjuan Zhao, Lexington, MA (US); Eric Peters, San Diego, CA (US); Shari Lynn Caplan, Lunenburg, MA (US); Changgang Lou, Portage, MI (US)

(72) Inventors: Jun Yuan, Boston, MA (US); Frederic Zecri, Brookline, MA (US); Philipp Grosche, Inzlingen (DE); Hongjuan Zhao, Lexington, MA (US); Eric Peters, San Diego, CA (US); Shari Lynn Caplan, Lunenburg, MA (US); Changgang Lou, Portage, MI (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/336,290

(22) Filed: Jul. 21, 2014

(65) Prior Publication Data

US 2015/0030594 A1 Jan. 29, 2015

Related U.S. Application Data

(60) Provisional application No. 62/015,848, filed on Jun. 23, 2014, provisional application No. 61/858,303, filed on Jul. 25, 2013.

(51) Int. Cl.

| | |
|---|---|
| *C07K 14/47* | (2006.01) |
| *C07K 7/08* | (2006.01) |
| *A61K 47/48* | (2006.01) |
| *A61K 45/06* | (2006.01) |
| *A61K 38/10* | (2006.01) |
| *C07K 16/00* | (2006.01) |
| *A61K 39/395* | (2006.01) |

(52) U.S. Cl.
CPC . *C07K 7/08* (2013.01); *A61K 38/10* (2013.01); *A61K 39/39533* (2013.01); *A61K 45/06* (2013.01); *A61K 47/48038* (2013.01); *A61K 47/48284* (2013.01); *A61K 47/48369* (2013.01); *C07K 14/47* (2013.01); *C07K 16/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,759,804 A | 6/1998 | Godiska et al. | |
| 6,492,324 B1 | 12/2002 | Hinuma et al. | |
| 6,555,339 B1 | 4/2003 | Liaw et al. | |
| 6,774,221 B1 | 8/2004 | Nishimura et al. | |
| 7,635,751 B2 | 12/2009 | Kitada et al. | |
| 7,736,646 B2 | 6/2010 | Krieg | |
| 7,947,280 B2 | 5/2011 | Ashley et al. | |
| 8,673,848 B2 | 3/2014 | Zecri et al. | |
| 2003/0092618 A1 | 5/2003 | Hinuma et al. | |
| 2003/0119021 A1 | 6/2003 | Koster et al. | |
| 2004/0082496 A1 | 4/2004 | Acton et al. | |
| 2004/0116336 A1 | 6/2004 | Kitada et al. | |
| 2005/0152836 A1 | 7/2005 | Ashley et al. | |
| 2006/0045880 A1 | 3/2006 | Krieg | |
| 2006/0159676 A1 | 7/2006 | Krieg | |
| 2007/0088244 A1 | 4/2007 | Miller et al. | |
| 2008/0031871 A1 | 2/2008 | Allen et al. | |
| 2008/0182779 A1 | 7/2008 | Ashley et al. | |
| 2011/0008346 A1 | 1/2011 | Duckers | |
| 2011/0097710 A1 | 4/2011 | Macrae et al. | |
| 2011/0123534 A1 | 5/2011 | Duckers | |
| 2011/0195077 A1 | 8/2011 | Glass et al. | |
| 2011/0305663 A1 | 12/2011 | Gosselin | |

(Continued)

FOREIGN PATENT DOCUMENTS

| | | |
|---|---|---|
| EP | 1116727 A1 | 7/2001 |
| EP | 2017355 A1 | 1/2009 |

(Continued)

OTHER PUBLICATIONS

Castan-laurell et al ('Apelin, a promising target for type 2 diabetes treatment?' Trends in Endocrinology and Metabolism v23(5) May 2012 pp. 234-241).*

(Continued)

*Primary Examiner* — Karlheinz R Skowronek
*Assistant Examiner* — Ronald Niebauer
(74) *Attorney, Agent, or Firm* — Sophie Binet Cross

(57) ABSTRACT

The invention provides a bioconjugates comprising a synthetic polypeptide of Formula I' (SEQ ID NO: 1):

$$X_1-X_2-X_3-X_4-X_5-X_6-X_7-X_8-X_9-X_{10}-X_{11}-X_{12}-X_{13} \quad \text{I'}$$

or an amide, an ester or a salt thereof, wherein X1, X2, X3, X4, X5, X6, X7, X8, X9, X10, X11, X12 and X13 are defined herein and a half-life extending moiety wherein the peptide and the half-life extending moiety are covalently linked or fuse, optionally via a linker. The polypeptides are agonist of the APJ receptor. The invention also relates to a method for manufacturing the bioconjugates of the invention, and its therapeutic uses such as treatment or prevention of acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia. The present invention further provides a combination of pharmacologically active agents and a pharmaceutical composition.

12 Claims, No Drawings

(56) References Cited

U.S. PATENT DOCUMENTS

| | | | |
|---|---|---|---|
| 2013/0196899 A1* | 8/2013 | Zecri et al. ............. 514/1.9 |
| 2014/0142022 A1 | 5/2014 | Zecri et al. |
| 2014/0155315 A1 | 6/2014 | Zecri et al. |
| 2014/0275489 A1 | 9/2014 | Stevis et al. |
| 2015/0031604 A1 | 1/2015 | Zecri et al. |

FOREIGN PATENT DOCUMENTS

| | | |
|---|---|---|
| EP | 2330125 A2 | 6/2011 |
| RU | 2457216 A | 7/2012 |
| WO | 00/24782 A2 | 5/2000 |
| WO | 0190123 A2 | 11/2001 |
| WO | 03063892 A1 | 8/2003 |
| WO | 2005023863 A1 | 3/2005 |
| WO | 2005106493 A1 | 11/2005 |
| WO | 2006009902 A2 | 1/2006 |
| WO | 2006041205 A1 | 4/2006 |
| WO | 2007039184 A2 | 4/2007 |
| WO | 2009033669 A2 | 3/2009 |
| WO | 2009033784 A2 | 3/2009 |
| WO | 2009033819 A2 | 3/2009 |
| WO | 2009075566 A1 | 6/2009 |
| WO | 2010053545 A2 | 5/2010 |
| WO | 2010115874 A1 | 10/2010 |
| WO | 2011056073 A2 | 5/2011 |
| WO | 2011133948 A2 | 10/2011 |
| WO | 2012/125408 A1 | 9/2012 |
| WO | 2012/170969 A2 | 12/2012 |
| WO | 2013/106437 A1 | 7/2013 |
| WO | WO2013111110 * | 8/2013 |
| WO | 2014/099984 A1 | 6/2014 |
| WO | 2015/013165 A2 | 1/2015 |
| WO | 2015/013167 A2 | 1/2015 |

OTHER PUBLICATIONS

Pitkin et al (International Union of Basic and Clinical Pharmacology LXXIV Apelin Receptor Nomenclature, Distribution, Pharmacology, and Function Pharmacological Reviews v62 2010 pp. 331-342).*

A. G. Japp et al.: "Acute Cardiovascular Effects of Apelin in Human: Potential Role in Patients With Chronic Heart Failure", Circulation, vol. 121, No. 16, Apr. 27, 2010, pp. 1818-1827.

Huang et al.: "Receptor-Fc fusion therapeutics, traps and MIMETIBODY technology", Current Opinion in Biotechnology, vol. 20, No. 6, (Dec. 2009), pp. 692-699.

Murza et al., "Elucidation of the Structure-Activity Relationships of Apelin: Influence of Unnatural Amino Acids on Binding, Signaling, and Plasma Stability," Chem Med Chem 7:318-325 (Feb. 2012).

Sidorova et al., "Synthesis and Cardioprotective properties of Apelin-12 and its Structural Analogs," Russian Journal of Bioorganic Chemistry 38(1):40-51 (Jan. 1, 2012).

Murza et al., "Elucidation of the Structure-Activity Relationships of Apelin: Influence of Unnatural Amino Acids on Binding, Signaling and Plasma Stability," Journal of Peptide Science 18(1):S104 (Sep. 2012).

Lee et al., "Modification of the Terminal Residue of Apelin-13 Antagonizes Its Hypotensive Action," Endocrinology 146 (1):231-236 (Oct. 14, 2004).

Francia et al., "The Apelin/APJ System From Vascular Biology to Heart Failure," High Blood Press Cardiovasc Prev 13 (4):159-162 (Oct. 22, 2006).

Zeng et al., "Effects and mechanisms of apelin-13 on ischemia/reperfusion injury in rat heart," Chinese Pharmacological Bulletin 23(1):82-85 (Jan. 2007).

Simpkin et al., "Apelin-13 and apelin-36 exhibit direct cardio protective activity against ischemia reperfusion injury," Basic Research in Cardiology 102(6):518-528 (Nov. 2007).

Zhang et al., "The Effect of Apelin-13 on Ischemia-Induced Cardiomyocyte Apoptosis in Acute Myocardial Ischemia Rats," Chinese Journal of Arteriosclerosis 2008-2009.

Fukase et al., "Synthetic Study on Peptide Antiobiotic Nisin. V. Total Synthesis of Nisin," Bull. Chem. Soc. Jpn. 65:2227-2240 (1992).

Rastaldo et al., "Apelin-13 limits infarct size and improves cardiac postischemic mechanical recovery only if given after ischemia" American Journal of Physiology—Heart and Circulatory Physiology 300(6):H2308-H2315 (Jun. 2011).

Charles, Christopher, "Update on apelin peptides as putative targets for cardiovascular drug discovery" Expert Opinion on Drug Discovery 6(6):633-644 , (Jun. 2011).

Tycinska et al., "Apelin in acute myocardial infarction and heart failure induced by ischemia," Clinica Chimica Acta 413: 406-410 (Nov. 25, 2011).

Dowd et al., "A human gene that shows identity with the gene encoding the angiotensin receptor is located on chromosome 11," Gene 136:355-360 (1993).

Habata et al., "Apelin, the natural ligand of the orphan receptor APJ, is abundantly secreted in the colostrum," Biochimica et Biophysica Acta 1452:25-35 (1999).

Hamada et al., "Evaluation of novel cyclic analogues of apelin," International Journal of molecular medicine 22:547-552 (2008).

Bernardes et al., "From Disulfide- to Thioether-Linked Glycoproteins," Angew, Chem. Int. Ed 47:2244-2247 (2008).

Ranganathan et al., "Triply bridged (1,3,5) cyclophanes from cystine and lanthionine linkers-a comparison," Tetrahedron 66:3923-3929 (2010).

Japp et al., "Vascular effects of apelin in vivo in man," Journal of the american college of cardiology 52:908-13 (2008).

Medhurst et al., "Pharmacological and immunohistochemical characterization of the APJ receptor and its endogenous ligand apelin," Journal of neurochemistry 84:1162-1172 (2003).

Macaluso and Glen, "Exploring the 'RPRL' Motif of apelin-13 through molecular simulation and biological evaluation of cyclic peptide analogues," ChemMedChem 5:1247-1253 (2010).

Macaluso et al., "Discovery of competitive apelin receptor (APJ) antagonist," ChemMedChem 6:1017-1023 (2011).

Pisarenko et al., Effects of structural analogues of apelin-12 in acute myocardial infarction in rats, Journal of Pharmacology and Pharmcotherapeutics, Jul.-Sep. 2013, vol. 4, Issue 3, pp. 198-203.

Pisarenko et. al, Apelin-12 and its structural analog enhance antioxidant defense in experimental myocardial ischemia and reperfusion, Mol. Cell Biochem (2014), 391:241-250.

Margathe et al., Structure-Activity Relationship Studies toward the Discovery of Selective Apelin Receptor Agonists, Journal of Medicinal Chemistry (2014), vol. 57, pp. 2908-2919.

Jia et al., Cardiovascular effects of a PEGylated apelin, Elsevier Inc., Peptides 38 (2012), pp. 181-188.

Corti Davide et al.: "A Neutralizing Antibody Selected from Plasma Cells That Binds to Group 1 and Group 2 Influenza A Hemagglutinins", Science, vol. 333, No. 6044, pp. 850-856, Aug. 12, 2011.

IUPAC Codes for Amino Acids, Amino Acid Codes, thinkpeptides, http://thinkpeptides.com/extras.html, (2015).

* cited by examiner

BIOCONJUGATES OF SYNTHETIC APELIN POLYPEPTIDES

This application claims benefit under 35 U.S.C. §119(e) of U.S. Provisional Application No. 61/858,303, filed Jul. 25, 2013; U.S. Provisional Application No. 62/015,848 filed Jun. 23, 2014; the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Sep. 26, 2014, is named PAT055781-US-NP$_{13}$ SL.txt and is 118,077 bytes in size.

FIELD OF THE INVENTION

The present invention relates to compositions comprising semi synthetic biologic molecules which are bioconjugates of an APJ agonist polypeptide and a half-life extending moiety. In particular, the bioconjugates of the invention exhibit greater resistance to proteolytic degradation via the action of peptidases as compared to their corresponding naked polypeptide. The invention further relates to methods of making said composition and using said compositions as pharmaceutically active agent in the treatment of cardiovascular diseases.

BACKGROUND OF THE INVENTION

The incidence of heart failure in the Western world is approximately 1/100 adults after 65 yrs of age. The most common pathology is a chronic deficit in cardiac contractility and, thereby, cardiac output, i.e., the effective volume of blood expelled by either ventricle of the heart over time. Patients with chronic heart failure can have acute episodes of decompensation, i.e., failure of the heart to maintain adequate blood circulation, where cardiac contractility declines further. There are ~500K hospitalizations per year for "acute decompensated heart failure" (ADHF) in the USA alone.

Current therapies for ADHF include diuretics, vasodilators, and inotropes, which directly increase cardiac contractility. Current intravenous inotropes (dobutamine, dopamine, milrinone, levosimendan) are used in the acute setting, despite their association with adverse events such as arrhythmia and increased long-term mortality. These liabilities have prevented their application in chronic heart failure. Digoxin is an oral inotrope, but is limited by a narrow therapeutic index, increased arrhythmogenic potential and contraindication in renal insufficiency.

A therapy for heart failure that increases cardiac contractility without arrhythmogenic or mortality liabilities is urgently needed for ADHF, but could also address the enormous unmet medical need in chronic heart failure.

Apelin is the endogenous ligand for the previously orphan G-protein-coupled receptor (GPCR), APJ, also referred to as apelin receptor, angiotension-like-1 receptor, angiotension II-like-1 receptor, and the like. The apelin/APJ pathway is widely expressed in the cardiovascular system and apelin has shown major beneficial cardiovascular effects in preclinical models. Acute apelin administration in humans causes peripheral and coronary vasodilatation and increases cardiac output (Circulation. 2010; 121:1818-1827). As a result, APJ agonism is emerging as an important therapeutic target for patients with heart failure. Activation of the apelin receptor APJ is thought to increase cardiac contractility and provide cardioprotection, without the liabilities of current therapies. However, the native apelins exhibit a very short half life and duration of action in vivo. The very short half life is a recognized major difficulty with the delivery of such therapeutic endogenous peptides due to rapid serum clearance and proteolytic degradation via the action of peptidases.

One way which has been currently used to overcome this disadvantage is to administer large dosage of therapeutic peptide of interest to the patient so that even if some therapeutic peptide is degraded, enough remains to be therapeutically effective. However, this method is uncomfortable to patients. Since most therapeutic peptides cannot be administered orally, the therapeutic peptide would have to be either constantly infused, frequently infused by intravenous injection or administered frequently by the inconvenient route of subcutaneous injections. The need for frequent administration also results in many potential peptide therapeutics having an unacceptable high projected cost of treatment. The presence of large amounts of degraded peptide may also generate undesired side effects.

Discomfort in administration and high costs are two reasons why most therapeutic peptides with attractive bioactivity profiles may not be developed as drug candidates.

Therefore, one approach to prolong half-life of peptides is to modify the therapeutic peptides in such a way that their degradation is slowed down while still maintaining biological activity. Such synthetically modified polypeptides have been described in unpublished U.S. patent application Ser. No. 13/747,621. Another approach includes reducing the rate of clearance by conjugating the peptides to molecules that prevent their elimination through kidney. Such bio-conjugates, however may still be susceptible to protease activity.

There is thus a need for modified therapeutic peptides with increased half-life in order to provide longer duration of action in vivo, while maintaining low toxicity yet retaining the therapeutic advantages of the modified peptides.

BRIEF DESCRIPTION OF THE INVENTION

This invention is directed to overcoming the problem of peptide degradation in the body by modifying the therapeutic peptide or polypeptide of interest, i.e. APJ agonists.

Therefore the aim of the present invention is to provide novel bioconjugates or multimer thereof, comprising a) a peptide or polypeptide which is useful as APJ agonist; and b) a half-life extending moiety; wherein the peptide and half-life extending moiety are covalently linked or fused, optionally via a linker.

The bioconjugate of the invention possess at least one of the following improvements over wild type apelin and other known apelin analogs: increased half-life; greater immunity to degradation upon administration and/or upon solubilization; and increased conformational constraints, all while exhibiting the same or greater biological activity as wild type apelin. The peptides and polypeptides of this invention are thus particularly useful for the treatment or prevention of cardiovascular diseases such as heart failure, disorders and conditions associated with heart failure, and disorders and conditions responsive to the activation of APJ receptor activity.

In one embodiment, the bioconjugates of the invention are particularly useful for the treatment or prevention of a disorder or condition associated with heart failure, or a disorder responsive to the activation (or agonism) of the APJ receptor activity. In another embodiment, the bioconjugates of the invention are useful in the treatment of acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

The invention pertains to bioconjugates of a peptide or polypeptide and a half-life extending moiety, pharmaceutical compositions thereof, and methods of manufacture and use thereof, as described herein.

Examples of peptide or polypeptide which forms the bioconjugate include the peptide and polypeptide according to any one of Formulae I to IX, or an amide, an ester or a salt thereof, as well as any peptide or polypeptide specifically listed herein, including but not limited to the experimental examples.

The invention therefore provides a bioconjugate or a multimer thereof, comprising:
a. a peptide or a polypeptide of formula (I') (SEQ ID NO: 1):

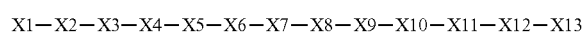

I' wherein:
X1 is the N-terminus of the polypeptide and is either absent or is selected from pE, R, Isn, Q, A, K, and 5-amino-valeric acid;
X2 is R, A, r, N-Me-R, K, H, hF, hK, F, E or Orn;
X3 is P, A, a, p, 4-PhP, K, D, pipecolic acid, or cysteine wherein the side chain of cysteine forms a disulfide bond with the side chain of the cysteine at the X7 position;
X4 is R, A, r, N-Me-R, F, E or cysteine wherein the side chain of cysteine forms a disulfide bond with the side chain of the cysteine at the X7 position;
X5 is L, Cha, A, D-L, N-Me-L, K, D, 4-PhF or F;
X6 and X12 are independently a natural or unnatural amino acid selected from C, c, hC, D-hC, K, D, Orn, Dab or E wherein the side chain of X6 and X12 are linked together via a covalent bond forming either a monosulfide (—S—), a disulfide (—S—S—) or an amide bond (—NHC(O)— or —C(O)—NH—); or alternatively X6 is K, X13 is absent and X12 is F or f wherein the C-terminus of X12 form an amide bond with the amino side chain of X6;
X7 is H, h, A, N-Me-A, a, Aib, K, Nal, F, P, Dap, N, E or cysteine wherein the side chain of the cysteine forms a disulfide bond with the side chain of the cysteine at position X3 or with the side chain of the cysteine at position X4;
X8 is K, k, F, f, A, hF, N-Me-R, E or 4-amino-Isn;
X9 is G, N-Me-G, A, D, L, R or Aib;
X10 is P, A, p, 4-PhP or pipecolic acid,
X11 is M, D-Nle, Nle, N-Me-Nle, M(O), A, F, Y, L, K, 3-PyA or Cha; and
X13 is the C-terminus and is absent or is selected from F, f, N-Me-F, Nal, D-Nal, 3-Br—F, (S)-☐-3-F, I, A, a, K, Dap, H and E;
wherein:
Nle is L-norleucine;
D-hC is D-homocysteine
hC is L-homocysteine;
hF is L-homophenylalanine;
hK is L-lysine;
Nal is L-naphathaline;
Orn is ornithine;
Aib is ☐aminoisobutyric acid;
Dab is (S)-diaminobutyric acid;
Dap is (S)-2,3-diaminopropionic acid;
M(O) is methionine sulfone;
Cha is (S)-☐-cyclohexylalanine;
4-amino-Isn is 4-aminopiperidine-4-carboxylic acid;
Isn is isonipecotinoyl;
pE is L-pyroglutamic acid;
3-PyA is 3-(3-pyridyl)-L-alanine;
4-PhF is 4-Phenyl-L-phenylalanine;
wherein the N-terminus and the C-terminus optionally form a ring together with 1, 2, 3 or 4 glycine amino acids; and
or an amide, an ester or a salt of the polypeptide; or a polypeptide substantially equivalent thereto; and
b. a half-life extending moiety;
wherein said peptide of polypeptide and said half-life extending moiety are covalently linked or fused, optionally via a linker.

As further explained herein, the art-recognized three letters or one letter abbreviations are used to represent amino acid residues that constitute the peptides and polypeptides of the invention. Except when preceded with "D," the amino acid is an L-amino acid. When the one letter abbreviation is a capital letter, it refers to the L-amino acid. When the one letter abbreviation is a lower case letter, it refers to the D-amino acid.

Any of the above-listed amino acid residues of Formula I', or its related formulae described herein, e.g., Formulae I, II to IX, may be substituted in a conservative fashion, provided the bioconjugate of the invention still retains functional activity and structural properties (e.g., half-life extension, protection from degradation, conformational constraint). Principle and examples of permissible conservative amino acid substitutions are further explained herein.

The half-life extending moiety of the invention can be covalently fused, attached, linked or conjugated to a peptide or polypeptide analog. A half-life extending moiety can be, for example, a polymer, such as polyethylene glycol (PEG), a cholesterol group, a carbohydrate or oligosaccharide; a fatty acid, or any natural or synthetic protein, polypeptide or peptide that binds to a salvage receptor. Preferably, the half-life extending moiety is covalently linked, optionally via a linker, to plasma protein (albumin and immunoglobulin) with long serum half-lives. In other embodiment, the half-life extending moiety is an albumin binding residue. An "Albumin binding residue" as used herein means a residue which binds non-covalently to human serum albumin. In one embodiment the albumin binding residue is a lipophilic residue. In another embodiment, the albumin binding residue is negatively charged at physiological pH. An albumin binding residue typically comprises a carboxylic acid which can be negatively charged. Examples of albumin binding residue includes fatty acids. In other embodiment, the half-life extending moiety is an IgG constant domain or fragment thereof (e.g., the Fc region), Human Serum Albumin (HSA), or albumin-binding polypeptides. Preferably, the half-life extending moiety portion of the bioconjugate is a human serum albumin or an Fc region. Most preferably, the half-life extending moiety portion of the bioconjugate is an Fc region.

The half-life extending moiety is attached in such a way so as enhance, and/or not to interfere with, the biological function of the constituent portions of the bio-conjugates of the invention, e.g., the peptide or polypeptide of Formula I', or its related formulae described herein (Formulae I-IX). In some embodiments, the polypeptide of the invention can be fused to a half-life extending moiety, optionally via a linker. The half-life extending moiety can be a protein such as an IgG constant domain or fragment thereof (e.g., the Fc region), Human Serum Albumin (HSA), a fatty acid or an albumin-binding polypeptides. Such proteins disclosed herein can also form multimers.

In some embodiments, the half-life extending moiety (e.g., HSA, Fc, fatty acid etc.) is covalently linked or fused to the N-terminus of the peptide or polypeptide of Formula I', or I-IX. In other embodiments, the half-life extending moiety (e.g., HSA, Fc, fatty acid etc.) is covalently linked or fused to C-terminus of the peptide or polypeptide of Formula I', or I-IX of the invention.

The bioconjugates of the invention, via activation of the APJ receptor, have utility in the treatment of acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

In a preferred embodiment the bioconjugates of the invention are useful in the treatment of acute decompensated heart failure (ADHF).

In another embodiment, the invention pertains to a method for treating disorder or disease responsive to the activation of the APJ receptor, in a subject in need of such treatment, comprising: administering to the subject an effective amount of a bioconjugate of the invention, such that the disorder or disease responsive to the activation of the APJ receptor in the subject is treated.

In yet another embodiment, the invention pertains to pharmaceutical compositions, comprising a bioconjugate of the invention and one or more pharmaceutically acceptable carriers.

In still another embodiment, the invention pertains to combinations including, a bioconjugate of the invention, and pharmaceutical combinations of one or more therapeutically active agents.

In another embodiment, the invention pertains to a method for activation of the APJ receptor in a subject in need thereof, comprising: administering to the subject a therapeutically effective amount of a bioconjugate of the invention.

These and other aspects of the invention will be elucidated in the following detailed description of the invention.

DETAILED DESCRIPTION OF THE INVENTION

Definition

For purposes of interpreting this specification, the following definitions will apply unless specified otherwise and whenever appropriate, terms used in the singular will also include the plural and vice versa.

As used herein, "disorders or diseases responsive to the modulation of the APJ receptor," "disorders and conditions responsive to the modulation of the APJ," "disorders and conditions responsive to the modulation of APJ receptor activity," "disorders responsive to the activation (or agonism) of the APJ receptor activity" and like terms include acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

As used herein, "Activation of APJ receptor activity," or "Activation of the APJ receptor," refers to an increase in the APJ receptor activity. The activation of the APJ receptor activity is also referred to as "agonism" of the APJ receptor, e.g., by administration of the peptides and polypeptides of the invention.

As used herein, the terms "polypeptide" and "peptide" are used interchangeably to refer to two or more amino acids linked together. Except for the abbreviations for the uncommon or unatural amino acids set forth in Table 1 below, the art-recognized three letter or one letter abbreviations are used to represent amino acid residues that constitute the peptides and polypeptides of the invention. Except when preceded with "D", the amino acid is an L-amino acid. When the one letter abbreviation is a capital letter, it refers to the L-amino acid. When the one letter abbreviation is a lower case letter, it refers to the D-amino acid. Groups or strings or amino acid abbreviations are used to represent peptides. Peptides are indicated with the N-terminus on the left and the sequence is written from the N-terminus to the C-terminus.

Peptides of the invention contain non-natural amino acids (i.e., compounds that do not occur in nature) and other amino acid analogs as are known in the art may alternatively be employed.

Certain non-natural amino acids can be introduced by the technology described in Deiters et al., J Am Chem Soc 125: 11782-11783, 2003; Wang and Schultz, Science 301:964-967, 2003; Wang et al., Science 292:498-500, 2001; Zhang et al., Science 303:371-373, 2004 or in U.S. Pat. No. 7,083,970. Briefly, some of these expression systems involve site-directed mutagenesis to introduce a nonsense codon, such as an amber TAG, into the open reading frame encoding a polypeptide of the invention. Such expression vectors are then introduced into a host that can utilize a tRNA specific for the introduced nonsense codon and charged with the non-natural amino acid of choice. Particular non-natural amino acids that are beneficial for purpose of conjugating moieties to the polypeptides of the invention include those with acetylene and azido side chains.

One or more of the natural or un-natural amino acids in a peptide of the invention may be modified, for example, by the addition of a chemical entity such as a carbohydrate group, a phosphate group, a farnesyl group, an isofarnesyl group, a fatty acid group ($C_qH_{q+1}C(O)_2H$ wherein q is 3 to 20), a linker for conjugation, functionalization, or other modification, etc. Said modifications may be done in a site-specific or non-site-specific manner. In a preferred embodiment, the modifications of the peptide lead to a more stable peptide (e.g., one exhibiting greater half-life in vivo). These modifications may include the incorporation of additional D-amino acids, etc. None of the modifications should substantially interfere with the desired biological activity of the peptide, but such modifications may confer desirable properties, e.g., enhanced biological activity, on the peptide.

Said modifications enhance the biological properties of the proteins of the invention relative to the wild-type proteins, as well as, in some cases, serving as points of attachment for, e.g., labels and protein half-life extension agents, and for purposes of affixing said variants to the surface of a solid support.

In certain embodiments, such modifications, e.g. site-specific modifications, are used to attach the half-life extending moiety, e.g., PEG groups to polypeptides, and/or peptides of the invention, for purposes of, e.g., extending half-life or otherwise improving the biological properties of said polypeptides, and/or peptides. Said techniques are described further herein.

In other embodiments, such modifications, e.g., site-specific modifications are used to attach other polymers and small molecules and recombinant protein sequences that extend half-life of the polypeptide of the invention. One such embodiment includes the attachment of fatty acids or specific albumin binding compounds to polypeptides, and/or peptides. In other embodiments, the modifications are made at a particular amino acid type and may be attached at one or more sites on the polypeptides.

In other embodiments, such modifications, e.g., site-specific modifications are used as means of attachment for the production of wild-type and/or variant multimers, e.g., dimers (homodimers or heterodimers) or trimers or tetramers. These multimeric protein molecules may additionally have groups such as PEG, sugars, and/or PEG-cholesterol conjugates attached or be fused either amino-terminally or carboxy-terminally to other proteins such as Fc, Human Serum Albumin (HSA), etc.

In other embodiments, such site-specific modifications are used to produce proteins, polypeptides and/or peptides wherein the position of the site-specifically incorporated pyrrolysine or pyrrolysine analogue or non-naturally occurring amino acids (para-acetyl-Phe, para-azido-Phe) allows for controlled orientation and attachment of such proteins, polypeptides and/or peptides onto a surface of a solid support or to have groups such as PEG, sugars and/or PEG-cholesterol conjugates attached.

In other embodiments, such site-specific modifications are used to site-specifically cross-link proteins, polypeptides and/or peptides thereby forming hetero-oligomers including, but not limited to, heterodimers and heterotrimers. In other embodiments, such site-specific modifications are used to site-specifically cross-link proteins, polypeptides and/or peptides thereby forming protein-protein conjugates, protein-polypeptide conjugates, protein-peptide conjugates, polypeptide-polypeptide conjugates, polypeptide-peptide conjugates or peptide-peptide conjugates. In other embodiments, a site specific modification may include a branching point to allow more than one type of molecule to be attached at a single site of a protein, polypeptide or peptide.

In other embodiments, the modifications listed herein can be done in a non-site-specific manner and result in protein-protein conjugates, protein-polypeptide conjugates, protein-peptide conjugates, polypeptide-polypeptide conjugates, polypeptide-peptide conjugates or peptide-peptide conjugates of the invention.

One of ordinary skill in the art will appreciate that various amino acid substitutions, e.g., conservative amino acid substitutions, may be made in the sequence of any of the polypeptides described herein, without necessarily decreasing its activity. As used herein, "amino acid commonly used as a substitute thereof" includes conservative substitutions (i.e., substitutions with amino acids of comparable chemical characteristics). For the purposes of conservative substitution, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid. Examples of amino acid substitutions include substituting an L-amino acid for its corresponding D-amino acid, substituting cysteine for homocysteine or other non natural amino acids having a thiol-containing side chain, substituting a lysine for homolysine, diaminobutyric acid, diaminopropionic acid, ornithine or other non natural amino acids having an amino containing side chain, or substituting an alanine for norvaline or the like.

The term "amino acid," as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission.

The term "naturally occurring" refers to materials which are found in nature and are not manipulated by man. Similarly, "non-naturally occurring," "un-natural," and the like, as used herein, refers to a material that is not found in nature or that has been structurally modified or synthesized by man. When used in connection with amino acids, the term "naturally occurring" refers to the 20 conventional amino acids (i.e., alanine (A or Ala), cysteine (C or Cys), aspartic acid (D or Asp), glutamic acid (E or Glu), phenylalanine (F or Phe), glycine (G or Gly), histidine (H or His), isoleucine (I or Ile), lysine (K or Lys), leucine (L or Leu), methionine (M or Met), asparagine (N or Asn), proline (P or Pro), glutamine (Q or Gln), arginine (R or Arg), serine (S or Ser), threonine (T or Thr), valine (V or Val), tryptophan W or Trp), and tyrosine (Y or Tyr)).

The terms "non-natural amino acid" and "unnatural amino acid," as used herein, are interchangeably intended to represent amino acid structures that cannot be generated biosynthetically in any organism using unmodified or modified genes from any organism, whether the same or different. The terms refer to an amino acid residue that is not present in the naturally occurring (wild-type) apelin protein sequence or the sequences of the present invention. These include, but are not limited to, modified amino acids and/or amino acid analogues that are not one of the 20 naturally occurring amino acids, selenocysteine, pyrrolysine (Pyl), or pyrroline-carboxy-lysine (Pcl, e.g., as described in PCT patent publication WO2010/48582). Such non-natural amino acid residues can be introduced by substitution of naturally occurring amino acids, and/or by insertion of non-natural amino acids into the naturally occurring (wild-type) Apelin protein sequence or the sequences of the invention. The non-natural amino acid residue also can be incorporated such that a desired functionality is imparted to the apelin molecule, for example, the ability to link a functional moiety (e.g., PEG). When used in connection with amino acids, the symbol "U" shall mean "non-natural amino acid" and "unnatural amino acid," as used herein.

In addition, it is understood that such "unnatural amino acids" require a modified tRNA and a modified tRNA synthetase (RS) for incorporation into a protein. These "selected" orthogonal tRNA/RS pairs are generated by a selection process as developed by Schultz et al. or by random or targeted mutation. As way of example, pyrroline-carboxy-lysine is a "natural amino acid" as it is generated biosynthetically by genes transferred from one organism into the host cells and as it is incorporated into proteins by using natural tRNA and tRNA synthetase genes, while p-aminophenylalanine (See, Generation of a bacterium with a 21 amino acid genetic code, Mehl R A, Anderson J C, Santoro S W, Wang L, Martin A B, King D S, Horn D M, Schultz PG. J Am Chem Soc. 2003 Jan. 29; 125(4):935-9) is an "unnatural amino acid" because, although generated biosynthetically, it is incorporated into proteins by a "selected" orthogonal tRNA/tRNA synthetase pair.

Modified encoded amino acids include, but are not limited to, hydroxyproline, -carboxyglutamate, O-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. The term "amino acid" also includes naturally occurring amino acids that are metabolites in certain organisms but are not encoded by the genetic code for incorporation into proteins. Such amino acids include, but are not limited to, ornithine, D-ornithine, and D-arginine.

The term "amino acid analogue," as used herein, refers to compounds that have the same basic chemical structure as a naturally occurring amino acid, by way of example only, an α-carbon that is bound to a hydrogen, a carboxyl group, an amino group, and an R group. Amino acid analogues include the natural and unnatural amino acids which are chemically blocked, reversibly or irreversibly, or their C-terminal carboxy group, their N-terminal amino group and/or their side-chain functional groups are chemically modified. Such analogues include, but are not limited to, methionine sulfoxide, methionine sulfone, S-(carboxymethyl)-cysteine, S-(carboxymethyl)-cysteine sulfoxide, S-(carboxymethyl)-cysteine sulfone, aspartic acid-(beta-methyl ester), N-ethylglycine, alanine carboxamide, homoserine, norleucine, and methionine methyl sulfonium.

TABLE 1

Un-natural or Non-natural Amino Acids as described in the invention:

| Symbol | Name | Structure |
|---|---|---|
| Aib | α-Aminoisobutyric acid | 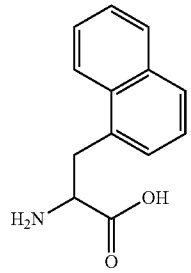 [SMILES: NC(Cc1cccc2ccccc12)C(=O)O] |
| M(O) | Methionine sulfone | 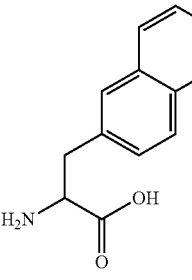 |

TABLE 1-continued

Un-natural or Non-natural Amino Acids as described in the invention:

| Symbol | Name | Structure |
|---|---|---|
| 1-Nal | 1-Naphthalanine | 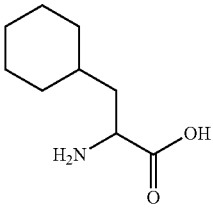 [SMILES: NC(CC1CCCCC1)C(=O)O] |
| 2-Nal | 2-Naphthalanine | 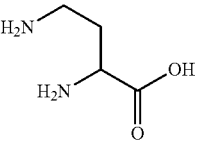 |
| Cha | β-Cyclohexylalanine | 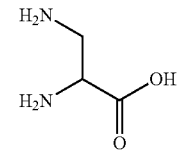 |
| Dab | Diaminobutyric acid | 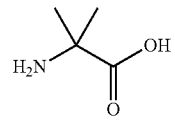 |
| Dap | 2,3-Diamino propionic acid | 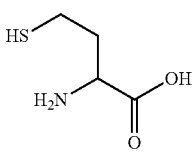 |
| hC | Homocysteine | 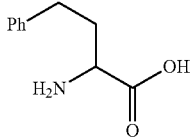 [SMILES: NC(CCc1ccccc1)C(=O)O] |
| hF | Homophenylalanine | 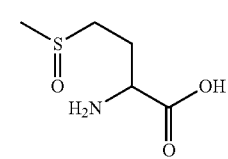 |

TABLE 1-continued

Un-natural or Non-natural Amino Acids as described in the invention:

| Symbol | Name | Structure |
|---|---|---|
| hK | Homolysine | 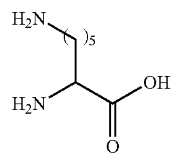 |
| Nle | Norleucine | 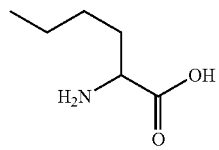 |
| Orn | Ornithine | 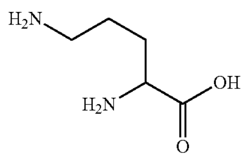 |
| β-3-F | β-3-phenylalanine | 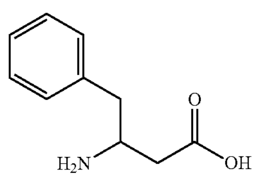 [SMILES: NC(CC(=O)O)Cc1ccccc1] |
| 4-amino-Isn | 4-Amino-piperidine-4-carboxylic acid (4 amino group form the peptidic bond) | 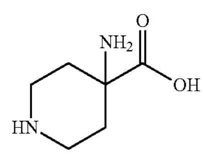 |
| Isn | Iso-nipecotinoic acid | 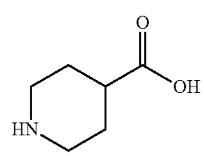 |
| pE | Pyroglutamic acid | 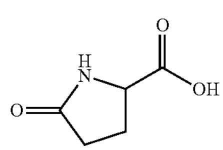 |
| 4-PhP | 4-Phenylproline | 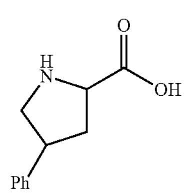 |
| | Pipecolinic acid | |

TABLE 1-continued

Un-natural or Non-natural Amino Acids as described in the invention:

| Symbol | Name | Structure |
|---|---|---|
| | 5-Aminovaleric acid | |
| O2Oc | 8-Amino-3,6-dioxa-octanoic acid | 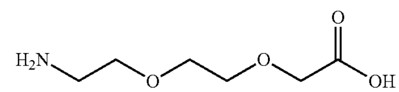 [SMILES: NCCOCCOCC(=O)O] |
| 3-PyA | 3-(3-pyridyl)-alanine | 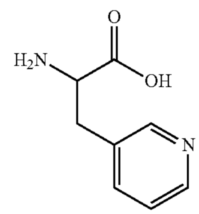 [SMILES: NC(Cc1cccnc1)C(=O)O] |
| 4-PhF | 4-phenyl-phenylalanine | 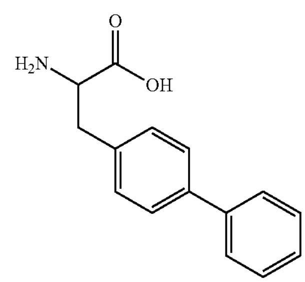 [SMILES: NC(Cc1ccc(-c2ccccc2)cc1)C(=O)O] |

Nal refers both to 1-Naphthalanine and 2-Naphthalanine, preferably 2-naphthalanine. 4-Phenylproline refers to both cis and trans 4-Phenylproline, preferably trans-4-phenylproline As used herein the term "amide" refers to an amide derivative of the carboxylic acid group at the C-terminus (e.g. —C(O)NH$_2$, —C(O)NH—C$_{1-6}$ alkyl, —C(O)NH—C1-2alkylphenyl, —C(O)NH—NHBn or —C(O)N(C$_{1-6}$ alkyl)$_2$).

The term "amide" also refer to derivative of the amino group at the N-terminus (e.g. —NHC(O)C$_{1-16}$alkyl, —NHC(O)(CH$_2$)$_n$Ph (n is an integer of 1 to 6), —NHC(O)(CH$_2$)$_2$CO$_2$H, 4-Cl-Ph-(CH$_2$)$_3$C(O)NH—, C$_{11}$H$_{23}$C(O)NH—(CH$_2$)$_2$—O—(CH$_2$)$_2$—O—CH$_2$—C(O)—NH—, C$_{13}$H$_{27}$C(O)NH—(CH$_2$)$_2$—O—(CH$_2$)$_2$—O—CH$_2$—C(O)—NH—; C$_{15}$H$_{27}$C(O)NH—(CH$_2$)$_2$—O—(CH$_2$)$_2$—O—CH$_2$—C(O)NH—, Ph-CH$_2$CH$_2$NHC(O)—NH— or CH$_3$(OCH$_2$CH$_2$)$_m$C(O)NH— (m is an integer of 1 to 12).

As used herein, the term "ester" refers to an ester derivative of the carboxylic acid group at the C-terminus (e.g —COOR) wherein R of the ester refers to C$_{1-6}$ alkyl groups such as methyl, ethyl, n-propyl, isopropyl, n-butyl, etc., C$_{3-8}$ cycloalkyl groups such as cyclopentyl, cyclohexyl, etc., C$_{6-10}$ aryl groups such as phenyl, α-naphthyl, etc., C$_{6-10}$ aryl-C$_{1-6}$ alkyl groups, for example phenyl-C$_{1-2}$ alkyl groups such as benzyl, phenethyl, benzhydryl, etc., and α-naphthyl-C$_{1-2}$ alkyl groups such as α-naphthylmethyl and the like. Mention may also be made of pivaloyloxymethyl ester and the like, which are commonly used as esters for oral administration.

When the polypeptides of the invention possess additional carboxyl or carboxylate groups in positions other than the C terminus, those polypeptides in which such groups are amidated or esterified also fall under the category of the polypeptide of the invention. In such cases, the esters may for example be the same kinds of esters as the C-terminal esters mentioned above.

The term alkyl refers to a fully saturated branched or unbranched (or straight chain or linear) hydrocarbon moiety, comprising 1 to 20 carbon atoms. Preferably the alkyl comprises 1 to 7 carbon atoms, and more preferably 1 to 4 carbon atoms.

The term aryl refers to monocyclic or bicyclic aromatic hydrocarbon groups having 6-10 carbon atoms in the ring portion. Representative examples of aryl are phenyl or naphthyl.

The term heteroaryl includes monocyclic or bicyclic heteroaryl, containing from 5-10 ring members selected from carbon atoms and 1 to 5 heteroatoms, and each heteroatoms is independently selected from O, N or S wherein S and N may be oxidized to various oxidation states. For bicyclic heteroaryl system, the system is fully aromatic (i.e. all rings are aromatic).

The term cycloalkyl refers to saturated or unsaturated but non-aromatic monocyclic, bicyclic or tricyclic hydrocarbon groups of 3-12 carbon atoms, preferably 3-8, or 3-7 carbon atoms. For bicyclic, and tricyclic cycloalkyl system, all rings are non-aromatic.

The term heterocyclyl refers to a saturated or unsaturated non-aromatic (partially unsaturated) ring which is a 4-, 5-, 6-, or 7-membered monocyclic, and contains at least one heteroatom selected from O, S and N, where the N and S can also optionally be oxidized to various oxidation states. In one embodiment, heterocyclyl moiety represents a saturated monocyclic ring containing from 5-7 ring atoms and optionally containing a further heteroatom, selected from O, S or N.

The term "APJ" (also referred to as "apelin receptor," "angiotensin-like-1 receptor," "angiotensin II-like-1 receptor," and the like) indicates a 380 residue, 7 transmembrane domain, Gi coupled receptor whose gene is localized on the long arm of chromosome 11 in humans (NCBI Reference Sequence: NP_005152.1, and encoded by NCBI Reference Sequence: NM_005161). APJ was first cloned in 1993 from genomic human DNA using degenerate oligonucleotide primers (O'Dowd et al. Gene, 136:355-60, 1993) and shares significant homology with angiotensin II receptor type 1. Despite this homology however, angiotensin II does not bind APJ. Although orphan for many years, the endogenous ligand has been isolated and named apelin (Tatemoto et al., Biochem Biophys Res Commun 251, 471-6 (1998)).

The term "apelin," indicates a 77 residue preprotein (NCBI Reference Sequence: NP_0059109.3, and encoded by NCBI Reference Sequence: NM_017413.3), which gets processed into biologically active forms of apelin peptides, such as apelin-36, apelin-17, apelin-16, apelin-13, apelin-12. The full length mature peptide, referred to as "apelin-36," comprises 36 amino acids, but the most potent isoform is the pyroglutamated form of a 13mer of apelin (apelin-13), referred to as "Pyr-1-apelin-13 or Pyr$^1$-apelin-13" Different apelin forms are described, for instance, in U.S. Pat. No. 6,492, 324B1.

The term "conjugate" and "bioconjugate" is used interchangeablly and is intended to refer to the entity formed as a result of a covalent attachment of an APJ agonist polypeptide or a polypeptide of Formula I' or I-IX, and a half-life extending moiety, via an optional linker. The term "Conjugate" or "bioconjugate" is also intended to include an entity formed as a result of a fusion between an APJ agonist polypeptide or a polypeptide of Formula I' or I-IX, and a half life extending moiety.

The term half-life extending moiety can be covalently linked/attached or fused to a peptide or polypeptide analog. A half-life extending moiety can be, for example, a polymer, such as polyethylene glycol (PEG), a fatty acid, a cholesterol group, a carbohydrate or oligosaccharide; or any natural or synthetic protein, polypeptide or peptide that binds to a salvage receptor. In other embodiment, the half-life extending moiety is an albumin binding residue. An "Albumin binding residue" as used herein means a residue which binds non-covalently to human serum albumin. In one embodiment the albumin binding residue is a lipophilic residue. In another embodiment, the albumin binding residue is negatively charged at physiological pH. An albumin binding residue typically comprises a carboxylic acid which can be negatively charged. Examples of albumin binding residue includes fatty acids. In other embodiment, the half-life extending moiety is covalently linked, optionally via a linker, to plasma protein (albumin and immunoglobulin) with long serum half-lives. For example, the half-life extending moiety is an IgG constant domain or fragment thereof (e.g., the Fc region), Human Serum Albumin (HSA), an albumin-binding polypeptides or residue such as for example fatty acids. Most preferably, the half-life extending moiety portion of the bioconjugate is an Fc region.

The term "increased half-life" or "increase serum half-life" or "extending half-life" is meant the positive change in circulating half-life of a modified biologically active molecule (e.g. apelin 13) relative to its non-modified form (or naked form of the peptide). Serum half-life is measured by taking blood samples at various time points after administration of the biologically active molecule, and determining the concentration of that molecule in each sample. Measuring the change in serum concentration with time allows calculation of the serum half-life of a modified molecule (e.g. conjugated molecule). By comparing the serum half-life of a modified molecule (e.g. conjugated molecule), with an unmodified molecule (e.g. apelin 13), the relative increase in serum half-life or t½ may be determined. The increase is desirably at least about two-fold, but a smaller increase may be useful.

Peptides or Polypeptides of the Invention

Various embodiments of the invention are described herein. It will be recognized that features specified in each embodiment may be combined with other specified features to provide further embodiments.

In embodiment 1 A, the invention therefore provides a bioconjugate, or a multimer thereof, comprising a. a peptide or a polypeptide formula (I) (SEQ ID NO: 2):

$$X1-X2-X3-X4-X5-X6-X7-X8-X9-X10-X11-X12-X13 \tag{I}$$

wherein:

X1 is the N-terminus of the polypeptide and is either absent or is selected from pE, R, Q, A, K, 5-amino-valeric acid and Isn;

X2 is R, A, r, N-Me-R, K, H, hF, hK or Orn;

X3 is P, A, a, p, 4-PhP, pipecolic acid, or cysteine wherein the side chain of cysteine forms a disulfide bond with the side chain of the cysteine at the X7 position;

X4 is R, A, r, N-Me-R or cysteine wherein the side chain of cysteine form a disulfide bond with the side chain of the cysteine at the X7 position;

X5 is L, Cha, A, D-L, N-Me-L or F;

X6 and X12 are independently a natural or unnatural amino acid selected from C, c, hC, D-hC, K, D, Orn, Dab or E wherein the side chain of X6 and X12 are linked together via a covalent bond;

or alternatively X6 is K, X13 is absent and X12 is F or f wherein the C-terminus of X12 form an amide bond with the amino side chain of X6;

X7 is H, h, A, N-Me-A, a, Aib, K, Nal, F, P, Dap, N or cysteine wherein the side chain of the cysteine form a disulfide bond with the side chain of the cysteine at position X3 or with the side chain of the cysteine at position X4;

X8 is K, k, F, f, A, hF, N-Me-R or 4-amino-Isn;

X9 is G, N-Me-G, A or Aib;

X10 is P, A, p, 4-PhP or pipecolic acid,

X11 is M, D-Nle, Nle, N-Me-Nle, M(O), A, F, Y, L, K or Cha; and

X13 is the C-terminus and is absent or is selected from F, f, N-Me-F, Nal, D-Nal, 3-Br—F, (S)-☐-3-F, I, A, a, K, Dap wherein:

Nle is L-norleucine;
D-hC is D-homocysteine
hC is L-homocysteine;
hF is L-homophenylalanine;
hK is L-lysine;
Nal is L-naphathaline;
Orn is ornithine;
Aib is ☐-aminoisobutyric acid;
Dab is (S)-diaminobutyric acid;
Dap is (S)-2,3-diaminopropionic acid;
M(O) is methionine sulfone;
Cha is (S)-☐-cyclohexylalanine;
4-amino-Isn is 4-Aminopiperidine-4-carboxylic acid;
Isn is isonipecotinoyl;
pE is L-pyroglutamic acid;

wherein the N-terminus and the C-terminus optionally form a ring together with 1, 2, 3 or 4 glycine amino acids; and or an amide, an ester or a salt of the polypeptide; or a polypeptide substantially equivalent thereto; and b. a half-life extending moiety; wherein said peptide or polypeptide and said half-life extending moiety are covalently linked or fused, optionally via a linker.

In embodiment 2, the invention pertains to a bioconjugate or a multimer thereof comprising:

a. a peptide or a polypeptide according to embodiment 1, 2 or 3, having Formula II (SEQ ID NO: 3):

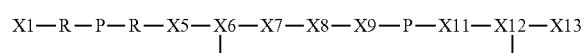

II wherein
X1 is absent, pE, R, Q or Isn;
X5 is L or Cha;
X7 is H, Aib, F, K;
X8 is K, F or 4-amino-Isn;
X9 is G or Aib;
X11 is Nle or Cha;
X13 is absent or is F, f, K;

X6 and X12 are independently a natural or unnatural amino acid selected from C, K, D, Orn, Dab or E wherein the side chain of X6 and X12 are linked together via a covalent bond; and wherein the N-terminus and the C-terminus optionally form a ring together with 1, 2, 3 or 4 glycine amino acids; or an amide, an ester or a salt of the polypeptide; or a polypeptide substantially equivalent thereto;

a. a half-life extending moiety and wherein said peptide or polypeptide and said half-life extending moiety are covalently linked or fused, optionally via a linker.

In yet a further aspect of anyone of the previous embodiments, more specifically of anyone of the previous embodiments, the invention pertains to a bioconjugate, or a multimer thereo, comprising a peptide or polypeptide of Formula I, I' or II wherein X6 and X12 are independently a natural or unnatural amino acid selected from C, K, D, Orn, Dab or E wherein the side chain of X6 and X12 are linked together via a covalent bond; or an amide, an ester or a salt of the polypeptide; or a polypeptide substantially equivalent thereto; and a half-life extending moiety; wherein said peptide or polypeptide and said half-life extending moiety are covalently linked or fused optionally via a linker.

In embodiment 3, the invention pertains to a bioconjugate, or a multimer thereof, comprising a peptide or polypeptide of Formula I, I' or II, according to anyone of the previous embodiments, wherein X6 and X12 are independently selected from K, Orn, Dab, E and D and wherein the side chain of X6 and X12 form together an amide bond; or an amide, an ester or a salt of the peptide or polypeptide; and a half-life extending moiety, wherein said peptide or polypeptide and half-life extending moiety are covalently linked or fused, optionally via a linker. In a further aspect of this embodiment, X6 is K, Orn or Dab and X12 is E or D and the side chain of X6 and X12 form an amide bond. In yet another aspect of this embodiment, X6 is K and X12 is E or D.

In embodiment 4, the invention pertains to a bioconjugate, or a multimer thereof, comprising a peptide or polypeptide of Formula I, I' or II, according to anyone of the previous embodiments, wherein X6 and X12 are independently C, c, D-hC or hC wherein the side chain of X6 and X12 form together a disulfide bond; or an amide, an ester or a salt of the peptide or polypeptide; and a half-life extending moiety, wherein said peptide or polypeptide and half-life extending moiety are covalently linked or fused, optionally via a linker. In a further aspect of this embodiment, X6 and X12 are C.

In embodiment 4A, the invention pertains to a bioconjugate, or a multimer thereof, comprising a peptide or polypeptide of Formula I, I' or II, according to anyone of the previous embodiments, more specifically of anyone of embodiments 1, 2 and 4, wherein X6 and X12 are independently C, c, D-hC or hC wherein the side chain of X6 and X12 form together a monosulfide (—S—) bond; or an amide, an ester or a salt of the peptide or polypeptide and a half-life extending moiety, wherein said peptide or polypeptide and half-life extending moiety are covalently linked or fused, optionally via a linker. In a further aspect of this embodiment, X6 and X12 are C.

In embodiment 5, certain bioconjugate of the invention comprise a peptide or polypeptide, according to anyone of embodiment 1, 2, 4, 4A and 4B, having Formula III (SEQ ID NO: 4):

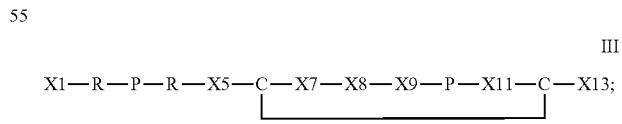

III or an amide, an ester or a salt of the polypeptide. In embodiment 5, the invention pertains to a bioconjugate or a multimer thereof, comprising a peptide or polypeptide of Formula III wherein the 2 cysteine at position 6 and 12 form a disulfide bond (—S—S—), a monosulfide bond (—S—). In a further aspect of embodiment 5 or 5A, the invention includes bioconjugate or a multimer thereof comprising a peptide or polypeptide of Formula III wherein the 2 cysteines in position 6 and 12 form a disulfide bond (—S—S—).

In embodiment 6, certain bioconjugates, or multimers thereof, comprise a peptide or polypeptide according to anyone of embodiment 1-5 having Formula IV (SEQ ID NO: 5):

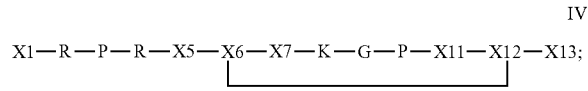
IV or an amide, an ester or a salt of the polypeptide, for conjugation with the half-life extending moiety.

In embodiment 7, certain bioconjugates, or multimers thereof, comprise a polypeptide according to anyone of embodiment 1, 2, and 4 to 6, having Formula V (SEQ ID NO: 6):

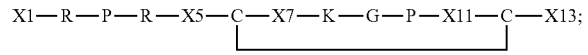
V or an amide, an ester or a salt of the polypeptide, for conjugation with the half-life extending moiety. In embodiment 7A, the invention pertains to a bioconjugate, a multimer thereof, comprising a peptide or polypeptide of Formula V wherein the 2 cysteine at position 6 and 12 form a disulfide bond (—S—S—), or a monosulfide bond (—S—). In a further aspect of embodiment 7 or 7A, the invention includes bioconjugate comprising a peptide or polypeptide of Formula V wherein the 2 cysteines in position 6 and 12 form a disulfide bond (—S—S—), for conjugation with the half-life extending moiety.

In embodiment 8, the invention pertains to a bioconjugate comprising a bicyclic peptide or polypeptide of Formula I or I' wherein X3 is cysteine and wherein the side chain of cysteine forms a disulfide bond with the side chain of the cysteine at the X7 position, and a half-life extending moiety wherein said peptide and said half-life extending moiety are covalently linked or fused, optionally via a linker. This embodiment is represented by a bioconjugate, or a multimer thereof, comprising a peptide or polypeptide of Formula VI (SEQ ID NO: 7):

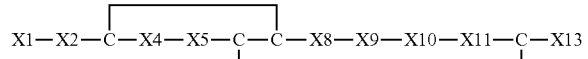
VI or an amide, an ester or a salt of the polypeptide for conjugation with a half-life extending moiety.

In embodiment 9, the invention pertains to a bioconjugate comprising a bicyclic peptide or polypeptide of Formula I or I' wherein X4 is cysteine and wherein the side chain of cysteine forms a disulfide bond with the side chain of the cysteine at the X7 position, and a half-life extending moiety wherein said peptide and said half-life extending moiety are covalently linked or fused, optionally via a linker. This embodiment is represented by a bioconjugate, or a multimer thereof, comprising a peptide or polypeptide of Formula VII (SEQ ID NO: 8):

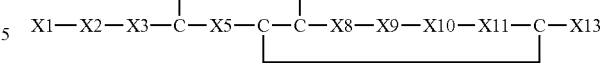
VII or an amide, an ester or a salt of the polypeptide for conjugation with the half-life extending moiety.

In embodiment 10, the invention pertains to a bioconjugate, or a multimer thereof, comprising a peptide or polypeptide of anyone of Formulae I to V, according to anyone of embodiment 1 to 7; wherein the N-terminus and the C-terminus optionally form a ring together with 1, 2, 3 or 4 glycine amino acids; or an amide, an ester or a salt of the polypeptide; or a polypeptide substantially equivalent thereto and a half-life extending moiety, wherein said peptide and half-life extending moiety are covalently linked or fused, optionally via a linker. This embodiment is represented by peptide or polypeptide having Formula VIII (SEQ ID NO: 9):

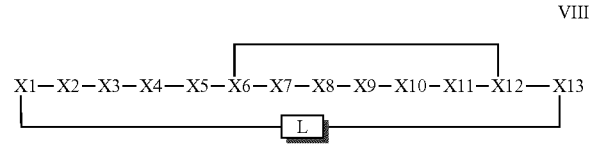
VIII wherein L is (G)r, G is glycine and r is 1, 2, 3 or 4; or a salt of the polypeptide. In this embodiment the half-life extending moiety is linked, optionally via a linker, to a functional group of a side chain (e.g. to an amino group on the side chain of K, Orn, Dab, Dap, hK or 4-amino-Isn).

In embodiment 10A, a further aspect of embodiment 10, the invention pertains to peptide or polypeptide of Formula VIII for conjugation with the half-life extending moiety wherein X1 is Q, X13 is F and r is 2 or an ester, an amide or a salt thereof;

In embodiment 11, the invention pertains to a bioconjugate, or a multimer thereof, comprising a peptide or polypeptide according to Formula I or I', according to embodiment 1 or 2, wherein X6 is K, X13 is absent and X12 is F or f wherein the C-terminus of X12 forms an amide bond with the amino side chain of X6, and a half-life extending moiety, wherein said peptide and half-life extending moiety are covalently linked or fused, optionally via a linker. This embodiment is represented by a peptide or polypeptide of Formula IX (SEQ ID NO: 10):

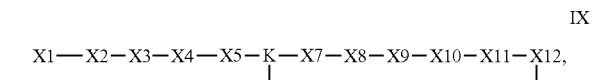
IX or an ester, an amide or a salt of the polypeptide, for conjugation with the half-life extending moiety. In a particular aspect of this embodiment, the peptide of Formula IX is preferably linked via its N-terminus, optionally via a linker, to the half-life extending moiety.

Any of the or below above-listed amino acid residues of Formula I', or its related formulae and all embodiments described herein, e.g., Formulae I, II to IX, may be substituted in a conservative fashion, provided the peptide or polypeptide of the invention still retains functional activity and structural properties (e.g., half-life extension, protection from degradation, conformational constraint). Principle and examples of permissible conservative amino acid substitutions are further explained herein.

The following embodiments can be used independently, collectively or in any combination or sub-combination:

In embodiment 12, the invention pertains to a bioconjugate, or a multimer thereof, comprising a peptide or a polypeptide according to any one of Formulae I', I to VII and IX, or any of any other classes and subclasses described supra, (i.e. according to anyone of the embodiments 1 to 9 and 11) or an amide, an ester or a salt thereof, wherein X1 is pE. In one aspect of this invention, the half-life extending moiety is linked, optionally via a linker to the C-terminus of the peptide. In another aspect of this invention, the half-life extending moiety is linked, optionally via a linker, to a side chain functional group of the peptide such as for example the amino acid functionality of a side chain of K, Orn, Dab, Dap, hK or 4-amino-Isn. One side chain amino acid of particular interest for linking the peptide to the half-life extending moiety is Lysine at position 8 (X8 is K).

In embodiment 12A, the invention pertains to a bioconjugate, or a multimer thereof, comprising a peptide or a polypeptide according to any one of Formulae I', I to VII and IX, or any of any other classes and subclasses described supra, (i.e. according to anyone of the embodiments 1 to 9 and 11) or an amide, an ester or a salt thereof, wherein X1 is A or Q. In a further aspect of this embodiment the peptide is fused or covalently linked to the half-life extending moiety via it's A or Q N-terminus.

In embodiment 13A, the invention pertains to bioconjugate, or a multimer thereof comprising a peptide or a polypeptide according to any one of Formulae I to VII, or any of any other classes and subclasses described supra, (i.e. according to anyone of embodiments 1 to 9), or an amide, an ester or a salt thereof, wherein X13 is F; or an amide, an ester or a salt of the polypeptide.

In embodiment 13B, the invention pertains to a bioconjugate, or a multimer thereof, comprising a peptide or a polypeptide according to any one of Formulae I to VII, or any of any other classes and subclasses described supra, (i.e. according to anyone of embodiments 1 to 9), or an amide, an ester or a salt thereof, wherein X13 is absent; or an amide, an ester or a salt of the polypeptide. In embodiment 13C, one aspect of embodiment 13B, The C-terminus is an amide. In embodiment 13D, a further aspect of embodiment 13C, the invention pertains to a bioconjugate, or a multimer thereof, comprising a peptide or a polypeptide according to any one of Formulae I to VII, or any of any other classes and subclasses described supra, or an amide, an ester or a salt thereof, wherein the C-terminus is an amide of Formula —C(O)R$^2$ and R$^2$ is —NH$_2$, —NH-Me, —NH—NHBn, or —NH—(CH$_2$)$_2$-Ph. In a prefered aspect of embodiment 13D, the invention pertains to bioconjugate comprising a peptide or a polypeptide according to any one of Formulae I to VII, or any of any other classes and subclasses described supra, or an amide, an ester or a salt thereof, wherein the C-terminus is an amide of Formula —C(O)R$^2$ and R$^2$ is —NH—(CH$_2$)$_2$-Ph.

In embodiment 14, the invention pertains to a bioconjugate, or a multimer thereof, comprising a peptide or a polypeptide according to anyone of Formulae I to IX, or any of any other classes and subclasses described supra, (i.e. according to anyone of embodiments 1 to 12), or an amide, an ester or a salt thereof, wherein X5 is L and a half-life extending moiety, wherein said peptide and half-life extending moiety are covalently linked or fused optionally via a linker.

In embodiment 15, the invention pertains to a bioconjugate, or a multimer thereof, comprising a peptide or a polypeptide according to anyone of Formulae I to V, VIII and IX, or any of any other classes and subclasses described supra (i.e. according to anyone of embodiments 1 to 7 and 10-14), or an amide, an ester or a salt thereof, wherein X7 is H, and a half-life extending moiety, wherein said peptide and half-life extending moiety are covalently linked or fused, optionally via a linker.

In embodiment 16, the invention pertains to a bioconjugate, or a multimer thereof, comprising a peptide or a polypeptide according to anyone of Formulae I to III and VI to IX, or any of any other classes and subclasses described supra, (i.e. according to anyone of embodiments 1 to 15), or an amide, an ester or a salt thereof, wherein X8 is K or F. In a further aspect of this embodiment, X8 is K, and a half-life extending moiety, wherein said peptide and half-life extending moiety are covalently linked or fused, optionally via a linker.

In embodiment 17, the invention pertains to a bioconjugate, or a multimer thereof, comprising a peptide and a polypeptide according to any one of Formulae I to III and VI to IX, or any of any other classes and subclasses described supra, (i.e. according to anyone of embodiments 1 to 16) or an amide, an ester or a salt thereof, wherein X9 is G, and a half-life extending moiety, wherein said peptide and half-life extending moiety are covalently linked or fused, optionally via a linker.

In embodiment 18, the invention pertains to a bioconjugate, or a multimer thereof comprising a peptide or polypeptide according to any one of Formulae I to IX, or any of any other classes and subclasses described supra, (i.e. according to anyone of embodiments 1 to 17), or an amide, an ester or a salt thereof, wherein X11 is Nle, and a half-life extending moiety, wherein said peptide and half-life extending moiety are covalently linked or fused, optionally via a linker.

In embodiment 18A, the invention pertains to a bioconjugate, or a multimer thereof, comprising a peptide or a polypeptide of embodiment 1, 2 or 3, wherein three of the amino acids X1 to X13 are different from the corresponding amino acids present in Pyr-1-apelin-13. In embodiment 18B, the invention pertains to a bioconjugate comprising a peptide or a polypeptide of embodiment 1, 2 or 3 wherein four of the amino acids X1 to X13 are different from the corresponding amino acids present in Pyr-1-apelin-13.

In another embodiment, X1, X2, X3, X4, X5, X6, X7, X8. X9, X10, X11, X12 and X13 amino acids, linker and half-life extending moieties are those defined by X1, X2, X3, X4, X5, X6, X7, X8, X9, X10, X11, X12 and X13 amino acids, linker and half-life extending moiety in the Examples section below.

Unless specified otherwise, the term "polypeptide" refers to a polypeptide of Formula (I') and subformulae thereof (Formulae I, II to IX); or an amide, an ester or a salt thereof.

Unless specified otherwise, the terms "polypeptides", "peptides", "APJ peptide agonists," and the like refer to peptides and polypeptides of Formula I' and subformulae thereof (Formulae I, II, III, IV, V, VI, VII, VIII or IX); or an amide, an ester or a salt thereof. The bioconjugates of the peptides and polypeptides of the invention demonstrate substantially equivalent or improved activity and/or plasma stability over known apelin peptides and polypeptides described herein, including but not limited to wild type apelin, apelin-13 and pyr-1-apelin-13.

The bioconjugates of the invention also encompass bioconjugates containing peptides and polypeptides which are at least about 95% identical to the peptides and polypeptides according to any one of Formulae I', I to IX, or an amide, an ester or a salt thereof, as well as to any peptides or polypeptides specifically listed herein, including but not limited to the experimental examples.

As used herein, the phrase "homologous amino acid sequence," or variations thereof, refers to sequences characterized by a homology, at the amino acid level, of at least a specified percentage and is used interchangeably with "sequence identity." Homologous amino acid sequences include those amino acid sequences which contain conservative amino acid substitutions and which polypeptides have the same binding and/or activity. In some embodiments, an amino acid sequence is homologous if it has at least 60% or greater, up to 99%, identity with a comparator sequence. In some embodiments, an amino acid sequence is homologous if it shares one or more, up to 60, amino acid substitutions, additions, or deletions with a comparator sequence. In some embodiments, the homologous amino acid sequences have no more than 5 or no more than 3 conservative amino acid substitutions.

Homology may also be at the polypeptide level. The degree or percentage identity of peptides or polypeptides of the invention, or portions thereof, and different amino acid sequences is calculated as the number of exact matches in an alignment of the two sequences divided by the length of the "invention sequence" or the "foreign sequence", whichever is shortest. The result is expressed as percent identity.

A polypeptide comprising an amino acid sequence having a homology of about 80-99.9%, preferably 90-99.9% to the amino acid sequence described in the specific examples, and possessing a plasma stability superior to apelin-13 or pyr-1-apelin-13, fall under the category of the polypeptide of the invention. In one embodiment, the plasma stability improvement is at least 2 fold. In one embodiment, the polypeptide of the invention has a plasma stability of at least 30 minutes. In another embodiment, the polypeptide of the invention has a plasma stability of at least 60 minutes, preferably at least 100 min and more preferably at least 150 minutes.

The term "substantially equivalent" means the nature of the receptor-binding activity, signal transduction activity and the like is equivalent. Thus, it is allowable that even differences among grades such as the strength of receptor binding activity and the molecular weight of the polypeptide are present.

A polypeptide as described herein, or a substantial equivalent thereto, by substitution, deletion, addition or insertion of one or more of amino acids may be mentioned as polypeptides containing an amino acid sequence substantial equivalent(s) in the above sense. A polypeptide as described herein, or a substantial equivalent thereto, by substitution of 1 to 5, preferably 1 to 3 and more preferably 1 or 2 amino acids with natural or un-natural amino acids may be mentioned as polypeptides containing an amino acid sequence substantial equivalent(s) in the above sense. Further modifications and alterations may include the replacement of an L-amino-acid with a D-amino acid, or other variation including, but not limited to, phosphorylation, carboxylation, alkylation and the like as long as the APJ agonistic activity of the peptide of polypeptide of Formulae I, II, III, IV, V, VI, VII, VIII or IX is maintained and the plasma stability is improved over the pyroglutamated form of apelin-13. For example, D-amino acid are well tolerated with respect to activity and stability of the polypeptide at position 2 (X2), position 3 (X3), positions 5, 6, 7 and 8 (X5, X6, X7 and X8), position 10 (X10) and position 13 (X13) of the cyclic peptides and polypeptides of Formulae I, II, III, IV, V, VI, VII, VIII or IX.

In one embodiment, the half-life extending moiety is covalently linked or fused to the N-terminus of the peptide of Formula I' or anyone of Formulae I to VII and IX, optionally via a linker moiety.

In another embodiment, the half-life extending moiety is covalently linked or fused to the C-terminus of the peptide of Formula I' or anyone of Formulae I to IX, optionally via a linker moiety In yet another embodiment, the half-life extending moiety is covalently linked or fused to a side chain of the peptide of Formula I' or anyone of Formulae I to IX, e.g. the half-life is attached to an amino group in the side chain of K, Orn, Dab, Dap, hK or 4-amino-Isn, optionally via a linker moiety. Preferably, the half-life extending moiety is attached to the N-terminus of the peptide of Formula I' or anyone of Formulae I-IX, optionally via a linker moiety.

Half-life Extending Moiety

The half-life extending moiety of the invention can be covalently fused, attached, linked or conjugated to a peptide or polypeptide analog. A half-life extending moiety can be, for example, a polymer, such as polyethylene glycol (PEG), a fatty acid, a cholesterol group, a carbohydrate or oligosaccharide; or any natural or synthetic protein, polypeptide or peptide that binds to a salvage receptor. Preferably, the half-life extending moiety is covalently linked, optionally via a linker, to plasma protein (albumin and immunoglobulin) with long serum half-lives. For example, the half-life extending moiety is an IgG constant domain or fragment thereof (e.g., the Fc region), Human Serum Albumin (HSA), fatty acid, or albumin-binding polypeptides. Preferably, the half-life extending moiety portion of the bioconjugate is Human Serum Albumin, a fatty acid or an Fc region.

Half-life extending moieties include Albumin, which refers to the most abundant protein in the blood plasma having a molecular weight of approximately between 65 and 67 kilodaltons in its monomeric form, depending on species of origin. The term "albumin" is used interchangeably with "serum albumin" and is not meant to define the source of albumin which forms a conjugate with the modified peptides of the invention. Thus, the term "albumin" as used herein may refer either to albumin purified from a natural source such as blood or serous fluids, or it may refer to chemically synthesized or recombinantly produced albumin. Modified peptides or polypeptides of the invention are preferentially tethered to the free thiol group of the cysteine-34 on the surface of the albumin, optionally via a linker.

Half-life extending moieties include fatty acids, which can be defined as a C6-70alkyl, a C6-70alkenyl or a C6-70alkynyl chain, each of which is substituted with at least one carboxylic acid (for example 1, 2, 3 or 4 CO2H) and optionally further substituted with hydroxyl group. Examples of fatty acid are defined by Formulae A1, A2 and A3:

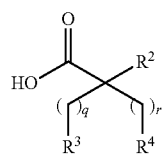

A1

-continued

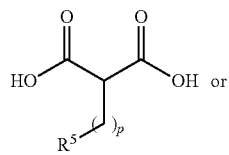
A2

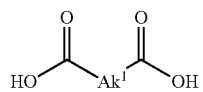
A3

$R^2$ is $CO_2H$, H;

$R^3$, $R^4$ and $R^5$ are independently of each other H, OH, $CO_2H$, —CH=$CH_2$ or —C≡CH;

$Ak^1$ is a branched $C_6$-$C_{30}$alkylene;

q, r and p are independently of each other an integer between 6 and 30; or an amide, an ester or a pharmaceutically acceptable salt thereof.

Examples of fatty acids are selected from:

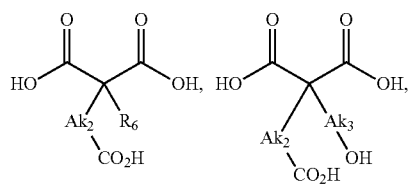

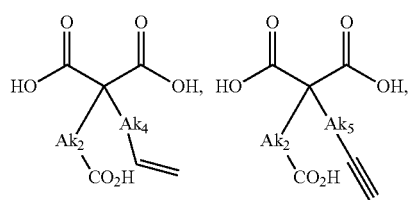

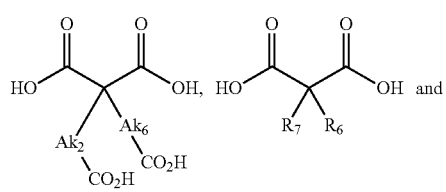

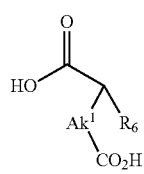

wherein $Ak^2$, $Ak^3$, $Ak^4$, $Ak^5$ and $Ak^6$ are independently a $(C_{8-20})$alkylene, $R^6$ and $R^7$ are independently $(C_{8-20})$alkyl.

More specifically, fatty acids are selected from:

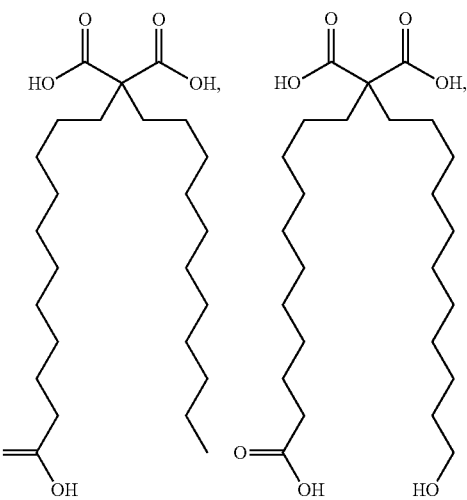

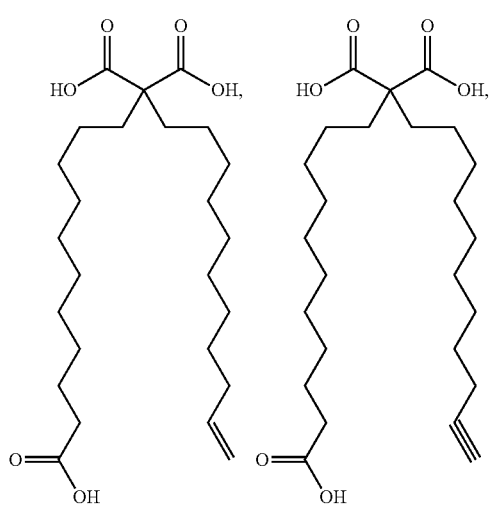

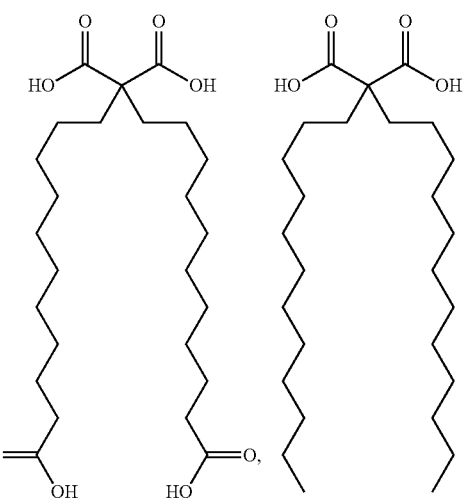

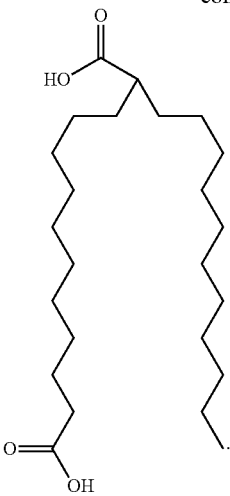

These fatty acid moieties have been described in co-filed U.S. application Ser. No. 62/015,862.

Half-life extending moieties include "native Fc" which refers to molecule or sequence comprising the sequence of a non-antigen-binding fragment resulting from digestion of whole antibody or produced by other means, whether in monomeric or multimeric form, and can contain the hinge region. The original immunoglobulin source of the native Fc is preferably of human origin and can be any of the immunoglobulins, although IgG1 and IgG2 are preferred. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a native Fc is a disulfide-bonded dimer resulting from papain digestion of an IgG (see Ellison et al., 1982, Nucleic Acids Res. 10: 4071-9). The term "native Fc" as used herein is generic to the monomeric, dimeric, and multimeric forms.

Half-life extending moieties include "Fc variant" which refers to a molecule or sequence that is modified from a native Fc but still comprises a binding site for the salvage receptor, FcRn (neonatal Fc receptor). International Publication Nos. WO 97/34631 and WO 96/32478 describe exemplary Fc variants, as well as interaction with the salvage receptor, and are hereby incorporated by reference. Thus, the term "Fc variant" can comprise a molecule or sequence that is humanized from a non-human native Fc. Furthermore, a native Fc comprises regions that can be removed because they provide structural features or biological activity that are not required for the bioconjugate of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

Half-life extending moieties include Fc variant wherein the C-terminus lysine has been deleted or replaced with alanine.

Half-time extending moieties refer to "Fc domain" which encompasses native Fc and Fc variants and sequences as defined above. As with Fc variants and native Fc molecules, the term "Fc domain" includes molecules in monomeric or multimeric form, whether digested from whole antibody or produced by other means. In some embodiments of the present invention, an Fc domain can be conjugated to a polypeptide of Formula I' or anyone of Formulae I-IX via, for example, a covalent bond between the Fc domain and the peptide sequence. Such Fc proteins can form multimers via the association of the Fc domains and both these Fc proteins and their multimers are an aspect of the present invention.

Half-life extending moieties include "modified Fc fragment", which shall mean an Fc fragment of an antibody comprising a modified sequence. The Fc fragment is a portion of an antibody comprising the $CH_2$, $CH_3$ and part of the hinge region. The modified Fc fragment can be derived from, for example, IgGI, IgG2, IgG3, or IgG4. FcLALA is a modified Fc fragment with a LALA mutation (L234A, L235A), which triggers ADCC with lowered efficiency, and binds and activates human complement weakly. Hessell et al. 2007 Nature 449:101-104. Additional modifications to the Fc fragment are described in, for example, U.S. Pat. No. 7,217,798.

The term "multimer" as applied to Fc domains or molecule comprising Fc domains refers to molecules having two or more polypeptide chains associated covalently. For example IgG molecules typically form dimers and therefore a bioconjugate comprising a dimeric IgG molecule would be fused to two polypeptide chains of Formula I'.

Linker

Any linker group is optional. When present, its chemical structure is not critical, since it serves primarily as a spacer.

The linker is a chemical moiety that contains two reactive groups/functional groups, one of which can react with the polypeptide and the other with the half-life extending moiety. The two reactive groups of the linker are linked via a linking group, structure of which is not critical as long as it does not interfere with the coupling of the linker to the peptide and the half-extending moiety.

The linker can be made up of amino acids linked together by peptide bonds. In some embodiments of the present invention, the linker is made up of from 1 to 20 amino acids linked by peptide bonds, wherein the amino acids are selected from the 20 naturally occurring amino acids. In various embodiments, the 1 to 20 amino acids are selected from the amino acids glycine, serine, alanine, proline, asparagine, glutamine, cysteine and lysine. In some embodiments, a linker is made up of a majority of amino acids that are sterically unhindered, such as glycine and alanine. In some embodiments, linkers are polyglycines, polyalanines, combinations of glycine and alanine (such as poly(Gly-Ala)), or combinations of glycine and serine (such as poly(Gly-Ser)). In some embodiments, a linker comprises a majority of amino acids selected from histidine, alanine, methionine, glutamine, asparagine and glycine. In some embodiments, linkers contain poly-histidine moiety. Examples of linkers are linkers which comprise the motif AH, MHA or AHA. Such motifs have been described in copending applications and co-filed U.S. application Ser. Nos. 62/015,854, 62/015,862 and 62/015,868, to be beneficial for selective conjugation at the N-terminus of a peptide or polypeptide.

Other examples of linkers comprises the motif GGGGSGGGGSGGGGS (SEQ ID NO: 11), GGGGSGGGGS (SEQ ID NO: 12), GGGGS (SEQ ID NO: 13), GS or GG.

In some other embodiment, the linker comprises recognition motifs for enzyme. An example is the LPXTG/A motif which can be included at the C-terminus wherein X is any amino acid, most commonly an E: Glutamic acid. (L: leucine, P: proline, T: threonine, G: Glycine, A; Alanine). (Carla P. Guimaraes et al.: "Site specific C-terminal and internal loop labeling of proteins using sortase-mediated reactions", Nature protocols, vol 8, No 9, 2013, 1787-1799)

In other embodiments, the linker comprises 1 to 20 amino acids which are selected from unnatural amino acids. While a linker of 3-15 amino acid residues is preferred for conjugation with the half-life extending moiety, the present invention contemplates linkers of any length or composition. A preferred non natural amino acid linker is O2Oc of the following formula:

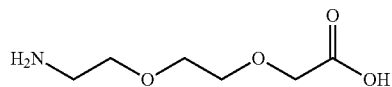

or its repeating units.

The linkers described herein are exemplary, and linkers that are much longer and which include other residues are contemplated by the present invention. Non-peptide linkers are also contemplated by the present invention.

The linking portion of the linker may comprise one or more alkyl groups, alkoxy groups, alkenyl groups, cycloalkyl groups, aryl groups, heteroaryl groups and heterocyclic groups or combination thereof. For example, alkyl linkers such as such as —NH—$(CH_2)_z$—C(O)— or —S—$(CH_2)_z$—C(O)— or —O—$(CH_2)_z$—C(O)— wherein z is 2-20 can be used. These alkyl linkers can further be substituted by any non-sterically hindering group, including, but not limited to, a lower alkyl (e.g., C1-C6), lower acyl, halogen (e.g., Cl, Br), CN, $NH_2$, or phenyl.

The linker can also be of polymeric nature. The linker may include polymer chains or units that are biostable or biodegradable. Polymers with repeat linkage may have varying degrees of stability under physiological conditions depending on bond lability. Polymers may contain bonds such as polycarbonates (—O—C(O)—O—), polyesters (—C(O)—O—), polyurethanes (—NH—C(O)—O—), polyamide (—C(O)—NH—). These bonds are provided by way of examples, and are not intended to limit the type of bonds employable in the polymer chains or linkers of the invention. Suitable polymers include, for example, polyethylene glycol (PEG), polyvinyl pyrrolidone, polyvinyl alcohol, polyamino acids, divinylether maleic anhydride, N-(2-hydroxypropyl)-methacrylicamide, dextran, dextran derivatives, polypropylene glycol, polyoxyethylated polyol, heparin, heparin fragments, polysaccharides, cellulose and cellulose derivatives, starch and starch derivatives, polyalkylene glycol and derivatives thereof, copolymers of polyalkylene glycols and derivatives thereof, polyvinyl ethyl ether, and the klike and mixtures thereof. A polymer linker is for example PEG. An exemplary non-peptide linker is a polyethylene glycol linker:

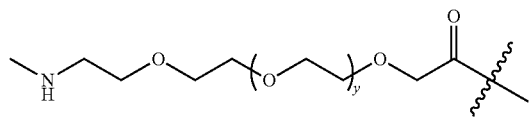

wherein the linker has a molecular weight of 100 to 5000 kD, for example, 100 to 500 kD.

Preferably, the linking moiety contains one or more amino acid moieties such as for example (O2Oc) unit or Glycine or serine, $C_{1-4}$alkylene-C(O)—, —NH—$C_{2-6}$alkylene-NH— or —NH—$CH_2CH_2$—O—$CH_2CH_2$—NH— diamino units or combination thereof and the linking moiety linked 2 reactive groups or functional groups.

Preferably, the reactive groups or functional groups are maleimide, thiol or pyridine-2-yldisulfanyl.

Preparation of the Peptide or Polypeptide and Peptide-linker Construct for Conjugation:

The apelin peptides and polypeptides and/or peptide-linker construct of the invention may be produced by either synthetic chemical processes or by recombinant methods or combination of both methods. The Apelin peptides and/or peptide-linker constructs may be prepared as full-length or may be synthesized as non-full length fragments and joined. The peptides and polypeptides or peptide-construct of the present invention can be produced by the per se known procedures for peptide synthesis. The methods for peptide synthesis may be any of a solid-phase synthesis and a liquid-phase synthesis. Thus, the peptide and polypeptide of interest can be produced by condensing a partial peptide or amino acid capable of constituting the protein with the residual part thereof and, when the product has a protective group, the protective group is detached whereupon a desired peptide can be manufactured. The known methods for condensation and deprotection include the procedures described in the following literature (1)-(5).

(1) M. Bodanszky and M. A. Ondetti, Peptide Synthesis, Interscience Publishers, New York, 1966,
(2) Schroeder and Luebke, The Peptide, Academic Press, New York, 1965,
(3) Nobuo lzumiya et al. Fundamentals and Experiments in Peptide Synthesis, Maruzen, 1975,
(4) Haruaki Yajima and Shumpei Sakakibara, Biochemical Experiment Series 1, Protein Chemistry IV, 205, 1977, and
(5) Haruaki Yajima (ed.), Development of Drugs-Continued, 14, Peptide Synthesis, Hirokawa Shoten.

After the reaction, the peptide can be purified and isolated by a combination of conventional purification techniques such as solvent extraction, column chromatography, liquid chromatography, and recrystallization. Where the peptide isolated as above is a free compound, it can be converted to a suitable salt by the known method. Conversely where the isolated product is a salt, it can be converted to the free peptide by the known method.

The amide of polypeptide can be obtained by using a resin for peptide synthesis which is suited for amidation. The resin includes chloromethyl resin, hydroxymethyl resin, benzhydrylamine resin, aminomethyl resin, 4-benzyloxybenzyl alcohol resin, 4-methylbenz-hydrylamine resin, PAM resin, 4-hydroxymethylmethylphenylacetamidomethyl resin, polyacrylamide resin, 4-(2',4'-dimethoxyphenyl-hydroxymethyl) phenoxy resin, 4-(2',4'-dimethoxyphenyl-Fmoc-aminomethyl)phenoxy resin, 2-chlorotrityl chloride resin, and so on. Using such a resin, amino acids whose α-amino groups and functional groups of side-chain have been suitably protected are condensed on the resin according to the sequence of the objective peptide by various condensation techniques which are known per se. At the end of the series of reactions, the peptide or the protected peptide is removed from the resin and the protective groups are removed and if necessary, disulfide bonds are formed to obtain the objective polypeptide.

For the condensation of the above-mentioned protected amino acids, a variety of activating reagents for peptide synthesis can be used such as HATU, HCTU or e.g. a carbodiimide. The carbodiimide includes DCC, N,N'-diisopropylcarbodiimide, and N-ethyl-N'-(3-dimethylaminopropyl) carbodiimide. For activation with such a reagent, a racemization inhibitor additive, e.g. HOBt or Oxyma Pure can be used. The protected amino acid can be directly added to the resin along with the activation reagents and racemization inhibitor or be pre-activated as symmetric acid anhydride, HOBt ester, or HOOBt ester then added to the resin. The solvent for the activation of protected amino acids or condensation with the resin can be properly selected from among those solvents which are known to be useful for peptide condensation reactions. For example, N,N-dimethylformamide, N-methylpyrrolidone, chloroform, trifluoroethanol, dimethyl sulfoxide, DMF, pyridine, dioxane, methylene chloride, tetrahydrofuran, acetonitrile, ethyl acetate, or suitable mixtures of them can be mentioned.

The reaction temperature can be selected from the range hitherto-known to be useful for peptide bond formation and is usually selected from the range of about −20° C.-50° C. The activated amino acid derivative is generally used in a proportion of 1.5-4 fold excess. If the condensation is found to be insufficient by a test utilizing the ninhydrin reaction, the condensation reaction can be repeated to achieve a sufficient condensation without removing the protective group. If repeated condensation still fails to provide a sufficient degree of condensation, the unreacted amino group can be acetylated with acetic anhydride or acetylimidazole.

The protecting group of amino group for the starting material amino acid includes Z, Boc, tertiary-amyloxycarbonyl, isobornyloxycarbonyl, 4-m ethoxybenzyloxycarbonyl, Cl—Z, Br—Z, adamantyloxycarbonyl, trifluoroacetyl, phthalyl, formyl, 2-nitrophenylsulfenyl, diphenylphosphinothioyl, or Fmoc. The carboxy-protecting group that can be used includes but is not limited to the above-mentioned $C_{1-6}$ alkyl, $C_{3-8}$ cycloalkyl and $C_{6-10}$aryl-$C_{1-2}$alkyl as well as 2-adamantyl, 4-nitrobenzyl, 4-methoxybenzyl, 4-chlorobenzyl, phenacyl, benzyloxycarbonylhydrazido, tertiary-butoxycarbonylhydrazido, and tritylhydrazido.

The hydroxy group of serine and threonine can be protected by esterification or etherification. The group suited for said esterification includes carbon-derived groups such as lower alkanoyl groups, e.g. acetyl etc., aroyl groups, e.g. benzoyl etc., benzyloxycarbonyl, and ethoxycarbonyl. The group suited for said etherification includes benzyl, tetrahydropyranyl, and tertiary-butyl. The protective group for the phenolic hydroxyl group of tyrosine includes Bzl, $Cl_2$-Bzl, 2-nitrobenzyl, Br—Z, and tertiary-butyl.

The protecting group of imidazole for histidine includes Tos, 4-methoxy-2,3,6-triethylbenzenesulfonyl, DNP, benzyloxymethyl, Bum, Boc, Trt, and Fmoc.

The activated carboxyl group of the starting amino acid includes the corresponding acid anhydride, azide and active esters, e.g. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt, etc. The activated amino group of the starting amino acid includes the corresponding phosphoramide.

The method for elimination of protective groups includes catalytic reduction using hydrogen gas in the presence of a catalyst such as palladium black or palladium-on-carbon, acid treatment with anhydrous hydrogen fluoride, methanesulfonic acid, trifluoromethanesulfonic acid, trifluoroacetic acid, or a mixture of such acids, base treatment with diisopropylethylamine, triethylamine, piperidine, piperazine, reduction with sodium metal in liquid ammonia. The elimination reaction by the above-mentioned acid treatment is generally carried out at a temperature of −20° C.-40° C. and can be conducted advantageously with addition of a cation acceptor such as anisole, phenol, thioanisole, m-cresol, p-cresol, dimethyl sulfide, 1,4-butanedithiol, 1,2-ethanedithiol. The 2,4-dinitrophenyl group used for protecting the imidazole group of histidine can be eliminated by treatment with thiophenol, while the formyl group used for protecting the indole group of tryptophan can be eliminated by alkali treatment with dilute sodium hydroxide solution or dilute aqueous ammonia as well as the above-mentioned acid treatment in the presence of 1,2-ethanedithiol, 1,4-butanedithiol.

The method for protecting functional groups which should not take part in the reaction of the starting material, the protective groups that can be used, the method of removing the protective groups, and the method of activating the functional groups that are to take part in the reaction can all be selected judicially from among the known groups and methods.

An another method for obtaining the amide form of the polypeptide comprises amidating the -carboxyl group of the C-terminal amino acid at first, then extending the peptide chain to the N-side until the desired chain length, and then selectively deprotecting the α-amino group of the C-terminal peptide and the α-carboxy group of the amino acid or peptide that is to form the remainder of the objective polypeptide and condensing the two fragments whose α-amino group and side-chain functional groups have been protected with suitable protective groups mentioned above in a mixed solvent such as that mentioned hereinbefore. The parameters of this condensation reaction can be the same as described hereinbefore. From the protected peptide obtained by condensation, all the protective groups are removed by the above-described method to thereby provide the desired crude peptide. This crude peptide can be purified by known purification procedures and the main fraction be lyophilized to provide the objective amidated polypeptide. To obtain an ester of the polypeptide, the a-carboxyl group of the C-terminal amino acid is condensed with a desired alcohol to give an amino acid ester and then, the procedure described above for production of the amide is followed.

Alternatively, recombinant expression methods are particularly useful. Recombinant protein expression using a host cell (a cell artificially engineered to comprise nucleic acids encoding the sequence of the peptide and which will transcribe and translate, and optionally, secrete the peptide into the cell growth medium) is used routinely in the art. For recombinant production process, a nucleic acid coding for amino acid sequence of the peptide would typically be synthesized by conventionaly methods and integrated into an expression vector. Such methods is particularly preferred for manufacture of the polypeptide compositions comprising the peptides fused to additional peptide sequences or other proteins or protein fragments or domains. The host cell can optionally be at least one selected from from E. Coli, COS-1, COS-7, HEK293, BHT21, CHO, BSC-1, Hep G2, 653, SP2/0, 293, heLa, myeloma, lymphoma, yeast, insect or plant cells, or any derivative, immortalized or transformed cell thereof.

The modified therapeutic peptides or polypeptides and/or peptide-linker construct include reactive groups which can react with available reactive functionalities on the half-life extending moiety to form a covalent bond. Reactive groups are chemical groups capable of forming a covalent bond. Reactive groups can generally be carboxy, phosphoryl, acyl group, ester or mixed anhydride, maleimide, imidate, pyridine-2-yl-disulfanyl, thereby capable of forming a covalent bond with functionalities like amino group, hydroxyl group, carboxy group or a thiol group at the target site of the Albumin or Fc domain. Reactive groups of particular interest for linking to an Albumin include maleimido-containing groups and pyridine-2-yl-disulfanyl containing group. Functionalities are groups on Albumin or Fc domain to which reactive groups on modified peptides or polypeptides are capable of reacting with to form covalent bonds. Functionalities include hydroxyl groups for bonding with ester reactive entities, thiol groups for reacting with maleimides, maleimido-containing groups or pyridine-2-yldisulfanyl, imidates and thioester groups; amino groups for bonding to carboxylic acid, phosphoryl groups, acyl group.

Schemes 1 to 3 describe the synthesis of peptide-Linker construct wherein the peptide is an APJ agonist peptide or a peptide according to anyone of Formulae I to IX.

Scheme 1 describes the synthesis of a maleimide containing linker attached to the N-terminus of an APJ agonist polypeptide or a polypeptide of Formula I to IX.

more preferably 3 to 6) according to well established amide coupling chemistry to generate (1A). The terminal amino functionality of (1A) is reacted with an activated acid (1B) wherein R is linear or branched alkylene, aryl, heteroaryl, cycloalkyl or combination thereof, in order to generate the peptide-maleimide containing linker construct (1C). The activated acid (1B) is commercially available or readily available from its corresponding carboxylic acid according to technique known to someone of ordinary skill in the art. Preferably, R is a linear alkylene, and more preferably R is —CH$_2$—CH$_2$—. Alternatively, for peptides containing an amino functionality in the side chain (for example peptide containing a lysine), orthogonal protecting group such as Alloc is required prior to the coupling reaction, followed by additional deprotection step in order to obtain (1C).

Schemes 2A and 2B describe the synthesis of pyridine-2-yl-disulfanyl containing linker attached to the N-terminus of

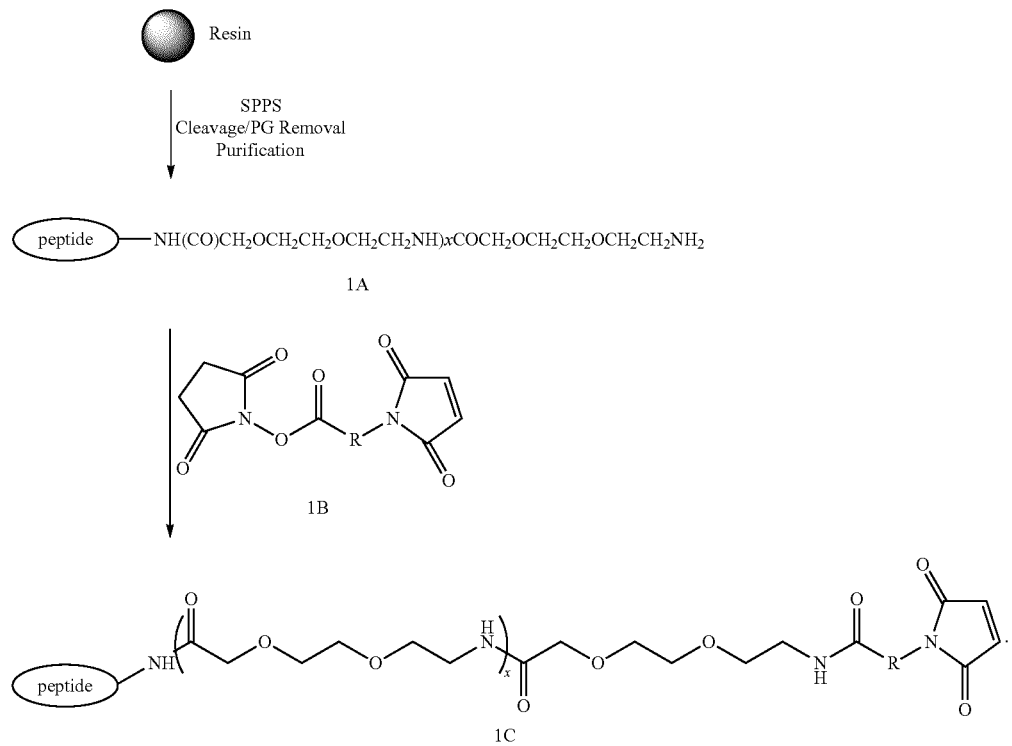

Scheme 1

The N-terminus of the peptide is coupled with one or more O2Oc amino acid units (x is 1 to 20, preferably 1 to 10 and more preferably 3 to 6)

an APJ agonist polypeptide or a polypeptide of Formula I to IX.

Scheme 2A

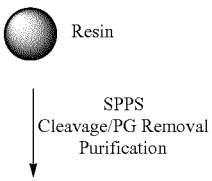

-continued

1A

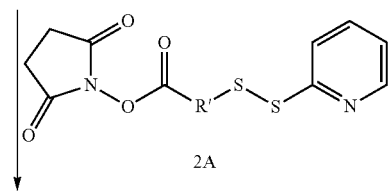

2A

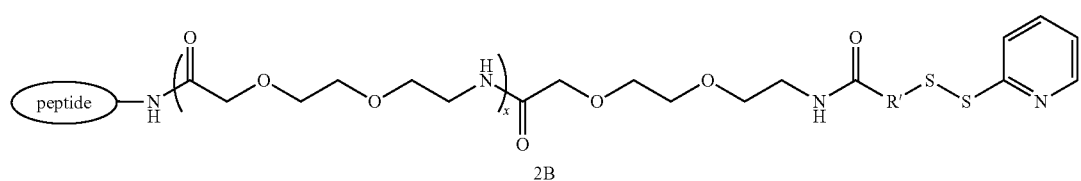

2B

Scheme 2B

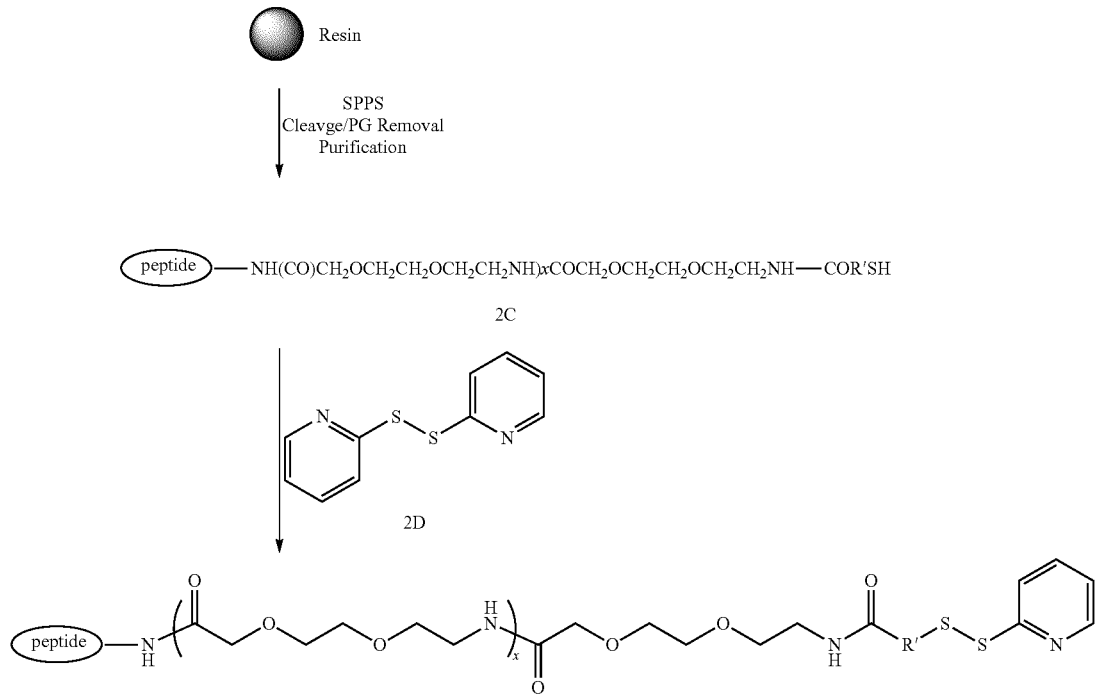

Peptide-Linker Construct (1A) is prepared as described in Scheme 1 and is further reacted with an activated acid of Formula (2A) wherein R' is a linear or branched alkylene, to generate a peptide-pyridine-2-yl-disulfanyl containing linker construct (2B). Activated acid (2A) is commercially available or is readily available from its corresponding carboxylic acid according to techniques known to someone of ordinary skill in the art. Preferably R' is is —CH$_2$—CH$_2$—. Alternatively, Peptide-Linker Construct (2C) can be prepared using HO$_2$C—R'—SH, or a protected form thereof (e.g. trityl or Acm groups, requiring additional deprotection steps), and further reacted with (2D) to generate peptide-pyridine-2-yl-disulfanyl containing linker construct (2B). Similarly to Scheme 1, orthogonal functional group (such as amino group of lysine) protection may be required prior to coupling reactions.

Similar functional groups are attached to the C-terminus of the peptide in a similar way as described in Schemes 1, 2A and 2B sing a diamino unit such as for example —NH—CH$_2$CH$_2$—NH— or —NH—CH$_2$CH$_2$—O—CH$_2$CH$_2$—NH—. Non limiting examples of such Peptide-Linker Conducts are:

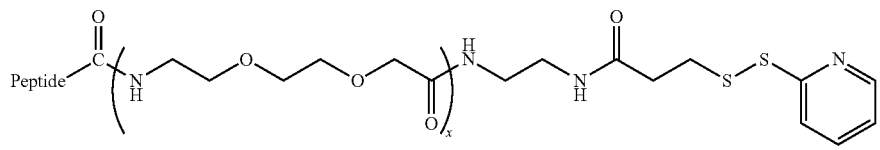
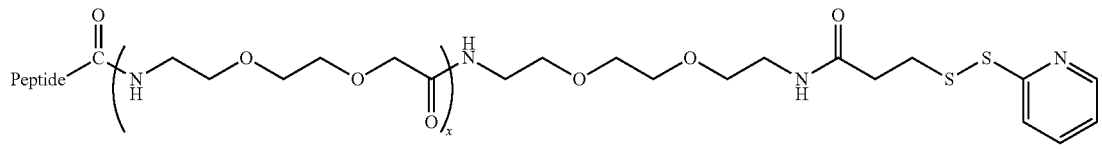
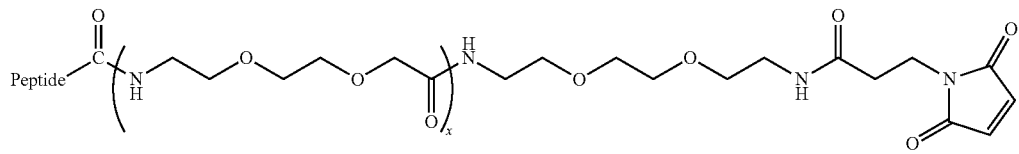
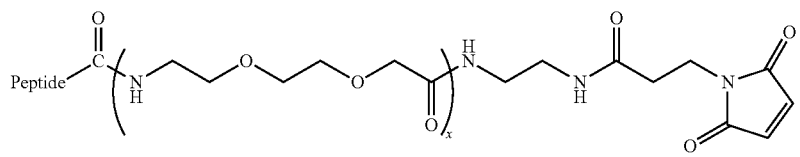
Alternatively maleimide or pyridine-2-yl-disulfanyl functional group can be attached to an APJ agonist polypeptide or a polypeptide of Formula I to IX according to schemes 3A, 3B and 3C:
Scheme 3A
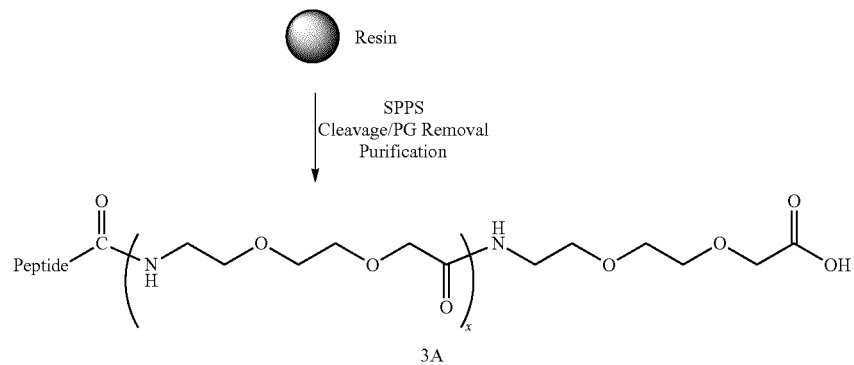
3A
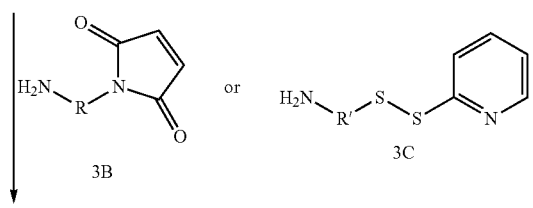
3B     3C

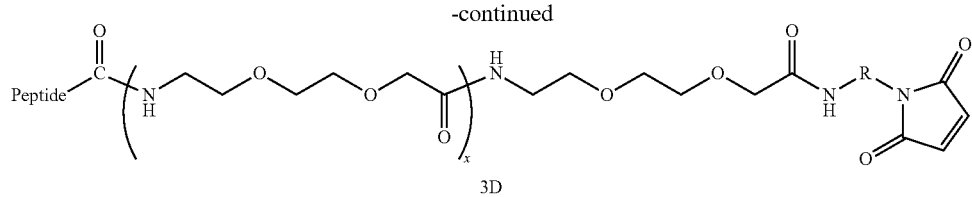

3D or

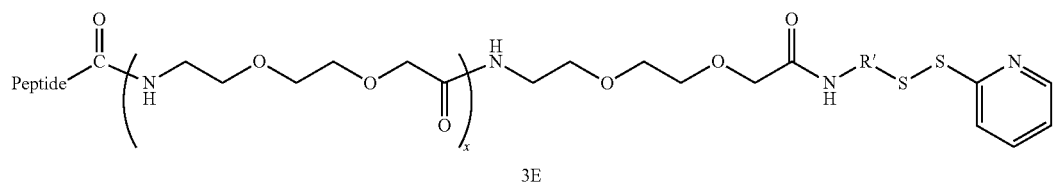

3E

The carboxylic acid group at the C-terminus of the peptide is coupled with one or more O2Oc amino acid units using standard amide coupling conditions to generate (3A). The terminal carboxylic acid functionality reacts with the amino group of (3B) or (3C) wherein R and R' are as defined above, in order to generate the activated peptide-linker constructs (3D) or (3E). Additionally, when a peptide contains a carboxy functionality side chain (e.g. Glu or Asp), orthogonal protecting group (e.g. O-Allyl) and additional deprotection steps are required.

Scheme 3B

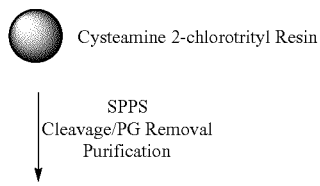 Cysteamine 2-chlorotrityl Resin

| SPPS
Cleavage/PG Removal
Purification
↓

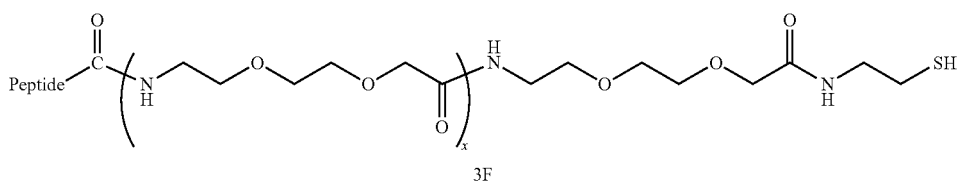

3F

↓

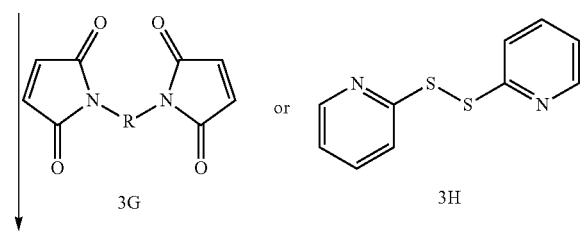

3G    or    3H

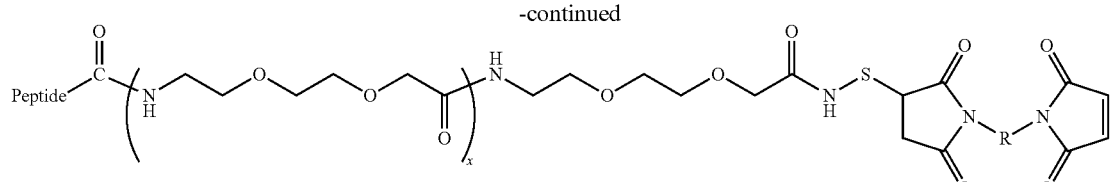
3I
or
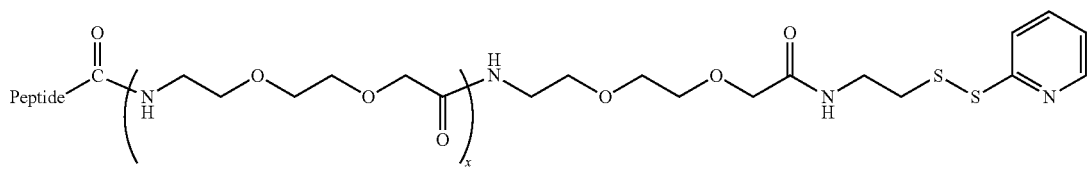
3E
Peptide-linker construct 3F can be obtained using a cysteamine 2-chlorotrityl Resin and then reacted with 3G or 3H to generate peptide-linker construct 3I or 3E respectively.
Scheme 3C
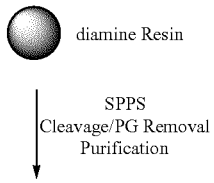
diamine Resin
SPPS
Cleavage/PG Removal
Purification
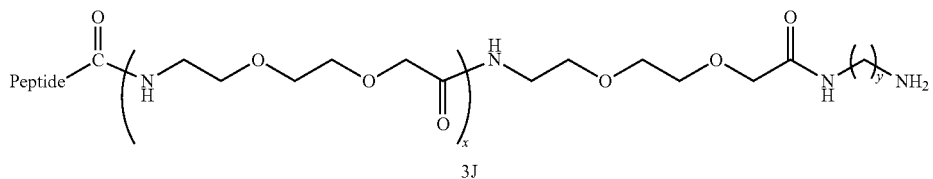
3J
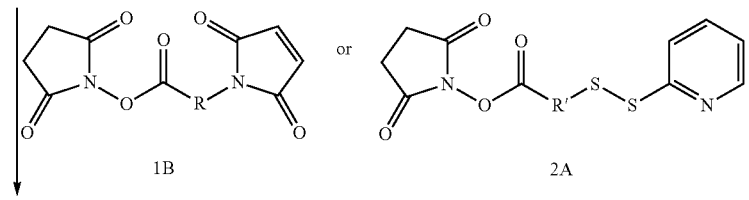
1B     2A

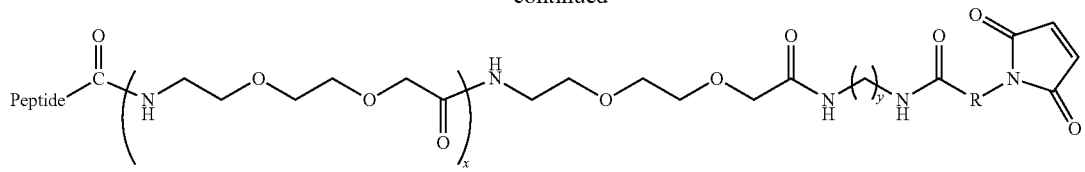

3K or

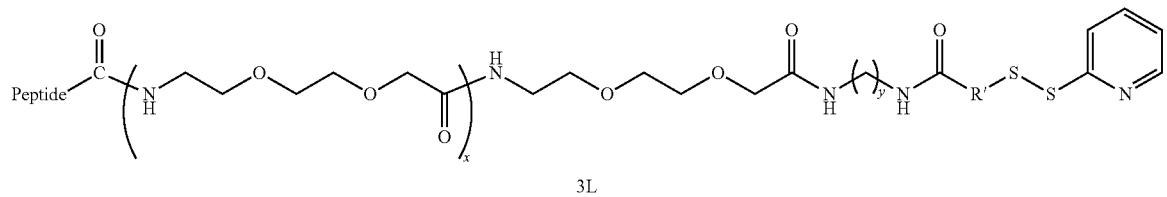

3L y is 1 to 10

Peptide-Linker Construct (3J) can be obtained from a diamine resin and be further reacted with (1B) or (2A) to generate a Peptide-Linker Construct of Formula 4K or 4L respectively. When the peptide contains amino functionality in its side chain (e.g. Lysine), someone of ordinary skill in the art would appreciate that additional orthogonal protection and deprotection steps are required.

Schemes 1 to 3C describe peptide-linker constructs, more particularly for use in the preparation of a bioconjugate with Albumin. The maleimide reactive group and the pyridine-2-yl-disulfanyl reactive group reacts with the —SH functionality of Cysteine 34 of the albumin.

Schemes 3D and 3E describes preparation of peptide-linker constructs for use in an azide-alkyne Huisgen cycloaddition, more commonly known as click chemistry.

Scheme 3D

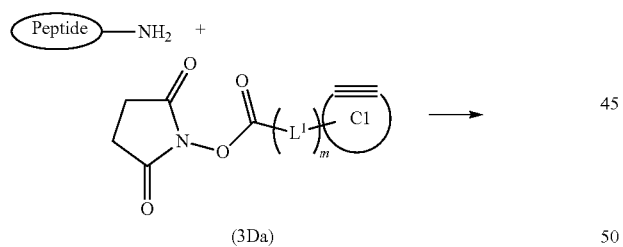

wherein m is 0 or 1, C1 is a mono, di or tricyclic carbocyclic or heterocyclic ring system optionally substituted with fluorine, $L^1$ is a C1-C20 alkylene linker wherein the alkylene chain is optionally substituted with oxo (=O), and wherein one or more carbon is replaced with O or NH. Cycloalkyne moieties (3Da) are readily available from commercial sources. Additionally, cyclic alkyne in click chemistry for protein labeling has been described in US 2009/0068738 which is herein incorporated by reference. Specific examples have been described below (example 20). The click handle can be introduced at the N-terminus of the peptide or on a lysine residue side chain.

Scheme 3E

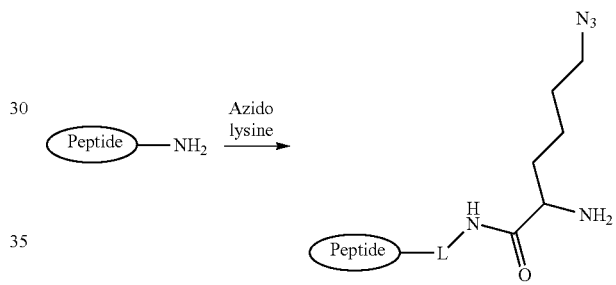

Scheme 3E describes the introduction of an Azido lysine residue at the N-terminus of an apelin peptide optionally via a linker L (such as for example one or more amino acids selected from glycine and serine). The azide functionality acts as a handle for click chemistry. Specific examples have been described in co-filed U.S. application Ser. No. 62/015,854.

Preparation of Half-life Extending Moiety-linker Construct:

Scheme 3F and 3G describes the preparation of a fatty acid-linker construct.

Scheme 3F

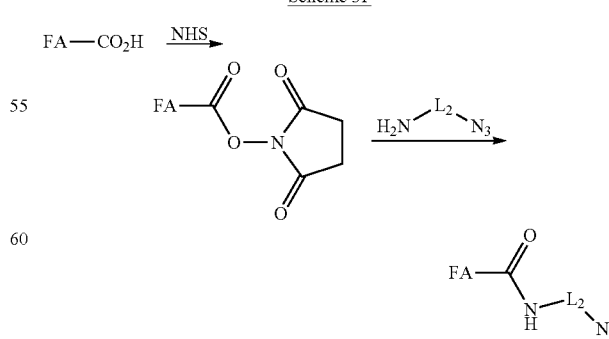

wherein FA is fatty acid, L2 is a linking moiety (for example PEG), NHS is N-hydroxysuccinimide. Such fatty acid-linker constructs are used for conjugation using click chemistry. In instances wherein the fatty acid contains functionalities such as hydroxyl or additional carboxylic acid, protection of such functionalities may be required.

Scheme 3G

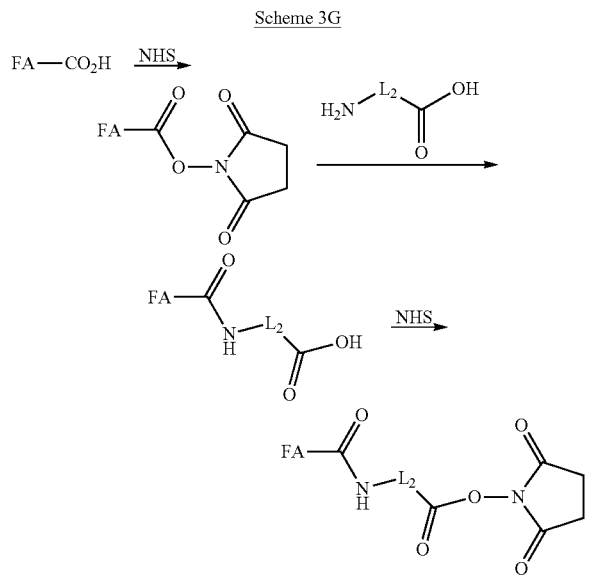

Wherein FA, NHS and L2 are defined above in Scheme 3F. Such fatty acid constructs are used for conjugation with an amino functionality on the peptide, preferably the N-terminus.

Scheme 3H describes the preparation of a Fc-linker construct

Scheme 3H

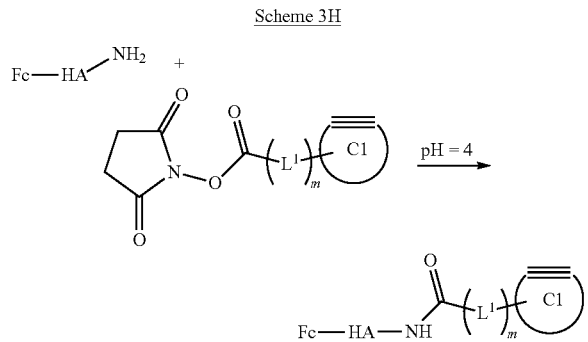

Fc-HA is a construct containing the sequence AH- at the N-terminus of the Fc. The construct is prepared using recombinant methods. The AH-sequence allows for selective modification of the N-terminus at a low pH. Such selective modification has been disclosed in cofiled U.S. application Ser. Nos. 62/015,868 and 62/015,862. Click handle is therefore introduced at the N-terminus of the Fc construct.

In yet another embodiment, the Fc construct is modified at the C-terminus to introduce a small Sortase recognition motif (LPXTG/A). Such Fc-recognition motif is prepared using recombinant methods. Example of such construct is: Fc-[GGGG]n-LPETGGLEVLFQGP (SEQ ID NO: 14) wherein the GGLEVLFQGP (SEQ ID NO: 15) is clipped during sortase treatment.

Preparation of the Fc APJ Peptide Fusion Protein

The biologically generated multimerized molecule, such as an antibody Fc comprising at least a part of cysteine containing region known as the hinge can be prepared from recombinant expressed protein product which has been secreted in multimerized (dimeric) form. The present invention also include modified Fc fusion proteins wherein the amino acid sequence of the Fc region has been altered relative to the amino acid sequence of the Fc- or constant region found in a naturally occurring antibody. For example, Fc-fusion protein may be engineered (i.e. modified) with mutations in order to obtain desired characteristics of FcRn binding affinity/or serum half-life. Example of modified Fc-fusion proteins have been disclosed in U.S. Pat. No. 7,217,798, which is incorporated by reference.

Fc-fusion proteins of this invention may also be altered synthetically, e.g. by attachment of the linker moiety and the peptide or polypeptide moiety. In addition, "modified" Fc-fusion proteins with Fc domain derived from recombinant antibodies can be made in any expression systems including both prokaryotic and eukaryotic expression system or using phage display methods.

Fc-Linker Constructs such as Fc-[GGGGS] (SEQ ID NO: 13), Fc-[GGGGS]2 (SEQ ID NO: 12), Fc-[GGGGS]3 (SEQ ID NO: 11), Fc-GG and Fc-GS, are described below in the experimental part. The [GGGGS] (SEQ ID NO: 13), [GGGGS]2 (SEQ ID NO: 12), [GGGGS]3. (SEQ ID NO: 11), GS and GG linker are attached either to the C-terminus of the Fc domain or to the N-terminus of the Fc domain, wherein Fc is a native Fc or a variant thereof. Example of Fc variant includes a Fc wherein the C-terminal Lysine has been deleted or replaced with Alanine.

Conjugates

In one embodiment of the present invention, a peptide or polypeptide according to anyone of Formula I to IX is conjugated (chemically/covalently attached) to the thiol functionality of cysteine 34 of the albumin.

In another embodiment of the present invention, a peptide or polypeptide of Formula I' or anyone of Formulae I-IX is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas a Fab is short-lived (Capon et al., 1989, Nature 337: 525-31). when joined together (with a therapeutic peptide or polypeptide, an Fc domain can provide longer half-life (C. Huang, Curr. Opin. Biotechnol., 2009, 20, 692-699).

In one embodiment, the Fc-Peptide refers to a bioconjugate in which the Fc sequence is fused to the N-terminus of the peptide. Alternatively, Peptide-Fc refers to a bioconjugate in which the Fc sequence is fused to the C-terminus of the peptide.

Preferred embodiments of the invention are Fc-Peptide conjugates comprising peptide or polypeptide of anyone of Formulae I', I-IX, as defined herein. In one aspect of this embodiment, the Fc-peptide is a bioconjugate in which Fc sequence is fused to polypeptide or peptide of anyone of Formulae I'-IX.

The Fc region can be a naturally occurring Fc region, or can be altered to improve certain qualities, such as therapeutic qualities, circulation time, or reduced aggregation.

Useful modifications of protein therapeutic agents by fusion with the "Fc" domain of an antibody are discussed in detail in PCT Publication No. WO 00/024782. This document discusses linkage to a "vehicle" such as polyethylene glycol (PEG), dextran, or an Fc region.

Preferred embodiments of the invention are bioconjugate comprising a peptide or polypeptide according to anyone of preceding embodiments and a half life extending moiety, wherein the half-life extending moiety is a Fc domain fused to a polypeptide of the invention via a linker. In one aspect of this invention, the linker has the following Formula:

-[GGGGS]n-, n is 1, 2 or 3 (SEQ ID NO: 16) or the linker is GG or GS and the polypeptide of any one of Formulae I and III to IX contains naturally occurring amino acids. Examples of polypeptides of the invention suitable for fusion with the Fc domain are: Q-R-P-R-L-C*-H-K-G-P-M-C*-F (SEQ ID NO: 17), Q-R-P-R-L-C*-H-K-G-P-M-C* (SEQ ID NO: 18) and Q-R-P-R-L-S-H-K-G-P-M-P-F (SEQ ID NO: 19). Preferred embodiments of the invention are Fc-Peptide fused bioconjugate as defined above, comprising a modified Fc fragment (e.g., an FcLALA) and a peptide or polypeptide of anyone of Formulae I', I-IX, as defined herein.

In yet another embodiment, the invention pertains to a bioconjugate according to any one of the preceding embodiments wherein the half-life extending moiety is a modified Fc domain wherein the C-terminal Lysine has been deleted or replaced with Alanine. Representative examples of this embodiment are examples 9, 10, 15 and 16. Such Fc variants have generated more stable fusion proteins with Apelin peptide/polypeptides.

Peptides fused to an Fc region have been found to exhibit a substantially greater half-life in vivo than the unfused counterpart. Also, a fusion to an Fc region allows for dimerization/multimerization of the polypeptide.

In another embodiments of the invention are bioconjugate comprising a peptide or polypeptide according to Formulae I-IX and a half life extending moiety, wherein the half-life extending moiety is a Fc domain which is chemically linked to a polypeptide.

Preparation Conjugates:

Schemes 4 and 5 illustrate chemical reactions for conjugation of an APJ agonist peptide or a peptide according to anyone of Formula I to IX and a half-life extending moiety such as an Fc domain or albumin.

Scheme 4 illustrates the conjugation of a peptide-linker of Formula 4A with Cysteine 34 of Human Serum Albumin

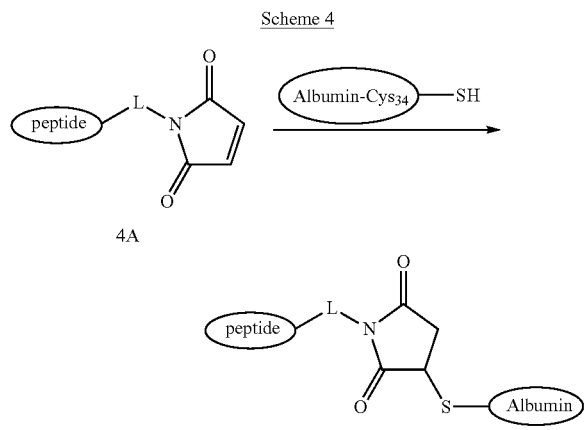

wherein L represent a linking moiety between the peptide and the maleimide functionality. In a particular embodiment, L is a linking moiety as disclosed in Scheme 1, 3A, 3B or 3C.

Scheme 5 illustrates the conjugation of a Peptide-Linker Construct of Formula 5A with Cysteine 34 of Albumin.

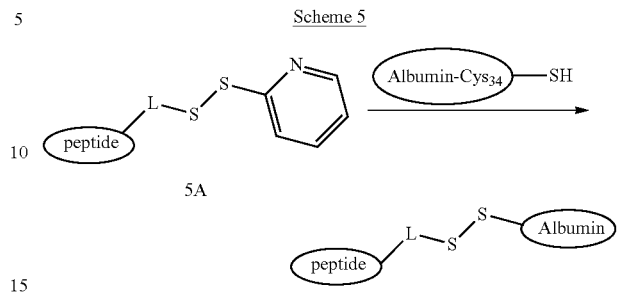

wherein L represents a linking moiety between the peptide and the —S—S-Pyridine functionality. In a particular embodiment, L is a linking moiety as disclosed in schemes 2, 3A, 3B or 3C.

Methods for making conjugates and peptide-linker constructs as described in Schemes 1-5 have also been described and exemplified in co-filed U.S. application Ser. No. 61/858,251, which is hereby incorporated by reference.

Other method of conjugation have been described in copending and co-filed U.S. application Ser. Nos. 62/015,862, 62/015,868 and 61/858,263. Such method includes selective N-acylation of a peptide and is summarized in Scheme 6.

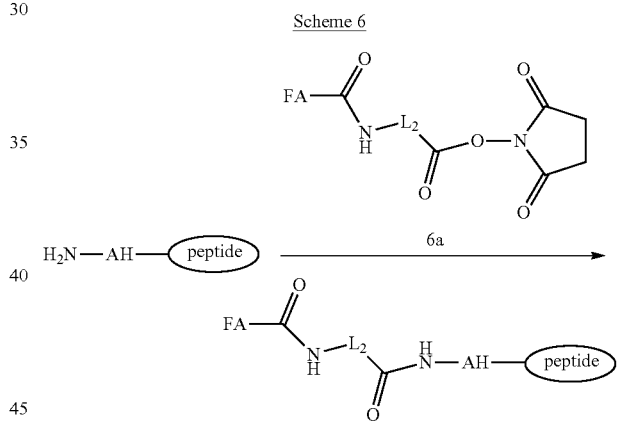

wherein AH— is a linker introduced on N-terminus of the peptide to facilitate reaction at the N-terminus, H is histidine, A is Alanine, FA is a fatty acid as described supra, for example a fatty acid of Formula A1 to A3, and L is a linking moieties (for example a PEG linking moiety). The Fatty acid Linker construct 6a (prepared as shown in Scheme 3G) is selectively introduced onto the peptide at the N-terminus when using low pH condition. Such method has been described in cofiled U.S. patent application Ser. Nos. 62/015,868 and 62/015,854.

Schemes 7 and 8 describes formation of conjugates according to the instant invention using click chemistry.

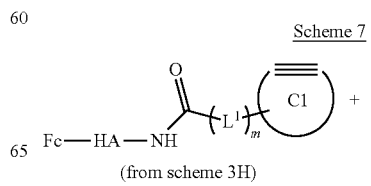

(from scheme 3H)

-continued

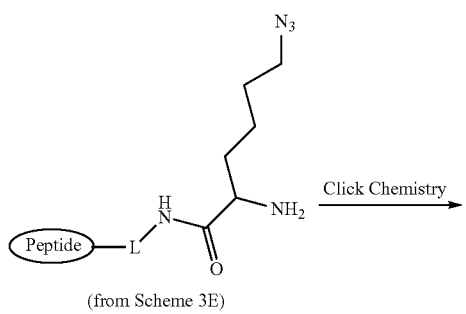

(from Scheme 3E)

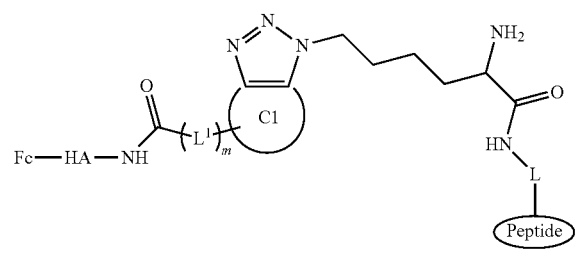

Scheme 8

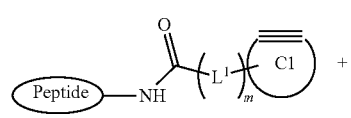

(Scheme 3D)

(Scheme 3F)

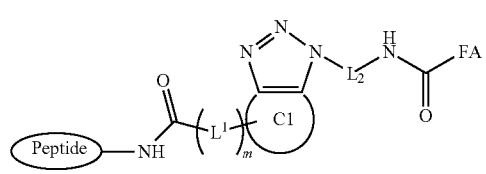

Scheme 9 describes the conjugation of an APJ peptide with a Fc construct using a sortase enzyme Scheme 9

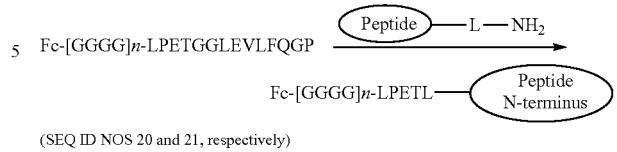

(SEQ ID NOS 20 and 21, respectively)

wherein n is 1, 2 or 3, L is an optional linker (for example a polyglycine linker)

Of particular interest are the following embodiments of the invention:

In embodiment 21, the invention pertains to the bioconjugate or multimer thereof according to anyone of preceding embodiments wherein the half-life extending moiety is an IgG constant domain or fragment thereof, a fatty acid or a Human Serum Albumin.

In embodiment 22, the invention pertains to the bioconjugate according to anyone of the preceding embodiments wherein the half-life extending moiety is a FcLALA modified Fc fragment with a LALA mutation (L234A, L235A).

In embodiment 23, the invention pertains to the bioconjugate according to anyone of embodiments 1, 4,-7, 13-17, 21 and 22 wherein the half-life extending moiety is a Fc domain which is fused to a polypeptide according to any one of Formulae I and III to IX via a linker and wherein the linker has the following Formula:

-[GGGGS]n-, n is 1, 2 or 3 (SEQ ID NO: 16) or the linker is GS or GG, and the polypeptide according to anyone of Formulae I and III to IX contais naturally occurring amino acids.

In embodiment 23A, the invention pertains to the bioconjugate according to embodiment 23 wherein the half-life extending moiety is a Fc variant wherein the C-terminal lysine has been deleted or replaced with alanine.

In embodiment 24, the invention pertains to the bioconjugate according to embodiment 23 wherein the polypeptide is a polypeptide of Formula I wherein:

X1 is the N-terminus of the polypeptide and is either absent or is selected from R, Q, A and K;
X2 is R, A, K, H, F or E;
X3 is P, A, K or D;
X4 is R, A, F or E;
X5 is L, A, K, D or F;
X6 and X12 are C and are linked together via a disulfide (—S—S—) bond;
X7 is H, A, K, F, P, N or E
X8 is K, F, A or E;
X9 is G, A, D, L or R;
X10 is P or A;
X11 is M, A, F, Y, L or K; and
X13 is the C-terminus and is absent or is selected from F, I, A, K, H and E.

In embodiment 25, the invention pertains to the bioconjugate according to embodiment 22, 23 or 24 wherein the polypeptide is:
Q-R-P-R-L-C*-H-K-G-P-M-C*-F (SEQ ID NO: 17).

In embodiment 26, the invention pertains to the bioconjugate or multimer thereof according to anyone of preceding embodiments wherein the half-life extending moiety is Human Serum Albumin.

In embodiment 27, the invention pertains to the bioconjugate according to embodiment 25 or 26 wherein the Human Serum Albumin is chemically linked to the N-terminus of a polypeptide of anyone of Formulae I to VII and IX via a linker of the following Formulae:

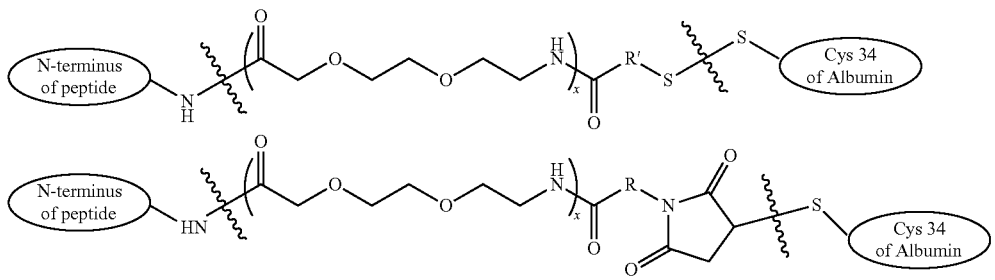

wherein x is 1-20, R is linear or branched alkylene, cycloalkyl, aryl of heteroaryl or combination thereof, R' is linear or branched alkylene, aryl or cycloalkyl or combination thereof.

In embodiment 28, the invention pertains to the bioconjugate according to embodiment 26 or 27 wherein the Human Serum Albumin is chemically linked to the C-terminus of a polypeptide of anyone of Formulae I to VII via a linker of the following Formulae:

wherein x is 1-20, R is linear or branched alkylene, cycloalkyl, aryl of heteroaryl or combination thereof, R' is linear or branched alkylene, aryl or cycloalkyl or combination thereof.

In other embodiment, the bioconjugate of the invention has the following formulae:

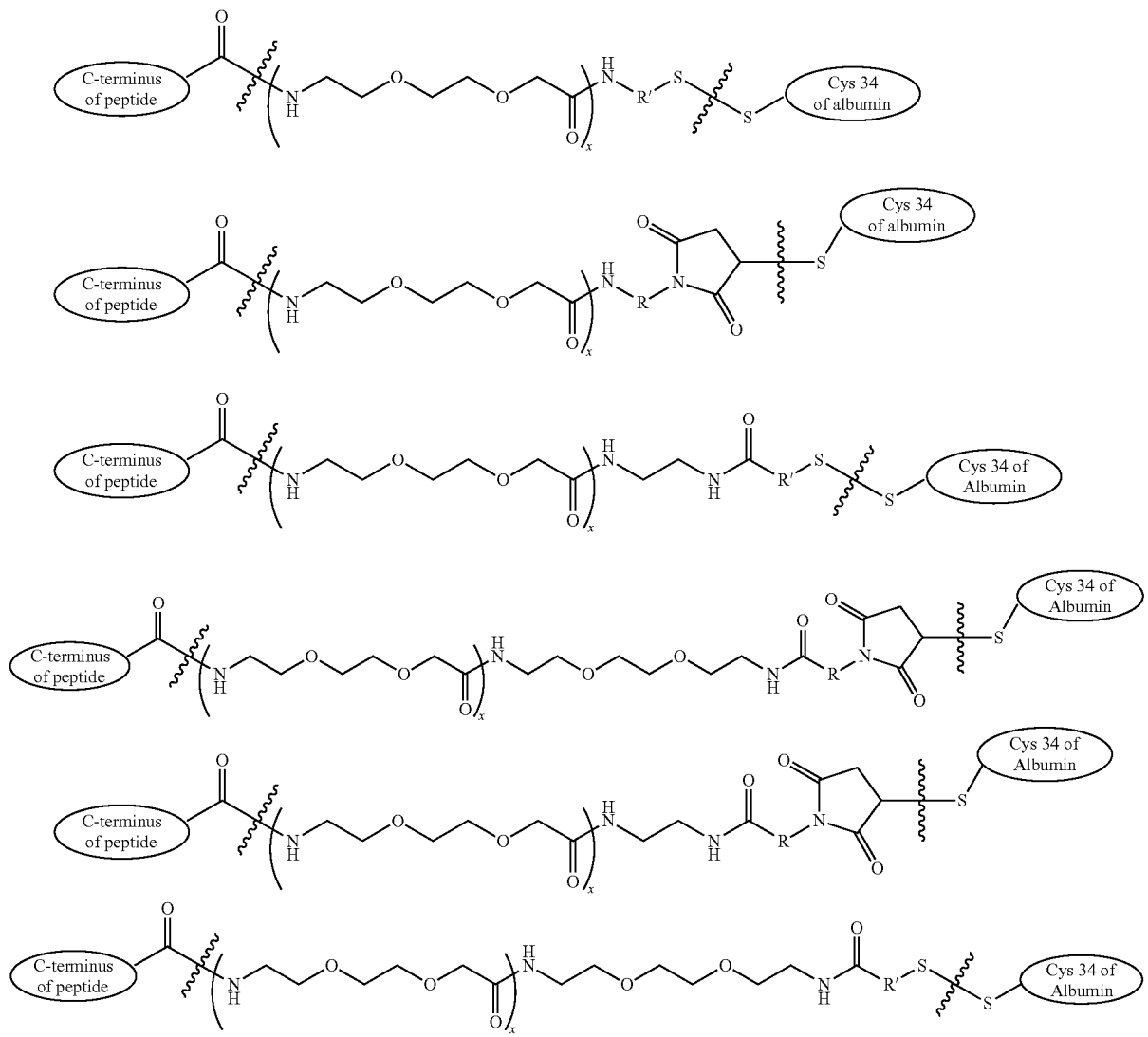

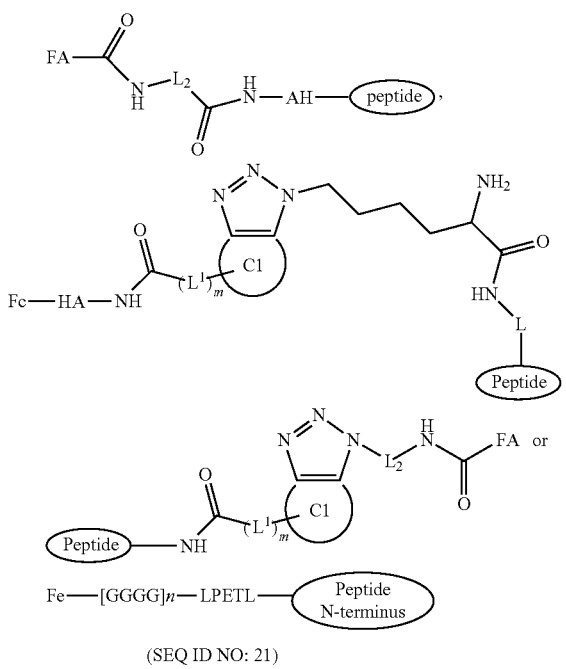

(SEQ ID NO: 21)

wherein peptide is the N-terminus of the peptide, A is alanine, H is histidine, m is 0 or 1, n is 0, 1, 2 or 3, L and L2 are linkers, C1 is a mono, di or tricyclic carbocyclic or heterocyclic ring system optionally substituted with fluorine and $L^1$ is a C1-C20 alkylene linker wherein the alkylene chain is optionally substituted with oxo (=O), and wherein one or more carbon is replaced with O or NH. In a particular aspect of this embodiment, L and L2 are PEG linkers.

Pharmaceutical Compositions

The bioconjugate of the instant invention may be administered in any of a variety of ways, including subcutaneously, intramuscularly, intravenously, intraperitoneally, inhalationally, intranasally, orally etc. Particularly preferred embodiments of the invention employ continuous intravenous administration of the bioconjuagtes of the instant invention, or an amide, ester, or salt thereof. The bioconjugates on the instant invention may be administered as a bolus or as a continuous infusion over a period of time. An implantable pump may be used. In certain embodiments of the invention, intermittent or continuous bioconjugates administration is continued for one to several days (e.g., 2-3 or more days), or for longer periods of time, e.g., weeks, months, or years. In some embodiments, intermittent or continuous bioconjugates administration is provided for at least about 3 days. In other embodiments, intermittent or continuous bioconjugate administration is provided for at least about one week. In other embodiments, intermittent or continuous bioconjugate administration is provided for at least about two weeks. It may be desirable to maintain an average plasma bioconjugate concentration above a particular threshold value either during administration or between administration of multiple doses. A desirable concentration may be determined, for example, based on the subject's physiological condition, disease severity, etc. Such desirable value(s) can be identified by performing standard clinical trials. Alternatively, the peptides and conjugates thereof could be delivered orally via FcRn mechanism. (Nat Rev Immunol. 7(9), 715-25, 2007; Nat Commun. 3; 3:610, 2012, Am J Physiol Gastrointest Liver Physiol 304: G262-G270, 2013).

In another aspect, the present invention provides a pharmaceutical composition comprising a bioconjugate of the present invention or and amide, an ester or a salt thereof and one or more pharmaceutically acceptable carriers. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, lyophilizates, powders or suppositories), or in a liquid form (including without limitation solutions, suspensions or emulsions). The pharmaceutical compositions can be subjected to conventional pharmaceutical operations such as aseptic manufacturing, sterilization and/or can contain conventional inert diluents, cake forming agents, tonicity agents, lubricating agents, or buffering agents, as well as adjuvants, such as preservatives, stabilizers, wetting agents, emulsifiers and buffers, etc.

Pharmaceutical compositions suitable for injectable use typically include sterile aqueous solutions (where water soluble) or dispersions and sterile powders for the extemporaneous preparation of sterile injectable solutions or dispersion.

For intravenous administration, suitable carriers include physiological saline, bacteriostatic water, Cremophor ELTM (BASF, Parsippany, N.J.) or phosphate buffered saline (PBS). In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, amino acids, sorbitol, sodium chloride in the composition. Prolonged absorption of the injectable compositions can be brought about by including in the composition an agent which delays absorption, for example, aluminum monostearate and gelatin.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Sterile injectable solutions can be prepared by incorporating the active compound in the required amount in an appropriate solvent with one or a combination of ingredients enumerated above, as required, followed by filtration sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive therapeutic agents are preferably delivered in the form of an aerosol spray from pressured container or dispenser which contains a suitable propellant, e.g., a gas such as carbon dioxide, or a nebulizer. It is noted that the lungs provide a large surface area for systemic delivery of therapeutic agents.

The agents may be encapsulated, e.g., in polymeric microparticles such as those described in U.S. publication 20040096403, or in association with any of a wide variety of other drug delivery vehicles that are known in the art. In other embodiments of the invention the agents are delivered in association with a charged lipid as described, for example, in U.S. publication 20040062718. It is noted that the latter system has been used for administration of a therapeutic polypeptide, insulin, demonstrating the utility of this system for administration of peptide agents.

Systemic administration can also be by transmucosal or transdermal means.

Suitable compositions for transdermal application include an effective amount of a bioconjugate of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

As used herein, the term "pharmaceutically acceptable salts" refers to salts that retain the biological effectiveness and properties of the bioconjugates of this invention and, which typically are not biologically or otherwise undesirable. In many cases, the bioconjugates of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

Method of the Invention:

Apelin family of peptides is the only known natural family of ligands for the G protein coupled APJ receptor. Apelin gene encodes a 77 aminoacid polypeptide, which gets processed into biologically active forms of apelin peptides, such as apelin-36, apelin-17, apelin-16, apelin-13, apelin-12 and pyroglutamate modified form of apelin-13 ($Pyr^1$-apelin-13). Any one of these apelin peptides, upon binding to APJ receptor, transduces the signal via Gi and Gq proteins. In cardiomyocytes, Gi or Gq coupling leads to changes in intracellular pH, PLC activation, and IP3 production that enhance myofilament calcium sensitivity and ultimately result in increased cardiac contractility. Gi coupling inhibits activated Gs, adenylyl cyclase and cAMP production and increases pAkt levels leading to cardioprotection. In vascular endothelial cells, APJ activation via Gi, pAKT leads to increased nitric oxide (NO) production, which increases smooth muscle relaxation resulting in overall vasodilation.

Patients with chronic stable heart failure have occasional acute episodes of decompensation, where cardiac contractility declines further and symptoms worsen. These exacerbations are referred to as acute decompensated heart failure (ADHF). Current therapies for ADHF include diuretics, vasodilators, and inotropes, which directly increase cardiac contractility. Current intravenous inotropes (dobutamine, dopamine, milrinone, levosimendan) are well known for their adverse events such as arrhythmia and increased long-term mortality. The synthetic apelin bioconjugate analogs of the instant invention provide a therapy for ADHF that increases cardiac contractility without arrhythmogenic or mortality liabilities and address the enormous unmet medical need in chronic heart failure.

Indeed, acute apelin treatment (5 min) in humans results in coronary vasodilatation and improved cardiac output. However, native apelins exhibit a very short $t_{1/2}$ (seconds) and duration of action (few minutes) in vivo. The potent synthetic bioconjugate APJ agonists of the instant invention have longer half lives compared to the native apelin.

Activation of APJ receptor in cardiomyocytes a) improve cardiac contractility via Gi/Gq, PLC and Ca2+, and b) provide cardioprotection via Gi, pAkt activation, but without increasing cAMP (as seen with other inotropes). In addition, APJ agonism in endothelial cells leads to arterial vasodilation, which further benefits heart failure by unloading the work of left ventricle. Taken together the bioconjugates of the instant invention can improve overall cardiac function, reduce arrhythmogenesis and provide survival benefit.

More recently, there have been a number of preclinical research publications focusing on the potential involvement of Apelin in diabetes and insulin resistance. Apelin has been shown to 1) lower blood glucose levels by improving glucose uptake in muscle, adipose and heart, 2) protect pancreatic beta cells from ER stress and subsequent apoptosis, 3) lower the insulin secretion in beta cells, and 4) regulate catecholamine induced lypolysis in adipose tissue. Activation of pAKT pathway has been implicated in these processes.

The bioconjugates comprising polypeptides according to anyone of formulae I to IX, or a pharmaceutically acceptable salt thereof, in free form or in pharmaceutically acceptable salt form, exhibit valuable pharmacological properties, e.g. APJ receptor agonsim properties, e.g. as indicated in in vitro and in vivo tests as provided in the next sections and are therefore indicated for therapy.

Bioconjugates of the invention or a pharmaceutically acceptable salt thereof, may be useful in the treatment of an indication selected from acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

Thus, as a further embodiment, the present invention provides the use of a bioconjugates as described herein, or a pharmaceutically acceptable salt thereof for the treatment of a disease which is associated with the APJ receptor activity. In a further embodiment, the therapy is selected from a disease which is responsive to the agonism of the APJ receptor. In another embodiment, the disease is selected from the aforementioned list, suitably acute decompensated heart failure. In yet another subset of this embodiment, the present invention provides the use of bioconjugates as described herein, or a pharmaceutically acceptable salt thereof, in the manufacture of a medicament, for the treatment of a disease which is associated with the APJ receptor activity.

Thus, as a further embodiment, the present invention provides the use of a bioconjugate or a pharmaceutically acceptable salt thereof, in therapy. In a further embodiment, the therapy is selected from a disease which may be treated by activation (agonism) of the APJ receptor.

In another embodiment, the invention provides a method of treating a disease which is responsive to the agonism of the APJ receptor, comprising administration of a therapeutically acceptable amount of a bioconjugate according to anyone of embodiments 1 to 31, or a multimer thereof. In a further embodiment, the disease is selected from the afore-mentioned list, suitably acute decompensated heart failure.

In yet another subset of this embodiment, the invention provides a method of treating a disease which is associated with the activity of the APJ receptor comprising administration of a therapeutically acceptable amount of a bioconjugate according to anyone of embodiments 1 to 31, or a multimer thereof.

The effective amount of a pharmaceutical composition or combination of the invention to be employed therapeutically will depend, for example, upon the therapeutic context and objectives. One skilled in the art will appreciate that the appropriate dosage levels for treatment will thus vary depending, in part, upon the molecule delivered, the indication for which the bioconjugate is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg.

The frequency of dosing will depend upon the pharmacokinetic parameters of the dual function protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The term "a therapeutically effective amount" of a bioconjugate of the present invention refers to an amount of the bioconjugate of the present invention that will elicit the biological or medical response of a subject, for example, amelioration of a symptom, alleviation of a condition, slow or delay disease progression, or prevention of a disease, etc. In one non-limiting embodiment, the term "a therapeutically effective amount" refers to the amount of the biconjugate of the present invention that, when administered to a subject, is effective to (1) at least partially alleviate, inhibit, prevent and/or ameliorate a condition, a disorder or a disease or a symptom thereof (i) ameliorated by the activation of the APJ receptor or (i) associated with the activity of the APJ receptor, or (iii) characterized by abnormal activity of the APJ receptor; or (2) activate the APJ receptor.

In another non-limiting embodiment, the term "a therapeutically effective amount" refers to the amount of the bioconjuagte of the present invention that, when administered to a cell, or a tissue, or a non-cellular biological material, or a medium, is effective to at least partially activate the APJ receptor. As will be appreciated by those of ordinary skill in the art, the absolute amount of a particular agent that is effective may vary depending on such factors as the desired biological endpoint, the agent to be delivered, the target tissue, etc. Those of ordinary skill in the art understand that "a therapeutically effective amount" may be administered in a single dose or may be achieved by administration of multiple doses. For example, in the case of an agent to treat heartfailure, an effective amount may be an amount sufficient to result in clinical improvement of the patient, e.g., increased exercise tolerance/capacity, increased blood pressure, decrease fluid retention, and/or improved results on a quantitative test of cardiac functioning, e.g., ejection fraction, exercise capacity (time to exhaustion), etc.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, the terms "prevent", "preventing" and "prevention" refer to the prevention of the recurrence, onset, or development of one or more symptoms of a disorder in a subject resulting from the administration of a therapy (e.g., a therapeutic agent), or the administration of a combination of therapies (e.g., a combination of therapeutic agents).

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The activity of a bioconjugate according to the present invention can be assessed by the following in vitro methods described below.

hAPJ Calcium Flux Assay:

Chem-5 APJ stable cells (Millipore #HTS068C) were plated in 384-well format with 10,000 cells/well in 25 ul growth media, then grown 24 hours in a 37° C. tissue culture incubator. One hour before the assay, 25 ul/well FLIPR Calcium 4 dye (Molecular Devices R8142) with 2.5 mM probenecid was added, and cells were incubated one hour in a 37° C. tissue culture incubator. Bioconjugates were solubilized in HBSS, HEPES & 0.1% BSA buffer, and serially-diluted 10-fold, from 50 uM to 5 pM, in triplicate. FLIPR Tetra was used to add bioconjugates to the cells with dye (1:5, for final bioconjugate concentrations ranging from 10 uM to 1 pM). FLIPR dye inside the cells emitted fluorescence after binding to calcium, while fluorescence from outside the cells was masked. Fluorescence was measured using 470-495 excitation and 515-575 emission wavelengths on the FLIPR Tetra. Readings were done for 3 minutes total, beginning 10 seconds before the bioconjugate addition. Maximum-minimum values were calculated and plotted for each bioconjugate concentration, and GraphPad prism software was used to calculate $EC_{50}$ values at the curve inflection points, for calcium flux stimulation by bioconjugates.

Plasma Stability Assay:

Materials:

Working solution: 1 mg/mL test article is prepared in Milli-Q water

Extraction solution: Methanol:Acetonitrile:Water (1:1:1) with 0.1% Formic Acid and 400 ng/mL Glyburide.

Plasma: Male Sprague-Dawley rat plasma (with sodium heparin), purchased from Bioreclamation LLC (Liverpool, N.Y.).

Whole blood: Male Sprague Dawley whole blood (with sodium heparin), purchased from Bioreclamation LLC (Liverpool, N.Y.)

Lung homogenate: Male rat Sprague Dawley lung was purchased from Bioreclamation LLC (Liverpool, N.Y.). The lung was homogenized using polytron homogenizer after addition of 5× volume of 1×PBS. The homogenate was centrifuged at 9000 rpm for 10 min at 4° C. The supernatant was centrifuged again at 3000 rpm for 30 min to make a clear supernatant. Protein concentration was determined using a commercial kit (Pierce, Thermo Scientific).

Sample Preparation Procedure: (peptides)

Test article was prepared in one of the following biological matrices: heparinized rat plasma, heparinized rat whole blood or lung homogenate. The plasma and whole blood sample was prepared at 5000 ng/mL by adding 5 uL of 1 mg/mL Working solution to 995 uL of rat plasma or whole blood. Lung homogenate samples were prepared by diluting lung homogenate to 1 mg/ml protein concentration with phosphate buffered saline (PBS), followed by addition of 5 uL Working solution to 995 uL diluted lung homogenate. The samples were incubated at 37° C. with gentle shaking (65~75 rpm) in a water bath incubator. At times 0 min, 5 min, 15 min, 30 min, 60 min, 120 and 240 min, 25 uL aliquots of incubation samples were transferred to 96-well plate and immediately protein precipitated using 150 uL of Extraction solution. After completion of incubation experiment, the sample plate was centrifuged at 4000 rpm at 4° C. for 10 minutes. Afterwards, a pipetting device (Tecan Temo) was used to transfer the supernatants to another plate and add 50 uL of water to all samples. The plate was vortexed prior to LC-MS analysis.

Sample Preparation Procedure (Conjugates)

Test article was prepared at 50,000 ng/mL by adding 5 uL of 1 mg/mL Working solution to 495 uL of rat plasma. The samples were incubated at 37° C. with gentle shaking (65~75 rpm) in a water bath incubator. At times 0 hr, 0.5 hr, 1 hr, 2 hr, 4 hr, 6 and 24 hr, 50 uL aliquots of incubation samples were transferred to 96-well plate and 100 uL 40 mM TCEP (tris(2-carboxyethyl)phosphine) was added to each sample. The reaction mixture was incubated at 37° C. for 1 hour. After completion of reaction, protein precipitation was performed using 300 uL of acetonitrile. The sample plate was centrifuged at 4000 rpm at 4° C. for 10 minutes. Afterwards, a pipetting device (Tecan Temo) was used to transfer 125 uL supernatants to another plate and adds 50 uL of water to all samples. The plate was vortexed prior to LC-MS analysis.

LC-MS Analysis of Stability Samples

HPLC: Agilent 1290 HPLC with autosampler
Column: MAC-MOD ACE C18, 3 μm, 30 mm×2.1 mm i.d.
Mobile phase A: 0.1% Formic acid in acetonitrile
Mobile phase B: 0.1% Formic acid in water
Gradient Program:

| Time (min) | Flow (mL) | Mobile Phase A(%) | Mobile Phase B(%) |
|---|---|---|---|
| 0 | 0.4 | 95 | 5 |
| 0.5 | 0.4 | 95 | 5 |
| 1.5 | 0.4 | 5 | 95 |
| 4.1 | 0.4 | 5 | 95 |
| 4.2 | 0.4 | 95 | 5 |
| 5 | 0.4 | 95 | 5 |

Mass spectrometer: Agilent Q-TOF 6530
Data acquisition mode: Full scan with mass range of 100-1000 m/z
Data acquisition and analysis software: MassHunter Data Analysis:

Stability assay: stability half-life, (t ½), values were determined by converting peak areas at each time point to percent remaining relative to initial (t=0) peak area.

Percent remaining=100×(sample peak area)÷(t=0 peak area)

The natural log of percent remaining values were calculated and plotted against sample time (Microsoft Excel). The slope of this line, k, was determined by linear regression (Microsoft Excel).

Stability half-life was then calculated by the formula, t ½=0.693÷k

TABLE 2

Activity and Stability of Bioconjugates

| Bioconjugate | hAPJ $Ca^{2+}$ Flux $EC_{50}$ [nM] | Surrogate activity-based Plasma stability t½ [min] |
|---|---|---|
| Example 1 | 47.2 | >1000 |
| Example 2 | 92.4 | >1000 |
| Example 3 | 52.0 | 24.3 |
| Example 4 | 9.2 | 212 |
| Example 5 | 8.4 | 334 |
| Example 6 | 8.9 | >1000 |
| Example 7 | 8.0 | >1000 |
| Example 8 | >1000 | — |
| Example 9 | 7.9 | >1000 |
| Example 10 | 7.6 | >1000 |
| Example 11 | 21.9 | >1000 |
| Example 12 | 26.2 | >1000 |
| Example 13 | 36.2 | >1000 |
| Example 14 | 3.8 | >1000 |
| Example 15 | 13.6 | >1000 |
| Example 16 | 15.8 | >1000 |
| Example 17 | 9.7 | >1000 |
| Example 18 | 32.0 | >1000 |
| Example 19 | 11.8 | >1000 |
| Example 20 | 65 | >1000 |
| Comparative Example: Pyr-1-Apelin-13 | 6.6 | 5.0 |

TABLE 3

Correlation beween plasma stabililty Assay and Surrogate Activity based Plasma Stability assay:

| Bioconjugate | Plasma stability t½ [min] | Surrogate Activity based Plasma stability t½ [min] |
|---|---|---|
| Example 2 | ~1440 | >1000 |
| Pyr-1-Apelin 13 | 6.6 | 5.0 |

The bioconjugate of the present invention may have an APJ receptor potency similar to apelin-13 or pyr-1-apelin-13. In one embodiment the bioconjugate of the present invention has an $EC_{50}$ of less than 100 nM. In another embodiment the bioconjugate of the invention has an $EC_{50}$ of less than 50 nM, preferably less than 25 nM and more preferably less than 15 nM. In yet another embodiment, the bioconjugate of the present invention has an $EC_{50}$ of less than 10 nM.

The bioconjugate of the present invention may have plasma stability superior to apelin-13 or pyr-1-apelin-13. In one embodiment, the plasma stability improvement is at least 2 fold. In one embodiment, the bioconjugate of the invention has a plasma stability of at least 30 minutes. In another embodiment, the bioconjugate of the invention has a plasma stability of at least 10 minutes, at least 40 min and more preferably at least 60 minutes.

The bioconjugate of the present invention may be administered either simultaneously with, or before or after, one or more other therapeutic agent. The bioconjugate of the present invention may be administered separately, by the same or different route of administration, or together in the same pharmaceutical composition as the other agents.

In one embodiment, the invention provides a product comprising a bioconjugate of anyone of embodiments 1 to 31, and at least one other therapeutic agent as a combined preparation for simultaneous, separate or sequential use in therapy. In one embodiment, the therapy is the treatment of a disease or condition responsive to the activation of the APJ receptor.

Products provided as a combined preparation include a composition comprising a bioconjugate of anyone of embodiments 1 to 31, and the other therapeutic agent(s) together in the same pharmaceutical composition, or a bioconjugate of anyone of embodiments 1 to 31, and the other therapeutic agent(s) in separate form, e.g. in the form of a kit.

In one embodiment, the invention provides a pharmaceutical composition comprising a bioconjugate of anyone of embodiments 1 to 31, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a bioconjugate according to anyone of embodiments 1 to 31. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the bioconjugate of the invention and the other therapeutic agent may be manufactured and/or formulated by the same or different manufacturers. Moreover, the bioconjugate of the invention and the other therapeutic may be brought together into a combination therapy: (i) prior to release of the combination product to physicians (e.g. in the case of a kit comprising the bioconjugate of the invention and the other therapeutic agent); (i) by the physician themselves (or under the guidance of the physician) shortly before administration; (iii) in the patient themselves, e.g. during sequential administration of a bioconjugate of the invention and the other therapeutic agent.

Accordingly, the invention provides the use of a bioconjugate according to anyone of embodiments 1 to 31, for treating a disease or condition responsive to the agonism of the APJ receptor, wherein the medicament is prepared for administration with another therapeutic agent. The invention also provides the use of another therapeutic agent for treating a disease or condition responsive to the agonism of the apelin receptor, wherein the medicament is administered with a bioconjugate according to anyone of embodiments 1 to 31.

The invention also provides a bioconjugate according to anyone of embodiments 1 to 31 for use in a method of treating a disease or condition responsive to the agonism of the APJ receptor, wherein the bioconjugate is prepared for administration with another therapeutic agent. The invention also provides another therapeutic agent for use in a method of treating a disease or condition responsive to the agonism of the APJ receptor, wherein the other therapeutic agent is prepared for administration with a bioconjugate according to anyone of embodiments 1 to 31.

The invention also provides the use of a bioconjugate according to anyone of embodiments 1 to 31, for treating a disease or condition responsive to the agonism of the APJ receptor, wherein the patient has previously (e.g. within 24 hours) been treated with another therapeutic agent. The invention also provides the use of another therapeutic agent for treating a disease or condition responsive to the agonism of the APJ receptor, wherein the patient has previously (e.g. within 24 hours) been treated with a bioconjugate according to anyone of embodiments 1 to 31.

In one embodiment, the other therapeutic agent is selected from inotropes, beta adrenergic receptor blockers, HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and a NEP inhibitor.

The term "in combination with" a second agent or treatment includes co-administration of the bioconjugate of the invention (e.g., a bioconjugate according to anyone of embodiments 1 to 31 or a bioconjugate otherwise described herein) with the second agent or treatment, administration of the compound of the invention first, followed by the second agent or treatment and administration of the second agent or treatment first, followed by the bioconjugate of the invention.

The term "second agent" includes any agent which is known in the art to treat, prevent, or reduce the symptoms of a disease or disorder described herein, e.g. a disorder or disease responsive to the activation of the APJ receptor, such as for example, acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

Examples of second agents include inotropes, beta adrenergic receptor blockers, HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and/or a NEP inhibitor.

Inotropes as used herein include for example dobutamine, isoproterenol, milrinone, amirinone, levosimendan, epinephrine, norepinephrine, isoproterenol and digoxin.

Beta adrenergic receptor blockers as used herein include for example acebutolol, atenolol, betaxolol, bisoprolol, carteolol, metoprolol, nadolol, propranolol, sotalol and timolol.

Anti-coagulants as used herein include Dalteparin, Danaparoid, Enoxaparin, Heparin, Tinzaparin, Warfarin.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rosuvastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moexipril, moveltopril, perindopril, quinapril, ramipril, spirapril, temocapril, and trandolapril, or, pharmaceutically acceptables salt thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R*,2R*)]]-1-[(1,1-dimethylethoxy)carbonyl]-L-prolyl-L-phenylalanyl-N-[2-hydroxy-5-methyl-1-(2-methylpropyl)-4-[[[2-methyl-1-[[(2-pyridinylmethyl)amino]carbonyl]butyl]amino]carbonyl]hexyl]-N-alfa-methyl-L-histidinamide); terlakiren (chemical name: [R-(R*,S*)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); Aliskiren (chemical name: (2S,4S,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide) and zankiren (chemical name: [1S-[1R*[R*(R*)],2S*,3R*]]-N-[1-(cyclohexylmethyl)-2,3-dihydroxy-5-methylhexyl]-alfa-[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

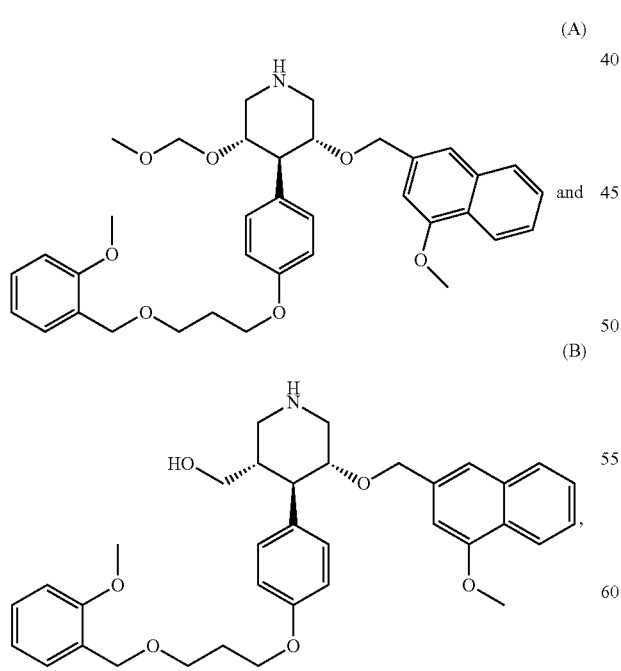

or, pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

The term "calcium channel blocker (CCB)" includes dihydropyridines (DHPs) and non-DHPs (e.g., diltiazem-type and verapamil-type GCBs). Examples include amlodipine, Bepridil, Diltiazem, felodipine, ryosidine, isradipine, lacidipine, nicardipine, nifedipine, niguldipine, niludipine, nimodipine, nisoldipine, nitrendipine, Verapamil and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F (SEQ ID NO: 22))

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

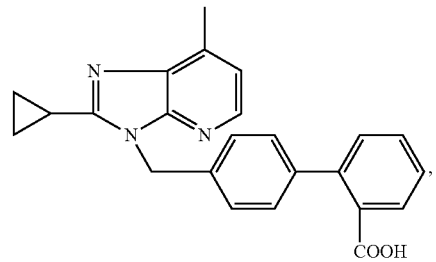 [SMILES: Cc1ccnc2c1nc(C1CC1)n2Cc1ccc(-c2ccccc2C(=O)O)cc1]

the compound with the designation SC-52458 of the following formula

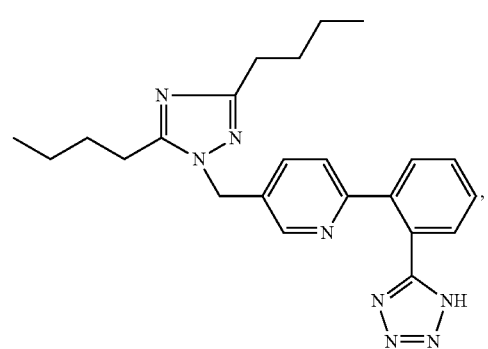 [SMILES: CCCCc1nc(CCCC)n(Cc2ccc(-c3ccccc3-c3nnn[nH]3)nc2)n1]

and the compound with the designation ZD-8731 of the following formula

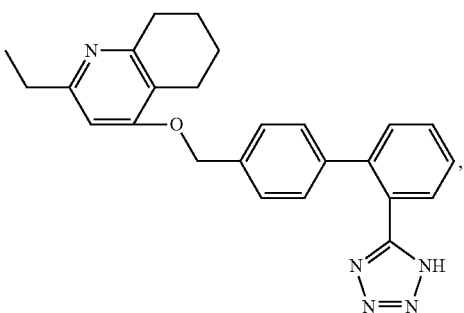 [SMILES: CCc1cc(OCc2ccc(-c3ccccc3-c3nnn[nH]3)cc2)c2c(n1)CCCC2]

or, in each case, a pharmaceutically acceptable salt thereof.

Preferred $AT_1$-receptor antagonist are candesartan, eprosartan, irbesartan, losartan, telmisartan, valsartan. Also preferred are those agents which have been marketed, most preferred is valsartan or a pharmaceutically acceptable salt thereof.

The term "anti-diabetic agent" includes insulin secretion enhancers that promote the secretion of insulin from pancreatic-cells. Examples include biguanide derivatives (e.g., metformin), sulfonylureas (SU) (e.g., tolbutamide, chlorpropamide, tolazamide, acetohexamide, 4-chloro-N-[(1-pyrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine] (cf. EP 196222 and EP 526171) of the formula

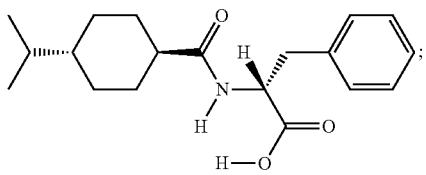 [SMILES: CC(C)[C@H]1CC[C@H](C(=O)N[C@H](Cc2ccccc2)C(=O)O)CC1]

repaglinide [(S)-2-ethoxy-4-{2-[[3-methyl-1-[2-(1-piperidinyl)phenyl]butyl]amino]-2-oxoethyl}benzoic acid] (cf. EP 589874, EP 147850 A2, in particular Example 11 on page 61, and EP 207331 A1); calcium (2S)-2-benzyl-3-(cis-hexahydro-2-isoindolinlycarbonyl)-propionate dihydrate (e.g., mitiglinide (cf. EP 507534)); and glimepiride (cf. EP 31058).

Further examples of second agents with which the bioconjugate of the invention can be used in combination include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV (dipeptidyl peptidase IV) inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 (glucagon like peptide-1) is an insulinotropic protein which is described, e.g., by W. E. Schmidt et al. in Diabetologia, 28, 1985, 704-707 and in U.S. Pat. No. 5,705, 483.

The term "GLP-1 agonists" includes variants and analogs of GLP-1(7-36)$NH_2$ which are disclosed in particular in U.S. Pat. Nos. 5,120,712, 5,118,666, 5,512,549, WO 91/11457 and by C. Orskov et al in J. Biol. Chem. 264 (1989) 12826. Further examples include GLP-1(7-37), in which compound the carboxy-terminal amide functionality of $Arg^{36}$ is displaced with Gly at the $37^{th}$ position of the GLP-1(7-36)$NH_2$ molecule and variants and analogs thereof including $GLN^9$-GLP-1(7-37), D-$GLN^9$-GLP-1(7-37), acetyl $LYS^9$-GLP-1 (7-37), $LYS^{18}$-GLP-1(7-37) and, in particular, GLP-1(7-37) OH, $VAL^8$-GLP-1(7-37), $GLY^8$-GLP-1(7-37), THR8-GLP-1 (7-37), $MET^8$-GLP-1(7-37) and 4-imidazopropionyl-GLP-1. Special preference is also given to the GLP agonist analog exendin-4, described by Greig et al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenyl]methyl}-thiazolidine-2,4-dione, 5-[3-(4-chlorophenyl]-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]methyl}thiazolidine-2,4-dione (pioglitazone), 5-{[4-(3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluorobenzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; α₂-adrenergic antagonists; and pharmaceutically acceptable salts thereof.

In one embodiment, the invention provides a combination, in particular a pharmaceutical combination, comprising a therapeutically effective amount of the bioconjugate according to anyone of embodiments 1 to 31, and one or more therapeutically active agents selected from β-adrenergic receptor blockers such as acebutolol, atenolol, betaxolol, bisoprolol, metoprolol, nadolol, propranolol, sotalol and timolol; angiotensin II receptor antagonists such as AT1 blockers; antidiabetic agents such as DPPIV inhibitors (e.g. vildagliptin) and GLP1 peptide agonist.

The term "obesity-reducing agent" includes lipase inhibitors (e.g., orlistat) and appetite suppressants (e.g., sibutramine and phentermine).

An aldosterone synthase inhibitor or a pharmaceutically acceptable salt thereof is understood to be an active ingredient that has the property to inhibit the production of aldosterone. Aldosterone synthase (CYP11B2) is a mitochondrial cytochrome P450 enzyme catalyzing the last step of aldosterone production in the adrenal cortex, i.e., the conversion of 11-deoxycorticosterone to aldosterone. The inhibition of the aldosterone production with so-called aldosterone synthase inhibitors is known to be a successful variant to treatment of hypokalemia, hypertension, congestive heart failure, atrial fibrillation or renal failure. Such aldosterone synthase inhibition activity is readily determined by those skilled in the art according to standard assays (e.g., US 2007/0049616).

The class of aldosterone synthase inhibitors comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. An example of non-steroidal aldosterone synthase inhibitor is the (+)-enantiomer of the hydrochloride of fadrozole (U.S. Pat. Nos. 4,617,307 and 4,889,861) of formula

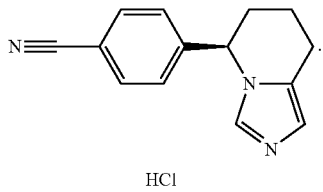

HCl or, if appropriate, a pharmaceutically acceptable salt thereof.

Aldosterone synthase inhibitors useful in said combination are compounds and analogs generically and specifically disclosed e.g. in US2007/0049616, in particular in the compound claims and the final products of the working examples, the subject-matter of the final products, the pharmaceutical preparations and the claims are hereby incorporated into the present application by reference to this publication. Preferred aldosterone synthase inhibitors suitable for use in the present invention include, without limitation 4-(6,7-dihydro-5H-pyrrolo[1,2-c]imidazol-5-yl)-3-methylbenzonitrile; 5-(2-chloro-4-cyanophenyl)-6,7-dihydro-5H-pyrrolo[1,2-c]imidazole-5-carboxylic acid (4-methoxybenzyl)methylamide; 4'-fluoro-6-(6,7,8,9-tetrahydro-5H-imidazo[1,5-a]azepin-5-yl)biphenyl-3-carbonitrile; 5-(4-Cyano-2-methoxyphenyl)-6,7-dihydro-5H-pyrrolo[1,2-c]imidazole-5-carboxylic acid butyl ester; 4-(6,7-Dihydro-5H-pyrrolo[1,2-c]imidazol-5-yl)-2-methoxybenzonitrile; 5-(2-Chloro-4-cyanophenyl)-6,7-dihydro-5H-pyrrolo[1,2-c]imidazole-5-carboxylic acid 4-fluorobenzyl ester; 5-(4-Cyano-2-trifluoromethoxyphenyl)-6,7-dihydro-5H-pyrrolo[1,2-c]imidazole-5-carboxylic acid methyl ester; 5-(4-Cyano-2-methoxyphenyl)-6,7-dihydro-5H-pyrrolo[1,2-c]imidazole-5-carboxylic acid 2-isopropoxyethyl ester; 4-(6,7-Dihydro-5H-pyrrolo[1,2-c]imidazol-5-yl)-2-methylbenzonitrile; 4-(6,7-dihydro-5H-pyrrolo[1,2-c]imidazol-5-yl)-3-fluorobenzonitrile; 4-(6,7-Dihydro-5H-pyrrolo[1,2-c]imidazol-5-yl)-2-methoxybenzonitrile; 3-Fluoro-4-(7-methylene-6,7-dihydro-5H-pyrrolo[1,2-c]imidazol-5-yl)benzonitrile; cis-3-Fluoro-4-[7-(4-fluoro-benzyl)-5,6,7,8-tetrahydro-imidazo[1,5-a]pyridin-5-yl]benzonitrile; 4'-Fluoro-6-(9-methyl-6,7,8,9-tetrahydro-5H-imidazo[1,5-a]azepin-5-yl)biphenyl-3-carbonitrile; 4'-Fluoro-6-(9-methyl-6,7,8,9-tetrahydro-5H-imidazo[1,5-a]azepin-5-yl)biphenyl-3-carbonitrile or in each case, the (R) or (S) enantiomer thereof; or if appropriable, a pharmaceutically acceptable salt thereof.

The term aldosterone synthase inhibitors also include compounds and analogs disclosed in WO2008/076860, WO2008/076336, WO2008/076862, WO2008/027284, WO2004/046145, WO2004/014914, WO2001/076574.

Furthermore Aldosterone synthase inhibitors also include compounds and analogs disclosed in U.S. patent applications US2007/0225232, US2007/0208035, US2008/0318978, US2008/0076794, US2009/0012068, US20090048241 and in PCT applications WO2006/005726, WO2006/128853, WO2006128851, WO2006/128852, WO2007065942, WO2007/116099, WO2007/116908, WO2008/119744 and in European patent application EP 1886695. Preferred aldosterone synthase inhibitors suitable for use in the present invention include, without limitation 8-(4-Fluorophenyl)-5,6-dihydro-8H-imidazo[5,1-c][1,4]oxazine; 4-(5,6-Dihydro-8H-imidazo[5,1-c][1,4]oxazin-8-yl)-2-fluorobenzonitrile; 4-(5,6-Dihydro-8H-imidazo[5,1-c][1,4]oxazin-8-yl)-2,6-difluorobenzonitrile; 4-(5,6-Dihydro-8H-imidazo[5,1-c][1,4]oxazin-8-yl)-2-methoxybenzonitrile; 3-(5,6-Dihydro-8H-imidazo[5,1-c][1,4]oxazin-8-yl)benzonitrile; 4-(5,6-Dihydro-8H-imidazo[5,1-c][1,4]oxazin-8-yl)phthalonitrile; 4-(8-(4-Cyanophenyl)-5,6-dihydro-8H-imidazo[5,1-c][1,4]oxazin-8-yl)benzonitrile; 4-(5,6-Dihydro-8H-imidazo[5,1-c][1,4]oxazin-8-yl)benzonitrile; 4-(5,6-Dihydro-8H-imidazo[5,1-c][1,4]oxazin-8-yl)naphthalene-1-carbonitrile; 8-[4-(1H-Tetrazol-5-yl)phenyl]-5,6-dihydro-8H-imidazo[5,1-c][1,4]oxazine as developed by Speedel or in each case, the (R) or (S) enantiomer thereof; or if appropriable, a pharmaceutically acceptable salt thereof.

Aldosterone synthase inhibitors useful in said combination are compounds and analogs generically and specifically disclosed e.g. in WO 2009/156462 and WO 2010/130796, in particular in the compound claims and the final products of the working examples, the subject-matter of the final products, the pharmaceutical preparations and the claims. Preferred Aldosterone Synthase inhibitors suitable for combination in the present invention include, 3-(6-Fluoro-3-methyl-2-pyridin-3-yl-1H-indol-1-ylmethyl)-benzonitrile hydrochloride, 1-(4-Methanesulfonyl-benzyl)-3-methyl-2-pyridin-3-yl-1H-indole, 2-(5-Benzyloxy-pyridin-3-yl)-6-chloro-1-methyl-1H-indole, 5-(3-Cyano-1-methyl-1H-indol-2-yl)-nicotinic acid ethyl ester, N-[5-(6-chloro-3-cyano-1-methyl-1H-indol-2-yl)-pyridin-3-ylmethyl]-ethanesulfonamide, Pyrrolidine-1-sulfonic acid 5-(6-chloro-3-cyano-1-methyl-1H-indol-2-yl)-pyridin-3-ylester, N-Methyl-N-[5-(1-methyl-1H-indol-2-yl)-pyridin-3-ylmethyl]-methanesulfonamide, 6-Chloro-1-methyl-2-{5-[(2-pyrrolidin-1-yl-ethylamino)-methyl]-pyridin-3-yl}-1H-indole-3-carbonitrile, 6-Chloro-2-[5-(4-methanesulfonyl-piperazin-1-ylmethyl)-pyridin-3-yl]-1-methyl-1H-indole-3-carbonitrile, 6-Chloro-1-methyl-2-{5-[(1-methyl-piperidin-4-ylamino)-methyl]-pyridin-3-yl}-1H-indole-3-carbonitrile, Morpholine-4-carboxylic acid [5-(6-chloro-3-cyano-1-methyl-1H-indol-2-yl)-pyridin-3-ylmethyl]-amide, N-[5-(6-Chloro-1-methyl-1H-indol-2-yl)-pyridin-3-ylmethyl]-ethanesulfonamide, C,C,C-Trifluoro-N-[5-(1-methyl-1H-indol-2-yl)-pyridin-3-ylmethyl]-methanesulfonamide, N-[5-(3-Chloro-4-cyano-phenyl)-pyridin-3-yl]-4-trifluoromethyl-benzenesulfonamide, N-[5-(3-Chloro-4-cyano-phenyl)-pyridin-3-yl]-1-phenyl-methanesulfonamide, N-(5-(3-chloro-4-cyanophenyl)pyridin-3-yl)butane-1-sulfonamide, N-(1-(5-(4-cyano-3-methoxyphenyl)pyridin-3-yl)ethyl)ethanesulfonamide, N-((5-(3-chloro-4-cyanophenyl)pyridin-3-yl)(cyclopropyl)methyl)ethanesulfonamide, N-(cyclopropyl(5-(1H-indol-5-yl)-pyridin-3-ylmethyl)ethanesulfonamide, N-(cyclopropyl(5-naphthalen-1-yl-pyridin-3-yl)methyl)ethanesulfonamide, Ethanesulfonic acid [5-(6-chloro-1-methyl-1H-pyrrolo[2,3-b]pyridin-2-yl)-pyridin-3-ylmethyl]-amide and Ethanesulfonic acid {[5-(3-chloro-4-cyano-phenyl)-pyridin-3-yl]-cyclopropyl-methyl}-ethyl-amide.

The term "endothelin receptor blocker" includes bosentan and ambrisentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. Nos. 6,140,343 and 6,197,786 (e.g., [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot.*, 49(8): 815-816 (1996), and *Bioorg. Med. Chem. Lett;* 6:1951-1954 (1996), respectively. Furthermore, the CETP inhibitors also include those disclosed in WO2000/017165, WO2005/095409, WO2005/097806, WO 2007/128568, WO2008/009435, WO 2009/059943 and WO2009/071509.

The term "NEP inhibitor" refers to a compound that inhibits neutral endopeptidase (NEP) EC 3.4.24.11. Examples include Candoxatril, Candoxatrilat, Dexecadotril, Ecadotril, Racecadotril, Sampatrilat, Fasidotril, Omapatrilat, Gemopatrilat, Daglutril, SCH-42495, SCH-32615, UK-447841, AVE-0848, PL-37 and (2R,4S)-5-Biphenyl-4-yl-4-(3-carboxy-propionylamino)-2-methyl-pentanoic acid ethyl ester or a pharmaceutically acceptable salt thereof. NEP inhibitors also include Phosphono/biaryl substituted dipeptide derivatives, as disclosed in U.S. Pat. No. 5,155,100. NEP inhibitors also include N-mercaptoacyl phenylalanine derivative as disclosed in PCT application Number WO 2003/104200. NEP inhibitors also include dual-acting antihypertensive agents as disclosed in PCT application Numbers WO 2008/133896, WO 2009/035543 or WO 2009/134741. Other examples include compounds disclosed in U.S. application Ser. Nos. 12/788,794; 12/788,766 and 12/947,029. NEP inhibitors also include compounds disclosed in WO 2010/136474, WO 2010/136493, WO 2011/061271 and US provisional applications No 61/414,171 and 61/414,163.

In one embodiment, the invention provides a method of activating the APJ receptor in a subject, wherein the method comprises administering to the subject a therapeutically effective amount of the bioconjugate according to anyone of the preceding embodiments, or a multimer thereof.

In one embodiment, the invention provides a method of treating a disorder or a disease responsive to the activation of the APJ receptor, in a subject, wherein the method comprises administering to the subject a therapeutically effective amount of bioconjugate according to anyone of the preceding embodiments, or a multimer thereof.

In one embodiment, the invention provides a method of treating a disorder or a disease responsive to the activation (agonism) of the APJ receptor, in a subject, wherein the disorder or the disease is selected from acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

In one embodiment, the invention provides a bioconjugate according to anyone of the preceding embodiments, or a multimer thereof, for use as a medicament.

In one embodiment, the invention provides the use of a bioconjugate according to anyone of the preceding embodiments, or a multimer thereof, in the manufacture of a medicament, for the treatment of a disorder or disease responsive to the activation of the APJ receptor. In another embodiment, the invention provides the use of a bioconjugate according to anyone of the preceding embodiments, or a multimer thereof, in the manufacture of a medicament, for the treatment of a disorder or disease responsive to the activation of the APJ receptor, wherein said disorder or disease is in particular selected from acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

Exemplification of the Invention: Peptide and Polypeptide Synthesis for Conjugation with a Half Life Extending Moiety.

| Abbreviation | Definition |
| --- | --- |
| AA | Amino acid |
| Ac | Acetyl |
| Acm | Acetamidomethyl |
| ACN | Acetonitrile |
| AcOH | Acetic acid |
| $Ac_2O$ | Acetic anhydride |

| Abbreviation | Definition |
|---|---|
| AM | Aminomethyl |
| BAL | Backbone amide linker |
| BSA | Bovine Serum Albumin |
| Boc | tert-Butyloxycarbonyl |
| DCM | Dichlormethane |
| DIC | N,N'-Diisopropylcarbodiimide |
| DIPEA | N,N'-Diisopropylethylamine |
| DMA | N,N'-Dimethylacetamide |
| DTT | dithiothreitol |
| DMF | N,N'-Dimethylformamide |
| DMSO | Dimethylsulfoxide |
| DVB | Divinylbenzene |
| EDT | Ethanedithiol |
| FA | Formic acid |
| Fmoc | 9-Fluorenylmethyloxycarbonyl |
| HATU | 2-(1H-9-Azabenzotriazole-1-yl)-1,1,3,3-tetramethyluronium hexafluorophosphate |
| HBSS | Hank's buffered salt solution |
| HCTU | 2-(6-Chloro-1H-Benzotriazole-yl)-1,1,3,3-tetramethyluronium hexafluorophosphate |
| HEPES | 4-(2-hydroxyethyl)-1-piperazineethanesulfonic acid |
| HFIP | Hexafluoroisopropanol |
| HOAt | 1-Hydroxy-7-azabenzotriazole |
| HPLC | High performance liquid chromatography |
| HSA | Human Serum Albumin |
| ivDde | (4,4-Dimethyl-2,6-dioxocyclohex-1-ylidene)-3-methylbutyl |
| LN | Logarithmus naturali (natural logarithm) |
| MPA | 3-(Maleimido)propionic acid |
| MeOH | Methanol |
| MS | Mass spectrometry |
| Nal | 2-Naphthylalanine |
| Nle | Norleucine |
| NMP | N-Methylpyrrolidine |
| Oxyma Pure | Ethyl 2-cyano-2-(hydroxyimino)acetate |
| Pbf | 2,2,4,6,7-Pentamethyldihydrobenzofuran-5-sulfonyl |
| pE | Pyroglutamate |
| PG | Protecting group |
| PBS | Phosphate buffered saline |
| Ph | Phenyl |
| PS | Polystyrene |
| POL | Polymer support |
| rt | Room temperature |
| SPPS | Solid phase peptide synthesis |
| SEC | Size-exclusion chromatography |
| tBuOH | tert-Butanol |
| TCEP | Tris(2-carboxyethyl)phosphine |
| TIPS/TIS | triisopropylsilane |
| TFA | Trifluoroacetic acid |
| THF | Tetrahydrofuran |
| TIS | Triisopropylsilane |
| TPA | 3-Mercaptopropanoic Acid |
| $t_R$ | Retention time |
| Trt | Trityl |
| UPLC | Ultra performance liquid chromatography |
| UV | Ultraviolet |

The peptides below were synthesized by standard solid phase Fmoc chemistry. The peptides were assembled on the Prelude™ peptide synthesizer (Protein Technologies, Inc., Tucson, USA). Peptides with a free carboxylic acid on the C-terminus were synthesized from 2-chlorotrityl chloride-PS-resin (ABCR, Karlsruhe, Germany. Peptides with an unsubstituted carboxamide on the C-terminus were synthesized from Fmoc protected Rink-Amide-AM-PS-resin (Merck, Darmstadt, Germany). Peptides with an N-monosubstituted carboxamide on the C-terminus were synthesized from BAL-AM-PS-resin loaded with amines (EMC Microcollections, Tübingen, Germany).

The peptides were purified by preparative reversed-phase HPLC. The following columns were used:

Waters SunFire Prep C18 OBD Column, 5 µm, 30×100 mm, Part No. 186002572 (one column or two columns in series)

Waters SunFire Prep C18 OBD Column, 5 µm, 30×50 mm, Part No. 186002572

Waters SunFire Prep C18 OBD Column, 5 µm, 30×150 mm, Part No. 186002797

Waters Atlantis Prep OBD T3 Column, 5 µm, 30×150 mm, Part No. 186003703

Waters XBridge Prep C8 OBD Column, 5 µm, 30×150 mm, Part No. 186003083

Machery-Nagel Nucleosil® 100-5 C18, 5 µm, 250×40 mm, Part No. 715340.400

Mobile phases consisted of eluent A (0.1% TFA in $H_2O$) and eluent B (ACN). Gradients were designed based on the specific requirements of the separation problem. Pure products were lyophilized from ACN/$H_2O$.

The products were analyzed by HPLC using UV detection at λ=214 nm and UPLC-MS using electrospray ionization.

The peptides that are exemplified in Table 4 were synthesized using the general procedures described below. Unsubstituted N- or C-termini are indicated by small italic H— or —OH, respectively.

TABLE 4

| Peptide | Sequence | Type of Ring | SEQ ID NO: |
|---|---|---|---|
| Peptide 1 | pE-R-P-R-L-K-H-F-G-P-Nle-D-Phenethylamine | Lactam $K^6$-$D^{12}$ | 23 |
| Peptide 2 | pE-R-P-R-L-K-H-F-G-P-Nle-E-Phenethylamine | Lactam $K^6$-$E^{12}$ | 24 |
| Peptide 3 | pE-R-P-R-L-Orn-H-F-G-P-Nle-D-Phenethylamine | Lactam $O^6$-$D^{12}$ | 25 |
| Peptide 4 | pE-R-P-R-L-Dab-H-F-G-P-Nle-D-Phenethylamine | Lactam $Dab^6$-$D^{12}$ | 26 |
| Peptide 5 | pE-R-P-R-L-K-F-K-G-P-Nle-F | Lactam $K^6$-C-terminus | 27 |
| Peptide 6 | pE-R-P-R-L-K-F-K-G-P-Nle-f | Lactam $K^6$-C-terminus | 28 |
| Peptide 7 | Q-R-P-R-L-C-F-K-G-P-Nle-C-F-G-G | Lactam N-terminus-C-terminus, Disulfide $C^6$-$C^{12}$ | 29 |
| Peptide 8 | pE-R-P-R-L-C-H-K-G-P-Nle-C-F-OH | Disulfide $C^6$-$C^{12}$ | 30 |
| Peptide 9 | pE-R-P-R-L-C-Aib-K-G-P-Nle-C-F-OH | Disulfide $C^6$-$C^{12}$ | 31 |
| Peptide 10 | pE-R-P-R-L-C-Aib-K-G-P-Nle-C-f-OH | Disulfide $C^6$-$C^{12}$ | 32 |

TABLE 4-continued

| Peptide | Sequence | Type of Ring | SEQ ID NO: |
|---|---|---|---|
| Peptide 11 | H-Isn-R-P-R-L-C-Aib-K-G-P-Nle-C-f-OH | Disulfide $C^6$-$C^{12}$ | 33 |
| Peptide 12 | pE-R-P-R-L-C-H-K-G-P-Nle-C-Phenethylamine | Disulfide $C^6$-$C^{12}$ | 34 |
| Peptide 13 | pE-R-P-R-L-C-H-K-G-P-Nle-C-f-OH | Disulfide $C^6$-$C^{12}$ | 35 |
| Peptide 14 | pE-R-P-R-Cha-C-H-K-G-P-Cha-C-F-OH | Disulfide $C^6$-$C^{12}$ | 36 |
| Peptide 15 | pE-R-P-R-L-C-F-K-G-P-Nle-C-F-OH | Disulfide $C^6$-$C^{12}$ | 37 |
| Peptide 16 | H-R-P-R-L-C-H-K-G-P-Nle-C-F-OH | Disulfide $C^5$-$C^{11}$ | 38 |
| Peptide 17 | H-R-R-P-R-L-C-H-K-G-P-Nle-C-F-OH | Disulfide $C^6$-$C^{12}$ | 39 |
| Peptide 18 | H-Isn-R-P-R-L-C-H-K-G-P-Nle-C-F-OH | Disulfide $C^6$-$C^{12}$ | 40 |
| Peptide 19 | pE-R-P-R-L-C-H-F-G-P-Nle-C-Phenethylamine | Disulfide $C^6$-$C^{12}$ | 41 |
| Peptide 20 | pE-R-P-R-L-C-H-K-Aib-P-Nle-C-F-OH | Disulfide $C^6$-$C^{12}$ | 42 |
| Peptide 21 | pE-R-P-R-L-C-H-(4-NH-Isn)-G-P-Nle-C-F-OH | Disulfide $C^6$-$C^{12}$ | 43 |
| Peptide 22 | pE-R-P-C-L-C-C-K-G-P-Nle-C-F-OH | Disulfides $C^6$-$C^{12}$, $C^4$-$C^7$ | 44 |
| Peptide 23 | pE-R-C-R-L-C-C-K-G-P-Nle-C-F-OH | Disulfides $C^6$-$C^{12}$, $C^3$-$C^7$ | 45 |
| Peptide 24 | pE-r-P-R-L-C-H-K-G-P-Nle-C-F-OH | Disulfide $C^6$-$C^{12}$ | 46 |
| Peptide 25 | pE-F-P-R-L-C-H-K-G-P-Nle-C-F-OH | Disulfide $C^6$-$C^{12}$ | 47 |
| Peptide 26 | pE-E-P-R-L-C-H-K-G-P-Nle-C-F-OH | Disulfide $C^6$-$C^{12}$ | 48 |
| Peptide 27 | pE-R-p-R-L-C-H-K-G-P-Nle-C-F-OH | Disulfide $C^6$-$C^{12}$ | 49 |
| Peptide 28 | pE-R-K-R-L-C-H-K-G-P-Nle-C-F-OH | Disulfide $C^6$-$C^{12}$ | 50 |
| Peptide 29 | pE-R-D-R-L-C-H-K-G-P-Nle-C-F-OH | Disulfide $C^6$-$C^{12}$ | 51 |
| Peptide 30 | pE-R-P-F-L-C-H-K-G-P-Nle-C-F-OH | Disulfide $C^6$-$C^{12}$ | 52 |
| Peptide 31 | pE-R-P-R-K-C-H-K-G-P-Nle-C-F-OH | Disulfide $C^6$-$C^{12}$ | 53 |
| Peptide 32 | pE-R-P-R-L-C-H-E-G-P-Nle-C-F-OH | Disulfide $C^6$-$C^{12}$ | 54 |
| Peptide 33 | pE-R-P-R-L-C-H-D-P-Nle-C-F-OH | Disulfide $C^6$-$C^{12}$ | 55 |
| Peptide 34 | pE-R-P-E-L-C-H-K-G-P-Nle-C-F-OH | Disulfide $C^6$-$C^{12}$ | 56 |
| Peptide 35 | pE-R-P-R-(4-PhF)-C-H-K-G-P-Nle-C-F-OH | Disulfide $C^6$-$C^{12}$ | 57 |
| Peptide 36 | pE-R-P-D-C-H-K-G-P-Nle-C-F-OH | Disulfide $C^6$-$C^{12}$ | 58 |
| Peptide 37 | pE-R-P-R-L-C-E-K-G-P-Nle-C-F-OH | Disulfide $C^6$-$C^{12}$ | 59 |
| Peptide 38 | pE-R-P-R-L-C-H-K-L-P-Nle-C-F-OH | Disulfide $C^6$-$C^{12}$ | 60 |
| Peptide 39 | pE-R-P-R-L-C-H-K-R-P-Nle-C-F-OH | Disulfide $C^6$-$C^{12}$ | 61 |
| Peptide 40 | pE-R-P-R-L-C-H-K-G-(Pipecolic acid)-Nle-C-F-OH | Disulfide $C^6$-$C^{12}$ | 62 |
| Peptide 41 | pE-R-P-R-L-C-H-K-G-P-(3-PyA)-C-F-OH | Disulfide $C^6$-$C^{12}$ | 63 |
| Peptide 42 | pE-R-P-R-L-C-H-K-G-P-Nle-C-H-OH | Disulfide $C^6$-$C^{12}$ | 64 |
| Peptide 43 | pE-R-P-R-L-C-H-K-G-P-Nle-C-E-OH | Disulfide $C^6$-$C^{12}$ | 65 |
| Peptide 44 | pE-R-P-R-L-C-H-K-G-P-Nle-C-OH | Disulfide $C^6$-$C^{12}$ | 66 |
| Peptide 45 | pE-R-P-R-L-C-H-K-G-P-Nle-hC-F-OH | Disulfide $C^6$-$C^{12}$ | 67 |
| Peptide 46 | pE-R-P-R-L-hC-H-K-G-P-Nle-hC-F-OH | Disulfide $C^6$-$C^{12}$ | 68 |
| Peptide 47 | pE-R-P-R-L-c-H-K-G-P-Nle-C-F-OH | Disulfide $C^6$-$C^{12}$ | 69 |
| Peptide 48 | pE-R-P-R-L-C-H-K-G-P-Nle-(D-hC)-F-OH | Disulfide $C^6$-$C^{12}$ | 70 |

TABLE 4-continued

| Peptide | Sequence | Type of Ring | SEQ ID NO: |
|---|---|---|---|
| Peptide 49 | pE-R-P-R-L-(D-hC)-H-K-G-P-Nle-(D-hC)-F-OH | Disulfide $C^6$-$C^{12}$ | 71 |
| Peptide 50 | pE-R-P-R-L-C-H-K-G-P-Nle-c-F-OH | Disulfide $C^6$-$C^{12}$ | 72 |
| Peptide 51 | pE-R-P-R-L-c-H-K-G-P-Nle-c-F-OH | Disulfide $C^6$-$C^{12}$ | 73 |
| Peptide 52 | pE-R-P-R-L-C-H-K-G-P-Nle-C-F-$NH_2$ | Disulfide $C^6$-$C^{12}$ | 74 |
| Peptide 53 | pE-R-P-R-L-C-H-K-G-P-Nle-C-$NH_2$ | Disulfide $C^6$-$C^{12}$ | 75 |
| Peptide 54 | pE-R-P-R-L-C-H-K-G-P-Nle-C-F-OH | Monosulfide $C^6$-$C^{12}$ | 76 |

Analytical Methods

1a) HPLC—Analytical Method A
Column: Bischoff UHC-640 (53×4.0 mm) with ProntoSil 120-3-C18-H, 3 µm; Part n°: 0604F185PS030
Eluent A: 0.07% TFA in water/Eluent B: 0.1% TFA in ACN
Flow: 1.5 ml/min
Temperature: 40° C.
Gradient:

| Time [min] | A [%] | B [%] |
|---|---|---|
| 0.0 | 95 | 5 |
| 10.0 | 0 | 100 |
| 12.0 | 0 | 100 |
| 12.2 | 95 | 5 |

1b) UPLC—Analytic Method B
Column: XBridge BEH300 C18 (100×4.6 mm), 3 µm; Part n°: 186003612
Eluent A: 0.1% TFA in water/Eluent B: 0.1% TFA in ACN
Flow: 1.0 ml/min
Temperature: 40° C.
Gradient:

| Time [min] | A [%] | B [%] |
|---|---|---|
| 0.0 | 98 | 2 |
| 18 | 2 | 98 |
| 20 | 2 | 98 |
| 22 | 98 | 2 |

2) UPLC-MS—Analytic Method C
Waters Acquity UPLC® BEH C18, 1.7 µm, 2.1×50 mm; Part n°: 186002350
Eluent A: 0.1% FA in water; Eluent B: 0.1% FA in ACN
Flow: 0.7 ml/min
Temperature: 40° C.
Gradient:

| Time [min] | A [%] | B [%] |
|---|---|---|
| 0.0 | 99 | 1 |
| 1.0 | 97 | 3 |
| 3.5 | 50 | 50 |
| 4.0 | 10 | 90 |
| 4.3 | 0 | 100 |
| 4.6 | 80 | 20 |

The analytical data for peptides 1 to 54 are summarized in Table 5 and was generated using the analytical methods described supra.

3) Analytical Method D:
XBridge C18 Column, 3.5 µm, 3.0×30 mm
Eluent: A: Water (0.1% formic acid); B: CAN
Flow rate: 2 mL/min
Gradient: 0 min 40% B; 40% to 95% B in 1.70 min; 2.0 min 95% B; 2.1 min 40% B
Mass Spectrometer: Single Quadrupole ESI scan range 150-1600
HPLC: Agilent 1100 series
Temperature: 40 C

TABLE 5

Peptide for conjugation with a half-life extending moiety

| | HPLC | | Mass spectrometry | | | | |
|---|---|---|---|---|---|---|---|
| Peptide | $t_R$ [min] | Meth. | $[M+2H]^{2+}$ (measured) | $[M+3H]^{3+}$ (measured) | Meth. | $[M+2H]^{2+}$ (calc.) | $[M+3H]^{3+}$ (calc.) |
| 1 | 4.16 | A | 766.3 | 511.2 | C | 766.4 | 511.3 |
| 2 | 4.18 | A | 773.5 | 515.8 | C | 773.4 | 516.0 |
| 3 | 4.14 | A | | 506.6 | C | 759.4 | 506.6 |
| 4 | 4.15 | A | 752.4 | 501.9 | C | 752.4 | 501.9 |
| 5 | 3.70 | A | | 484.5 | C | 726.4 | 484.6 |
| 6 | 3.84 | A | | 484.5 | C | 726.4 | 484.6 |
| 7 | 3.85 | A | | 553.6 | C | 829.9 | 553.6 |
| 8 | 3.43 | A | 768.1 | 512.4 | C | 768.4 | 512.6 |
| 9 | 3.77 | A | | 495.2 | C | 742.4 | 495.3 |
| 10 | 3.74 | A | 742.5 | 495.1 | C | 742.4 | 495.3 |
| 11 | 3.61 | A | 742.9 | 495.2 | C | 742.4 | 495.3 |
| 12 | 3.62 | A | | 497.8 | C | 746.4 | 497.9 |
| 13 | 3.49 | A | 768.3 | 512.5 | C | 768.4 | 512.6 |
| 14 | 4.14 | A | 808.5 | 539.2 | C | 808.4 | 539.3 |
| 15 | 3.99 | A | 773.4 | 515.8 | C | 773.4 | 515.9 |
| 16 | 3.36 | A | | 475.5 | C | 712.9 | 475.6 |
| 17 | 3.28 | A | | 527.5 | C | 790.9 | 527.6 |
| 18 | 3.36 | A | | 512.5 | C | 768.4 | 512.6 |
| 19 | 4.38 | A | 756.0 | 504.2 | C | 755.9 | 504.3 |
| 20 | 3.17 | A | 782.6 | 522.0 | C | 782.4 | 521.9 |
| 21 | 3.45 | A | | 512.0 | C | 767.4 | 511.9 |
| 22 | 4.16 | A | 723.7 | | C | 723.8 | 482.9 |
| 23 | 3.85 | A | 753.0 | 502.5 | C | 753.3 | 502.6 |
| 24 | 3.39 | A | | 512.5 | C | 768.4 | 512.6 |
| 25 | 4.08 | A | 763.8 | 509.4 | C | 763.9 | 509.6 |
| 26 | 3.59 | A | 754.8 | 503.6 | C | 754.9 | 503.6 |
| 27 | 3.36 | A | | 512.5 | C | 768.4 | 512.6 |
| 28 | 3.14 | A | | 522.8 | C | 783.9 | 522.9 |
| 29 | 3.36 | A | | 518.5 | C | 777.4 | 518.6 |
| 30 | 3.91 | A | 763.8 | 509.4 | C | 763.9 | 509.6 |
| 31 | 3.05 | A | | 517.5 | C | 775.9 | 517.6 |
| 32 | 3.67 | A | 768.7 | 512.8 | C | 768.9 | 512.9 |
| 33 | 3.47 | A | | 531.7 | C | 797.4 | 531.9 |
| 34 | 3.60 | A | 754.9 | 503.6 | C | 754.9 | 503.6 |
| 35 | 3.91 | A | | 549.1 | C | 823.4 | 549.3 |
| 36 | 3.10 | A | 769.2 | 513.1 | C | 769.4 | 513.2 |
| 37 | 3.58 | A | 764.2 | 509.7 | C | 764.4 | 509.9 |
| 38 | 3.82 | A | | 531.1 | C | 796.4 | 531.3 |

TABLE 5-continued

Peptide for conjugation with a half-life extending moiety

| | HPLC | | Mass spectrometry | | | | |
|---|---|---|---|---|---|---|---|
| Peptide | $t_R$ [min] | Meth. | $[M + 2H]^{2+}$ (measured) | $[M + 3H]^{3+}$ (measured) | Meth. | $[M + 2H]^{2+}$ (calc.) | $[M + 3H]^{3+}$ (calc.) |
| 39 | 3.16 | A | | 545.5 | C | 817.9 | 545.6 |
| 40 | 3.54 | A | | 517.1 | C | 775.4 | 517.3 |
| 41 | 2.53 | A | | 524.1 | C | 785.9 | 524.3 |
| 42 | 2.49 | A | | 509.2 | C | 763.4 | 509.3 |
| 43 | 2.73 | A | 759.3 | 506.5 | C | 759.4 | 506.6 |
| 44 | 2.72 | A | 694.5 | | C | 694.8 | 463.6 |
| 45 | 3.38 | A | | 517.1 | C | 775.4 | 517.3 |
| 46 | 3.45 | A | | 521.9 | C | 782.4 | 521.9 |
| 47 | 3.52 | A | 768.4 | 512.5 | C | 768.4 | 512.6 |
| 48 | 3.43 | A | 775.3 | 517.1 | C | 775.4 | 517.3 |
| 49 | 3.83 | A | 782.3 | 521.8 | C | 782.4 | 521.9 |
| 50 | 3.42 | A | 768.1 | 512.4 | C | 768.4 | 512.6 |
| 51 | 3.66 | A | 768.3 | 512.4 | C | 768.4 | 512.6 |
| 52 | 3.22 | A | | 512.3 | C | 767.9 | 512.3 |
| 53 | 2.71 | A | 694.3 | 463.1 | C | 694.4 | 463.2 |

General Synthesis Procedures

1) Loading of First Amino Acid onto 2-chlorotrityl Chloride Resin and Fmoc-Removal 2-Chlorotrityl chloride resin (1 eq., 1.0-1.6 mmol/g) was washed thoroughly with DCM. The desired amino acid (typically 0.5-2 eq. relative to the resin, considering 1.6 mmol/g loading) was dissolved in DCM (approx. 10 mL per gram of resin) and DIPEA (4 eq. relative to the resin, considering 1.6 mmol/g loading). The solution was added to the resin and the suspension was shaken at it for 19 h. The resin was drained and then thoroughly washed sequentially with DCM/MeOH/DIPEA (17:2:1), DCM, DMA, DCM.

For Fmoc removal and determination of the loading the resin was shaken repeatedly with piperidine/DMA (1:4) or 4-methylpiperidine/DMA (1:4) (12×10 mL per gram of initial resin) and washed with DMA (2×10 mL per gram of initial resin). The combined solutions were diluted with MeOH to a volume V of 250 mL per gram of initial resin. A 2 mL aliquot ($V_a$) of this solution was diluted further to 250 mL ($V_t$) with MeOH. The UV absorption was measured at 299.8 nm against a reference of MeOH, giving absorption A. The resin was thoroughly washed sequentially with DMA, DCM, DMA, DCM and dried in high vacuum at 40° C., affording m g of resin.

The loading of the resin is calculated according to the formula:

$$\text{Loading [mol/g]} = (A \times V_t \times V)/(d \times \epsilon \times V_a \times m)$$

(with d: width of cuvette; $\epsilon$=7800 L mol$^{-1}$ cm$^{-1}$)

2) Solid Phase Peptide Synthesis on Prelude™ Synthesizer

2a) Synthesis Cycle A

The resin was washed with DMA. Fmoc was removed by repetitive treatment with 4-methylpiperidine/DMA (1:4). The resin was washed with DMA. Coupling was done by addition of the Fmoc-amino acid (3 eq.; 0.2 M solution in NMP), HCTU (3 eq.; 0.3 M solution in NMP), and DIPEA (3.3 eq.; 0.66 M solution in NMP) followed by mixing of the suspension with nitrogen at it for typically 15 min to 4 h depending on the specific requirements. After washing with DMA the coupling step was typically repeated 1 to 3 times depending on the specific requirements. After washing with DMA capping was performed by addition of a mixture of Ac$_2$O/pyridine/DMA (1:1:8) and subsequent mixing of the suspension at rt. The resin was washed with DMA.

2b) Synthesis Cycle B

The resin was washed with DMA. Fmoc was removed by repetitive treatment with piperidine/DMA (1:4). The resin was washed with DMA. Coupling was done by addition of the Fmoc-amino acid (3 eq.; 0.3 M solution in NMP), HCTU (3 eq.; 0.3 M solution in NMP), and DIPEA (4.5 eq.; 0.9 M solution in NMP) followed by mixing of the suspension with nitrogen at rt for typically 15 min to 4 h depending on the specific requirements. After washing with DMA the coupling step was typically repeated 1 to 3 times depending on the specific requirements. After washing with DMA capping was performed by addition of a mixture of Ac$_2$O/pyridine/DMA (1:1:8) and subsequent mixing of the suspension at rt. The resin was washed with DMA.

2c) Synthesis Cycle C

The resin was washed with DMA. Fmoc was removed by repetitive treatment with piperidine/DMA (1:4). The resin was washed with DMA. Coupling was done by addition of the Fmoc-amino acid (3 eq.; 0.3 M solution in NMP), HCTU (3 eq.; 0.3 M solution in NMP), and DIPEA (6 eq.; 0.9 M solution in NMP) followed by mixing of the suspension with nitrogen at it for typically 15 min to 4 h depending on the specific requirements. After washing with DMA the coupling step was typically repeated 1 to 3 times depending on the specific requirements. After washing with DMA capping was performed by addition of a mixture of Ac$_2$O/pyridine/DMA (1:1:8) and subsequent mixing of the suspension at rt. The resin was washed with DMA.

2d) Synthesis Cycle D

The resin was washed with DMA. Fmoc was removed by repetitive treatment with 4-methylpiperidine/DMA (1:4). The resin was washed with DMA. Coupling was done by addition of a mixture of the Fmoc-amino acid and Oxyma Pure (3 eq. each; 0.2 M of both in NMP) and DIC (3 eq.; 0.3 M solution in NMP) followed by mixing of the suspension with nitrogen at it for typically 15 min to 4 h depending on the specific requirements. After washing with DMA the coupling step was typically repeated 1 to 3 times depending on the specific requirements. After washing with DMA capping was performed by addition of a mixture of Ac$_2$O/pyridine/DMA (1:1:8) and subsequent mixing of the suspension at rt. The resin was washed with DMA.

3) Cleavage from Resin with or without Concomitant Removal of Protecting Groups

3a) Cleavage Method A

The resin (0.1 mmol) was shaken at it for 2 h with 95% aq. TFA/EDT/TIS (95:2.5:2.5) (3 mL). The cleavage solution was filtered off, and fresh solution was added (3 mL). The suspension was shaken at it for 1 h then the cleavage solution was filtered off. Fresh solution was added (3 mL) and the suspension was shaken at it for 1 h. The cleavage solution was filtered off. The combined cleavage solutions were poured slowly onto a mixture of cold heptane/diethyl ether (1:1) (35 mL), giving a precipitate. The suspension was centrifuged and the supernatant poured off. The residue was washed with cold heptane/diethyl ether (1:1) (10 mL), the suspension was centrifuged and the supernatant was poured off. The solid was dried in high vacuum.

3b) Cleavage Method B

The resin (0.1 mmol) was treated with 95% aq. TFA/EDT (4:1) (0.75 mL) and the suspension was shaken at it for 1 h. A mixture of 95% aq. TFA (2.18 mL) and TIS (75 μL) was added and shaking at rt was resumed for 1 h. The cleavage solution was filtered off then 95% aq. TFA/EDT/TIS (95:2.5:2.5) (3 mL) was added to the resin and the suspension was shaken at rt for 1 h. The cleavage solution was filtered off and collected and fresh solution was added (3 mL). The suspension was shaken at rt for 1 h then the cleavage solution was filtered off. The combined cleavage solutions were poured onto cold heptane/diethyl ether (1:1) (35 mL). The precipitate thus formed was left to settle, centrifuged then the supernatant was carefully poured off. The precipitate was washed once with cold heptane/diethyl ether (1:1) (10 mL), the suspension was centrifuged and the supernatant was poured off. The residue was dried in high vacuum.

3c) Cleavage Method C

HFIP/DCM (30:70) (5 mL) was added to the resin (0.1 mmol) and the suspension was stirred at rt for 1.5 h. The cleavage solution was filtered off and collected and fresh HFIP/DCM (30:70) (5 mL) was added. The suspension was stirred at rt for 30 min. The cleavage solution was filtered off and collected. The resin was washed with DCM (2×5 mL) which was also collected. The combined cleavage and washing solutions were concentrated to dryness in high vacuum. The residue was lyophilized from tBuOH/H$_2$O (1:1).

4) Cyclization Methods

4a) Cyclization Method A (Disulfide Formation)

The fully deprotected linear precursor peptide was dissolved in H$_2$O/DMSO (9:1) or (4:1) to give typically a concentration of 1-15 mg/mL. The reaction mixture was then stirred at rt for typically 40 h depending on the requirements and then concentrated to dryness in high vacuum.

4b) Cyclization Method B (Disulfide Formation)

The fully deprotected linear precursor peptide (1 eq.) was dissolved in H$_2$O to give typically a concentration of 10 mg/mL. A solution of 50 mM I$_2$ in AcOH (1.2 eq.) was added in one portion to the stirred solution and the reaction was stirred for 10 min at rt. 0.5 M Ascorbic acid in H$_2$O (1.5 eq) was added to quench the excess of I$_2$. The solution was concentrated to near dryness in vacuo.

4c) Cyclization Method C (Selective Formation of Two Disulfides)

The partially protected linear precursor peptide (1 eq.) (two cysteines were protected with Acm and two cysteines unprotected) was dissolved in AcOH/H$_2$O (4:1) to give typically a concentration of 1 mg/mL. 50 mM I$_2$ in AcOH (2 eq.) was added and the reaction mixture was stirred at rt for 1 h. Further 50 mM I$_2$ in AcOH (10 eq.) was added portionwise over 4 h. After 21 h, the reaction mixture was concentrated to near dryness in vacuo and 1 M ascorbic acid in H$_2$O was added in excess to quench unreacted I$_2$.

4d) Cyclization Method D (Lactam Formation Between Side Chains)

The fully deprotected linear precursor peptide (1 eq.) and HATU (1.5 eq.) were dissolved in NMP (peptide concentration: typically 1 mmol/L). DIPEA (3 eq.) was added and the solution stirred at rt for 90 min. The reaction mixture was concentrated to dryness in vacuo.

4e) Cyclization Method E (Lactam Formation Between Side Chain and C-terminus)

A solution of the peptide (1 eq.), HATU (1.3 eq.) and HOAt (1.3 eq.) in DMF (peptide concentration: 2.6 mmol/L) was treated with 2,6-lutidine (20 eq.) and the reaction was stirred at rt for 2 h. The reaction mixture was concentrated to dryness in vacuo.

In the following the syntheses of representative examples are described.

Peptide 1 Synthesis of pE-R-P-R-L-K-H-F-G-P-Nle-D-Phenethylamine (lactam K$^6$-D$^{12}$) (SEQ ID NO: 23)

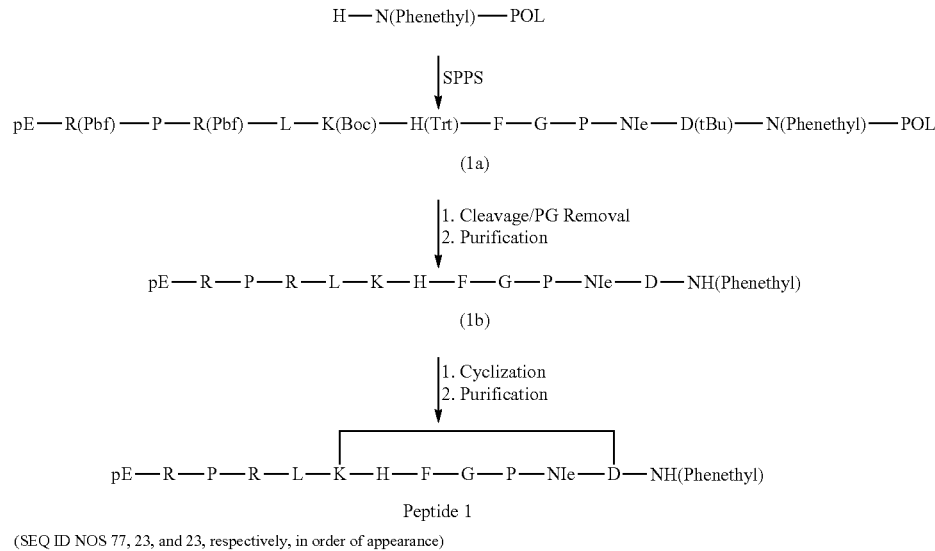

(SEQ ID NOS 77, 23, and 23, respectively, in order of appearance)

Preparation of Intermediate 1a (Assembly of Linear Peptide)

Phenethylamine-BAL-PS resin (167 mg, 0.100 mmol) was subjected to solid phase peptide synthesis on the Prelude™ peptide synthesizer. Coupling was performed as follows:

| Coupling | AA | Number of couplings × Reaction time | Synthesis cycle |
|---|---|---|---|
| 1 | D(tBu) | 2 × 4 h | C |
| 2 | Nle | 1 × 3 h | C |
| 3 | P | 2 × 45 min | C |
| 4 | G | 2 × 90 min | C |
| 5 | F | 1 × 3 h | C |
| 6 | H(Trt) | 2 × 45 min | C |
| 7 | K(Boc) | 2 × 4 h | C |
| 8 | L | 4 × 1 h | C |
| 9 | R(Pbf) | 4 × 1 h | C |
| 10 | P | 2 × 90 min | C |
| 11 | R(Pbf) | 4 × 1 h | C |
| 12 | pE | 2 × 90 min | C |

Preparation of Intermediate 1b (Cleavage from the Resin with Concomitant Protecting Group Removal then Purification)

A mixture of 95% aq. TFA/EDT/TIS (95:2.5:2.5) (2 mL) was added to Intermediate 1a (0.1 mmol) and the suspension was shaken at rt for 2.5 h. The cleavage solution was filtered off, and fresh cleavage solution (2 mL) was added. The suspension was shaken at rt for 45 min then the cleavage solution was filtered off. Fresh solution (2 mL) was added and the suspension was shaken at rt for 45 min. The cleavage solution was filtered off and the resin was washed with 95% aq. TFA (1 mL). The combined cleavage solutions were poured onto a mixture of cold heptane/diethyl ether (1:1) (35 mL), giving a precipitate. The suspension was centrifuged and the supernatant poured off. The residue was washed with cold heptane/diethyl ether (1:1) (20 mL), the suspension was centrifuged and the supernatant was poured off. The solid was dried in high vacuum. The crude was purified by preparative HPLC and lyophilized from ACN/H$_2$O to afford Intermediate 1b as a white solid in two batches of different qualities: Batch A (35.9 mg (98% purity), 0.018 mmol) and batch B (52.9 mg (80% purity), 0.021 mmol).

Preparation of Peptide 1

(Cyclization and Purification)

Both batches from the previous step were treated separately following the same protocol:

Batch A: A solution of the peptide (35.9 mg (98% purity), 0.018 mmol) and HATU (10.0 mg, 0.026 mmol) in NMP (18 mL) and DIPEA (9.2 µL, 0.053 mmol) was stirred at rt for 2 h.

Batch B: A solution of the peptide (52.9 mg (80% purity), 0.021 mmol) and HATU (14.5 mg, 0.038 mmol) in NMP (26 mL) and DIPEA (13.0 µL, 0.076 mmol) was stirred at rt for 2 h.

Each of the batches was concentrated to dryness in vacuo. The product was isolated by preparative HPLC. Pure fractions of both purifications were combined and lyophilized from ACN/H$_2$O to give Peptide 1 as a white solid (52.0 mg, 0.025 mmol).

The pure product was analyzed by analytical HPLC (Analytical method A: t$_R$=4.16 min) and UPLC-MS (Analytical method C; measured: [M+3]$^{3+}$=511.2; calculated: [M+3]$^{3+}$=511.3).

Peptide 5 Synthesis pE-R-P-R-L-K-F-K-G-P-Nle-F (Lactam K$^6$-C-Terminus) (SEQ ID NO: 27)

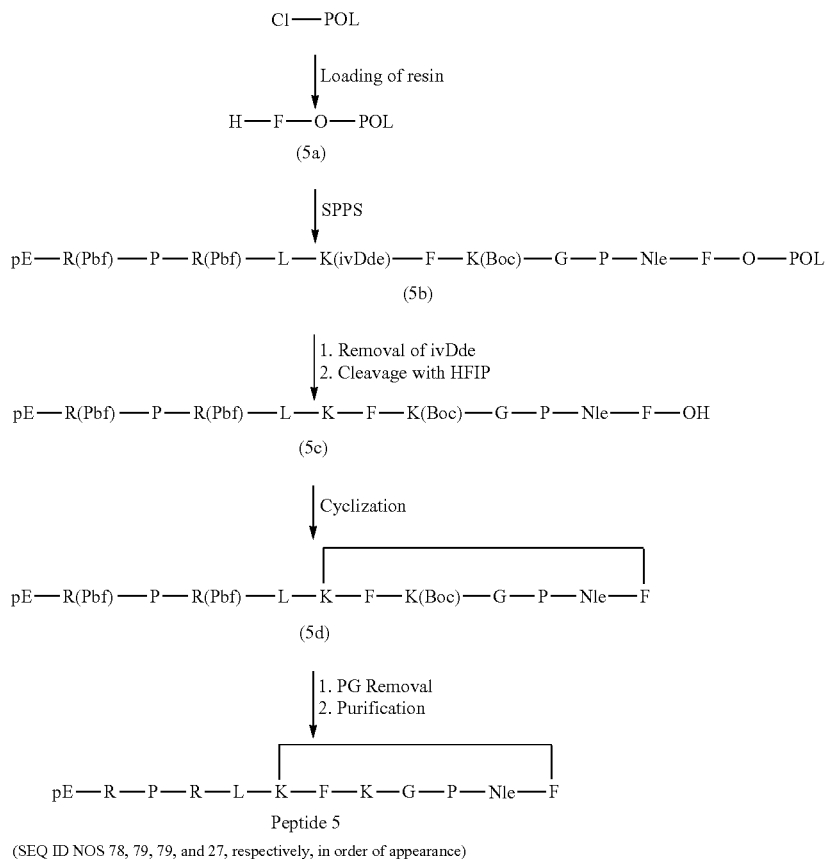

(SEQ ID NOS 78, 79, 79, and 27, respectively, in order of appearance)

Preparation of Intermediate 5a (Loading of 2-chlorotrityl Chloride Resin with Fmoc-F—OH, Fmoc Removal and Determination of the Loading of the Resin)

2-Chlorotrityl chloride resin (10.0 g, 16.0 mmol) was reacted with a solution of Fmoc-F—OH (6.24 g, 32.0 mmol) in DCM (100 mL) and DIPEA (11.2 mL, 64.0 mmol) in analogy to the general procedure described above to give Intermediate 5a (12.8 g, loading=0.79 mmol/g).

Preparation of Intermediate 5b (Assembly of Linear Peptide)

Intermediate 5a (0.100 mmol) was subjected to solid phase peptide synthesis on the Prelude™ peptide synthesizer. Coupling was performed as follows:

| Coupling | AA | Number of couplings × Reaction time | Synthesis cycle |
| --- | --- | --- | --- |
| 2 | Nle | 2 × 90 min | B |
| 3 | P | 2 × 30 min | B |
| 4 | G | 2 × 90 min | B |
| 5 | K(ivDde) | 2 × 30 min | B |
| 6 | F | 2 × 30 min | B |
| 7 | K(Boc) | 4 × 1 h | B |
| 8 | L | 2 × 30 min | B |
| 9 | R(Pbf) | 4 × 1 h | B |
| 10 | P | 2 × 90 min | B |
| 11 | R(Pbf) | 4 × 1 h | B |
| 12 | pE | 2 × 90 min | B |

Preparation of Intermediate 5c (Removal of ivDde and Cleavage from the Resin)

Intermediate 5b (0.100 mmol) was treated six times for 10 min with a solution of hydrazine monohydrate (0.081 mL, 1.67 mmol) in DMA (4 mL). Then the resin was treated three times for 20 min with a solution of hydrazine monohydrate (0.081 mL, 1.67 mmol) in THF (4 mL). The resin was washed with DCM (3×). HFIP/DCM (30:70) (5 mL) was added to the resin (0.100 mmol) and the suspension was stirred at rt for 1.5 h. The cleavage solution was filtered off and fresh HFIP/DCM (30:70) (5 mL) was added. The suspension was stirred at rt for 30 min. The cleavage solution was filtered off. The resin was washed with DCM (2×5 mL). The combined cleavage and washing solutions were concentrated to dryness in vacuo. The residue was lyophilized from tBuOH/H$_2$O (1:1) to give Intermediate 5c (187 mg, 0.090 mmol).

Preparation of Peptide 5

(Cyclization and Removal of Protecting Groups)

A solution of Intermediate 5c (187 mg, 0.090 mmol), HATU (44.6 mg, 0.117 mmol) and HOAt (16.0 mg, 0.117 mmol) in DMF (35 mL) was treated with 2,6-lutidine (0.210 mL, 1.80 mmol) and the reaction was stirred at rt for 2 h. The reaction mixture was concentrated to dryness in vacuo. The residue Intermediate 5d was dissolved in 95% aq. TFA/EDT/TIS (95:2.5:2.5) (5 mL) and the solution was stirred at rt for 2.5 h. The cleavage solution was poured onto cold heptane/diethyl ether (1:1) (30 mL), giving a precipitate. The suspension was centrifuged and the supernatant poured off. The residue was washed with cold heptane/diethyl ether (1:1) (10 mL), the suspension was centrifuged and the supernatant was poured off. The washing step was repeated once. The residue was dried in high vacuum. The product was isolated by preparative HPLC and lyophilized from ACN/H$_2$O to afford Peptide 5 as a white solid (41.4 mg, 0.023 mmol).

The pure product was analyzed by analytical HPLC (Analytical method A: $t_R$=3.70 min) and UPLC-MS (Analytical method C; measured: $[M+3]^{3+}$=484.5; calculated: $[M+3]^{3+}$=484.6).

Peptide 7 Synthesis Q-R-P-R-L-C-F-K-G-P-Nle-C-F-G-G (Lactam N-terminus-C-terminus) (SEQ ID NO: 29)

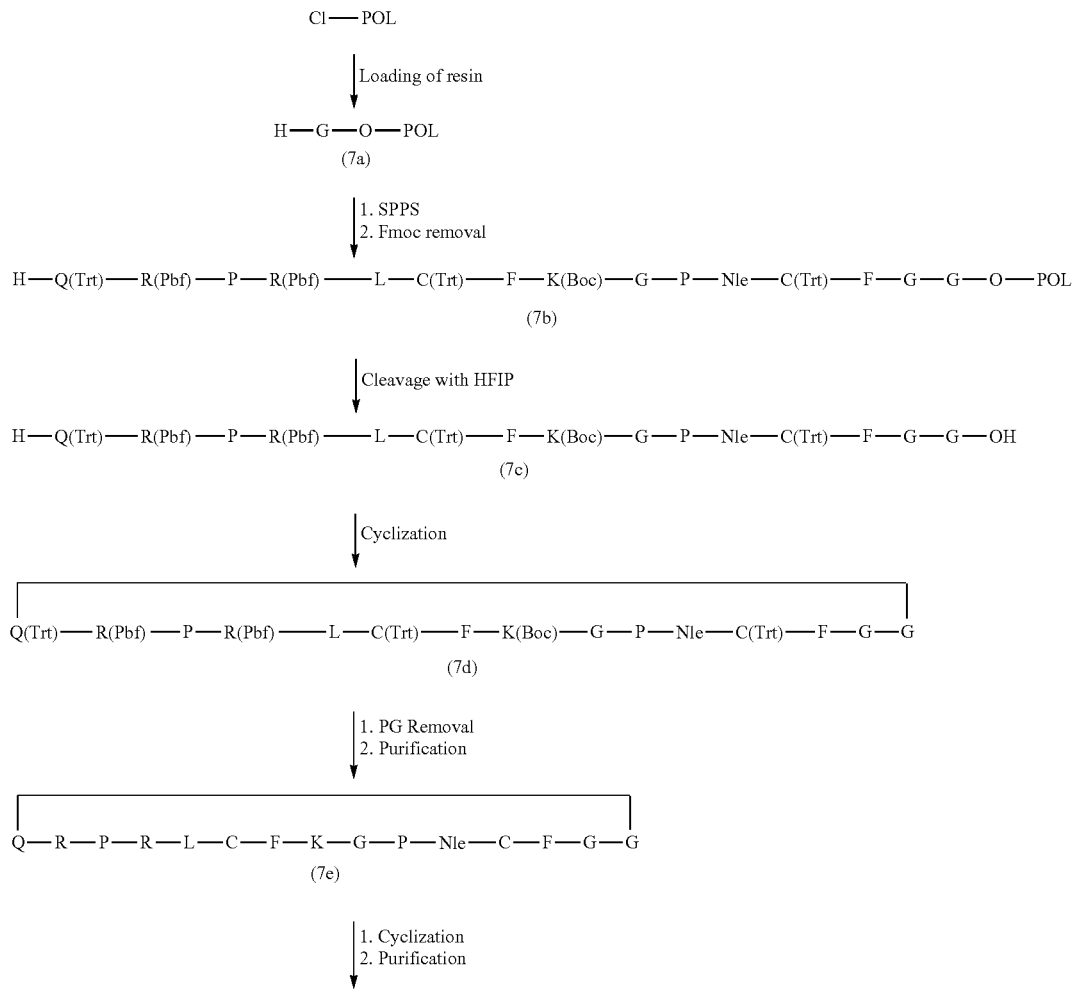

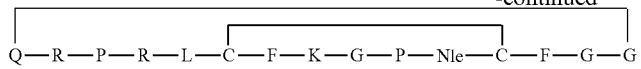

Peptide 7
(SEQ ID NOS 80, 80, 80, 29, and 29, respectively, in order of appearance)

Preparation of Intermediate 7a
(Loading of 2-chlorotrityl Chloride Resin with with Fmoc-Gly-OH, Fmoc Removal and Determination of the Loading of the Resin)
2-Chlorotrityl chloride resin (2.00 g, 3.20 mmol) was reacted with a solution of Fmoc-Gly-OH (0.476 g, 1.60 mmol) in DCM (20 mL) and DIPEA (2.24 mL, 12.8 mmol) in analogy to the general procedure described above to give Intermediate 7a (2.22 g; loading=0.68 mmol/g).
Preparation of Intermediate 7b
(Assembly of Linear Peptide and Fmoc Removal)
Intermediate 7a (147 mg, 0.100 mmol) was subjected to solid phase peptide synthesis on the Prelude™ peptide synthesizer. Coupling was performed as follows:

| Coupling | AA | Number of couplings × Reaction time | Synthesis cycle |
|---|---|---|---|
| 1 | G | 2 × 30 min | B |
| 2 | F | 2 × 30 min | B |
| 3 | C(Trt) | 2 × 30 min | B |
| 4 | Nle | 2 × 90 min | B |
| 5 | P | 2 × 30 min | B |
| 6 | G | 2 × 90 min | B |
| 7 | K(Boc) | 2 × 30 min | B |
| 8 | F | 2 × 30 min | B |
| 9 | C(Trt) | 2 × 30 min | B |
| 10 | L | 2 × 30 min | B |
| 11 | R(Pbf) | 4 × 1 h | B |
| 12 | P | 2 × 90 min | B |
| 13 | R(Pbf) | 4 × 1 h | B |
| 14 | Q(Trt) | 2 × 90 min | B |

After assembly of the peptide Fmoc was removed by repetitive treatment with piperidine/DMA (1:4). The resin was washed with DMA to afford Intermediate 7b (0.100 mmol).
Preparation of Intermediate 7c
(HFIP Cleavage from the Resin)
HFIP/DCM (30:70) (3 mL) was added to Intermediate 7b (0.100 mmol) and the suspension was shaken at rt for 1.5 h. The cleavage solution was filtered off and fresh HFIP/DCM (30:70) (3 mL) was added. The suspension was shaken at rt for 30 min. The cleavage solution was filtered off. The resin was washed with DCM (2×3 mL). The combined cleavage and washing solutions were concentrated to dryness in vacuo. The residue was lyophilized from tBuOH/H$_2$O (1:1) to give Intermediate 7c (203 mg, 0.067 mmol).
Preparation of Intermediate 7d
(Backbone Cyclization)
A solution of Intermediate 7c (203 mg, 0.067 mmol), HATU (33.3 mg, 0.088 mmol) and HOAt (11.9 mg, 0.088 mmol) in DMF (40 mL) was treated with 2,6-lutidine (0.157 ml, 1.35 mmol) and the reaction was stirred at rt for 2 h. The reaction mixture was concentrated to dryness in vacuo to afford Intermediate 7d (0.067 mmol).
Preparation of Intermediate 7e
(Removal of Protecting Groups then Purification)
A mixture of 95% aq. TFA/EDT/TIS (95:2.5:2.5) (3 mL) was added to Intermediate 7d (0.067 mmol) and the suspension was shaken at rt for 2.5 h. The solution was poured onto a mixture of cold heptane/diethyl ether (1:1) (30 mL), giving a precipitate. The suspension was centrifuged and the supernatant poured off. The residue was washed with cold heptane/diethyl ether (1:1) (10 mL), the suspension was centrifuged and the supernatant was poured off. The washing step was repeated once. The solid was dried in high vacuum. The crude was purified by preparative HPLC and lyophilized from ACN/H$_2$O to afford Intermediate 7e as a white solid (33.6 mg, 0.017 mmol).
Preparation of Peptide 7
(Cyclization and Purification)
Intermediate 7e (33.6 mg, 0.017 mmol) was dissolved in H$_2$O/DMSO (9:1) (30 mL). The reaction mixture was stirred at rt for 40 h then concentrated to dryness in vacuo. The crude was purified by preparative HPLC and lyophilized from ACN/H$_2$O to afford Peptide 7 as a white solid (21.0 mg; 0.010 mmol).
The pure product was analyzed by analytical HPLC (Analytical method A: t$_R$=3.85 min) and UPLC-MS (Analytical method C; measured: [M+3]$^{3+}$=553.6; calculated: [M+3]$^{3+}$=553.6).
Peptide 8 Synthesis of pE-R-P-R-L-C-H-K-G-P-Nle-C-F-OH (disulfide C$^6$-C$^{12}$) (SEQ ID NO: 30)

Cl—POL

↓ Loading of resin

H—F—O—POL
(8a)

↓ SPPS

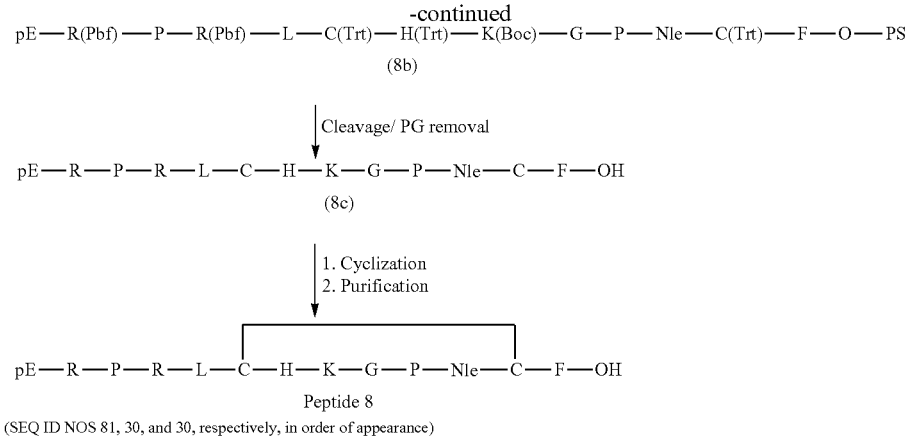

(SEQ ID NOS 81, 30, and 30, respectively, in order of appearance)

Preparation of Intermediate 8a (Loading of 2-chlorotrityl Chloride Resin with Fmoc-F—OH, Fmoc Removal and Determination of the Loading of the Resin)

2-Chlorotrityl chloride resin (40.0 g, 64.0 mmol) was washed with DCM (3×). A solution of Fmoc-F—OH (24.8 g, 64.0 mmol) in DCM (400 mL) and DIPEA (44.7 mL, 256 mmol) was added and the suspension was shaken for 22 h at rt. The resin was washed thoroughly with DCM/MeOH/DIPEA (17:2:1) (3×), DCM (3×), DMA (3×), DCM (3×).

The resin was then treated four times for 10 min with a mixture of piperidine/DMA (1:4) (400 mL) followed by washing with DMA (2×180 ml). The piperidine/DMA solutions and DMA washing solutions were collected for determination of the loading of the resin. 1 mL of the combined solutions was diluted to 500 mL with MeOH and the UV absorption at 299.8 nm was measured to be A=0.368. This corresponds to an Fmoc amount of 46.2 mmol.

The resin was washed thoroughly with DCM (3×), DMA (3×), DCM (3×) and dried in vacuo to give Intermediate 8a (50.7 g; loading=0.91 mmol/g).

Preparation of Intermediate 8b (Assembly of Linear Peptide)

Intermediate 8a (2.64 g, 2.40 mmol) was subjected to solid phase peptide synthesis on the Prelude™ peptide synthesizer. Coupling was performed as follows:

| Coupling | AA | Number of couplings × Reaction time | Synthesis cycle |
|---|---|---|---|
| 1 | C(Trt) | 2 × 30 min | D |
| 2 | Nle | 2 × 15 min | A |
| 3 | P | 2 × 15 min | A |
| 4 | G | 2 × 30 min | A |
| 5 | K(Boc) | 2 × 15 min | A |
| 6 | H(Trt) | 2 × 15 min | A |
| 7 | C(Trt) | 2 × 60 min | D |
| 8 | L | 2 × 15 min | A |
| 9 | R(Pbf) | 4 × 1 h | A |
| 10 | P | 2 × 15 min | A |
| 11 | R(Pbf) | 4 × 1 h | A |
| 12 | pE | 2 × 15 min | A |

Preparation of Intermediate 8c (Cleavage from the Resin with Concomitant Protecting Group Removal)

Intermediate 8b (2.40 mmol) was carefully washed with DCM (4×). A mixture of 95% aq. TFA/EDT/TIS (95:2.5:2.5) (50 mL) was added and the suspension was shaken at rt for 1 h. The cleavage solution was filtered off, and fresh cleavage solution (35 mL) was added. The suspension was shaken at rt for 1 h then the cleavage solution was filtered off. Fresh solution (35 mL) was added and the suspension was shaken at rt for 1 h. The cleavage solution was filtered off. The combined cleavage solutions were poured slowly onto a stirred mixture of cold heptane/diethyl ether (1:1) (500 mL), giving a precipitate. The suspension was stirred at rt for 2 h and then the precipitate was allowed to settle down. The supernatant was sucked off with a frit. The residue was washed with cold heptane/diethyl ether (1:1) (2×100 mL), the supernatant was sucked off with a frit. The solid was dried in high vacuum to afford Intermediate 8c as an off-white solid (3.75 g, 1.88 mmol).

Preparation of Peptide 8

(Cyclization and Purification)

Intermediate 8c (3.75 g, 1.88 mmol) was dissolved in $H_2O$ (375 mL). A solution of 50 mM $I_2$ in AcOH (45.1 mL, 2.26 mmol) was added in one portion to the stirred solution and the solution was stirred for 10 min at rt. 0.5 M Ascorbic acid in $H_2O$ (5.64 mL, 2.82 mmol) was added to quench the excess of $I_2$. The solution was concentrated to near dryness. The reaction was performed in two portions: 0.188 mmol scale and 1.69 mmol scale. The crudes were combined for purification. The crude was purified by preparative HPLC and lyophilized from ACN/$H_2O$ to afford Peptide 8 as a white solid (1.53 g, 0.767 mmol).

The pure product was analyzed by analytical HPLC (Analytical method A: $t_R$=3.43 min) and UPLC-MS (Analytical method C; measured: $[M+3]^{3+}$=512.4; calculated: $[M+3]^{3+}$=512.6).

Alternatively, the crude Peptide 8 was dissolved in water (500 mL of water/mmol of polypeptide) and was converted into the acetate salt with the aid of an ion exchange resin (i.e. Amberlite IRA-67 (Acetate-Form)(200 g/mmol of polypeptide) and purified by preparative HPLC (C8 modified reversed phase silica gel from Daisogel, gradient: ACN/$H_2O$: 3% ACN and 97% [mixture 0.3% Acetic acid/water] up to 12% ACN and 88% [mixture 0.3% Acetic acid/water]) and lyophilized to afford an acetate salt of Peptide 8 as a white solid (60-100% yield).

The salt stoichiometry was evaluated based on the analysis of the acetic acid content (ion chromatography) and water content and was determined to range between 1:3 and 1:4 (polypeptide:acetate).

Peptide 9 Synthesis of pE-R-P-R-L-C-Aib-K-G-P-Nle-C-F-OH (Disulfide $C^6$-$C^{12}$) (SEQ ID NO: 31)

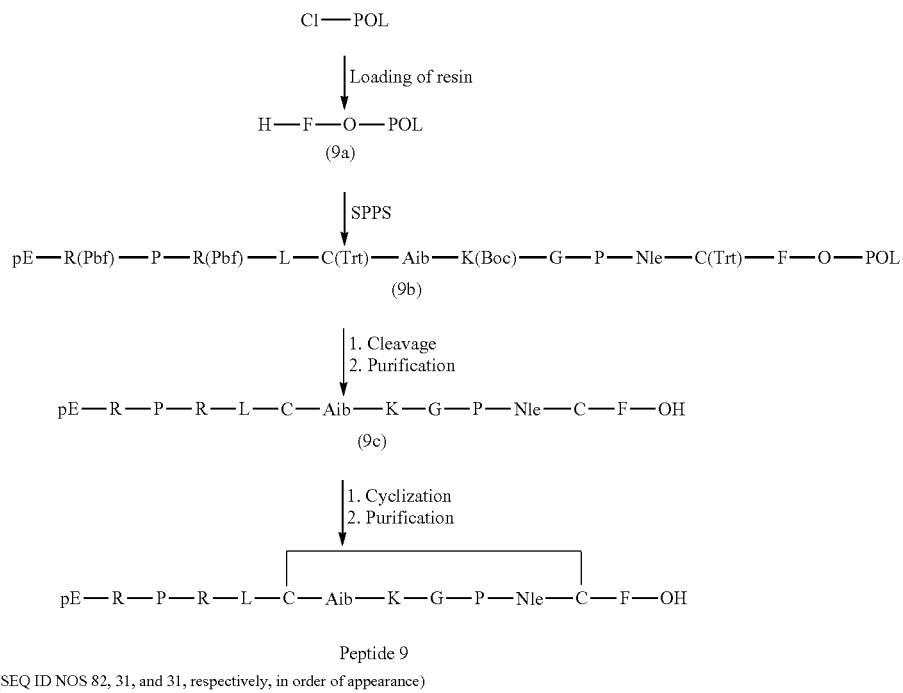

Peptide 9
(SEQ ID NOS 82, 31, and 31, respectively, in order of appearance)

Preparation of Intermediate 9a (Loading of 2-chlorotrityl Chloride Resin with Fmoc-F—OH, Fmoc Removal and Determination of the Loading of the Resin)

2-Chlorotrityl chloride resin (10.0 g, 16.0 mmol) was reacted with a solution of Fmoc-F—OH (6.20 g, 16.0 mmol) in DCM (100 mL) and DIPEA (11.2 mL, 64.0 mmol) in analogy to the general procedure described above to give Intermediate 9a (11.6 g, loading=0.87 mmol/g).

Preparation of Intermediate 9b (Assembly of Linear Peptide)

Intermediate 9a (345 mg, 0.300 mmol) was subjected to solid phase peptide synthesis on the Prelude™ peptide synthesizer. Coupling was performed as follows:

| Coupling | AA | Number of couplings × Reaction time | Synthesis cycle |
|---|---|---|---|
| 1 | C(Trt) | 2 × 15 min | B |
| 2 | Nle | 2 × 15 min | B |
| 3 | P | 2 × 15 min | B |
| 4 | G | 2 × 30 min | B |
| 5 | K(Boc) | 2 × 15 min | B |
| 6 | Aib | 2 × 15 min | B |
| 7 | C(Trt) | 2 × 15 min | B |
| 8 | L | 2 × 15 min | B |
| 9 | R(Pbf) | 4 × 1 h | B |
| 10 | P | 2 × 15 min | B |
| 11 | R(Pbf) | 4 × 1 h | B |
| 12 | pE | 2 × 15 min | B |

Preparation of Intermediate 9c (Cleavage from the Resin with Concomitant Protecting Group Removal then Purification)

A mixture of 95% aq. TFA/EDT/TIS (95:2.5:2.5) (9 mL) was added to Intermediate 9b (0.300 mmol) and the suspension was shaken at rt for 2 h. The cleavage solution was filtered off, and fresh cleavage solution (4 mL) was added. The suspension was shaken at rt for 1 h then the cleavage solution was filtered off. Fresh solution (4 mL) was added and the suspension was shaken at rt for 1 h. The cleavage solution was filtered off. The combined cleavage solutions were poured onto a mixture of cold heptane/diethyl ether (1:1) (100 mL), giving a precipitate. The suspension was centrifuged and the supernatant poured off. The residue was washed with cold heptane/diethyl ether (1:1) (40 mL), the suspension was centrifuged and the supernatant was poured off. The solid was dried in high vacuum.

The crude was purified by preparative HPLC and lyophilized from ACN/H$_2$O to afford Intermediate 9c as a white solid (188 mg, 0.103 mmol).

Preparation of Peptide 9

(Cyclization and Purification)

Intermediate 9c (188 mg, 0.103 mmol) was dissolved in H$_2$O/DMSO (9:1) (180 mL). The reaction mixture was stirred at rt for 40 h then concentrated to dryness in vacuo. The crude was purified by preparative HPLC and lyophilized from ACN/H$_2$O to afford Peptide 9 as a white solid (97 mg; 0.053 mmol).

The pure product was analyzed by analytical HPLC (Analytical method A: $t_R$=3.77 min) and UPLC-MS (Analytical method C; measured: $[M+3]^{3+}$=495.2; calculated: $[M+3]^{3+}$=495.3).

Peptide 22 Synthesis pE-R-P-C-L-C-C-K-G-P-Nle-C-F-OH (disulfides $C^4$-$C^7$ and $C^6$-$C^{12}$) (SEQ ID NO: 44)

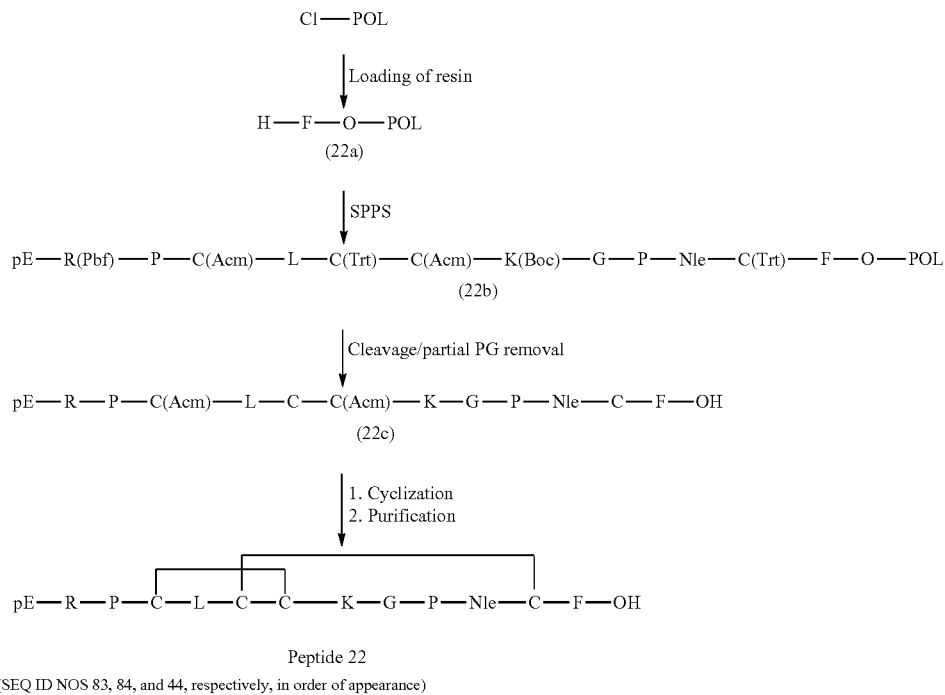

Peptide 22
(SEQ ID NOS 83, 84, and 44, respectively, in order of appearance)

Preparation of Intermediate 22a (Loading of 2-chlorotrityl Chloride Resin with Fmoc-F—OH, Fmoc Removal and Determination of the Loading of the Resin)

2-Chlorotrityl chloride resin (10.0 g, 16.0 mmol) was reacted with a solution of Fmoc-F—OH (6.20 g, 16.0 mmol) in DCM (100 mL) and DIPEA (11.2 mL, 64.0 mmol) in analogy to the general procedure described above to give Intermediate 22a (11.6 g, loading=0.87 mmol/g).

Preparation of Intermediate 22b (Assembly of Linear Peptide)

Intermediate 22a (115 mg, 0.100 mmol) was subjected to solid phase peptide synthesis on the Prelude™ peptide synthesizer. Coupling was performed as follows:

| Coupling | AA | Number of couplings × Reaction time | Synthesis cycle |
|---|---|---|---|
| 1 | C(Trt) | 2 × 15 min | B |
| 2 | Nle | 2 × 15 min | B |
| 3 | P | 2 × 15 min | B |
| 4 | G | 2 × 90 min | B |
| 5 | K(Boc) | 2 × 15 min | B |
| 6 | C(Acm) | 2 × 15 min | B |
| 7 | C(Trt) | 2 × 15 min | B |
| 8 | L | 2 × 15 min | B |
| 9 | C(Acm) | 2 × 15 min | B |
| 10 | P | 2 × 15 min | B |
| 11 | R(Pbf) | 4 × 1 h | B |
| 12 | pE | 2 × 15 min | B |

Preparation of Intermediate 22c (Cleavage from the Resin with Concomitant Partial Protecting Group Removal)

Intermediate 22b (0.100 mmol)) was carefully washed with DCM (4×). A mixture of 95% aq. TFA/EDT (4:1) (0.750 mL) was added and the suspension was shaken at rt for 1 h. A mixture of TFA/H$_2$O (95:5) (2.18 mL) and TIS (75 μL) was added to the suspension and shaking at rt was continued for 1 h. The cleavage solution was filtered off and a mixture of 95% aq. TFA/EDT/TIS (95:2.5:2.5) (3 mL) was added to the resin. The suspension was shaken at rt for 1 h the cleavage solution was filtered off. Fresh solution was added (3 mL) and the suspension was shaken at rt for 1 h. The cleavage solution was filtered off. The combined cleavage solutions were poured onto cold heptane/diethyl ether (1:1) (35 mL), giving a precipitate. The suspension was centrifuged and the supernatant poured off. The residue was washed with cold heptane/diethyl ether (1:1) (10 mL), the suspension was centrifuged and the supernatant was poured off. The washing step was repeated once. The residue was dried in high vacuum. The crude product was purified by preparative HPLC and lyophilized from ACN/H$_2$O to afford Intermediate 22c as a white solid (51.1 mg, 0.028 mmol).

Preparation of Peptide 22

(One-pot Formation of Two Disulfides)

Intermediate 22c (51.1 mg, 0.028 mmol) was dissolved in AcOH (48 mL) and H$_2$O (12 mL). A 50 mM solution of I$_2$ in AcOH (1.12 mL, 56 μmol) was added and the yellow solution was stirred at rt. Further 50 mM I$_2$ in AcOH (5.61 mL, 0.281 mmol) was added portion wise over 4 h. After 21 h, the reaction mixture was concentrated to 2 mL in vacuo and 1 M ascorbic acid in H$_2$O (6 mL) was added to quench the excess of I$_2$. The product was isolated by preparative HPLC and lyophilized from ACN/H$_2$O to afford Peptide 22 as a white solid (19.3 mg, 0.012 mmol).

The pure product was analyzed by analytical HPLC (Analytical method A: $t_R$=4.16 min) and UPLC-MS (Analytical method C; measured: $[M+2]^{2+}$=723.7; calculated: $[M+2]^{2+}$=723.8).

Peptide 52 Synthesis of pE-R-P-R-L-C-H-K-G-P-Nle-C-F-NH2 (disulfide $C^6$-$C^{12}$) (SEQ ID NO: 74)

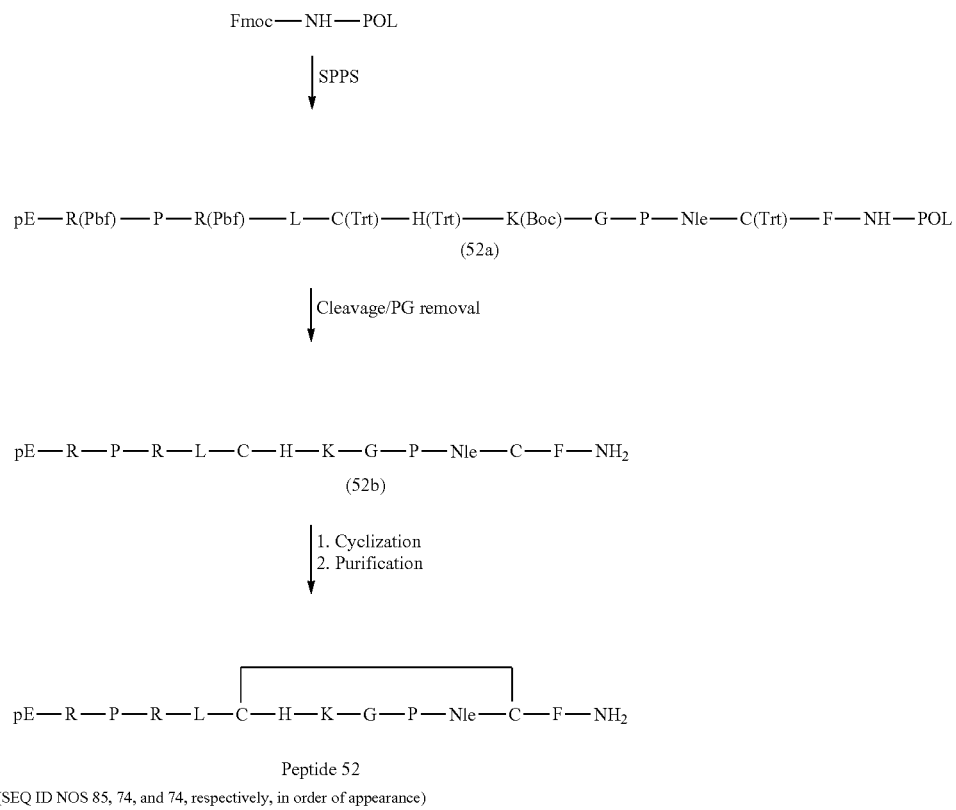

Peptide 52
(SEQ ID NOS 85, 74, and 74, respectively, in order of appearance)

Preparation of Intermediate 52a
(Assembly of Linear Peptide)

Fmoc protected Rink-Amide-AM-PS-resin (217 mg, 0.100 mmol) was subjected to solid phase peptide synthesis on the Prelude™ peptide synthesizer. Coupling was performed as follows:

| Coupling | AA | Number of couplings × Reaction time | Synthesis cycle |
|---|---|---|---|
| 1 | F | 2 × 15 min | A |
| 2 | C(Trt) | 2 × 30 min | D |
| 3 | Nle | 2 × 15 min | A |
| 4 | P | 2 × 15 min | A |
| 5 | G | 2 × 30 min | A |
| 6 | K(Boc) | 2 × 15 min | A |
| 7 | H(Trt) | 2 × 15 min | A |
| 8 | C(Trt) | 2 × 1 h | D |
| 9 | L | 2 × 15 min | A |
| 10 | R(Pbf) | 4 × 1 h | A |
| 11 | P | 2 × 15 min | A |
| 12 | R(Pbf) | 4 × 1 h | A |
| 13 | pE | 2 × 15 min | A |

Preparation of Intermediate 52b
(Cleavage from the Resin with Concomitant Protecting Group Removal)

A mixture of 95% aq. TFA/EDT/TIS (95:2.5:2.5) (3 mL) was added to Intermediate 52a (0.1 mmol) and the suspension was shaken at rt for 1.5 h. The cleavage solution was filtered off, and fresh cleavage solution (2 mL) was added. The suspension was shaken at rt for 45 min then the cleavage solution was filtered off. Fresh solution (2 mL) was added and the suspension was shaken at rt for 45 min. The combined cleavage solutions were poured onto a mixture of cold heptane/diethyl ether (1:1) (35 mL), giving a precipitate. The suspension was centrifuged and the supernatant poured off. The residue was washed with cold heptane/diethyl ether (1:1) (10 mL), the suspension was centrifuged and the supernatant was poured off. The solid was dried in high vacuum. The crude product Intermediate 52b was used in the next step without purification.

Preparation of Peptide 52
(Cyclization and Purification)

Intermediate 52b (0.100 mmol) was dissolved in $H_2O$ (20 mL). A solution of 50 mM $I_2$ in AcOH (2.4 mL, 0.120 mmol) was added in one portion to the stirred solution and the solution was stirred for 30 min at rt. 0.5 M Ascorbic acid in $H_2O$ (0.30 mL, 0.300 mmol) was added to quench the excess of $I_2$. The solution was concentrated to near dryness. The crude was purified by preparative HPLC and lyophilized from ACN/$H_2O$ to afford Peptide 52 as a white solid (50.5 mg, 0.025 mmol).

The pure product was analyzed by analytical HPLC (Analytical method A: $t_R$=3.22 min) and UPLC-MS (Analytical method C; measured: $[M+3]^{3+}$=512.3; calculated: $[M+3]^{3+}$=512.3).

The other peptides were synthesized in analogy:
Peptides 2 to 4 were synthesized in analogy to Peptide 1.
Peptide 6 was synthesized in analogy to Peptide 5.
Peptides 10 to 21 were synthesized in analogy to Peptide 9.
Peptide 23 was synthesized in analogy to Peptide 22.
Peptides 24 to 51 were synthesized in analogy to Peptide 8.
Peptide 53 was synthesized in analogy to Peptide 52.
Peptide 54: pE-R-P-R-L-C-H-K-G-P-Nle-C-F-OH (SEQ ID NO: 76)with a monosulfide linkage between the 2 Cysteines at position 6 and 12 $[C^6-C^{12}]$

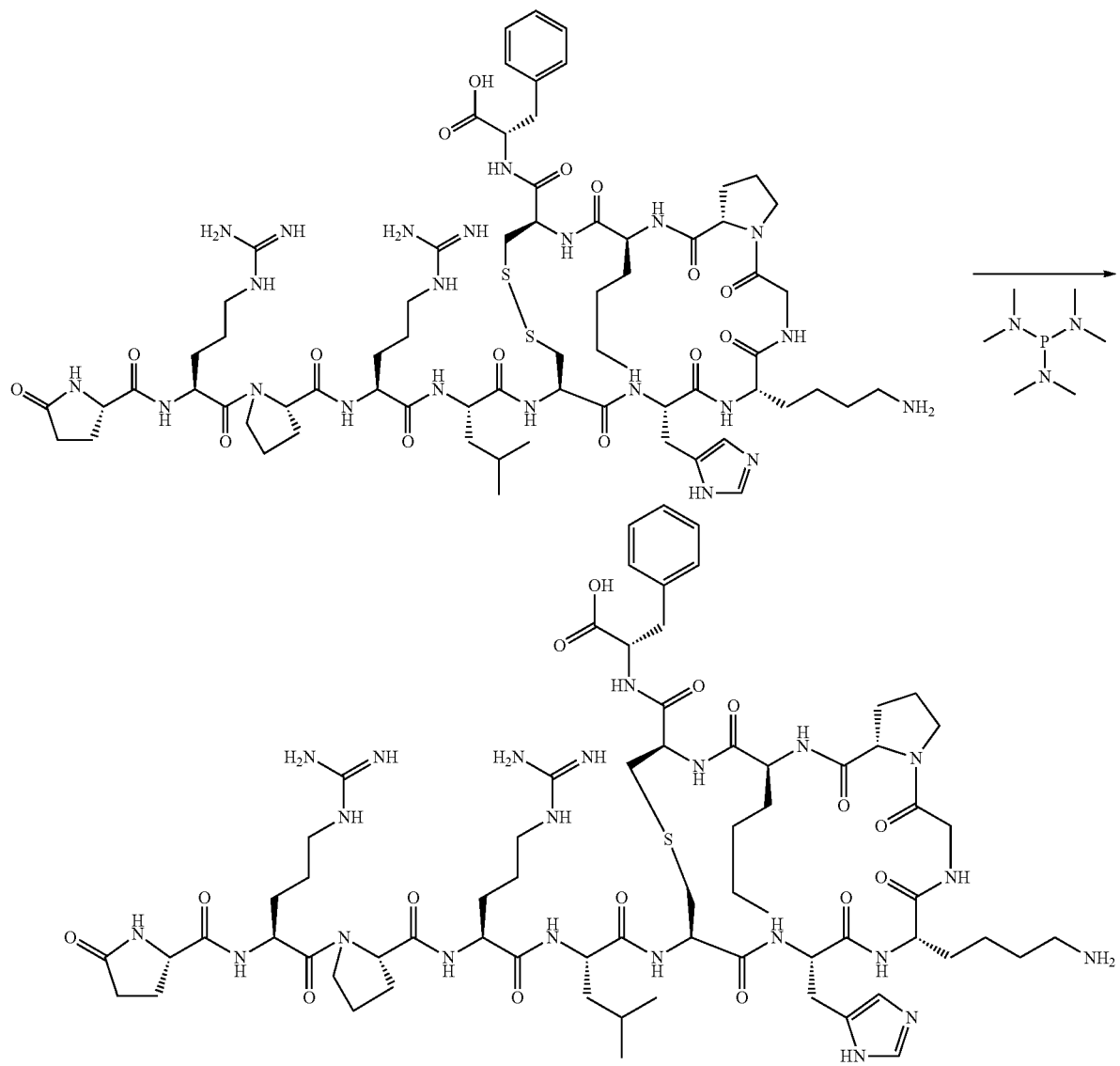

The mixture of Peptide 8 (S)-2-((3S,6R,11R,14S,17S,25aS)-14-((1H-imidazol-5-yl)methyl)-17-(4-aminobutyl)-3-butyl-11-((S)-2-((S)-5-guanidino-2-((S)-1(S)-5-guanidino-2-((S)-5-oxopyrrolidine-2-carboxamido)pentanoyl)pyrrolidine-2-carboxamido)pentanamido)-4-methylpentanamido)-1,4,12,15,18,21-hexaoxodocosahydro-1H-pyrrolo[2,1-j][1,2,5,8,11,14,17,20]dithiahexaazacyclotricosine-6-carboxamido)-3-phenylpropanoic acid TFA salts (30 mg, 0.015 mmol) and N,N,N',N',N'',N''-hexamethylphosphinetriamine (12.3 mg, 0.075 mmol) in PBS pH 9.2 buffer (1 mL) was stirred at RT for 3 days. The reaction mixture was purified by preparative HPLC (Sunfire C18, 0.1% TFA in water/MeCN) twice, and the product fraction was lyophilized to give Peptide 54 as a white powder (4 mg, 13.4%). [M+2H]2+ (calc.)=752.88, [M+2H]2+ (measured)=752.40, [M+3H]3+ (calc.)=502.26, [M+3H]3+ (measured)=501.94. HPLC (analytical method B), $t_R$=6.93 min.

The Peptides 1 to 54 can be purified and isolated as described supra and/or by a combination of conventional purification techniques such as solvent extraction, column chromatography, liquid chromatography and recrystallization. Where the polypeptide isolated in the above Examples is a free compound, it can be converted to a suitable salt by the known method. Therefore, Peptides 1 to 54 can be converted into their corresponding salt (e.g. hydrochloride, hydrobromide, sulfate, phosphate, citrate, acetate, lactate or another pharmaceutical salt for suitable for injection) with a polypeptide:salt ratio ranging from 1:1 to 1:4. For example, Peptides 1 to 54 can be dissolved in water and converted into a salt using ion-exchange resins. Conversely where the isolated peptide is a salt, it can be converted to the free peptide by known method or directly to a different salt with the aid of ion-exchange resins.

Peptide-linker Construct 1 and 2 were synthesized as follow:

The Peptide-Linker products were analyzed by analytical HPLC using UV detection at λ=214 nm (Column: XBridge BEH300 C18 (100×4.6 mm), 3 µm; Part n°: 186003612) Mobile phases consisted of eluent A (0.1% TFA in $H_2O$), eluent B (0.4% TFA in ACN). Additional characterization of the products was done by UPLC-MS (Column: Waters Acquity UPLC® BEH C18, 1.7 µm, 2.1×50 mm; Part n°:

186002350) equipped with a diode array detector and using electrospray ionization. Mobile phases consisted of Eluent A: 0.05% FA +3.75 mM ammonium acetate in water; Eluent B: 0.04% FA in ACN.

The peptides were synthesized by standard solid phase Fmoc chemistry. The peptides were assembled on Liberty microwave peptide synthesizer (CEM Corporation, North Carolina, USA). Peptides with a free carboxylic acid on the C-terminus were synthesized from 2-chlorotrityl chloride-PS-resin (AnaSpec, Inc., California, USA).

The peptides were purified by preparative reversed-phase HPLC. The following columns were used: Waters SunFire Prep C18 OBD Column, 5 µm, 30×50 mm, Part No. 186002570.

Mobile phases consisted of eluent A (0.1% TFA in $H_2O$) and eluent B (ACN). Gradients were designed based on the specific requirements of the separation problem. Pure products were lyophilized from $ACN/H_2O$.

The products were analyzed by analytical HPLC using UV detection at λ=214 nm (Column: XBridge BEH300 C18 (100×4.6 mm), 3 µm; Part n°: 186003612) Mobile phases consisted of eluent A (0.1% TFA in $H_2O$), eluent B (0.1% TFA in ACN). Additional characterization of the products was done by UPLC-MS (Column: Waters Acquity UPLC® BEH C18, 1.7 µm, 2.1×50 mm; Part n°: 186002350) equipped with a diode array detector and using electrospray ionization. Mobile phases consisted of Eluent A: 0.05% FA+3.75 mM ammonium acetate in water; Eluent B: 0.04% FA in ACN.

The peptides-linker constructs that are exemplified below were synthesized using the general procedures described below. Unsubstituted N- or C-termini are indicated by small italic H— or —OH, respectively.

Analytical Methods for Peptide-linker Construct 1 and 2
1) UPLC-MS—Analytical Method D
  Waters Acquity UPLC® BEH C18, 1.7 µm, 2.1×50 mm; Part n°: 186002350
  Eluent A: 0.05% FA+3.75 mM ammonium acetate in water; Eluent B: 0.04% FA in ACN
  Flow: 1.0 ml/min
  Temperature: 50° C.
  Gradient: 2 to 44% in 1.7 min
2) UPLC-HRMS—Analytic Method E
  Waters Acquity UPLC® BEH C18, 1.7 µm, 2.1×50 mm; Part n°: 186002350
  Eluent A: 0.1% FA; Eluent B: 0.1% FA in ACN
  Flow: 1.0 ml/min
  Temperature: 50° C.
  Gradient: 2 to 98% in 4.4 min
3) UPLC-MS—Analytic Method F
  Waters Acquity UPLC® BEH300 SEC guard column, 4.6×30 mm; Part n°: 186005793
  Eluent A: 0.1% FA in water; Eluent B: 0.04% FA in ACN
  Flow: 1.0 ml/min
  Gradient: 50% B for 6 min
4) UPLC-MS—Analytic Method G
  Waters Acqufty UPLC® ProSwift RP-3, 1.7 µm, 4.6×50 mm; Part n°: 064298
  Eluent A: 0.1% FA in water; Eluent B: 0.08% FA in ACN
  Flow: 2.0 ml/min (3 to 80% B in 2 min)-flow 1.8 ml/min
  Temperature: 40° C.
  Gradient: 2 to 98% in 3 min General Procedure for Peptide-Linker Construct 1 and 2
1) Loading of First Amino Acid onto 2-chlorotrityl Chloride Resin and Fmoc-removal 2-Chlorotrityl chloride resin (1 eq., 1.0-1.6 mmol/g) was washed thoroughly with DCM. The desired amino acid (typically 0.5-2 eq. relative to the resin, considering 1.6 mmol/g loading) was dissolved in DCM (approx. 10 mL per gram of resin) and DIPEA (4 eq. relative to the resin, considering 1.6 mmol/g loading). The solution was added to the resin and the suspension was shaken at rt for 19 h. The resin was drained and then thoroughly washed sequentially with DCM/MeOH/DIPEA (17:2:1), DCM, DMA, DCM.

For Fmoc removal and determination of the loading the resin was shaken repeatedly with piperidine/DMA (1:4) or 4-methylpiperidine/DMA (1:4) (12×10 mL per gram of initial resin) and washed with DMA (2×10 mL per gram of initial resin). The combined solutions were diluted with MeOH to a volume V of 250 mL per gram of initial resin. A 2 mL aliquot (Va) of this solution was diluted further to 250 mL (Vt) with MeOH. The UV absorption was measured at 299.8 nm against a reference of MeOH, giving absorption A. The resin was thoroughly washed sequentially with DMA, DCM, DMA, DCM and dried in high vacuum at 40° C., affording mg of resin.

The loading of the resin is calculated according to the formula:

$$\text{Loading [mol/g]} = (A \times V_t \times V)/(d \times \epsilon \times V_a \times m)$$

(with d: width of cuvette; $\epsilon$=7800 L mol$^{-1}$ cm$^{-1}$)

2) Solid Phase Peptide Synthesis on Liberty™ Synthesizer

Synthesis Cycle

The resin was washed with DMF and DCM. Fmoc was removed by treatment with 20% piperidine or 20% 4-Me-piperidine/DMF (typically 7 ml per 0.1 mmol twice). The resin was washed with DMF and. Coupling was done by addition of the Fmoc-amino acid (5 eq.; 0.2 M solution in DMF), HCTU (5 eq.; 0.5 M solution in DMF), and DIPEA (10 eq.; 2 M solution in NMP) followed by mixing of the suspension with nitrogen at 75 or 50° C. for typically 5 to 50 min with microwave power 0 to 20 watts depending on the specific requirements. After washing with DMF the coupling step might be repeated once depending on the specific requirements. The resin was washed with DMF and DCM.

3) Cleavage from Resin with or without Concomitant Removal of Protecting Groups

The resin (0.1 mmol) was shaken at rt for 3 h with 95% aq. TFA//TIS/DTT (95:2.5:2.5) (3 mL). The cleavage solution was filtered off. The resin was rinsed once with 95% aq. TFA (1 mL). The combined cleavage and washing solutions were poured slowly onto a mixture of cold heptane/diethyl ether (1:1) (10-15 mL), giving a precipitate. The suspension was centrifuged and the supernatant poured off. Diethyl ether (10 mL) were added to the residue, the suspension was vortexed for 3 min and centrifuged, and the supernatant was poured off, The wash process was repeated twice. The solid was dried in high vacuum.

4) Disulfide Formation

Cyclization Method:

The fully deprotected linear precursor peptide (1 eq.) was dissolved in $H_2O$ to give typically a concentration of about 10-25 mM. A solution of 50 mM $I_2$ in AcOH (1-2 eq.) was added in one portion to the stirred solution and the reaction was stirred at rt until complete conversion is achieved. 0.5 M Ascorbic acid in $H_2O$ was added to quench the excess of $I_2$.

Peptide-Linker Construct 1: MPA-O2Oc-O2Oc-O2Oc-O2Oc-Q-R-P-R-L-C*-H-F-G-P-Nle-C*-f-OH (SEQ ID NO: 86) wherein MPA is 3-maleimidopropionic acid

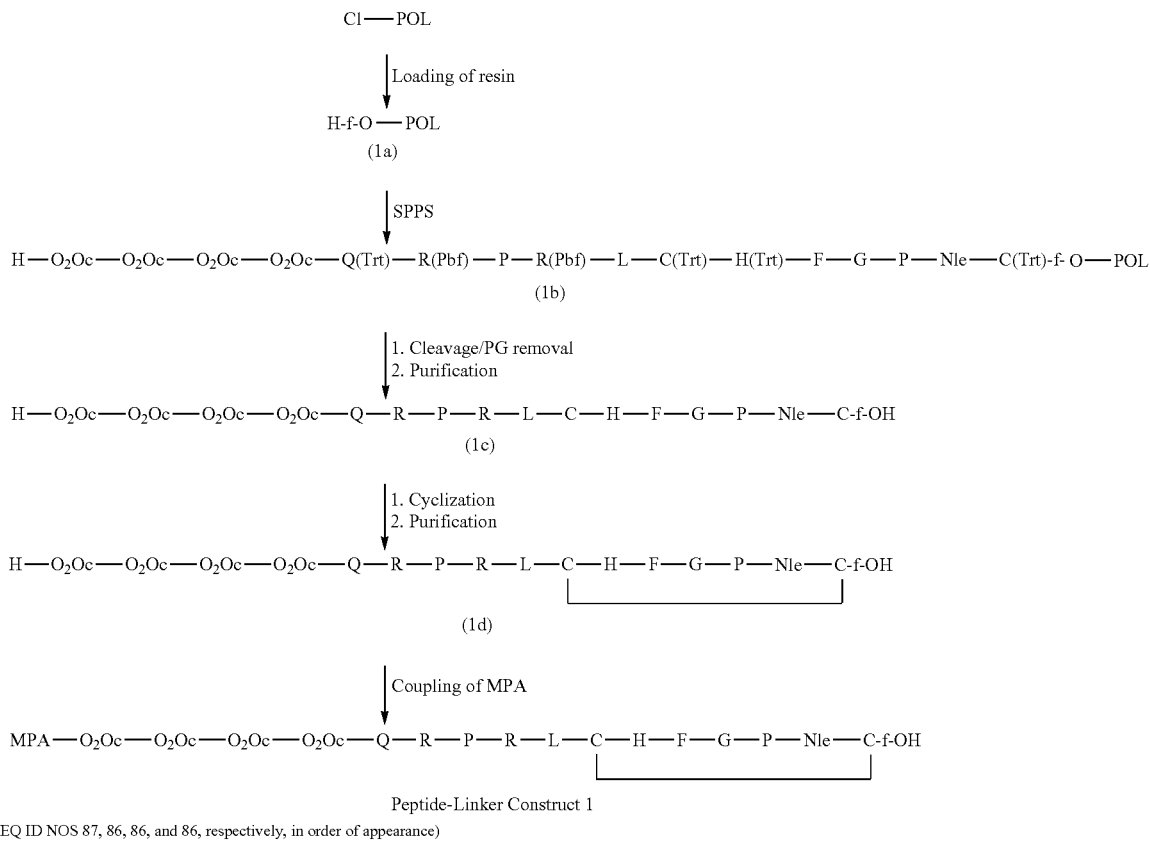

Peptide-Linker Construct 1
(SEQ ID NOS 87, 86, 86, and 86, respectively, in order of appearance)

Preparation of Intermediate 1a (Loading of 2-chlorotrityl Chloride Resin with Fmoc-f-OH, Fmoc Removal and Determination of the Loading of the Resin)

2-Chlorotrityl chloride resin (5.0 g, 8.01 mmol) was reacted with a solution of Fmoc-f-OH (3.10 g, 8.01 mmol) in DCM (50 mL) and DIPEA (5.59 mL, 32.0 mmol) in analogy to the general procedure described above to give Intermediate 1a (5.87 g, loading=0.897 mmol/g).

Preparation of Intermediate 1b (Assembly of Linear Peptide)
Intermediate 1a (0.250 mmol) was subjected to solid phase peptide synthesis on the Liberty™ microwave peptide synthesizer. Coupling was performed as follows:

| Coupling | AA | Number of couplings × Reaction time | Temperature °C. | Microwave power |
|---|---|---|---|---|
| 1 | C(Trt) | 1 × 2 min | 50 | 0 |
|   |        | 1 × 4 min | 50 | 25 |
| 2 | Nle | 1 × 7.5 min | 50 | 20 |
| 3 | P | 1 × 7.5 min | 50 | 20 |
| 4 | G | 1 × 7.5 min | 50 | 20 |
| 5 | F | 1 × 7.5 min | 50 | 20 |
| 6 | H(Trt) | 1 × 2 min | 50 | 0 |
|   |        | 1 × 4 min | 50 | 25 |
| 7 | C(Trt) | 1 × 2 min | 50 | 0 |
|   |        | 1 × 4 min | 50 | 25 |
| 8 | L | 1 × 7.5 min | 50 | 25 |
| 9 | R(Pbf) | 2 × 42 min | 50 | 0 |
| 10 | P | 2 × 7.5 min | 50 | 25 |
|    |   | 1 × 7.5 min | 50 | 25 |

-continued

| Coupling | AA | Number of couplings × Reaction time | Temperature °C. | Microwave power |
|---|---|---|---|---|
| 11 | R(Pbf) | 2 × 42 min | 50 | 0 |
|    |        | 2 × 7.5 min | 50 | 25 |
| 12 | Q(Trt) | 1 × 7.5 min | 50 | 25 |
| 13 | O2Oc | 1 × 7.5 min | 50 | 25 |
| 14 | O2Oc | 1 × 7.5 min | 50 | 25 |
| 15 | O2Oc | 1 × 7.5 min | 50 | 25 |
| 16 | O2Oc | 1 × 7.5 min | 50 | 25 |

Preparation of Intermediate 1c (Cleavage from the Resin with Concomitant Protecting Group Removal then Purification)

A solution made of 1.54 g of DTT and 0.75 mL of thioanisole in 6 mL of TFA/TIPS/Water (95:2.5:2.5) was added to Intermediate 1b (0.25 mmol) and the suspension was shaken at rt for 5 hr. The cleavage solution was filtered off and the resin was washed with 95% aq. TFA (1 mL). The combined cleavage and washing solutions were poured onto cold diethyl ether (40 mL), giving a precipitate. The suspension was centrifuged and the supernatant poured off. Diethyl ether (40 mL) were added to the residue, the suspension was vortexed for 3 min and centrifuged, and the supernatant was poured off, The wash process was repeated 3 three times. The solid was dried in high vacuum. The crude was purified by preparative HPLC and lyophilized from ACN/H$_2$O to afford Intermediate 1c as a white powder (178 mg, 71 μmol).

The pure product was analyzed by UPLC-MS (Analytical method D; t$_R$=1.33 min; measured: [M+2H]$^{2+}$=1078.1; calculated: [M+2H]$^{2+}$=1078.3).

Preparation of Intermediate 1d
(Cyclization and Purification)

Intermediate 1c (178 mg, 71 µmol) was dissolved in H$_2$O (2.0 mL). A solution of 50 mM I$_2$ in AcOH (I2 (50 mM in HOAc) (1.85 mL, 93 µmol) was added in one portion to the stirred solution and the solution was stirred overnight at rt until LC/MS showed the reaction was complete. 0.5 M Ascorbic acid in H$_2$O was added to quench the excess of I$_2$. The crude was purified by preparative HPLC and lyophilized from ACN/H$_2$O to afford Intermediate 1d as a white powder (92 mg, 35 µmol).

The pure product was analyzed by UPLC-MS (Analytical method D; $t_R$=1.44 min; measured: [M+2]$^{2+}$=1077.4; calculated: [M+2]$^{2+}$=1077.2).

Preparation of Peptide-linker Construct 1

A mixture of Preparation of Intermediate 1d (30 mg, 12 µmol), 3-(maleimido)propionic acid N-hydroxysuccinimide ester (3.06 mg, 12 µmol) and sodiumbicarbonate solution (50 µL, 1M) in DMF (1 mL) was shaked at 25° C. for 2 hrs, The reaction mixture was diluted with MeOH and filtered. The solution was purified by preparative HPLC and lyophilized from ACN/H$_2$O to afford Peptide-Linker Construct 1 as a white powder (12 mg, 4.54 µmol).

The pure product was analyzed by UPLC-MS (Analytical method D; $t_R$=1.59 min; measured: [M+2]$^{2+}$=1153.0; calculated: [M+2]$^{2+}$=1152.8).

Peptide-Linker Construct 2: PPA-O2Oc-O2Oc-O2Oc-O2Oc-Q-R-P-R-L-C*-H-F-G-P-Nle-C*-f-OH (SEQ ID NO:86) wherein PPA is 3-(2-Pyridyldithio)Propionic Acid A mixture of preparation of Intermediate 1d (27 mg, 10.4 µmol), 3-(2-pyridyldithio)propionic acid N-hydroxysuccinimide ester (5.7 mg, 18 µmol) and sodiumbicarbonate solution (72 µL, 1M) in DMF (1 mL) was shaked at 25° C. for 2 hrs, The reaction mixture was diluted with MeOH and filtered. The solution was purified by preparative HPLC and lyophilized from ACN/H$_2$O to afford Peptide-Linker Construct 2 as a white powder (10 mg, 3.71 µmol).

The pure product was analyzed by UPLC-MS (Analytical method D; $t_R$=1.71 min; measured: [M+2]$^{2+}$=1175.7; calculated: [M+2]$^{2+}$=1175.9).

Example 1

Albumin-MPA-O2Oc-O2Oc-O2Oc-O2Oc-Q-R-P-R-L-C*-H-F-G-P-Nle-C*-f-OH (SEQ ID NO: 86)

Step 1: Albumin Decapping
Decapping with TCEP

To a solution of albumin (500 mg, Aldrich, lyophilized powder, from human serum) in 10 mL of PBS 1× buffer in a 15 mL tube was added a solution of TCEP hydrochloride (1.074 mg in bio-grade purified water) once. The resultant solution was shaked at rt for 1 hr, then desalted and washed with two Amicon Ultra-4 centrifugal filters (30K MWCO). The filters were spinned at 4K g for 40 mins and the filtrates were discarded. 3 mL of bio-grade purified water was added to each filter for each wash (spinned at 14K g for 10 mins) and the wash process was repeated 3 times. The decapped HSA was dissolved in water (~20 mL in total). The solution was transferred to a 50 mL Falcon tube, and lyophilized to give a crystalline powder (500 mg).

The pure product was analyzed by UPLC-MS (Analytical method F; measured: 66439.0; expected: 66437).

Determination of the Number of Free Thiol Group in Decapped HSA

To a solution of this decapped HSA (2 mg) in 400 µL of PBS pH 7.4 in a 2 mL tube was added a solution of 6-maleimidohexanoic acid (13 µg) in water. The resultant solution was shaked at rt for 2 hr. UPLC-MS (Analytical method G) showed mono-adduct formation only, measured: 66649.0; expected: 66648.

Decapping with DTT

To a solution of albumin (400 mg, Aldrich, lyophilized powder, from human serum) in 5 mL of PBS 1× buffer in a 15 mL tube was added a solution of DTT (0.232 µl, 2 mg/mL in bio-grade purified water) once. The resultant solution was shaked at rt for 2 hr, then desalted and washed with twenty Amicon Ultra-0.5 centrifugal filters (10K MWCO). The filters were spinned at 14K g for 10 mins and the filtrates were discarded. Bio-grade purified water was added to the top of each filter for each wash (spinned at 14K g for 10 mins) and the wash process was repeated 6 times. The decapped HSA was dissolved in water (~20 mL in total). The solution was transferred to a 50 mL Falcon tube, and lyophilized to give a crystalline powder (376 mg).

The pure product was analyzed by UPLC-MS (Analytical method G; measured: 66438.5; expected: 66437).

Determination of the Number of Free Thiol Group in Decapped HSA

To a solution of this decapped HSA (3 mg) in 400 µL of PBS pH 7.4 in a 2 mL tube was added a solution of 3-maleimidopropionic acid (25 µg) in water. The resultant solution was shaked at rt overnight. UPLC-MS (Analytical method G) showed mono-adduct formation only, measured: 66608.0; expected: 66606.

Decapping with Cysteine

To a solution of albumin (120 mg, Aldrich, lyophilized powder, from human serum) in 1 mL of 50 mM PBS buffer pH 8.0 in a 2 mL tube was added cysteine (10.94 mg) once. The resultant solution was shaked at rt for 1 hr, then desalted and washed with two Amicon Ultra-0.5 centrifugal filters (10K MWCO). The filters were spinned at 14K g for 10 mins and the filtrates were discarded. Bio-grade purified water was added to the top of each filter for each wash (spinned at 14K g for 10 min) and the wash process was repeated 5 times. The decapped HSA was dissolved in water (4 mL in total). The solution was transferred to a 15 mL Falcon tube, and lyophilized to give a crystalline powder (108 mg).

The pure product was analyzed by UPLC-MS (Analytical method G; measured: 66439; expected: 66437).

Determination of the Number of Free Thiol Group in Decapped HSA

To a solution of this decapped HSA (3 mg) in 500 µL of PBS pH 7.4 in a 2 mL tube was added a solution of 3-maleimidopropionic acid (15 µg) in water. The resultant solution was shaked at rt for 1 hr. UPLC-MS (Analytical method G) showed mono-adduct formation only, measured: 66608.0; expected: 66606.

Step 2: Peptide-linker Construct/Albumin Conjugation

A solution of decapped HSA (97 mg) in PBS buffer was treated with a solution of Peptide-Linker Construct 1 (11.6 mg in water). The resultant solution was shaked at rt overnight, then desalted and washed with 6 Amicon Ultra-0.5 centrifugal filters (10K MWCO). The filters were spinned at 13K g for 10 min and the filtrates were discarded. Bio-grade purified water was added to the top of each filter for each wash (spinned at 13K g for 10 min) and the wash process was repeated 6 times. The conjugate was dissolved in water (4 mL in total). The solution was transferred to a 15 mL Falcon tube, and lyophilized to give a crystalline powder (90.5 mg).

The pure product was analyzed by UPLC-MS (Analytical method G; measured: 68742.5; expected: 68741).

Example 2

Albumin-TPA-O2Oc-O2Oc-O2Oc-O2Oc-Q-R-P-R-
L-C*-H-F-G-P-Nle-C*-f-OH (SEQ ID NO: 86)
wherein TPA is: 3-mercaptopropanoic acid A solution of decapped HSA (65.8 mg) in PBS buffer (1 mL) portionwise (100 ul in every 30 min) was added a solution of Peptide-Linker Construct 2 (8 mg) and sodium bicarbonate (8.92 uL, 1M) in PBS buffer (1 mL). After addition, the resultant solution was shaked at it overnight, then desalted and washed with 4 Amicon Ultra-0.5 centrifugal filters (10K MWCO). The filters were spinned at 13K g for 10 min and the filtrates were discarded. Bio-grade purified water was added to the top of each filter for each wash (spinned at 13K g for 10 mins) and the wash process was repeated 5 times. The conjugate was dissolved in water (4 mL in total). The solution was transferred to a 15 mL Falcon tube, and lyophilized to give a crystalline powder (65.6 mg).

The pure product was analyzed by UPLC-MS (Analytical method G; measured: 68677; expected: 68678).

Example 3

Albumin-MPA-NHCH$_2$CH$_2$CH$_2$_
OCH$_2$CH$_2$OCH$_2$CH$_2$O-CH$_2$CH$_2$CH$_2$NH-C(O)
CH$_2$CH$_2$C=O-A-R-P-R-L-S-H-K-G-P-Nle-P-F-OH
(SEQ ID NO: 88)

Example 3 was synthesized as example 1. The pure product was analyzed by UPLC-MS (Analytical method G, measured: 68367; expected: 68366)

Fc-apelin Construct Cloning:

The DNA fragments below were generated by standard PCR techniques using the vector pPL1146 as a template with the following primers: A 5' primer was designed that contains a NheI site followed by sequence corresponding to the 5' end of the human Fc contained in vector pPL1146. 3' primers were designed to contain a EcoRI site, Apelin sequence for the appropriate construct, a glycine serine linker and sequence complimentary to the 3' end of the human Fc contained in pPL1146. Following amplification, each of the four fragments was restriction digested with both NheI and EcoRI restriction enzymes, isolated and purified, and ligated into vector pPL1146 digested and purified in the same manner. The ligations were transformed into *E coli* cells and colonies containing the correct plasmids were identified by DNA sequencing. Sequences shown are for the sense strand and run in the 5-prime to 3-prime direction.

Fc-apelin fusion (example 4 to Example 7)

Fc-apelin Protein Expression and Purification:

Expression plasmid DNA was transfected into HEK293T cells at a density of ~10 E6 cells per ml using standard polyethyline imine methods. 500 ml cultures were then grown in Freestyle Media (Gibco) in 3 L flasks for 3 days at 37° C.

Fc-apelin proteins were purified from clarified conditioned media with protein A sepharose FF. Briefly 500 ml of conditioned media was batch bound to 2 ml Protein A sepharose at 4° C. overnight. The protein A sepharose was transferred to a disposable column and washed extensively with PBS. Fc-apelin proteins were eluted with 0.1M glycine, pH 2.7, neutralized with 1 M tris-HCl, pH 9 and dialyzed versus PBS. Yields were 10 to 20 mg per 500 ml conditioned media and endotoxin levels were low (<1 EU/mg) as measured by the Charles River ENDOSAFE PTS test.

Quality Control of Fc-apelin Proteins:

LC/MS of Native Fc-Apelin Proteins: Peaks were heterogeneous and about 3 kDa larger than expected for dimers. This is characteristic of N-linked glycosylation expected for Fc which has a consensus N-linked glycosylation site.

LC/MS of Reduced, N-Deglycosylated Fc-Apelin Proteins: gave sharp peaks. The molecular weight for Fc-apelin 3 and 4, and Fc-Cys was as expected while the molecular weights of Fc-apelin 1 & 2 and Cys-Fc were consistent with cleavage of the C-terminal amino acid. The cysteines at the C-terminus appear to protect the protein from cleavage.

Analytical Size Exclusion on Superdex 200: Fc-Apelin proteins have between 89 and 100% dimer, 0 to 10% tetramer, and 0 to 1% aggregate.

Reducing SDS/PAGE: All proteins migrated as predominately monomers of the expected size.

Nucleotide Sequence:

Fc-Apelin fusion: Example 4(SEQ ID NO: 89)

```
GCTAGCCACCATGGAAACTGACACCCTGCTGCTGTGGGTCCTGCTGCTGT
GGGGTGCCTGGCAGCACTGGCGATAAGACACACACTTGCCCCCCTTGTCC
AGCACCAGAGGCAGCTGGAGGACCAAGCGTGTTCCTGTTTCCACCCAAGC
CTAAAGACACACTGATGATCTCAAGGACCCCAGAAGTCACATGCGTGGTC
GTGGACGTGTCTCACGAGGACCCCGAAGTCAAGTTCAACTGGTACGTGGA
TGGCGTCGAGGTGCATAATGCTAAGACCAAACCCCGAGAGGAACAGTACA
ACAGCACCTATCGGGTCGTGTCCGTCCTGACAGTGCTGCACCAGGATTGG
CTGAACGGCAAAGAGTATAAGTGCAAAGTGAGTAATAAGGCTCTGCCTGC
ACCAATCGAGAAAACAATTTCTAAGGCTAAAGGGCAGCCAAGAGAACCCC
AGGTGTACACTCTGCCTCCATCTAGGGAGGAAATGACAAAGAACCAGGTC
AGTCTGACTTGTCTGGTGAAAGGCTTCTACCCCTCCGACATCGCAGTGGA
GTGGGAATCTAATGGCCAGCCTGAAAACAATTACAAGACCACACCCCCTG
TGCTGGACTCCGATGGGTCTTTCTTTCTGTATTCTAAGCTGACCGTGGAT
AAAAGTCGGTGGCAGCAGGGAAACGTCTTCTCATGCAGCGTGATGCACGA
GGCCCTGCACAATCATTACACACAGAAGTCCCTGTCTCTGAGTCCAGGCA
AAGGTGGCGGAGGCAGCGGCGGTGGAGGCAGCCAGCGGCCCCGGCTGAGC
CACAAGGGCCCCATGCCCTTCTAAGAATTC
```

Fc-Apelin fusion: Example 5(SEQ ID NO: 90)

```
GCTAGCCACCATGGAAACTGACACCCTGCTGCTGTGGGTCCTGCTGCTG
TGGGTGCCTGGCAGCACTGGCGATAAGACACACACTTGCCCCCCTTGTCC
AGCACCAGAGGCAGCTGGAGGACCAAGCGTGTTCCTGTTTCCACCCAAGC
CTAAAGACACACTGATGATCTCAAGGACCCCAGAAGTCACATGCGTGGTC
GTGGACGTGTCTCACGAGGACCCCGAAGTCAAGTTCAACTGGTACGTGGA
TGGCGTCGAGGTGCATAATGCTAAGACCAAACCCCGAGAGGAACAGTACA
ACAGCACCTATCGGGTCGTGTCCGTCCTGACAGTGCTGCACCAGGATTGG
CTGAACGGCAAAGAGTATAAGTGCAAAGTGAGTAATAAGGCTCTGCCTGC
ACCAATCGAGAAAACAATTTCTAAGGCTAAAGGGCAGCCAAGAGAACCCC
```

AGGTGTACACTCTGCCTCCATCTAGGGAGGAAATGACAAAGAACCAGGTC

AGTCTGACTTGTCTGGTGAAAGGCTTCTACCCCTCCGACATCGCAGTGGA

GTGGGAATCTAATGGCCAGCCTGAAAACAATTACAAGACCACACCCCCTG

TGCTGGACTCCGATGGGTCTTTCTTTCTGTATTCTAAGCTGACCGTGGAT

AAAAGTCGGTGGCAGCAGGGAAACGTCTTCTCATGCAGCGTGATGCACGA

GGCCCTGCACAATCATTACACACAGAAGTCCCTGTCTCTGAGTCCAGGCA

AAGGTGGCGGAGGCAGCGGCGGTGGAGGCAGCGGAGGTGGCGGAAGCCAG

CGGCCCCGGCTGAGCCACAAGGGCCCCATGCCCTTCTAA GAATTC

Fc-Apelin fusion: Example 6 (SEQ ID NO:91)

GCTAGC CACCATGGAAACTGACACCCTGCTGCTGTGGGTCCTGCTGCTGT

GGGTGCCTGCTAGCCACCATGGAAACTGACACCCTGCTGCTGTGGGTCCT

GCTGCTGTGGGTGCCTGGCAGCACTGGCGATAAGACACACACTTGCCCCC

CTTGTCCAGCACCAGAGGCAGCTGAGGACCAAGCGTGTTCCTGTTTCCA

CCCAAGCCTAAAGACACACTGATGATCTCAAGGACCCCAGAAGTCACATG

CGTGGTCGTGGACGTGTCTCACGAGGACCCCGAAGTCAAGTTCAACTGGT

ACGTGGATGGCGTCGAGGTGCATAATGCTAAGACCAAACCCCGAGAGGAA

CAGTACAACAGCACCTATCGGGTCGTGTCCGTCCTGACAGTGCTGCACCA

GGATTGGCTGAACGGCAAAGAGTATAAGTGCAAAGTGAGTAATAAGGCTC

TGCCTGCACCAATCGAGAAAACAATTTCTAAGGCTAAAGGGCAGCCAAGA

GAACCCCAGGTGTACACTCTGCCTCCATCTAGGGAGGAAATGACAAAGAA

CCAGGTCAGTCTGACTTGTCTGGTGAAAGGCTTCTACCCCTCCGACATCG

CAGTGGAGTGGGAATCTAATGGCCAGCCTGAAAACAATTACAAGACCACA

CCCCCTGTGCTGGACTCCGATGGGTCTTTCTTTCTGTATTCTAAGCTGAC

CGTGGATAAAAGTCGGTGGCAGCAGGGAAACGTCTTCTCATGCAGCGTGA

TGCACGAGGCCCTGCACAATCATTACACACAGAAGTCCCTGTCTCTGAGT

CCAGGCAAAGGTGGCGGAGGCAGCGGCGGTGGAGGCAGCCAGCGGCCCCG

GCTGTGCCACAAGGGCCCCATGTGCTTCTAA GAATTC

Fc-Apelin fusion: Example 7 (SEQ ID NO: 92)

GCTAGC CACCATGGAAACTGACACCCTGCTGCTGTGGGTCCTGCTGCTGT

GGGTGCCTGGCAGCACTGGCGATAAGACACACACTTGCCCCCCTTGTCCA

GGCACCAGAGGCAGCTGAGGACCAAGCGTGTTCCTGTTTCCACCCAAGCC

TAAAGACACACTGATGATCTCAAGGACCCCAGAAGTCACATGCGTGGTCG

TGGACGTGTCTCACGAGGACCCCGAAGTCAAGTTCAACTGGTACGTGGAT

GGCGTCGAGGTGCATAATGCTAAGACCAAACCCCGAGAGGAACAGTACAA

CAGCACCTATCGGGTCGTGTCCGTCCTGACAGTGCTGCACCAGGATTGGC

TGAACGGCAAAGAGTATAAGTGCAAAGTGAGTAATAAGGCTCTGCCTGCA

CCAATCGAGAAAACAATTTCTAAGGCTAAAGGGCAGCCAAGAGAACCCCA

GGTGTACACTCTGCCTCCATCTAGGGAGGAAATGACAAAGAACCAGGTCA

GTCTGACTTGTCTGGTGAAAGGCTTCTACCCCTCCGACATCGCAGTGGAG

TGGGAATCTAATGGCCAGCCTGAAAACAATTACAAGACCACACCCCCTGT

GCTGGACTCCGATGGGTCTTTCTTTCTGTATTCTAAGCTGACCGTGGATA

AAAGTCGGTGGCAGCAGGGAAACGTCTTCTCATGCAGCGTGATGCACGAG

GCCCTGCACAATCATTACACACAGAAGTCCCTGTCTCTGAGTCCAGGCAA

AGGTGGCGGAGGCAGCGGCGGTGGAGGCAGCGGAGGTGGCGGAAGCCAGC

GGCCCCGGCTGTGCCACAAGGGCCCCATGTGCTTCTAA GAATTC

Primer Sequences:

| | |
|---|---|
| FcA 1-fwd | GCTTGCTAGCCACCATGGAAACTG (SEQ ID NO: 93) |
| FcA 1-rev | GTTGATTGAATTCTTAGAAGGGCATGGGGCCCTTGTGGCTCAG CCGGGGCCGCTGGCTGCCTCCACCGCCGCTGCCTCCGCCACCT TTGCCTGGACTCAGAGACAGGG (SEQ ID NO: 94) |
| FcA 2-rev | GTTGATTGAATTCTTAGAAGGGCATGGGGCCCTTGTGGCTCAG CCGGGGCCGCTGGCTGCCTCCACCGCCGCTGCCTCCACCGCCG CTGCCTCCGCCACCTTTGCCTGGACTCAGAGACAGGG (SEQ ID NO: 95) |
| FcA 3-rev | GTTGATTGAATTCTTAGAAGCACATGGGGCCCTTGTGGCACAG CCGGGGCCGCTGGCTGCCTCCACCGCCGCTGCCTCCGCCACCT TTGCCTGGACTCAGAGACAGGG (SEQ ID NO: 96) |
| FcA 4-rev | GTTGATTGAATTCTTAGAAGCACATGGGGCCCTTGTGGCACAG CCGGGGCCGCTGGCTTCCGCCACCTCCGCTGCCTCCACCGCCG CTGCCTCCGCCACCTTTGCCTGGACTCAGAGACAGGG (SEQ ID NO: 97) |

Example 4

Fc-Apelin fusion

```
  1 METDTLLLWV LLLWVPGSTG DKTHTCPPCP APEAAGGPSV
    FLFPPKPKDT

51 LMISRTPEVT CVVVDVSHED PEVKFNWYVD GVEVHNAKTK
    PREEQYNSTY

101 RVVSVLTVLH QDWLNGKEYK CKVSNKALPA PIEKTISKAK
    GQPREPQVYT

151 LPPSREEMTK NQVSLTCLVK GFYPSDIAVE WESNGQPENN
    YKTTPPVLDS

201 DGSFFLYSKL TVDKSRWQQG NVFSCSVMHE ALHNHYTQKS
    LSLSPGKGGG

251 GSGGGGSQRPRLSHKGPMPF (SEQ ID NO: 98)
``` wherein GGGGSGGGGS (SEQ ID NO: 12) represents the linker and QRPRLSHKGPMPF (SEQ IF NO:19) is the polypeptide.

Example 5

Fc-Apelin fusion

```
  1  METDTLLLWV LLLWVPGSTG DKTHTCPPCP APEAAGGPSV
     FLFPPKPKDT

51  LMISRTPEVT CVVVDVSHED PEVKFNWYVD GVEVHNAKTK
     PREEQYNSTY

101  RVVSVLTVLH QDWLNGKEYK CKVSNKALPA PIEKTISKAK
     GQPREPQVYT

151  LPPSREEMTK NQVSLTCLVK GFYPSDIAVE WESNGQPENN
     YKTTPPVLDS

201  DGSFFLYSKL TVDKSRWQQG NVFSCSVMHE ALHNHYTQKS
     LSLSPGKGGG

251  GSGGGGSGGGGSQRPRLSHKGPMPF  (SEQ ID NO: 99)
``` wherein GGGGSGGGGSGGGGS (SEQ ID NO: 11) represents the linker and QRPRLSHKGPMPF (SEQ ID NO: 19) is the polypeptide.

Example 6

Fc-Apelin fusion

```
  1  METDTLLLWV LLLWVPGSTG DKTHTCPPCP APEAAGGPSV
     FLFPPKPKDT

51  LMISRTPEVT CVVVDVSHED PEVKFNWYVD GVEVHNAKTK
     PREEQYNSTY

101  RVVSVLTVLH QDWLNGKEYK CKVSNKALPA PIEKTISKAK
     GQPREPQVYT

151  LPPSREEMTK NQVSLTCLVK GFYPSDIAVE WESNGQPENN
     YKTTPPVLDS

201  DGSFFLYSKL TVDKSRWQQG NVFSCSVMHE ALHNHYTQKS
     LSLSPGKGGG

251  GSGGGGSQRPRLC*HKGPMC*F  (SEQ ID NO: 100)
``` wherein GGGGSGGGGS (SEQ ID NO: 12) represents the linker and QRPRLC*HKGPMC*F (SEQ ID NO: 17) is the polypeptide.

Example 7

Fc-Apelin fusion

```
  1  METDTLLLWV LLLWVPGSTG DKTHTCPPCP APEAAGGPSV
     FLFPPKPKDT

51  LMISRTPEVT CVVVDVSHED PEVKFNWYVD GVEVHNAKTK
     PREEQYNSTY

101  RWWSVLTVLH QDWLNGKEYK CKVSNKALPA PIEKTISKAK
     GQPREPQVYT

151  LPPSREEMTK NQVSLTCLVK GFYPSDIAVE WESNGQPENN
     YKTTPPVLDS

201  DGSFFLYSKL TVDKSRWQQG NVFSCSVMHE ALHNHYTQKS
     LSLSPGKGGG

251  GSGGGGSGGG GSQRPRLC*HKGPMC*F  (SEQ ID NO: 101)
``` wherein GGGGSGGGGSGGGGS (SEQ ID NO: 11) represents the linker and QRPRLC*HKGPMC*F (SEQ ID NO: 17) is the polypeptide.

Fc-Apelin Construct Cloning:

The Fc-Apelin DNA fragment shown below was generated by standard PCR techniques using the vector pPL1146 containing the mouse Ig Kappa signal sequence followed by the human Fc downstream of a CMV promoter, as a template. A forward primer (5'-GCT TGC TAG CCA CCA TGG AAA CTG-3') (SEQ ID NO: 93) was designed that contains a NheI site followed by sequences corresponding to the 5' end of the signal sequence contained in vector pPL1146. A reverse primer (5'-GTT GAT TGA ATT CTT AGA AGC ACA TGG GGC CCT TGT GGC ACA GCC GGG GCC GCT GGC TTC CGC CAC CTC CGC TGC CTC CAC CGC CGC TGC CTC CGC CAC CTG CGC CTG GAC TCA GAG ACA GGG-3') (SEQ IF NO: 102) was designed to contain a EcoRI site, apelin sequence, a glycine serine linker and sequence complementary to the 3' end of the human Fc contained in pPL1146. Following amplification, the fragment was restriction digested with both NheI and EcoRI, isolated and purified from an agarose gel, and ligated into vector pPL1146 digested and purified in the same manner. The ligations were transformed into E. coli DH5□ cells and colonies containing the correct plasmids were identified by DNA sequencing. Modifications in the Fc fusion, linker and/or apelin sequences of other Fc-Apelin fusions shown were generated by standard site-directed mutagenesis protocols using example 9 as a template. Example 8 containing an Fc fusion at the C-terminus of apelin was codon optimized by gene synthesis (GeneArt) and the insert cloned into vector pPL1146 as described above. Sequences shown are for the sense strand and run in the 5' to 3' direction.

Fc-Apelin Protein Expression and Purification:

Fc-Apelin expression plasmid DNA was transfected into HEK293T cells at a density of $1 \times 10^6$ cells per ml using standard polyethylenimine methods. 500 ml cultures were then grown in FreeStyle 293 Medium (Life Technologies) in 3 L flasks for 4 days at 37° C.

Fc-Apelin protein was purified from clarified conditioned media. Briefly 500 ml of conditioned media was flowed over a 5 ml HiTrap MabSelect SuRe column (GE Life Sciences) at 4 ml/min. The column was washed with 20 column volumes of PBS containing 0.1% Triton X-114 and then the Fc-Apelin protein was eluted with 0.1M glycine, pH 2.7, neutralized with 1 M Tris-HCl, pH 9 and dialyzed against PBS. Protein yields were 10 to 20 mg per 500 ml conditioned media and endotoxin levels were <1 EU/mg as measured by the Charles River ENDOSAFE PTS test.

Quality Control of Fc-apelin Proteins:

LC/MS of Native Fc-Apelin Proteins: Peaks were heterogeneous and about 3 kDa larger than expected for dimers. This is characteristic of N-linked glycosylation expected for Fc which has a consensus N-linked glycosylation site.

LC/MS of Reduced, N-Deglycosylated Fc-Apelin Proteins: Peaks were sharp. The molecular weight for Example 8 was 488 daltons less than theoretical, of which 130 daltons is likely due to loss of the C-terminal lysine residue of Fc. The molecular weight for example 9 to example 19 was 2 or 3 daltons less than expected, likely due to Cysteine ×2 reduction or Cys ×2 reduction with an additional modification (i.e. deamidation of Asn to Asp), respectively.

Analytical Size Exclusion on Superdex 200: Fc-Apelin proteins have between 89 and 100% dimer, 0 to 10% tetramer, and 0 to 1% aggregate.

Reducing SDS/PAGE: All proteins migrated as predominately monomers of the expected size.

Nucleotide Sequence

Ex 8    GCTAGCCACCATGGAAACCGACACCCTGCTGCTGTGGGTGCTG
CTGCTGTGGGTGCCAGGCAGCACAGGCGATAAGGGCAGCCAGA
GGCCTAGACTGTGCCACAAGGGCCCCATGTGCTTTGGCGGCGG
AGGATCTGGCGGAGGCGGCAGCGATAAGACCCACACCTGTCCT
CCATGCCCTGCCCCTGAAGCTGCTGGCGGCCCTAGCGTGTTCC
TGTTCCCCCCAAAGCCCAAGGACACCCTGATGATCAGCCGGAC
CCCCGAAGTGACCTGCGTGGTGGTGGATGTGTCCCACGAGGAC
CCTGAAGTGAAGTTCAATTGGTACGTGGACGGCGTGGAAGTGC
ACAACGCCAAGACCAAGCCCAGAGAGGAACAGTACAACAGCAC
CTACCGGGTGGTGTCCGTGCTGACCGTGCTGCACCAGGACTGG
CTGAACGGCAAAGAGTACAAGTGCAAGGTGTCCAACAAGGCCC
TGCCTGCCCCCATCGAGAAAACCATCAGCAAGGCCAAGGGCCA
GCCCCGCGAACCCCAGGTGTACACACTGCCCCCTAGCCGGGAA
GAGATGACCAAGAACCAGGTGTCCCTGACCTGTCTCGTGAAGG
GCTTCTACCCCTCCGATATCGCCGTGGAATGGGAGAGCAACGG
CCAGCCCGAGAACAACTACAAGACCACCCCCCCTGTGCTGGAC
AGCGACGGCTCATTCTTCCTGTACAGCAAGCTGACAGTGGACA
AGAGCCGGTGGCAGCAGGGCAACGTGTTCAGCTGCAGCGTGAT
GCACGAGGCCCTGCACAACCACTACACCCAGAAGTCCCTGAGC
CTGAGCCCCGGCAAATGAGAATTC (SEQ ID NO: 103)

Ex 9    GCTAGCCACCATGGAAACTGACACCCTGCTGCTGTGGGTCCTG
CTGCTGTGGGTGCCTGGCAGCACTGGCGATAAGACACACACTT
GCCCCCCTTGTCCAGCACCAGAGGCAGCTGGAGGACCAAGCGT
GTTCCTGTTTCCACCCAAGCCTAAAGACACACTGATGATCTCA
AGGACCCCAGAAGTCACATGCGTGGTCGTGGACGTGTCTCACG
AGGACCCCGAAGTCAAGTTCAACTGGTACGTGGATGGCGTCGA
GGTGCATAATGCTAAGACCAAACCCCGAGAGGAACAGTACAAC
AGCACCTATCGGGTCGTGTCCGTCCTGACAGTGCTGCACCAGG
ATTGGCTGAACGGCAAAGAGTATAAGTGCAAAGTGAGTAATAA
GGCTCTGCCTGCACCAATCGAGAAAACAATTTCTAAGGCTAAA
GGGCAGCCAAGAGAACCCCAGGTGTACACTCTGCCTCCATCTA
GGGAGGAAATGACAAAGAACCAGGTCAGTCTGACTTGTCTGGT
GAAAGGCTTCTACCCCTCCGACATCGCAGTGGAGTGGGAATCT
AATGGCCAGCCTGAAAACAATTACAAGACCACACCCCCTGTGC
TGGACTCCGATGGGTCTTTCTTTCTGTATTCTAAGCTGACCGT

GGATAAAAGTCGGTGGCAGCAGGGAAACGTCTTCTCATGCAGC
GTGATGCACGAGGCCCTGCACAATCATTACACACAGAAGTCCC
TGTCTCTGAGTCCAGGCGGTGGCGGAGGCAGCGGCGGTGGAGG
CAGCGGAGGTGGCGGAAGCCAGCGGCCCCGGCTGTGCCACAAG
GGCCCCATGTGCTTCTAAGAATTC (SEQ ID NO: 104)

Ex 10   GCTAGCCACCATGGAAACTGACACCCTGCTGCTGTGGGTCCTG
CTGCTGTGGGTGCCTGGCAGCACTGGCGATAAGACACACACTT
GCCCCCCTTGTCCAGCACCAGAGGCAGCTGGAGGACCAAGCGT
GTTCCTGTTTCCACCCAAGCCTAAAGACACACTGATGATCTCA
AGGACCCCAGAAGTCACATGCGTGGTCGTGGACGTGTCTCACG
AGGACCCCGAAGTCAAGTTCAACTGGTACGTGGATGGCGTCGA
GGTGCATAATGCTAAGACCAAACCCCGAGAGGAACAGTACAAC
AGCACCTATCGGGTCGTGTCCGTCCTGACAGTGCTGCACCAGG
ATTGGCTGAACGGCAAAGAGTATAAGTGCAAAGTGAGTAATAA
GGCTCTGCCTGCACCAATCGAGAAAACAATTTCTAAGGCTAAA
GGGCAGCCAAGAGAACCCCAGGTGTACACTCTGCCTCCATCTA
GGGAGGAAATGACAAAGAACCAGGTCAGTCTGACTTGTCTGGT
GAAAGGCTTCTACCCCTCCGACATCGCAGTGGAGTGGGAATCT
AATGGCCAGCCTGAAAACAATTACAAGACCACACCCCCTGTGC
TGGACTCCGATGGGTCTTTCTTTCTGTATTCTAAGCTGACCGT
GGATAAAAGTCGGTGGCAGCAGGGAAACGTCTTCTCATGCAGC
GTGATGCACGAGGCCCTGCACAATCATTACACACAGAAGTCCC
TGTCTCTGAGTCCAGGCAAAGGTAGCCAGCGGCCCCGGCTGTG
CCACAAGGGCCCCATGTGCTTCTAAGAATTC
(SEQ ID NO: 105)

Ex 11   GCTAGCCACCATGGAAACTGACACCCTGCTGCTGTGGGTCCTG
CTGCTGTGGGTGCCTGGCAGCACTGGCGATAAGACACACACTT
GCCCCCCTTGTCCAGCACCAGAGGCAGCTGGAGGACCAAGCGT
GTTCCTGTTTCCACCCAAGCCTAAAGACACACTGATGATCTCA
AGGACCCCAGAAGTCACATGCGTGGTCGTGGACGTGTCTCACG
AGGACCCCGAAGTCAAGTTCAACTGGTACGTGGATGGCGTCGA
GGTGCATAATGCTAAGACCAAACCCCGAGAGGAACAGTACAAC
AGCACCTATCGGGTCGTGTCCGTCCTGACAGTGCTGCACCAGG
ATTGGCTGAACGGCAAAGAGTATAAGTGCAAAGTGAGTAATAA
GGCTCTGCCTGCACCAATCGAGAAAACAATTTCTAAGGCTAAA
GGGCAGCCAAGAGAACCCCAGGTGTACACTCTGCCTCCATCTA
GGGAGGAAATGACAAAGAACCAGGTCAGTCTGACTTGTCTGGT
GAAAGGCTTCTACCCCTCCGACATCGCAGTGGAGTGGGAATCT
AATGGCCAGCCTGAAAACAATTACAAGACCACACCCCCTGTGC
TGGACTCCGATGGGTCTTTCTTTCTGTATTCTAAGCTGACCGT
GGATAAAAGTCGGTGGCAGCAGGGAAACGTCTTCTCATGCAGC

-continued

GTGATGCACGAGGCCCTGCACAATCATTACACACAGAAGTCCC
TGTCTCTGAGTCCAGGCAAAGGTGGCCAGCGGCCCCGGCTGTG
CCACAAGGGCCCCATGTGCTTCTAAGAATTC (SEQ ID NO: 106)

Ex 12  GCTAGCCACCATGGAAACTGACACCCTGCTGCTGTGGGTCCTG
CTGCTGTGGGTGCCTGGCAGCACTGGCGATAAGACACACACTT
GCCCCCCTTGTCCAGCACCAGAGGCAGCTGGAGGACCAAGCGT
GTTCCTGTTTCCACCCAAGCCTAAAGACACACTGATGATCTCA
AGGACCCCAGAAGTCACATGCGTGGTCGTGGACGTGTCTCACG
AGGACCCCGAAGTCAAGTTCAACTGGTACGTGGATGGCGTCGA
GGTGCATAATGCTAAGACCAAACCCCGAGAGGAACAGTACAAC
AGCACCTATCGGGTCGTGTCCGTCCTGACAGTGCTGCACCAGG
ATTGGCTGAACGGCAAAGAGTATAAGTGCAAAGTGAGTAATAA
GGCTCTGCCTGCACCAATCGAGAAAACAATTTCTAAGGCTAAA
GGGCAGCCAAGAGAACCCCAGGTGTACACTCTGCCTCCATCTA
GGGAGGAAATGACAAAGAACCAGGTCAGTCTGACTTGTCTGGT
GAAAGGCTTCTACCCCTCCGACATCGCAGTGGAGTGGGAATCT
AATGGCCAGCCTGAAAACAATTACAAGACCACACCCCCTGTGC
TGGACTCCGATGGGTCTTTCTTTCTGTATTCTAAGCTGACCGT
GGATAAAAGTCGGTGGCAGCAGGGAAACGTCTTCTCATGCAGC
GTGATGCACGAGGCCCTGCACAATCATTACACACAGAAGTCCC
TGTCTCTGAGTCCAGGCAAAGGTGGCGGAGGCAGCCAGCGGCC
CCGGCTGTGCCACAAGGGCCCCATGTGCTTCTAAGAATTC (SEQ ID NO: 107)

Ex 13  GCTAGCCACCATGGAAACTGACACCCTGCTGCTGTGGGTCCTG
CTGCTGTGGGTGCCTGGCAGCACTGGCGATAAGACACACACTT
GCCCCCCTTGTCCAGCACCAGAGGCAGCTGGAGGACCAAGCGT
GTTCCTGTTTCCACCCAAGCCTAAAGACACACTGATGATCTCA
AGGACCCCAGAAGTCACATGCGTGGTCGTGGACGTGTCTCACG
AGGACCCCGAAGTCAAGTTCAACTGGTACGTGGATGGCGTCGA
GGTGCATAATGCTAAGACCAAACCCCGAGAGGAACAGTACAAC
AGCACCTATCGGGTCGTGTCCGTCCTGACAGTGCTGCACCAGG
ATTGGCTGAACGGCAAAGAGTATAAGTGCAAAGTGAGTAATAA
GGCTCTGCCTGCACCAATCGAGAAAACAATTTCTAAGGCTAAA
GGGCAGCCAAGAGAACCCCAGGTGTACACTCTGCCTCCATCTA
GGGAGGAAATGACAAAGAACCAGGTCAGTCTGACTTGTCTGGT
GAAAGGCTTCTACCCCTCCGACATCGCAGTGGAGTGGGAATCT
AATGGCCAGCCTGAAAACAATTACAAGACCACACCCCCTGTGC

-continued

TGGACTCCGATGGGTCTTTCTTTCTGTATTCTAAGCTGACCGT
GGATAAAAGTCGGTGGCAGCAGGGAAACGTCTTCTCATGCAGC
GTGATGCACGAGGCCCTGCACAATCATTACACACAGAAGTCCC
TGTCTCTGAGTCCAGGCAAAGGTGGCGGAGGCAGCGGCGGTGG
AGGCAGCGGAGGTGGCGGAAGCCAGCGGCCCCGGCTGTGCCAC
AAGGGCCCCATGTGCTAGTAAGAATTC (SEQ ID NO:
108)

Ex 14  GCTAGCCACCATGGAAACTGACACCCTGCTGCTGTGGGTCCTG
CTGCTGTGGGTGCCTGGCAGCACTGGCGATAAGACACACACTT
GCCCCCCTTGTCCAGCACCAGAGGCAGCTGGAGGACCAAGCGT
GTTCCTGTTTCCACCCAAGCCTAAAGACACACTGATGATCTCA
AGGACCCCAGAAGTCACATGCGTGGTCGTGGACGTGTCTCACG
AGGACCCCGAAGTCAAGTTCAACTGGTACGTGGATGGCGTCGA
GGTGCATAATGCTAAGACCAAACCCCGAGAGGAACAGTACAAC
AGCACCTATCGGGTCGTGTCCGTCCTGACAGTGCTGCACCAGG
ATTGGCTGAACGGCAAAGAGTATAAGTGCAAAGTGAGTAATAA
GGCTCTGCCTGCACCAATCGAGAAAACAATTTCTAAGGCTAAA
GGGCAGCCAAGAGAACCCCAGGTGTACACTCTGCCTCCATCTA
GGGAGGAAATGACAAAGAACCAGGTCAGTCTGACTTGTCTGGT
GAAAGGCTTCTACCCCTCYGACATCGCAGTGGAGTGGGAATCT
AATGGCCAGCCTGAAAACAATTACAAGACCACACCCCCTGTGC
TGGACTCCGATGGGTCTTTCTTTCTGTATTCTAAGCTGACCGT
GGATAAAAGTCGGTGGCAGCAGGGAAACGTCTTCTCATGCAGC
GTGATGCACGAGGCCCTGCACAATCATTACACACAGAAGTCCC
TGTCTCTGAGTCCAGGCGCAGGTGGCGGAGGCAGCGGCGGTGG
AGGCAGCGGAGGTGGCGGAAGCCAGCGGCCCCGGCTGTGCCAC
AAGGGCCCCATGTGCTAAGAATTC (SEQ ID NO: 109)

Ex 15  GCTAGCCACCATGGAAACTGACACCCTGCTGCTGTGGGTCCTG
CTGCTGTGGGTGCCTGGCAGCACTGGCGATAAGACACACACTT
GCCCCCCTTGTCCAGCACCAGAGGCAGCTGGAGGACCAAGCGT
GTTCCTGTTTCCACCCAAGCCTAAAGACACACTGATGTCTCAA
GGACCCCAGAAGTCACATGCGTGGTCGTGGACGTGTCTCACGA
GGACCCCGAAGTCAAGTTCAACTGGTACGTGGATGGCGTCGAG
GTGCATAATGCTAAGACCAAACCCCGAGAGGAACAGTACAACA
GCACCTATCGGGTCGTGTCCGTCCTGACAGTGCTGCACCAGGA
TTGGCTGAACGGCAAAGAGTATAAGTGCAAAGTGAGTAATAAG
GCTCTGCCTGCACCAATCGAGAAAACAATTTCTAAGGCTAAAG
GGCAGCCAAGAGAACCCCAGGTGTACACTCTGCCTCCATCTAG
GGAGGAAATGACAAAGAACCAGGTCAGTCTGACTTGTCTGGTG

-continued

AAAGGCTTCTACCCCTCCGACATCGCAGTGGAGTGGGAATCTA

ATGGCCAGCCTGAAAACAATTACAAGACCACACCCCCTGTGCT

GGACTCCGATGGGTCTTTCTTTCTGTATTCTAAGCTGACCGTG

GATAAAAGTCGGTGGCAGCAGGGAAACGTCTTCTCATGCAGCG

TGATGCACGAGGCCCTGCACAATCATTACACACAGAAGTCCCT

GTCTCTGAGTCCAGGCGGTGGCGGAGGCAGCGGCGGTGGAGGC

AGCGGAGGTGGCGGAAGCCAGCGGCCCCGGCTGTGCCACAAGG

GCCCCATGTGCTAAGAATTC (SEQ ID NO: 110)

Ex 16 GCTAGCCACCATGGAAACTGACACCCTGCTGCTGTGGGTCCTG

CTGCTGTGGGTGCCTGGCAGCACTGGCGATAAGACACACACTT

GCCCCCCTTGTCCAGCACCAGAGGCAGCTGGAGGACCAAGCGT

GTTCCTGTTTCCACCCAAGCCTAAAGACACACTGATGATCTCA

AGGACCCCAGAAGTCACATGCGTGGTCGTGGACGTGTCTCACG

AGGACCCCGAAGTCAAGTTCAACTGGTACGTGGATGGCGTCGA

GGTGCATAATGCTAAGACCAAACCCCGAGAGGAACAGTACAAC

AGCACCTATCGGGTCGTGTCCGTCCTGACAGTGCTGCACCAGG

ATTGGCTGAACGGCAAAGAGTATAAGTGCAAAGTGAGTAATAA

GGCTCTGCCTGCACCAATCGAGAAAACAATTTCTAAGGCTAAA

GGGCAGCCAAGAGAACCCCAGGTGTACACTCTGCCTCCATCTA

GGGAGGAAATGACAAAGAACCAGGTCAGTCTGACTTGTCTGGT

GAAAGGCTTCTACCCCTCCGACATCGCAGTGGAGTGGGAATCT

AATGGCCAGCCTGAAAACAATTACAAGACCACACCCCCTGTGC

TGGACTCCGATGGGTCTTTCTTTCTGTATTCTAAGCTGACCGT

GGATAAAAGTCGGTGGCAGCAGGGAAACGTCTTCTCATGCAGC

GTGATGCACGAGGCCCTGCACAATCATTACACACAGAAGTCCC

TGTCTCTGAGTCCAGGCAAAGGTAGCCAGCGGCCCCGGCTGTG

CCACAAGGGCCCCATGTGCTAAGAATTC (SEQ ID NO: 111)

Ex 17 GCTAGCCACCATGGAAACTGACACCCTGCTGCTGTGGGTCCTG

CTGCTGTGGGTGCCTGGCAGCACTGGCGATAAGACACACACTT

GCCCCCCTTGTCCAGCACCAGAGGCAGCTGGAGGACCAAGCGT

GTTCCTGTTTCCACCCAAGCCTAAAGACACACTGATGATCTCA

AGGACCCCAGAAGTCACATGCGTGGTCGTGGACGTGTCTCACG

AGGACCCCGAAGTCAAGTTCAACTGGTACGTGGATGGCGTCGA

GGTGCATAATGCTAAGACCAAACCCCGAGAGGAACAGTACAAC

AGCACCTATCGGGTCGTGTCCGTCCTGACAGTGCTGCACCAGG

ATTGGCTGAACGGCAAAGAGTATAAGTGCAAAGTGAGTAATAA

GGCTCTGCCTGCACCAATCGAGAAAACAATTTCTAAGGCTAAA

GGGCAGCCAAGAGAACCCCAGGTGTACACTCTGCCTCCATCTA

GGGAGGAAATGACAAAGAACCAGGTCAGTCTGACTTGTCTGGT

GAAAGGCTTCTACCCCTCCGACATCGCAGTGGAGTGGGAATCT

AATGGCCAGCCTGAAAACAATTACAAGACCACACCCCCTGTGC

TGGACTCCGATGGGTCTTTCTTTCTGTATTCTAAGCTGACCGT

GGATAAAAGTCGGTGGCAGCAGGGAAACGTCTTCTCATGCAGC

GTGATGCACGAGGCCCTGCACAATCATTACACACAGAAGTCCC

TGTCTCTGAGTCCAGGCAAAGGTGGCCAGCGGCCCCGGCTGTG

CCACAAGGGCCCCATGTGCTAAGAATTC (SEQ ID NO: 112)

Ex 18 GCTAGCCACCATGGAAACTGACACCCTGCTGCTGTGGGTCCTG

CTGCTGTGGGTGCCTGGCAGCACTGGCGATAAGACACACACTT

GCCCCCCTTGTCCAGCACCAGAGGCAGCTGGAGGACCAAGCGT

GTTCCTGTTTCCACCCAAGCCTAAAGACACACTGATGATCTCA

AGGACCCCAGAAGTCACATGCGTGGTCGTGGACGTGTCTCACG

AGGACCCCGAAGTCAAGTTCAACTGGTACGTGGATGGCGTCGA

GGTGCATAATGCTAAGACCAAACCCCGAGAGGAACAGTACAAC

AGCACCTATCGGGTCGTGTCCGTCCTGACAGTGCTGCACCAGG

ATTGGCTGAACGGCAAAGAGTATAAGTGCAAAGTGAGTAATAA

GGCTCTGCCTGCACCAATCGAGAAAACAATTTCTAAGGCTAAA

GGGCAGCCAAGAGAACCCCAGGTGTACACTCTGCCTCCATCTA

GGGAGGAAATGACAAAGAACCAGGTCAGTCTGACTTGTCTGGT

GAAAGGCTTCTACCCCTCCGACATCGCAGTGGAGTGGGAATCT

AATGGCCAGCCTGAAAACAATTACAAGACCACACCCCCTGTGC

TGGACTCCGATGGGTCTTTCTTTCTGTATTCTAAGCTGACCGT

GGATAAAAGTCGGTGGCAGCAGGGAAACGTCTTCTCATGCAGC

GTGATGCACGAGGCCCTGCACAATCATTACACACAGAAGTCCC

TGTCTCTGAGTCCAGGCAAAGGTGGCGGAGGCAGCCAGCGGCC

CCGGCTGTGCCACAAGGGCCCCATGTGCTAAGAATTC (SEQ ID NO: 113)

Ex 19 GCTAGCCACCATGGAAACTGACACCCTGCTGCTGTGGGTCCTG

CTGCTGTGGGTGCCTGGCAGCACTGGCGATAAGACACACACTT

GCCCCCCTTGTCCAGCACCAGAGGCAGCTGGAGGACCAAGCGT

GTTCCTGTTTCCACCCAAGCCTAAAGACACACTGATGATCTCA

AGGACCCCAGAAGTCACATGCGTGGTCGTGGACGTGTCTCACG

AGGACCCCGAAGTCAAGTTCAACTGGTACGTGGATGGCGTCGA

GGTGCATAATGCTAAGACCAAACCCCGAGAGGAACAGTACAAC

AGCACCTATCGGGTCGTGTCCGTCCTGACAGTGCTGCACCAGG

ATTGGCTGAACGGCAAAGAGTATAAGTGCAAAGTGAGTAATAA

-continued

```
         GGCTCTGCCTGCACCAATCGAGAAAACAATTTCTAAGGCTAAA
         GGGCAGCCAAGAGAACCCCAGGTGTACACTCTGCCTCCATCTA
         GGGAGGAAATGACAAAGAACCAGGTCAGTCTGACTTGTCTGGT
         GAAAGGCTTCTACCCCTCCGACATCGCAGTGGAGTGGGAATCT
         AATGGCCAGCCTGAAAACAATTACAAGACCACACCCCCTGTGC
         TGGACTCCGATGGGTCTTTCTTTCTGTATTCTAAGCTGACCGT
         GGATAAAAGTCGGTGGCAGCAGGGAAACGTCTTCTCATGCAGC
         GTGATGCACGAGGCCCTGCACAATCATTACACACAGAAGTCCC
         TGTCTCTGAGTCCAGGCAAAGGTGGCGGAGGCAGCCAGCGGCC
         CCGGCTGTGCCACAAGGGCCCCATGTGCTAAGAATTC
         (SEQ ID NO: 114)
Ex 20    GCTAGCCACCATGGAAACTGACACCCTGCTGCTGTGGGTCCTG
         CTGCTGTGGGTGCCTGGCAGCACTGGCGCTCATGATAAGACAC
         ACACATGCCCCCCTTGTCCAGCACCAGAGGCAGCTGGAGGACC
         AAGCGTGTTCCTGTTTCCACCCAAGCCTAAAGACACACTGATG
         ATCTCAAGGACCCCAGAAGTCACATGCGTGGTCGTGGACGTGT
         CTCACGAGGACCCCGAAGTCAAGTTCAACTGGTACGTGGATGG
         CGTCGAGGTGCATAATGCTAAGACCAAACCCCGAGAGGAACAG
         TACAACAGCACCTATCGGGTCGTGTCCGTCCTGACAGTGCTGC
         ACCAGGATTGGCTGAACGGCAAAGAGTATAAGTGCAAAGTGAG
         TAATAAGGCTCTGCCTGCACCAATCGAGAAAACAATTTCTAAG
         GCTAAAGGGCAGCCAAGAGAACCCCAGGTGTACACTCTGCCTC
         CATCTAGGGAGGAAATGACAAAGAACCAGGTCAGTCTGACTTG
         TCTGGTGAAAGGCTTCTACCCCTCCGACATCGCAGTGGAGTGG
         GAATCTAATGGCCAGCCTGAAAACAATTACAAGACCACACCCC
         CTGTGCTGGACTCCGATGGGTCTTTCTTTCTGTATTCTAAGCT
         GACCGTGGATAAAAGTCGGTGGCAGCAGGGAAACGTCTTCTCA
         TGCAGCGTGATGCACGAGGCCCTGCACAATCATTACACACAGA
         AGTCCCTGTCTCTGAGTCCAGGCAAATGAGAATTC
         (SEQ ID NO: 115)
```

Example 9

Fc-apelin Fusion

```
  1 METDTLLLWV LLLWVPGSTG DKTHTCPPCP APEAAGGPSV
    FLFPPKPKDT
 51 LMISRTPEVT CVVVDVSHED PEVKFNWYVD GVEVHNAKTK
    PREEQYNSTY
101 RVVSVLTVLH QDWLNGKEYK CKVSNKALPA PIEKTISKAK
    GQPREPQVYT
151 LPPSREEMTK NQVSLTCLVK GFYPSDIAVE WESNGQPENN
    YKTTPPVLDS
201 DGSFFLYSKL TVDKSRWQQG NVFSCSVMHE ALHNHYTQKS
    LSLSPGA*GGG*
251 *GSGGGGSGGGGS*QRPRLC*HKGPMC*F (SEQ ID NO: 116)
``` wherein GGGGSGGGGSGGGGS (SEQ ID NO: 11) represents the linker and QRPRLC*HKGPMC*F (SEQ ID NO:17) is the polypeptide.

Example 10

Fc-apelin Fusion

```
  1 METDTLLLWV LLLWVPGSTG DKTHTCPPCP APEAAGGPSV
    FLFPPKPKDT
 51 LMISRTPEVT CVVVDVSHED PEVKFNWYVD GVEVHNAKTK
    PREEQYNSTY
101 RVVSVLTVLH QDWLNGKEYK CKVSNKALPA PIEKTISKAK
    GQPREPQVYT
151 LPPSREEMTK NQVSLTCLVK GFYPSDIAVE WESNGQPENN
    YKTTPPVLDS
201 DGSFFLYSKL TVDKSRWQQG NVFSCSVMHE ALHNHYTQKS
    LSLSPG*GGGG*
251 *SGGGGSGGGGS*QRPRLC*HKGPMC*F (SEQ ID NO: 117)
``` wherein GGGGSGGGGSGGGGS (SEQ ID NO: 11) represents the linker and QRPRLC*HKGPMC*F (SEQ ID NO: 17) is the polypeptide.

Example 11

Fc-apelin Fusion

```
  1 METDTLLLWV LLLWVPGSTG DKTHTCPPCP APEAAGGPSV
    FLFPPKPKDT
 51 LMISRTPEVT CVVVDVSHED PEVKFNWYVD GVEVHNAKTK
    PREEQYNSTY
101 RVVSVLTVLH QDWLNGKEYK CKVSNKALPA PIEKTISKAK
    GQPREPQVYT
151 LPPSREEMTK NQVSLTCLVK GFYPSDIAVE WESNGQPENN
    YKTTPPVLDS
201 DGSFFLYSKL TVDKSRWQQG NVFSCSVMHE ALHNHYTQKS
    LSLSPGK*GS*Q
251 RPRLC*HKGPMC*F (SEQ ID NO: 118)
``` wherein GS represents the linker and QRPRLC*HKGPMC*F (SEQ ID NO: 17) is the polypeptide.

Example 12

Fc-apelin Fusion

```
  1 METDTLLLWV LLLWVPGSTG DKTHTCPPCP APEAAGGPSV
    FLFPPKPKDT

51 LMISRTPEVT CVVVDVSHED PEVKFNWYVD GVEVHNAKTK
    PREEQYNSTY

101 RVVSVLTVLH QDWLNGKEYK CKVSNKALPA PIEKTISKAK
    GQPREPQVYT

151 LPPSREEMTK NQVSLTCLVK GFYPSDIAVE WESNGQPENN
    YKTTPPVLDS

201 DGSFFLYSKL TVDKSRWQQG NVFSCSVMHE ALHNHYTQKS
    LSLSPGKGGQ

251 RPRLC*HKGPMC*F (SEQ ID NO: 119)
``` wherein GG represents the linker and QRPRLC*HKGPMC*F (SEQ ID NO 17) is the polypeptide.

Example 13

Fc-apelin Fusion

```
  1 METDTLLLWV LLLWVPGSTG DKTHTCPPCP APEAAGGPSV
    FLFPPKPKDT

51 LMISRTPEVT CVVVDVSHED PEVKFNWYVD GVEVHNAKTK
    PREEQYNSTY

101 RVVSVLTVLH QDWLNGKEYK CKVSNKALPA PIEKTISKAK
    GQPREPQVYT

151 LPPSREEMTK NQVSLTCLVK GFYPSDIAVE WESNGQPENN
    YKTTPPVLDS

201 DGSFFLYSKL TVDKSRWQQG NVFSCSVMHE ALHNHYTQKS
    LSLSPGKGGG

251 GSQRPRLC*HKGPMC*F (SEQ ID NO: 120)
``` wherein GGGGS (SEQ ID NO: 13) represents the linker and QRPRLC*HKGPMC*F (SEQ ID NO 17) is the polypeptide.

Example 14

Fc-apelin Fusion

```
  1 METDTLLLWV LLLWVPGSTG DKTHTCPPCP APEAAGGPSV
    FLFPPKPKDT

51 LMISRTPEVT CVVVDVSHED PEVKFNWYVD GVEVHNAKTK
    PREEQYNSTY

101 RVVSVLTVLH QDWLNGKEYK CKVSNKALPA PIEKTISKAK
    GQPREPQVYT

151 LPPSREEMTK NQVSLTCLVK GFYPSDIAVE WESNGQPENN
    YKTTPPVLDS

201 DGSFFLYSKL TVDKSRWQQG NVFSCSVMHE ALHNHYTQKS
    LSLSPGKGGG

251 GSGGGGSGGGGSQRPRLC*HKGPMC* (SEQ ID NO: 121)
``` wherein GGGGS GGGGS GGGGS (SEQ ID NO: 11) represents the linker and QRPRLC*HKGPMC* (SEQ ID NO: 18) is the polypeptide.

Example 15

Fc-apelin Fusion

```
  1 METDTLLLWV LLLWVPGSTG DKTHTCPPCP APEAAGGPSV
    FLFPPKPKDT

51 LMISRTPEVT CVVVDVSHED PEVKFNWYVD GVEVHNAKTK
    PREEQYNSTY

101 RVVSVLTVLH QDWLNGKEYK CKVSNKALPA PIEKTISKAK
    GQPREPQVYT

151 LPPSREEMTK NQVSLTCLVK GFYPSDIAVE WESNGQPENN
    YKTTPPVLDS

201 DGSFFLYSKL TVDKSRWQQG NVFSCSVMHE ALHNHYTQKS
    LSLSPGAGGG

251 GSGGGGSGGGGSQRPRLC*HKGPMC* (SEQ ID NO: 122)
``` wherein GGGGS GGGGS GGGGS (SEQ ID NO: 11) represents the linker and QRPRLC*HKGPMC* (SEQ ID NO: 18) is the polypeptide.

Example 16

Fc-apelin Fusion

```
  1 METDTLLLWV LLLWVPGSTG DKTHTCPPCP APEAAGGPSV
    FLFPPKPKDT

51 LMISRTPEVT CVVVDVSHED PEVKFNWYVD GVEVHNAKTK
    PREEQYNSTY

101 RVVSVLTVLH QDWLNGKEYK CKVSNKALPA PIEKTISKAK
    GQPREPQVYT

151 LPPSREEMTK NQVSLTCLVK GFYPSDIAVE WESNGQPENN
    YKTTPPVLDS

201 DGSFFLYSKL TVDKSRWQQG NVFSCSVMHE ALHNHYTQKS
    LSLSPGGGGG

251 SGGGGSGGGGSQRPRLC*HKGPMC* (SEQ ID NO: 123)
``` wherein GGGGS GGGGS GGGGS (SEQ ID NO: 11) represents the linker and QRPRLC*HKGPMC* (SEQ ID NO: 18) is the polypeptide.

Example 17

Fc-apelin Fusion

```
  1 METDTLLLWV LLLWVPGSTG DKTHTCPPCP APEAAGGPSV
    FLFPPKPKDT

51 LMISRTPEVT CVVVDVSHED PEVKFNWYVD GVEVHNAKTK
    PREEQYNSTY

101 RVVSVLTVLH QDWLNGKEYK CKVSNKALPA PIEKTISKAK
    GQPREPQVYT

151 LPPSREEMTK NQVSLTCLVK GFYPSDIAVE WESNGQPENN
    YKTTPPVLDS

201 DGSFFLYSKL TVDKSRWQQG NVFSCSVMHE ALHNHYTQKS
    LSLSPGKGSQ

251 RPRLC*HKGPMC* (SEQ ID NO: 124)
``` wherein GS represents the linker and QRPRLC*HKGPMC* (SEQ ID NO: 18) is the polypeptide.

Example 18

Fc-apelin Fusion

```
  1 METDTLLLWV LLLWVPGSTG DKTHTCPPCP APEAAGGPSV
    FLFPPKPKDT

51 LMISRTPEVT CVVVDVSHED PEVKFNWYVD GVEVHNAKTK
    PREEQYNSTY

101 RVVSVLTVLH QDWLNGKEYK CKVSNKALPA PIEKTISKAK
    GQPREPQVYT

151 LPPSREEMTK NQVSLTCLVK GFYPSDIAVE WESNGQPENN
    YKTTPPVLDS

201 DGSFFLYSKL TVDKSRWQQG NVFSCSVMHE ALHNHYTQKS
    LSLSPGKGGQ

251 RPRLC*HKGPMC* (SEQ ID NO: 125)
``` wherein GG represents the linker and QRPRLC*HKGPMC* (SEQ ID NO: 18) is the polypeptide.

Example 19

Fc-apelin Fusion

```
  1 METDTLLLWV LLLWVPGSTG DKTHTCPPCP APEAAGGPSV
    FLFPPKPKDT

51 LMISRTPEVT CVVVDVSHED PEVKFNWYVD GVEVHNAKTK
    PREEQYNSTY

101 RVVSVLTVLH QDWLNGKEYK CKVSNKALPA PIEKTISKAK
    GQPREPQVYT

151 LPPSREEMTK NQVSLTCLVK GFYPSDIAVE WESNGQPENN
    YKTTPPVLDS

201 DGSFFLYSKL TVDKSRWQQG NVFSCSVMHE ALHNHYTQKS
    LSLSPGKGGG

251 GSQRPRLC*HKGPMC* (SEQ ID NO: 126)
``` wherein GGGGS (SEQ ID NO: 13) represents the linker and QRPRLC*HKGPMC* (SEQ ID NO: 18) is the polypeptide.

Example 20

Apelin Cyclic Peptide Conjugated to a Fatty Acid Via a BCN-PEG Linker

Step 1: Apelin Peptide-BCN Linker (BCN is ((1R,8S,9s)-Bicyclo[6.1.0]non-4-yn-9-ylmethyl N-carbonate)

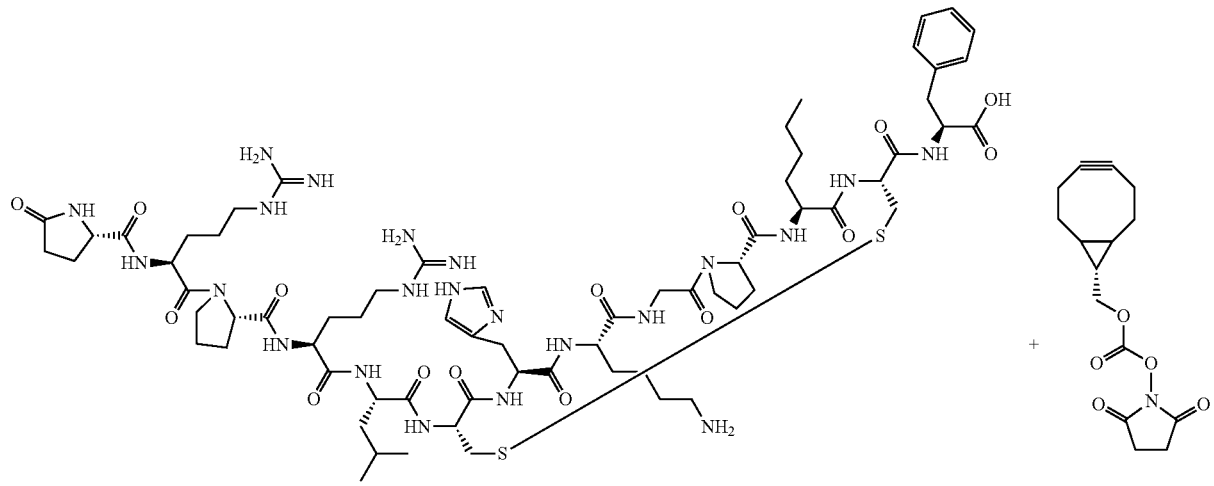

-continued

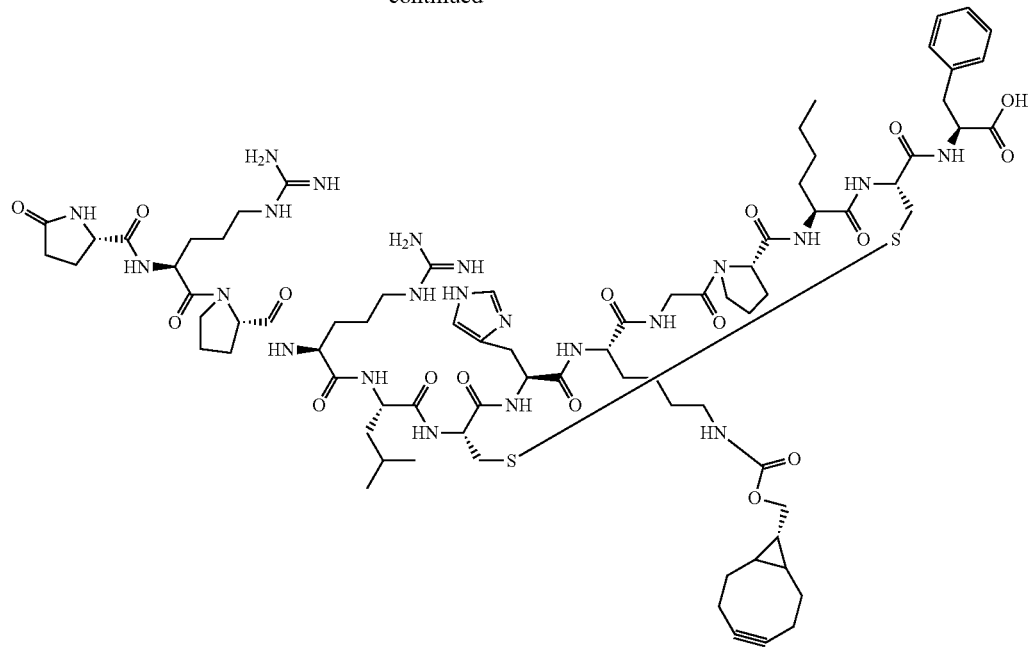

A mixture of pE-R-P-R-L-C*-H-K-G-P-Nle-C*-F-OH (Disulfide $C^6$-$C^{12}$) (SEQ ID NO: 30) 50 mg, 0.033 mmol, as prepared in U.S. Pat. No. 8,673,848), sodium bicarbonate (18 mg, 0.215 mmol) and water (40 uL) in DMF (0.5 mL) was stirred at RT for 10 mins, then (1R,8S)-bicyclo[6.1.0]non-4-yn-9-ylmethyl succinimidyl carbonate (Berry &associates, 18 mg, 0.065 mmol) was added. The reaction mixture was stirred at RT for 90 mins. A mixture of +1 and +2 additions was observed by LCMS, so mixture was purified by mass triggered HPLC (Peptide Method 5 25-50% ACN 5 min gradient: Conditions: Sunfire 30×50 mm 5 um column ACN/H$_2$O w/0.1% TFA 75 ml/min 1.5 ml injection): rt 3.2 min (+1), rt 4.65 min, 4.9min (+1 and +2 mixture). LCMS confirms desired +1 product in 61% yield and +1, +2 mixture in 18% yield. LCMS: (Basic Eluent A: Water+5 mM Ammonium Hydroxide Eluent B: ACN Acidic Column: Sunfire C18 3.5 μm 3.0×30 mm-40° C. Basic Column: XBridge C18 3.5 μm 3.0×30 mm-40° C.) Retention time: 0.98 mins; MS $[M+2]^{2+}$: observed: 856.0, calculated: 865.0245.

Step 2: Di-tert-butyl 2-(undec-10-yn-1-yl)malonate

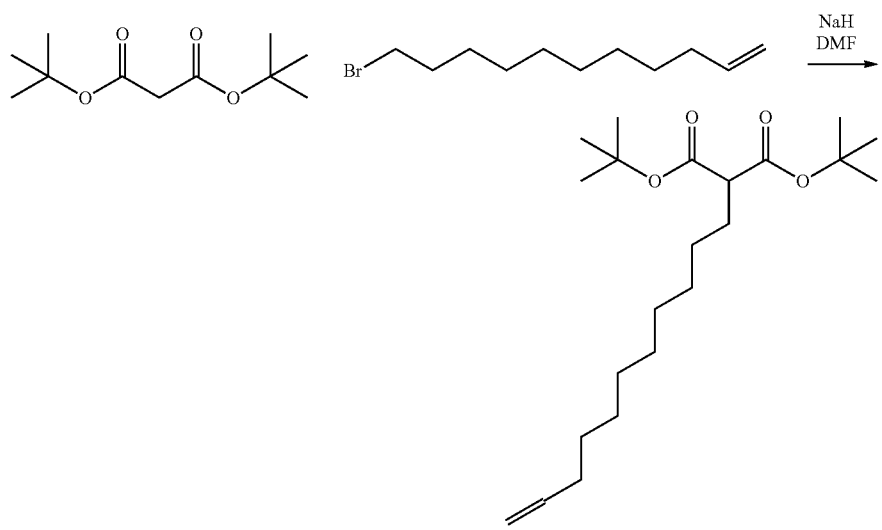

Di-tert-butyl malonate (800 mg, 3.70 mmol) is dissolved in DMF (9 mL) at 0° C. under N$_2$ and NaH (148 mg, 3.70 mmol) is added. The reaction is stirred 30 minutes at 0° C. and 11-bromo-dec-1-ene (3.33 mmol) is added slowly dropwise, resulting in a yellow solution. The reaction is stirred at 0° C. for 2 hours then warmed to r.t. and stirred for 16 hours. The mixture is taken up in EtOAc (75 mL) and washed with H$_2$O (25 mL). The aqueous layer is extracted with EtOAc (75 mL) and the combined organic layers are dried over Na₂SO₄, filtered and concentrated. The mixture is purified via flash column (12 g silica cartridge, 0-20% EtOAc/heptanes) and fractions are concentrated to yield the desired product.

Step 3: 11,11-di-tert-butyl 1-ethyl docos-21-ene-1,11,11-tricarboxylate

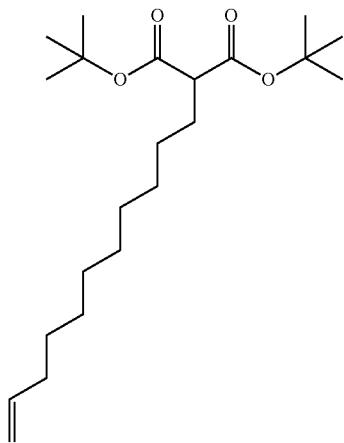

+

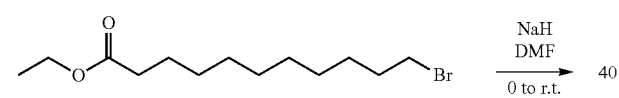

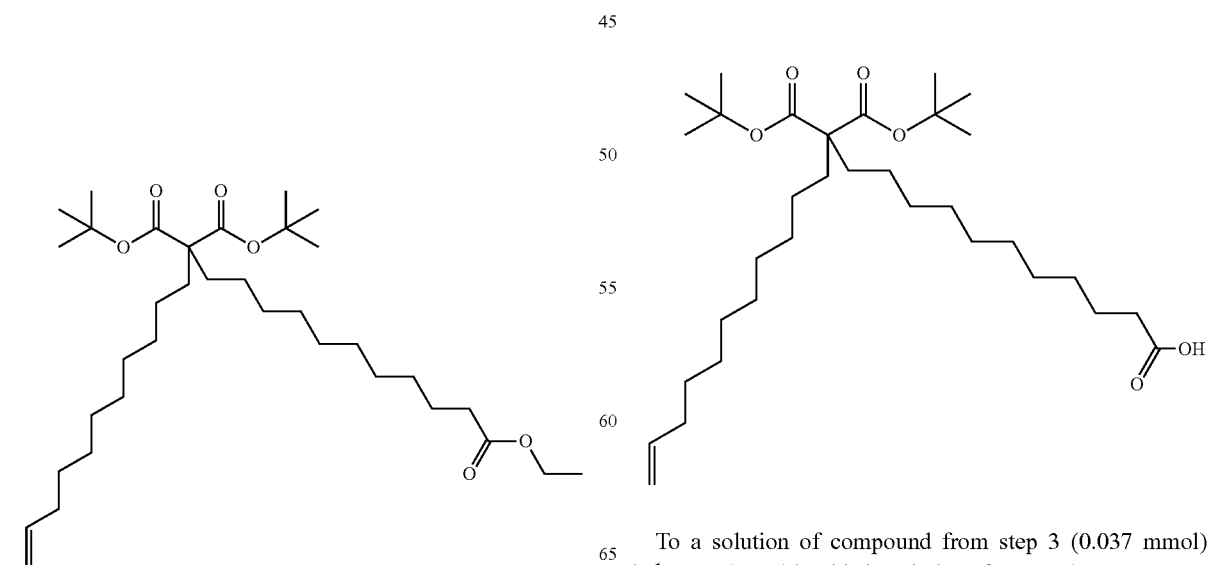

Compound from step 2 (0.442 mmol) is dissolved in DMF (2 mL) at 0° C. and NaH (21.23 mg, 0.531 mmol) is added. The reaction stirred at 0° C. for 15 minutes and ethyl 11-bromoundecanoate (143 mg, 0.486 mmol) is added slowly dropwise. The reaction is warmed to r.t. and stirred for 16 hours. The mixture is diluted with EtOAc (40 mL) and washed once with H₂O (20 mL). The aqueous layer is extracted once with EtOAc (40 mL) and the organic layers are combined, dried over Na₂SO₄, filtered and concentrated. The sample is dissolved in 1 mL DCM and purified via flash column (12 g silica column, 0-20% EtOAc/heptane, 15 min). The fractions are combined and concentrated to give the desired product.

Step 4: 12,12-bis(tert-butoxycarbonyl)tricos-22-enoic acid

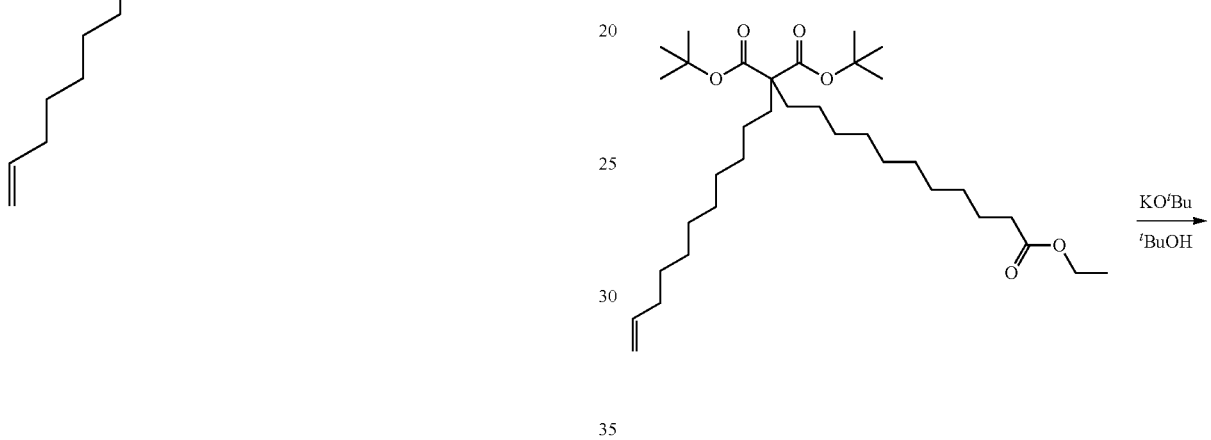

To a solution of compound from step 3 (0.037 mmol) in ᵗBuOH (1 mL) is added a solution of KOtBu (114 mg, 1.012 mmol) in ᵗBuOH (2 mL) at 30° C. under N2. The mixture is stirred at r.t. and monitored by TLC (1:1 EtOAc/hexanes, KMnO₄, reflux). After the reaction is completed, the reaction mixture is quenched with 1 M HCl (20 mL) and extracted twice with EtOAc (25 mL). The organic layers are combined, dried over Na₂SO₄, filtered and concentrated. The material was carried on to the next step without further purification.

Step 5: Docos-21-ene-1,11,11-tricarboxylic acid

Step 6: 2-(((2,5-Dioxopyrrolidin-1-yl)oxy)carbonyl)-2-(undec-10-en-1-yl)tridecanedioic acid

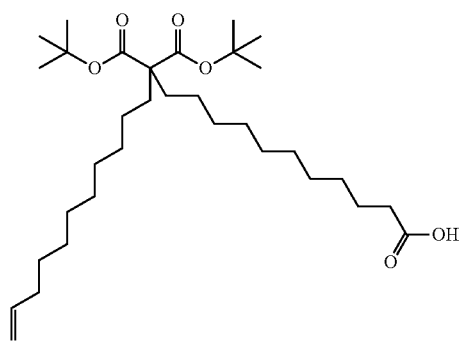

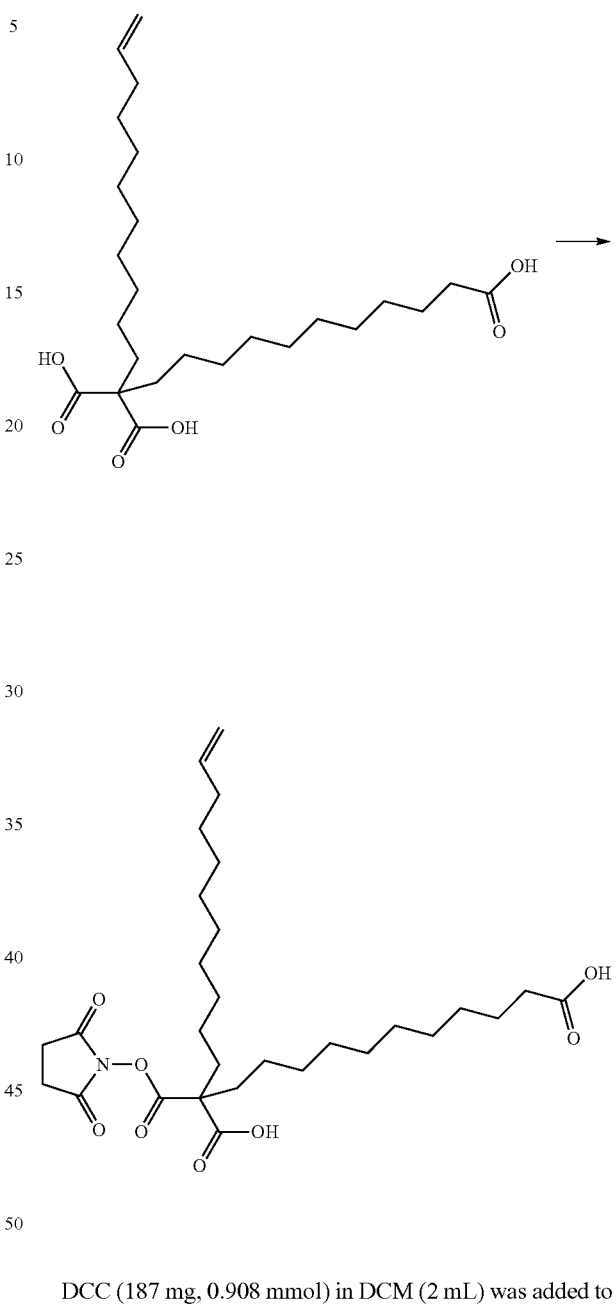

TFA (2 mL) is added to a compound from step 4 (0.022 mmol) and the reaction is stirred at r.t. for 1 hour. The mixture is diluted with DCM (10 mL) and concentrated. The material is taken up in EtOAc (10 mL) and washed with H₂O (20 mL). The organic layer is dried over Na₂SO₄, filtered and concentrated. The crude material is dissolved in 1 mL MeOH and purified via MS-triggered HPLC (Sunfire 30×50 mm 5 um column ACN/H2O w/0.1% TFA 75 ml/min, 1.5 ml injection, 45-70% ACN over 3.5 min).

DCC (187 mg, 0.908 mmol) in DCM (2 mL) was added to a solution of N-hydroxysuccinimide (99 mg, 0.862 mmol) and docos-21-ene-1,11,11-tricarboxylic acid (Intermediate 45: 400 mg, 0.908 mmol) in DCM (7 mL) and THF (0.7 mL). The reaction was stirred overnight before the solvent was evaporated. The residue was purified by HPLC (Sunfire C18 30×50 mm; 55-80% ACN/water+0.1% TFA) to yield the title compound (155 mg, 0.288 mmol, 32%): by LCMS Method D Rt=1.51 min, M+H 538.3; ¹H NMR (400 MHz, CHLOROFORM-d) δ ppm 1.16-1.46 (m, 28 H) 1.60-1.87 (m, 3 H) 1.91-2.17 (m, 5 H) 2.38 (t, J=7.03 Hz, 2 H) 2.86 (br. s., 4 H) 3.68 (dd, J=11.25, 7.34 Hz, 1 H) 3.78 (dd, J=11.31, 5.20 Hz, 1 H) 3.99-4.10 (m, 1 H).

Step 7: Fatty Acid-PEG Linker

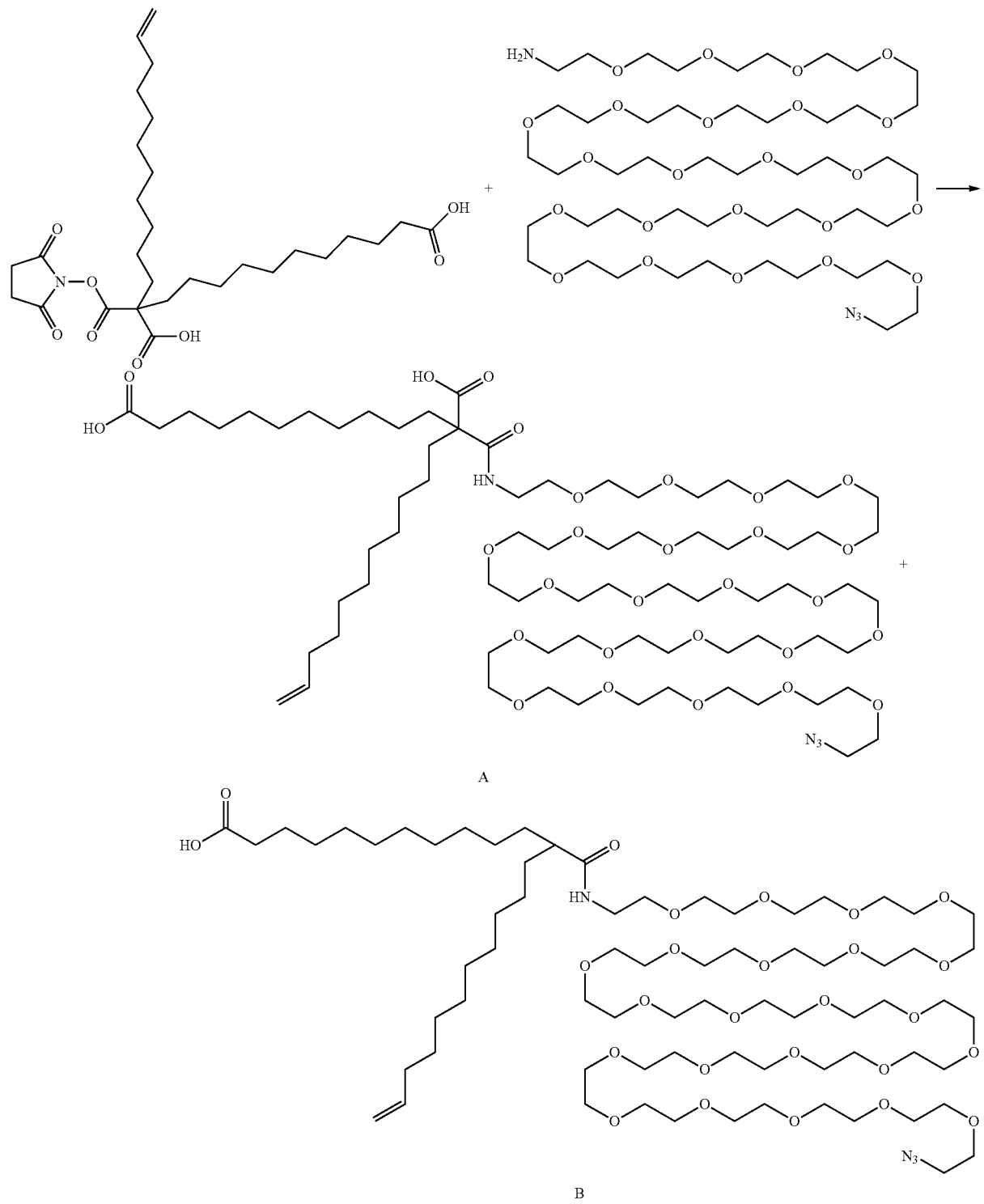

Azido-dPEG23-amine (Quanta Biodesign: 164 mg, 0.149 mmol) and compound from step 6 (80 mg, 0.149 mmol) were dissolved in THF (2.5 mL). DIPEA (39 µL, 0.233 mmol) was added and the reaction agitated overnight. The solvent was evaporated and the residue purified by HPLC (Sunfire C18 30×50 mm; 45-70% ACN/water+0.1% TFA) to yield compounds A (97 mg, 0.061 mmol, 41%) and B (32 mg, 0.021 mmol, 14%): LCMS Method D Rt=1.35 min, $[M+2H]^{+2}$ 761.9; $^1$H NMR (400 MHz, ACETONITRILE-d3) δ ppm 1.05-1.18 (m, 3 H) 1.19-1.32 (m, 20 H) 1.36 (t, J=7.15 Hz, 1 H) 1.48-1.59 (m, 2 H) 1.65-1.75 (m, 2 H) 2.01-2.06 (m, 2 H) 2.25 (t, J=7.46 Hz, 2 H) 3.33-3.39 (m, 2 H) 3.39-3.44 (m, 2 H)

129
3.50-3.67 (m, 98 H) 4.84-4.95 (m, 1 H) 4.95-5.06 (m, 1 H) 5.83 (ddt, J=17.07, 10.29, 6.68, 6.68 Hz, 1 H) 7.31 (t, J=5.44 Hz, 1 H); LCMS method D Rt=1.50 min, [M+2H]$^{+2}$ 739.9; $^1$H NMR (400 MHz, ACETONITRILE-d3) δ ppm 1.16-1.42 (m, 30 H) 1.42-1.63 (m, 5 H) 2.00-2.07 (m, 2 H) 2.22-2.28 (m, 2 H) 2.40-2.52 (m, 2 H) 3.25-3.33 (m, 2 H) 3.33-3.42 (m, 2 H) 3.42-3.50 (m, 2 H) 3.50-3.68 (m, 88 H) 4.86-5.06 (m, 2 H) 5.83 (ddt, J=17.04, 10.26, 6.71, 6.71 Hz, 1 H) 6.40-6.74 (m, 1 H).
130
Step 8
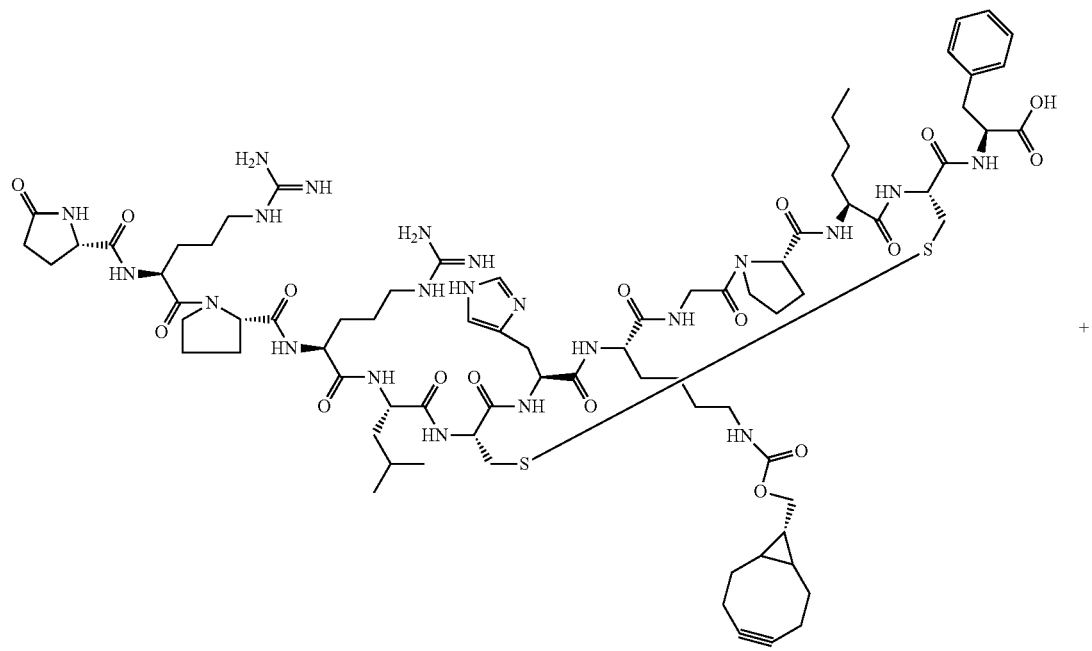
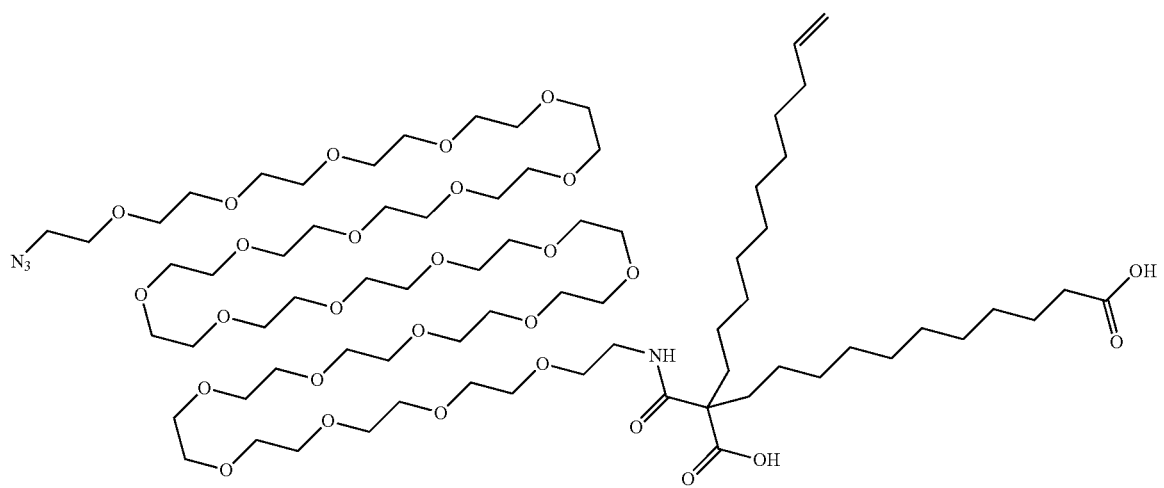

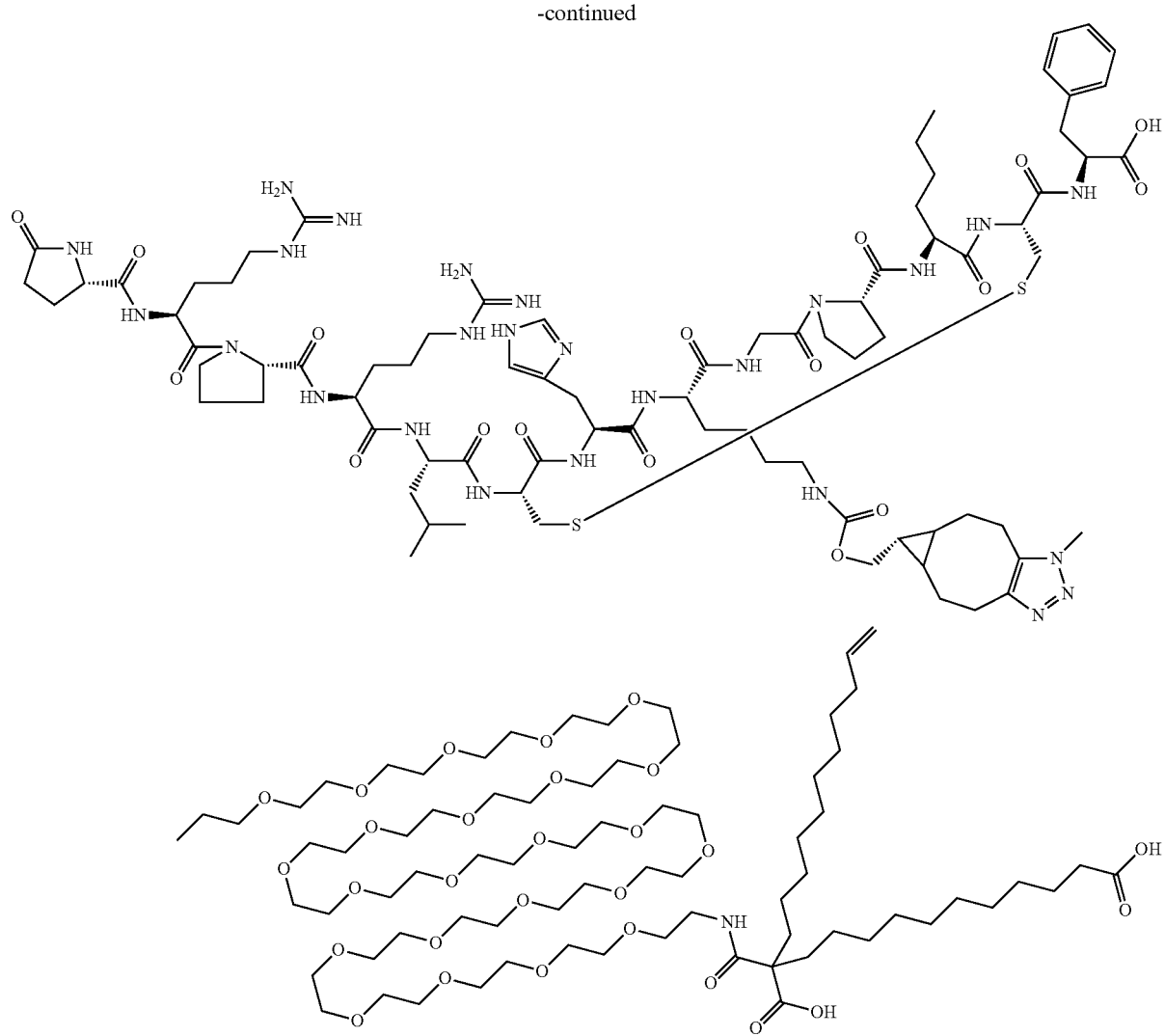

Example 20

A mixture of pE-R-P-R-L-C*-H-$N^6$-[[(1α,8α,9α)-bicyclo[6.1.0]non-4-yn-9-ylmethoxy]carbonyl]-K-G-P-Nle-C*-F-OH(Disulfide $C^6$-$C^{12}$) (SEQ ID NO: 127) (21.33 mg, 0.014 mmol) and compound from step 7 (24 mg, 0.014 mmol) was stirred at RT for about 3 hrs. The reaction was complete by LCMS and was lyophilized to give the titled product (23 mg, 48%). LCMS (Waters Acquity UPLC BEH C18 1.7 um 2.1× 50 mm, 50° C., Eluent A: Water+0.1% Formic Acid, Eluent B: Acetonitrile+0.1% Formic Acid, gradient 2% to 98% B/A over 5.15 mins): Retention time: 2.22 mins; MS $[M+2]^{2+}$: observed: 1616.9464, calculated: 1616.976.

Example 21

Fc Conjugation to a APJ Peptide Using Sortase and Sortase Recognition Motif

General Scheme (SEQ ID NOS 128, 128, 129, 130, and 130, respectively, in order of appearance):

General Scheme (SEQ ID NOS 128, 128, 129, 130, and 130, respectively, in order of appearance):

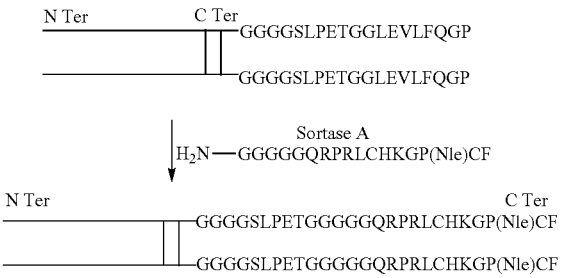

Step 1: Preparation of Fc-Sortase Construct

Construct Cloning:

A DNA fragment containing the mouse Ig kappa chain signal peptide followed by a human Fc and a sortase recognition sequence (LPXTG) (SEQ ID NO: 131) was codon optimized by gene synthesis (GeneArt) with 5'-NheI and 3'-EcoRI restriction sites. The resulting sequence was restric- Fc-Sortase

```
GCTAGCCACCATGGAAACCGACACCCTGCTGCTGTGGGTGCTGCTGCTG

TGGGTGCCAGGCAGCACCGGCGATAAGACCCACACCTGTCCTCCCTGTC

CTGCCCCTGAAGCTGCTGGCGGCCCTAGCGTGTTCCTGTTCCCCCCAAA

GCCCAAGGACACCCTGATGATCAGCCGGACCCCCGAAGTGACCTGCGTG

GTGGTGGATGTGTCCCACGAGGACCCTGAAGTGAAGTTCAATTGGTACG

TGGACGGCGTGGAAGTGCACAACGCCAAGACCAAGCCCAGAGAGGAACA

GTACAACAGCACCTACCGGGTGGTGTCCGTGCTGACCGTGCTGCACCAG

GACTGGCTGAACGGCAAAGAGTACAAGTGCAAGGTGTCCAACAAGGCCC

TGCCAGCCCCCATCGAGAAAACCATCAGCAAGGCCAAGGGCCAGCCCCG

CGAACCCCAGGTGTACACACTGCCCCCTAGCCGGGAAGAGATGACCAAG

AACCAGGTGTCCCTGACCTGTCTCGTGAAGGGCTTCTACCCCTCCGATA

TCGCCGTGGAATGGGAGAGCAACGGCCAGCCCGAGAACAACTACAAGAC

CACCCCCCCTGTGCTGGACAGCGACGGCTCATTCTTCCTGTACAGCAAG

CTGACAGTGGACAAGAGCCGGTGGCAGCAGGGCAACGTGTTCAGCTGCA

GCGTGATGCACGAGGCCCTGCACAACCACTACACCCAGAAGTCCCTGAG

CCTGAGCCCTGGAAAAGGCGGCGGAGGCTCTCTGCCTGAAACAGGCGGA

CTGGAAGTGCTGTTCCAGGGCCCCTAAGAATTC (SEQ ID NO: 132)
```

Sequence of the Fc Sortase Construct:

```
  1 METDTLLLWV LLLWVPGSTG DKTHTCPPCP APEAAGGPSV
    FLFPPKPKDT

51 LMISRTPEVT CVVVDVSHED PEVKFNWYVD GVEVHNAKTK
    PREEQYNSTY

101 RVVSVLTVLH QDWLNGKEYK CKVSNKALPA PIEKTISKAK
    GQPREPQVYT

151 LPPSREEMTK NQVSLTCLVK GFYPSDIAVE WESNGQPENN
    YKTTPPVLDS

201 DGSFFLYSKL TVDKSRWQQG NVFSCSVMHE ALHNHYTQKS
    LSLSPGKGGG

251 GSLPETGGLEVLFQGP (SEQ ID NO: 133)
``` wherein GGGGS (SEQ ID NO: 13) represents the linker and LPETGGLEVLFQGP (SEQ ID NO: 134) the sortase recognition motif (note: the GGLEVLFQGP (SEQ ID NO: 15) is clipped during sortase treatment).

Protein Expression and Purification:

Fc-sortase expression plasmid DNA was transfected into HEK293T cells at a density of $1 \times 10^6$ cells per ml using standard polyethylenimine methods. 500 ml cultures were then grown in FreeStyle 293 Medium (Life Technologies) in 3 L flasks for 4 days at 37° C. Fc-sortase protein was purified from clarified conditioned media. Briefly, 500 ml of conditioned media was flowed over a 5 ml HiTrap MabSelect SuRe column (GE Life Sciences) at 4 ml/min. The column was washed with 20 column volumes of PBS containing 0.1% Triton X-114 and then the Fc-sortase protein was eluted with 0.1M glycine, pH 2.7, neutralized with 1 M Tris-HCl, pH 9 and dialyzed against PBS. Protein yields were 10 to 20 mg per 500 ml conditioned media and endotoxin levels were <1 EU/mg as measured by the Charles River ENDOSAFE PTS test.

Quality Control of Fc-sortase Protein

LC/MS of Native Fc-sortase Protein: Peak was heterogeneous and about 3 kDa larger than expected for dimers. This is characteristic of N-linked glycosylation expected for Fc which has a consensus N-linked glycosylation site.

LC/MS of Reduced, N-Deglycosylated Fc-sortase Protein: Peak was sharp. The molecular weight was 2 daltons less than theoretical, likely due to Cysteine ×2 reduction.

Analytical Size Exclusion on Superdex 200: Fc-sortase protein had between 89 and 100% dimer, 0 to 10% tetramer, and 0 to 1% aggregate.

Reducing SDS/PAGE: The protein migrated predominately as a monomer of the expected size.

Step 2: Preparation of Apelin Peptide H$_2$N-GGGGGQRPRLC*HKGP(Nle)C*F-COOH (SEQ ID NO: 129) for Sortase Conjugation

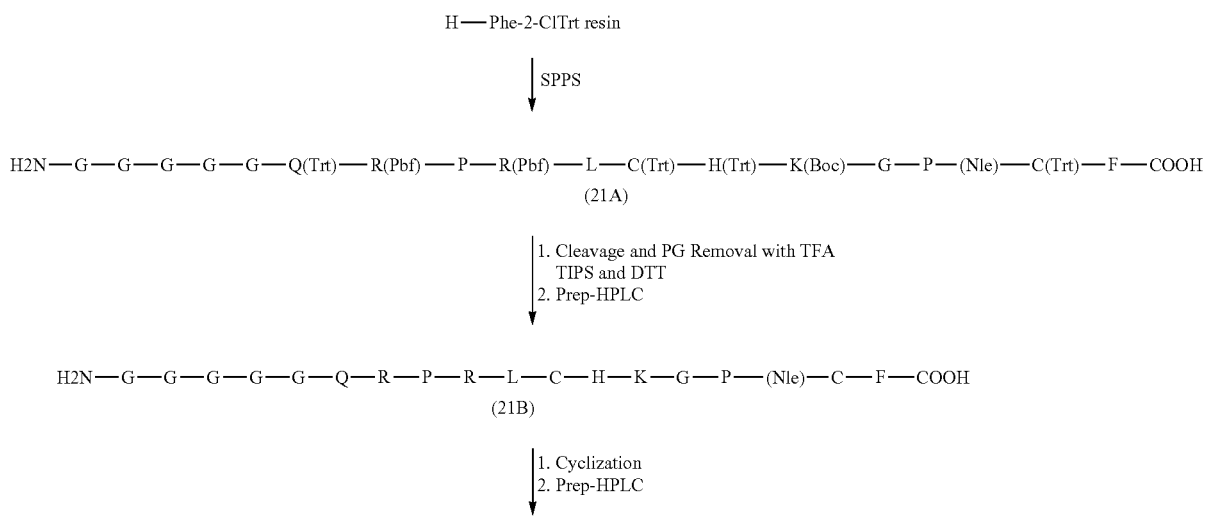

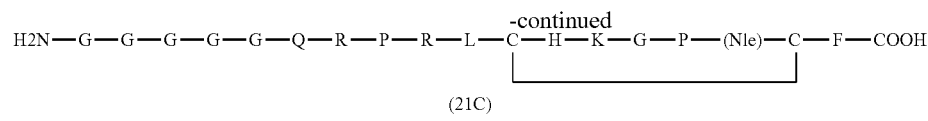

(21C)

(SEQ ID NOS 128, 128, 129, 130, and 130, respectively, in order of appearance)

Step 2a: Preparation of Intermediate 21A

Two batches of H-Phe-2-ClTrt resin (Novabiochem, 0.342 g, 0.25 mmol, 0.73 mmol/g) were subjected to solid phase peptide synthesis on an automatic peptide synthesizer (CEM LIBERTY) with standard double Arg for the Arg residues. Amino acids were prepared as 0.2 M solutions in DMF.

A coupling cycle was defined as follows:

Amino acid coupling: AA (4.0 eq.), HATU (4.0 eq.), DIEA (25 eq.)

Washing: DMF (3×10 mL, 1 min each time).

Fmoc deprotection: Piperidine/DMF (1:4) (10 mL, 75° C. for 1 min, then 10 mL, 75° C. for 3 min).

Washing: DMF (4×10 mL, 1 min each time).

| Coupling | AA | Number of couplings × Reaction time | Reaction Temperature |
|---|---|---|---|
| 1 | Fmoc-L-Cys(Trt)-OH | 1 × 6 min | 2 min at 25° C. 4 min at 50° C. |
| 2 | Fmoc-L-Nle-OH | 1 × 5 min | 75° C. |
| 3 | Fmoc-L-Pro-OH | 1 × 5 min | 75° C. |
| 4 | Fmoc-L-Gly-OH | 1 × 5 min | 75° C. |
| 5 | Fmoc-Lys(Boc)-OH | 1 × 5 min | 75° C. |
| 6 | Fmoc-L-His(Trt)-OH | 1 × 5 min | 75° C. |
| 7 | Fmoc-L-Cys(Trt)-OH | 1 × 6 min | 2 min at 25° C. 4 min at 50° C. |
| 8 | Fmoc-L-Leu-OH | 1 × 5 min | 75° C. |
| 9 | Fmoc-L-Arg(Pbf)-OH | 2 × 30 min | 25 min at 25° C. 5 min at 75° C. |
| 10 | Fmoc-L-Pro-OH | 1 × 5 min | 75° C. |
| 11 | Fmoc-L-Arg(Pbf)-OH | 2 × 30 min | 25 min at 25° C. 5 min at 75° C. |
| 12 | Fmoc-L-Gln(Trt)-OH | 1 × 5 min | 75° C. |
| 13 | Fmoc-Gly-Gly-Gly-OH | 1 × 5 min | 75° C. |
| 14 | Fmoc-Gly-OH | 1 × 5 min | 75° C. |
| 15 | Fmoc-Gly-OH | 1 × 5 min | 75° C. |

After the assembly of the peptide, each batch of resin was washed with DMF (3×10 mL), DCM (3×10 mL). The combined peptide resin was dried under vacuum at room temperature to give Intermediate 21A, (1.454 g, 0.5 mmol).

Step 2b: Preparation of Intermediate 21B, H₂N-GGGGGQR-PRLCHKGP(Nle)CF-COOH (SEQ ID NO: 129)

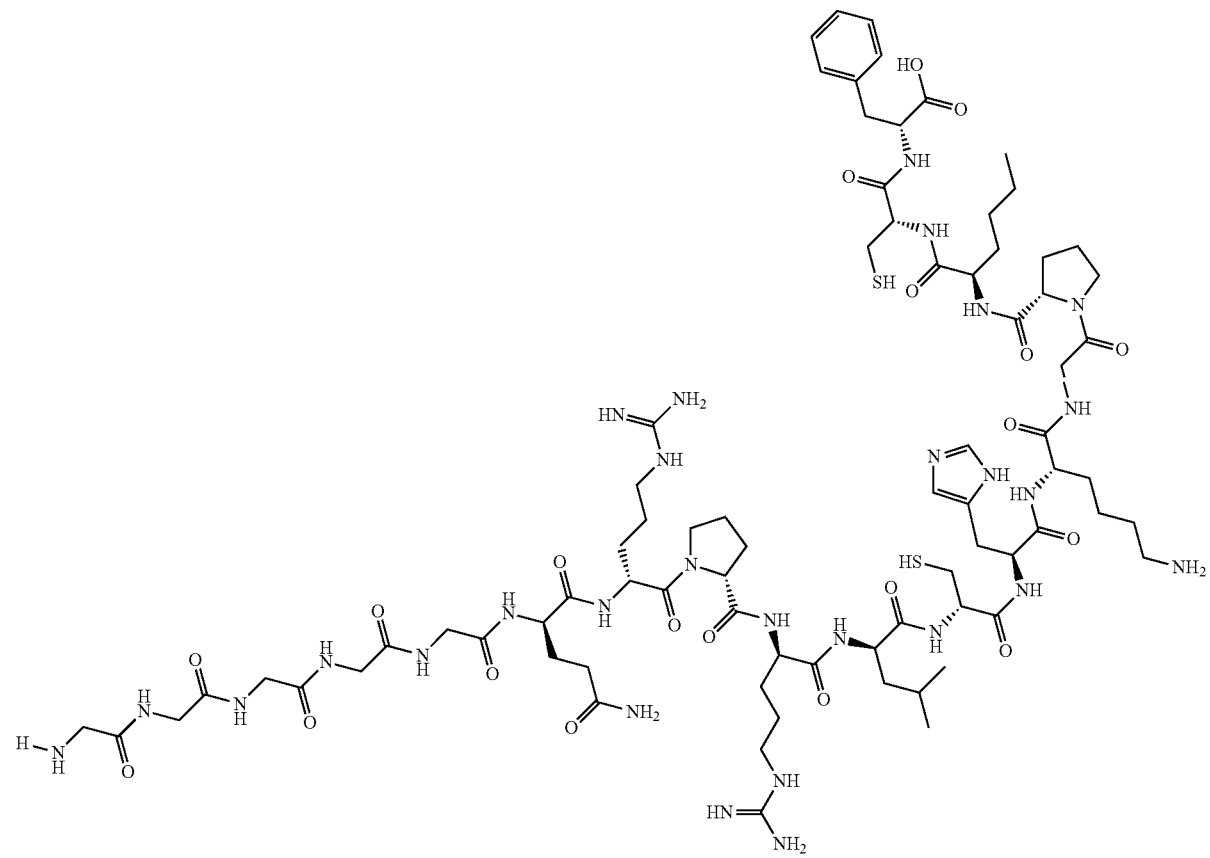 [SMILES: CCCC[C@@H](NC(=O)[C@@H]1CCCN1C(=O)CNC(=O)[C@H](CCCCN)NC(=O)[C@H](Cc1cnc[nH]1)NC(=O)[C@@H](CS)NC(=O)[C@@H](CC(C)C)NC(=O)[C@@H](CCCNC(=N)N)NC(=O)[C@H]1CCCN1C(=O)[C@@H](CCCNC(=N)N)NC(=O)[C@@H](CCC(N)=O)NC(=O)CNC(=O)CNC(=O)CNC(=O)CNC(=O)CN)C(=O)N[C@H](CS)C(=O)N[C@H](Cc1ccccc1)C(=O)O]

1) Cleavage and Protecting Group Removal

To intermediate 21A (1.454 g, 0.5 mmol) was added 6 mL solution of 95% TFA/2.5% H$_2$O/2.5% TIPS and DTT (1.452 g, 10.00 mmol), the resulting mixture was shaked at room temperature for 3 hours, then filtered. The filtrate was dropped into 80 mL of cold ether, then centrifuged at 4000 rpm for 5 minutes. The solvent was removed and the white solid was washed with ether (3×80 mL), vortexed and centrifuged. The solid was dried under high vacuum at 25° C. for 1 hour.

2) Purification

The above white solid was then purified by preparative HPLC (Sunfire™ Prep C18 OBD™ 30 ×50 mm 5 um column ACN/H$_2$O w/0.1% TFA 75 ml/min, 10-30% ACN 8 min gradient). The product fraction was lyophilized to give intermediate 21B as TFA salt (213 mg, 23%).

Step 3: Preparation of H$_2$N-GGGGGQRPRLC*HKGP(Nle)C*F-COOH (disulfide C$^{11}$-C$^{17}$) (SEQ ID NO: 129) intermediate 21C To intermediate 21B (213 mg, 0.166 mmol) in 3.85 mL of H$_2$O was added I$_2$ (50 mM in AcOH, 4.63 mL, 0.232 mmol) dropwise. The mixture was shaked at room temperature overnight. LC/MS showed the reaction completed. To the reaction mixture was added several drops of 0.5 M of ascorbic acid solution (MeOH/H$_2$O=1/1) until the color of the solution disappeared. The mixture was diluted with MeOH for HPLC purification. The purification was carried out by preparative HPLC (Sunfire™ Prep C18 OBD™ 30×50 mm 5 um column ACN/H2O w/0.1% TFA 75 ml/min, 7.5-20% ACN 8 min gradient). The product fraction was lyophilized to give H$_2$N-GGGGGQRPRLC*HKGP(Nle)C*F-COOH (disulfide C$^{11}$-C$^{17}$) (SEQ ID NO: 129) intermediate 21C as TFA salt (65 mg, 31%). LC/MS (QT2, ProductAnalysis-HRMS-Acidic, Waters Acquity UPLC BEH C18 1.7 um 2.1×50 mm, 50° C., Eluent A: Water+0.1% Formic Acid, Eluent B: Acetonitrile+0.1% Formic Acid, gradient 2% to 98% B/A over 5.15 mins): Retention time: 0.79 mins; MS [M+2]$^{2+}$: observed: 919.9562.

Step 3: Sortase Conjugation of Fc-Sortase and Intermediate 21C

1) Chemoenzymatic Sortase Conjugation

On ice bath, to the Fc-LPETGG (SEG ID NO: 136) (1397 µl, 0.081 µmol) in PBS (pH7.4) buffer solution was added the solution of H$_2$N-GGGGGQRPRLC*HKGP(Nle)C*F-COOH (disulfide C$^{11}$-C$^{17}$) (SEQ ID NO: 129) (148 µL, 4.04 µmoL, 50 mg/mL) in Tris-8.0 buffer, followed by 520 µM of sortase A* (155 µL, 0.081 82 moL) in 50 mM Tris-Cl pH7.4, 150 mM NaCl. The mixture was shaked at room temperature overnight. LC/MS showed the reaction completed.

(Sortase A*): Sequence of Sortase A Mutant:

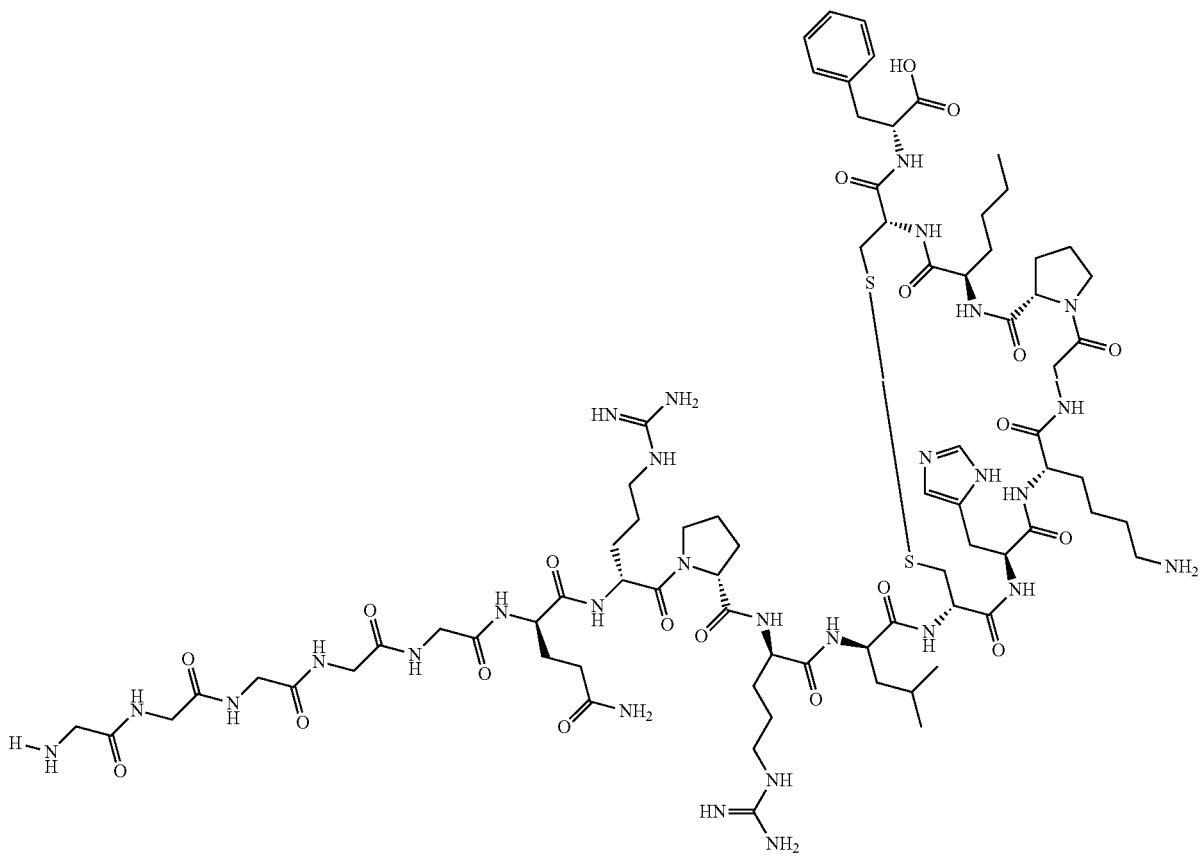 [SMILES: CCCC[C@H]1NC(=O)[C@@H]2CCCN2C(=O)CNC(=O)[C@H](CCCCN)NC(=O)[C@H](Cc2cnc[nH]2)NC(=O)[C@H](NC(=O)[C@@H](CC(C)C)NC(=O)[C@@H](CCCNC(=N)N)NC(=O)[C@H]2CCCN2C(=O)[C@@H](CCCNC(=N)N)NC(=O)[C@@H](CCC(N)=O)NC(=O)CNC(=O)CNC(=O)CNC(=O)CNC(=O)CN)CSSC[C@H](C(=O)N[C@H](Cc2ccccc2)C(=O)O)NC1=O]

MQAKPQIPKDKSKVAGYIEIPDADIKEPVYPGPATREQLNRGVSFAKEN

QSLDDQNISIAGHTFIDRPNYQFTNLKAAKKGSMVYFKVGNETRKYKMT

SIRNVKPTAV<u>E</u>VLDEQKGKDKQLTLITCDDYNEETGVWETRKIFVATEV

KLEHHHHHH (SEQ ID NO: 137)

where the bold letters represent amino acids which were mutated and the underlined letters represent amino acids described (Chen et al., PNAS, Vol 108, No 28, 2011, 11399-11403) which are not conserved in the original sequence of S aureus sortase A (Mazmanian et al. Science (Washington, D.C.) (1999), 285(5428), 760-763)

The sortase A mutant was expressed in *E. coli* and purified by affinity chromatography exploring the polyhistidine tag comprised at its C-terminus, following established protocols (Carla P. Guimaraes et al.: "Site specific C-terminal and internal loop labeling of proteins using sortase-mediated reactions", Nature protocols, vol 8, No 9, 2013, 1787-1799).

2) Purification and Desalting

The above solution was flowed over a 5 mL HiTrap Mab Select SuRe column (GE Lifesciences #11-0034-95) at 4 mL/min on ATTA XPRESS. Example 21 was washed on the column with 20 column volumes (CV) PBS+0.1% Triton 114 and eluted with 0.1M glycine, pH 2.7, neutralized with 1 M tris-HCl, pH 9 and dialyzed versus PBS. The purified solution was desalted by using Zeba Sping Desalting Column, 5 mL (89891) to give 2 mL target solution, the average concentration was 1.62 mg/mL, and the recoverage was 68%. LCMS (QT2, Protein_20-70 kDa_3 min, AcQuity ProSwift RP-3U 4.6×50 mm, 1.0 mL/min, Eluent A: Water+0.1% Formic Acid, Eluent B: Acetonitrile+0.1% Formic Acid, gradient 2% to 98% B/A over 3 mins): $R_f$=1.55 minutes, MS [M+H] 59346.5000.

The bioconjugates in the examples above have been found to have $EC_{50}$ values in the range of about 0.01 nM to about 1100 nM for APJ receptor potency. The bioconjugate in the examples above have been found to have a plasma stability higher than 2 minutes, higher than 5 minutes, higher than 10 minutes, higher than 20 minutes, higher than 50 minutes and higher than 60 minutes.

It can be seen that the biconjugates of the invention are useful as agonist of the APJ receptor and therefore useful in the treatment of diseases and conditions responsive the activation of the APJ receptor, such as the diseases disclosed herein.

Having thus described exemplary embodiments of the present invention, it should be noted by those of ordinary skill in the art that the within disclosures are exemplary only and that various other alternatives, adaptations, and modifications may be made within the scope of the present invention. Accordingly, the present invention is not limited to the specific embodiments as illustrated therein.

What is claimed is:

1. A bioconjugate or a multimer thereof, comprising:
   a) a peptide or polypeptide having the following formula V (SEQ ID NO: 6):

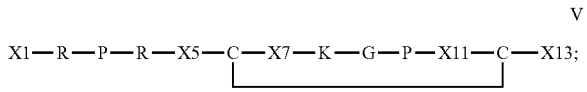

V wherein:
   X1 is the N-terminus of the polypeptide and is either absent or is selected from R, Q, A and K;
   X5 is L, A, K, D or F;
   wherein the side chain of the two Cysteines (C) are linked together via a covalent bond forming a disulfide (—S—S—);
   X7 is H, A, K, F, P, N or E;
   X11 is M, A, F, Y, L or K; and
   X13 is the C-terminus and is absent or is selected from F, I, A, K, H and E;
   or an amide, an ester or a salt of the polypeptide; and
   b) a half-life extending moiety;
   wherein the half-life extending moiety is a Fc domain which is fused to said polypeptide via a linker and wherein the linker has the following Formula:
   -[GGGGS]n-, n is 1, 2 or 3 (SEQ ID NO: 16) or the linker is GG or GS.

2. The bioconjugate according to claim 1 wherein the half-life extending moiety is a FcLALA modified Fc fragment with a LALA mutation (L234A, L235A).

3. The bioconjugate according to claim 2 wherein the polypeptide is: Q-R-P-R-L-C*-H-K-G-P-M-C*-F (SEQ ID NO: 17).

4. A Combination comprising a therapeutically effective amount of a bioconjugate according to claim 1, and one or more therapeutically active co-agent.

5. A combination according to claim 4 wherein the co-agent is selected from inotropes, beta adrenergic receptor blockers, HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and/or a NEP inhibitor.

6. A pharmaceutical composition comprising a therapeutically effective amount of a bioconjugate according to claim 1, and one or more pharmaceutically acceptable carriers.

7. The bioconjugate according to claim 1 wherein X1 is A or Q; and the peptide is fused to the half-life extending moiety via its A or Q N-terminus.

8. The bioconjugate according to claim 1 wherein X5 is L.

9. The bioconjugate according to claim 1 wherein X7 is H.

10. The bioconjugate according to claim 1 wherein X13 is absent or F.

11. The bioconjugate according to claim 1 having any one of SEQ ID NO: 100, 101 and 116 to 126.

12. The bioconjugate according to claim 1 having SEQ ID NO: 100.

* * * * *

SEQUENCE LISTING

```
<160> NUMBER OF SEQ ID NOS: 139

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu, Arg, Isn, Gln, Ala, Lys, 5-amino-
      valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      homoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-Ph-Pro, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp,
      4-Ph-Phe or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu or Cys
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
```

```
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-Ph-Pro or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, Met(O), Ala, Phe,
      Tyr, Leu, Lys, 3-Py-Ala or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu or absent
<220> FEATURE:
<223> OTHER INFORMATION: See specification as filed for detailed
      description of substitutions and preferred embodiments

<400> SEQUENCE: 1

Xaa Xaa Xaa Xaa Xaa Xaa Xaa Xaa Xaa Xaa Xaa Xaa Xaa
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu, Arg, Gln, Ala, Lys, 5-amino-valeric
      acid, Isn or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      homoLys or Orn
<220> FEATURE:
<221> NAME/KEY: MOD_RES
<222> LOCATION: (3)..(3)
<223> OTHER INFORMATION: Pro, Ala, D-Ala, D-Pro, 4-Ph-Pro, pipecolic
      acid or Cys
<220> FEATURE:
<221> NAME/KEY: MOD_RES
<222> LOCATION: (4)..(4)
<223> OTHER INFORMATION: Arg, Ala, D-Arg, N-Me-Arg or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, or Cys
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg
      or 4-amino-Isn
<220> FEATURE:
<221> NAME/KEY: MOD_RES
<222> LOCATION: (9)..(9)
<223> OTHER INFORMATION: Gly, N-Me-Gly, Ala or Aib
```

```
<220> FEATURE:
<221> NAME/KEY: MOD_RES
<222> LOCATION: (10)..(10)
<223> OTHER INFORMATION: Pro, Ala, D-Pro, 4-Ph-Pro or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, Met(O), Ala, Phe,
      Tyr, Leu, Lys or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap or absent
<220> FEATURE:
<223> OTHER INFORMATION: See specification as filed for detailed
      description of substitutions and preferred embodiments

<400> SEQUENCE: 2

Xaa Xaa Xaa Xaa Xaa Xaa Xaa Xaa Xaa Xaa Xaa Xaa Xaa
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu, Arg, Gln, Isn or absent
<220> FEATURE:
<221> NAME/KEY: MOD_RES
<222> LOCATION: (5)..(5)
<223> OTHER INFORMATION: Leu or Cha
<220> FEATURE:
<221> NAME/KEY: MOD_RES
<222> LOCATION: (6)..(6)
<223> OTHER INFORMATION: Cys, Lys, Asp, Orn, Dab or Glu
<220> FEATURE:
<221> NAME/KEY: MOD_RES
<222> LOCATION: (7)..(7)
<223> OTHER INFORMATION: His, Aib, Phe or Lys
<220> FEATURE:
<221> NAME/KEY: MOD_RES
<222> LOCATION: (8)..(8)
<223> OTHER INFORMATION: Lys, Phe or 4-amino-Isn
<220> FEATURE:
<221> NAME/KEY: MOD_RES
<222> LOCATION: (9)..(9)
<223> OTHER INFORMATION: Gly or Aib
<220> FEATURE:
<221> NAME/KEY: MOD_RES
<222> LOCATION: (11)..(11)
<223> OTHER INFORMATION: Nle or Cha
<220> FEATURE:
<221> NAME/KEY: MOD_RES
<222> LOCATION: (12)..(12)
<223> OTHER INFORMATION: Cys, Lys, Asp, Orn, Dab or Glu
<220> FEATURE:
<221> NAME/KEY: MOD_RES
<222> LOCATION: (13)..(13)
<223> OTHER INFORMATION: Phe, D-Phe, Lys or absent
<220> FEATURE:
<223> OTHER INFORMATION: See specification as filed for detailed
      description of substitutions and preferred embodiments

<400> SEQUENCE: 3

Xaa Arg Pro Arg Xaa Xaa Xaa Xaa Xaa Pro Xaa Xaa Xaa
```

```
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu, Arg, Isn, Gln, Ala, Lys, 5-amino-
      valeric acid or absent
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp,
      4-Ph-Phe or Phe
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu or Cys
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (11)..(11)
<223> OTHER INFORMATION: Met, D-Nle, Nle, N-Me-Nle, Met(O), Ala, Phe,
      Tyr, Leu, Lys, 3-Py-Ala or Cha
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu or absent
<220> FEATURE:
<223> OTHER INFORMATION: See specification as filed for detailed
      description of substitutions and preferred embodiments

<400> SEQUENCE: 4

Xaa Arg Pro Arg Xaa Cys Xaa Xaa Xaa Pro Xaa Cys Xaa
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu, Arg, Isn, Gln, Ala, Lys, 5-amino-
      valeric acid or absent
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp,
      4-Ph-Phe or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
```

```
<223> OTHER INFORMATION: His, D-His, Ala, N-Me-Ala, D-Ala, Aib, Lys,
      Nal, Phe, Pro, Dap, Asn, Glu or Cys
<220> FEATURE:
<221> NAME/KEY: MOD_RES
<222> LOCATION: (11)..(11)
<223> OTHER INFORMATION: Met, D-Nle, Nle, N-Me-Nle, Met(O), Ala, Phe,
      Tyr, Leu, Lys, 3-Py-Ala or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu or absent
<220> FEATURE:
<223> OTHER INFORMATION: See specification as filed for detailed
      description of substitutions and preferred embodiments

<400> SEQUENCE: 5

Xaa Arg Pro Arg Xaa Xaa Xaa Lys Gly Pro Xaa Xaa Xaa
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu, Arg, Isn, Gln, Ala, Lys, 5-amino-
      valeric acid or absent
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp,
      4-Ph-Phe or Phe
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu or Cys
<220> FEATURE:
<221> NAME/KEY: MOD_RES
<222> LOCATION: (11)..(11)
<223> OTHER INFORMATION: Met, D-Nle, Nle, N-Me-Nle, Met(O), Ala, Phe,
      Tyr, Leu, Lys, 3-Py-Ala or Cha
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu or absent
<220> FEATURE:
<223> OTHER INFORMATION: See specification as filed for detailed
      description of substitutions and preferred embodiments

<400> SEQUENCE: 6

Xaa Arg Pro Arg Xaa Cys Xaa Lys Gly Pro Xaa Cys Xaa
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: PyroGlu, Arg, Isn, Gln, Ala, Lys, 5-amino-
      valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      homoLys, Phe, Glu or Orn
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp,
      4-Ph-Phe or Phe
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-Ph-Pro or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, Met(O), Ala, Phe,
      Tyr, Leu, Lys, 3-Py-Ala or Cha
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu or absent
<220> FEATURE:
<223> OTHER INFORMATION: See specification as filed for detailed
      description of substitutions and preferred embodiments

<400> SEQUENCE: 7

Xaa Xaa Cys Xaa Xaa Cys Cys Xaa Xaa Xaa Xaa Cys Xaa
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu, Arg, Isn, Gln, Ala, Lys, 5-amino-
      valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      homoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-Ph-Pro, Lys, Asp,
      pipecolic acid or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp,
      4-Ph-Phe or Phe
<220> FEATURE:
<221> NAME/KEY: MOD_RES
<222> LOCATION: (8)..(8)
```

```
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-Ph-Pro or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, Met(O), Ala, Phe,
      Tyr, Leu, Lys, 3-Py-Ala or Cha
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu or absent
<220> FEATURE:
<223> OTHER INFORMATION: See specification as filed for detailed
      description of substitutions and preferred embodiments

<400> SEQUENCE: 8

Xaa Xaa Xaa Cys Xaa Cys Cys Xaa Xaa Xaa Xaa Cys Xaa
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu, Arg, Isn, Gln, Ala, Lys, 5-amino-
      valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      homoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-Ph-Pro, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp,
      4-Ph-Phe or Phe
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu or Cys
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
<221> NAME/KEY: MOD_RES
<222> LOCATION: (9)..(9)
```

```
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-Ph-Pro or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, Met(O), Ala, Phe,
      Tyr, Leu, Lys, 3-Py-Ala or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (13)..(13)
<223> OTHER INFORMATION: Phe, D-Phe, N-Me-Phe, Nal, D-Nal, 3-Br-Phe,
      (S)-Beta-3-Phe, Ile, Ala, D-Ala, Lys, Dap, His, Glu or absent
<220> FEATURE:
<221> NAME/KEY: misc_feature
<222> LOCATION: (14)..(17)
<223> OTHER INFORMATION: This region may encompass 1-4 Gly residues
      wherein some positions may be absent
<220> FEATURE:
<223> OTHER INFORMATION: See specification as filed for detailed
      description of substitutions and preferred embodiments

<400> SEQUENCE: 9

Xaa Xaa Xaa Xaa Xaa Xaa Xaa Xaa Xaa Xaa Xaa Xaa Xaa Gly Gly Gly
1               5                   10                  15

Gly

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu, Arg, Isn, Gln, Ala, Lys, 5-amino-
      valeric acid or absent
<220> FEATURE:
<221> NAME/KEY: MOD_RES
<222> LOCATION: (2)..(2)
<223> OTHER INFORMATION: Arg, Ala, D-Arg, N-Me-Arg, Lys, His, homoPhe,
      homoLys, Phe, Glu or Orn
<220> FEATURE:
<221> NAME/KEY: MOD_RES
<222> LOCATION: (3)..(3)
<223> OTHER INFORMATION: Pro, Ala, D-Ala, D-Pro, 4-Ph-Pro, Lys, Asp,
      pipecolic acid or Cys
<220> FEATURE:
<221> NAME/KEY: MOD_RES
<222> LOCATION: (4)..(4)
<223> OTHER INFORMATION: Arg, Ala, D-Arg, N-Me-Arg, Phe, Glu or Cys
<220> FEATURE:
<221> NAME/KEY: MOD_RES
<222> LOCATION: (5)..(5)
<223> OTHER INFORMATION: Leu, Cha, Ala, D-Leu, N-Me-Leu, Lys, Asp,
      4-Ph-Phe or Phe
<220> FEATURE:
<221> NAME/KEY: MOD_RES
<222> LOCATION: (7)..(7)
<223> OTHER INFORMATION: His, D-His, Ala, N-Me-Ala, D-Ala, Aib, Lys,
      Nal, Phe, Pro, Dap, Asn, Glu or Cys
<220> FEATURE:
<221> NAME/KEY: MOD_RES
<222> LOCATION: (8)..(8)
<223> OTHER INFORMATION: Lys, D-Lys, Phe, D-Phe, Ala, homoPhe, N-Me-Arg,
      Glu or 4-amino-Isn
<220> FEATURE:
```

```
<221> NAME/KEY: MOD_RES
<222> LOCATION: (9)..(9)
<223> OTHER INFORMATION: Gly, N-Me-Gly, Ala, Asp, Leu, Arg or Aib
<220> FEATURE:
<221> NAME/KEY: MOD_RES
<222> LOCATION: (10)..(10)
<223> OTHER INFORMATION: Pro, Ala, D-Pro, 4-Ph-Pro or pipecolic acid
<220> FEATURE:
<221> NAME/KEY: MOD_RES
<222> LOCATION: (11)..(11)
<223> OTHER INFORMATION: Met, D-Nle, Nle, N-Me-Nle, Met(O), Ala, Phe,
      Tyr, Leu, Lys, 3-Py-Ala or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab or Glu
<220> FEATURE:
<223> OTHER INFORMATION: See specification as filed for detailed
      description of substitutions and preferred embodiments

<400> SEQUENCE: 10

Xaa Xaa Xaa Xaa Xaa Lys Xaa Xaa Xaa Xaa Xaa Xaa
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser Gly Gly Gly Gly Ser Gly Gly Gly Gly Ser
1               5                   10                  15

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Ser Gly Gly Gly Gly Ser
1               5                   10

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly Ser
1               5

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14
```

```
Gly Gly Gly Gly Leu Pro Glu Thr Gly Gly Leu Glu Val Leu Phe Gln
1               5                   10                  15
Gly Pro

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Leu Glu Val Leu Phe Gln Gly Pro
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(15)
<223> OTHER INFORMATION: This sequence may encompass 1-3 "Gly Gly Gly
      Gly Ser" repeating units wherein some positions may be absent

<400> SEQUENCE: 16

Gly Gly Gly Gly Ser Gly Gly Gly Gly Ser Gly Gly Gly Gly Ser
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Arg Pro Arg Leu Cys His Lys Gly Pro Met Cys Phe
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Arg Pro Arg Leu Cys His Lys Gly Pro Met Cys
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Arg Pro Arg Leu Ser His Lys Gly Pro Met Pro Phe
1               5                   10
```

```
<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: This region may encompass 1-3 "Gly Gly Gly Gly"
      repeating units wherein some positions may be absent

<400> SEQUENCE: 20

Gly Gly Gly Gly Gly Gly Gly Gly Gly Gly Gly Gly Leu Pro Glu Thr
1               5                   10                  15

Gly Gly Leu Glu Val Leu Phe Gln Gly Pro
            20                  25

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: This region may encompass 1-3 "Gly Gly Gly Gly"
      repeating units wherein some positions may be absent

<400> SEQUENCE: 21

Gly Gly Gly Gly Gly Gly Gly Gly Gly Gly Gly Gly Leu Pro Glu Thr
1               5                   10                  15

Leu

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Trp Phe Lys Ala Phe Tyr Asp Lys Val Ala Glu Lys Phe Lys Glu
1               5                   10                  15

Ala Phe

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 23
```

Glu Arg Pro Arg Leu Lys His Phe Gly Pro Leu Asp
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 24

Glu Arg Pro Arg Leu Lys His Phe Gly Pro Leu Glu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (6)..(6)
<223> OTHER INFORMATION: Orn
<220> FEATURE:
<221> NAME/KEY: MOD_RES
<222> LOCATION: (11)..(11)
<223> OTHER INFORMATION: Nle

<400> SEQUENCE: 25

Glu Arg Pro Arg Leu Xaa His Phe Gly Pro Leu Asp
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (6)..(6)
<223> OTHER INFORMATION: Dab
<220> FEATURE:
<221> NAME/KEY: MOD_RES
<222> LOCATION: (11)..(11)
<223> OTHER INFORMATION: Nle

<400> SEQUENCE: 26

Glu Arg Pro Arg Leu Xaa His Phe Gly Pro Leu Asp
1               5                   10

<210> SEQ ID NO 27

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 27

Glu Arg Pro Arg Leu Lys Phe Lys Gly Pro Leu Phe
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: D-Phe

<400> SEQUENCE: 28

Glu Arg Pro Arg Leu Lys Phe Lys Gly Pro Leu Phe
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Nle

<400> SEQUENCE: 29

Gln Arg Pro Arg Leu Cys Phe Lys Gly Pro Leu Cys Phe Gly Gly
1               5                   10                  15

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
```

```
<223> OTHER INFORMATION: Nle

<400> SEQUENCE: 30

Glu Arg Pro Arg Leu Cys His Lys Gly Pro Leu Cys Phe
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (7)..(7)
<223> OTHER INFORMATION: Aib
<220> FEATURE:
<221> NAME/KEY: MOD_RES
<222> LOCATION: (11)..(11)
<223> OTHER INFORMATION: Nle

<400> SEQUENCE: 31

Glu Arg Pro Arg Leu Cys Xaa Lys Gly Pro Leu Cys Phe
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (7)..(7)
<223> OTHER INFORMATION: Aib
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (13)..(13)
<223> OTHER INFORMATION: D-Phe

<400> SEQUENCE: 32

Glu Arg Pro Arg Leu Cys Xaa Lys Gly Pro Leu Cys Phe
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Isn
<220> FEATURE:
<221> NAME/KEY: MOD_RES
<222> LOCATION: (7)..(7)
<223> OTHER INFORMATION: Aib
```

```
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (13)..(13)
<223> OTHER INFORMATION: D-Phe

<400> SEQUENCE: 33

Xaa Arg Pro Arg Leu Cys Xaa Lys Gly Pro Leu Cys Phe
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 34

Glu Arg Pro Arg Leu Cys His Lys Gly Pro Leu Cys
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (13)..(13)
<223> OTHER INFORMATION: D-Phe

<400> SEQUENCE: 35

Glu Arg Pro Arg Leu Cys His Lys Gly Pro Leu Cys Phe
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (5)..(5)
<223> OTHER INFORMATION: Cha
<220> FEATURE:
```

```
<221> NAME/KEY: MOD_RES
<222> LOCATION: (11)..(11)
<223> OTHER INFORMATION: Cha

<400> SEQUENCE: 36

Glu Arg Pro Arg Ala Cys His Lys Gly Pro Ala Cys Phe
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 37

Glu Arg Pro Arg Leu Cys Phe Lys Gly Pro Leu Cys Phe
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Nle

<400> SEQUENCE: 38

Arg Pro Arg Leu Cys His Lys Gly Pro Leu Cys Phe
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Nle

<400> SEQUENCE: 39

Arg Arg Pro Arg Leu Cys His Lys Gly Pro Leu Cys Phe
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Isn
```

```
<220> FEATURE:
<221> NAME/KEY: MOD_RES
<222> LOCATION: (11)..(11)
<223> OTHER INFORMATION: Nle

<400> SEQUENCE: 40

Xaa Arg Pro Arg Leu Cys His Lys Gly Pro Leu Cys Phe
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 41

Glu Arg Pro Arg Leu Cys His Phe Gly Pro Leu Cys
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (9)..(9)
<223> OTHER INFORMATION: Aib
<220> FEATURE:
<221> NAME/KEY: MOD_RES
<222> LOCATION: (11)..(11)
<223> OTHER INFORMATION: Nle

<400> SEQUENCE: 42

Glu Arg Pro Arg Leu Cys His Lys Xaa Pro Leu Cys Phe
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (8)..(8)
<223> OTHER INFORMATION: 4-NH-Isn
<220> FEATURE:
<221> NAME/KEY: MOD_RES
<222> LOCATION: (11)..(11)
<223> OTHER INFORMATION: Nle
```

```
<400> SEQUENCE: 43

Glu Arg Pro Arg Leu Cys His Xaa Gly Pro Leu Cys Phe
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 44

Glu Arg Pro Cys Leu Cys Cys Lys Gly Pro Leu Cys Phe
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 45

Glu Arg Cys Arg Leu Cys Cys Lys Gly Pro Leu Cys Phe
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (11)..(11)
<223> OTHER INFORMATION: Nle

<400> SEQUENCE: 46

Glu Arg Pro Arg Leu Cys His Lys Gly Pro Leu Cys Phe
1               5                   10

<210> SEQ ID NO 47
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 47

Glu Phe Pro Arg Leu Cys His Lys Gly Pro Leu Cys Phe
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 48

Glu Glu Pro Arg Leu Cys His Lys Gly Pro Leu Cys Phe
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (3)..(3)
<223> OTHER INFORMATION: D-Pro
<220> FEATURE:
<221> NAME/KEY: MOD_RES
<222> LOCATION: (11)..(11)
<223> OTHER INFORMATION: Nle

<400> SEQUENCE: 49

Glu Arg Pro Arg Leu Cys His Lys Gly Pro Leu Cys Phe
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
```

<221> NAME/KEY: MOD_RES
<222> LOCATION: (11)..(11)
<223> OTHER INFORMATION: Nle

<400> SEQUENCE: 50

Glu Arg Lys Arg Leu Cys His Lys Gly Pro Leu Cys Phe
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 51

Glu Arg Asp Arg Leu Cys His Lys Gly Pro Leu Cys Phe
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 52

Glu Arg Pro Phe Leu Cys His Lys Gly Pro Leu Cys Phe
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 53

Glu Arg Pro Arg Lys Cys His Lys Gly Pro Leu Cys Phe
1               5                   10

<210> SEQ ID NO 54
<211> LENGTH: 13
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 54

Glu Arg Pro Arg Leu Cys His Glu Gly Pro Leu Cys Phe
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 55

Glu Arg Pro Arg Leu Cys His Lys Asp Pro Leu Cys Phe
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 56

Glu Arg Pro Glu Leu Cys His Lys Gly Pro Leu Cys Phe
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (5)..(5)
<223> OTHER INFORMATION: 4-Ph-Phe
<220> FEATURE:
```

```
<221> NAME/KEY: MOD_RES
<222> LOCATION: (11)..(11)
<223> OTHER INFORMATION: Nle

<400> SEQUENCE: 57

Glu Arg Pro Arg Phe Cys His Lys Gly Pro Leu Cys Phe
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 58

Glu Arg Pro Arg Asp Cys His Lys Gly Pro Leu Cys Phe
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 59

Glu Arg Pro Arg Leu Cys Glu Lys Gly Pro Leu Cys Phe
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 60

Glu Arg Pro Arg Leu Cys His Lys Leu Pro Leu Cys Phe
1               5                   10

<210> SEQ ID NO 61
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 61

Glu Arg Pro Arg Leu Cys His Lys Arg Pro Leu Cys Phe
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (10)..(10)
<223> OTHER INFORMATION: Pipecolic acid
<220> FEATURE:
<221> NAME/KEY: MOD_RES
<222> LOCATION: (11)..(11)
<223> OTHER INFORMATION: Nle

<400> SEQUENCE: 62

Glu Arg Pro Arg Leu Cys His Lys Gly Xaa Leu Cys Phe
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: 3-Py-Ala

<400> SEQUENCE: 63

Glu Arg Pro Arg Leu Cys His Lys Gly Pro Ala Cys Phe
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
```

```
<221> NAME/KEY: MOD_RES
<222> LOCATION: (11)..(11)
<223> OTHER INFORMATION: Nle

<400> SEQUENCE: 64

Glu Arg Pro Arg Leu Cys His Lys Gly Pro Leu Cys His
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 65

Glu Arg Pro Arg Leu Cys His Lys Gly Pro Leu Cys Glu
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 66

Glu Arg Pro Arg Leu Cys His Lys Gly Pro Leu Cys
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: HomoCys

<400> SEQUENCE: 67

Glu Arg Pro Arg Leu Cys His Lys Gly Pro Leu Cys Phe
1               5                   10
```

```
<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (6)..(6)
<223> OTHER INFORMATION: HomoCys
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: HomoCys

<400> SEQUENCE: 68

Glu Arg Pro Arg Leu Cys His Lys Gly Pro Leu Cys Phe
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (6)..(6)
<223> OTHER INFORMATION: D-Cys
<220> FEATURE:
<221> NAME/KEY: MOD_RES
<222> LOCATION: (11)..(11)
<223> OTHER INFORMATION: Nle

<400> SEQUENCE: 69

Glu Arg Pro Arg Leu Cys His Lys Gly Pro Leu Cys Phe
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: D-HomoCys

<400> SEQUENCE: 70
```

Glu Arg Pro Arg Leu Cys His Lys Gly Pro Leu Cys Phe
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (6)..(6)
<223> OTHER INFORMATION: D-HomoCys
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: D-HomoCys

<400> SEQUENCE: 71

Glu Arg Pro Arg Leu Cys His Lys Gly Pro Leu Cys Phe
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: D-Cys

<400> SEQUENCE: 72

Glu Arg Pro Arg Leu Cys His Lys Gly Pro Leu Cys Phe
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (6)..(6)
<223> OTHER INFORMATION: D-Cys
<220> FEATURE:
<221> NAME/KEY: MOD_RES
<222> LOCATION: (11)..(11)
<223> OTHER INFORMATION: Nle

```
<220> FEATURE:
<221> NAME/KEY: MOD_RES
<222> LOCATION: (12)..(12)
<223> OTHER INFORMATION: D-Cys

<400> SEQUENCE: 73

Glu Arg Pro Arg Leu Cys His Lys Gly Pro Leu Cys Phe
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 74

Glu Arg Pro Arg Leu Cys His Lys Gly Pro Leu Cys Phe
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 75

Glu Arg Pro Arg Leu Cys His Lys Gly Pro Leu Cys
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (11)..(11)
<223> OTHER INFORMATION: Nle

<400> SEQUENCE: 76

Glu Arg Pro Arg Leu Cys His Lys Gly Pro Leu Cys Phe
1               5                   10

<210> SEQ ID NO 77
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (2)..(2)
<223> OTHER INFORMATION: Arg(Pbf)
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (6)..(6)
<223> OTHER INFORMATION: Lys(Boc)
<220> FEATURE:
<221> NAME/KEY: MOD_RES
<222> LOCATION: (7)..(7)
<223> OTHER INFORMATION: His(Trt)
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: Asp(tBu)

<400> SEQUENCE: 77

Glu Arg Pro Arg Leu Lys His Phe Gly Pro Leu Asp
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (2)..(2)
<223> OTHER INFORMATION: Arg(Pbf)
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (6)..(6)
<223> OTHER INFORMATION: Lys(ivDde)
<220> FEATURE:
<221> NAME/KEY: MOD_RES
<222> LOCATION: (8)..(8)
<223> OTHER INFORMATION: Lys(Boc)
<220> FEATURE:
<221> NAME/KEY: MOD_RES
<222> LOCATION: (11)..(11)
<223> OTHER INFORMATION: Nle

<400> SEQUENCE: 78

Glu Arg Pro Arg Leu Lys Phe Lys Gly Pro Leu Phe
1               5                   10

<210> SEQ ID NO 79
```

-continued

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (2)..(2)
<223> OTHER INFORMATION: Arg(Pbf)
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (8)..(8)
<223> OTHER INFORMATION: Lys(Boc)
<220> FEATURE:
<221> NAME/KEY: MOD_RES
<222> LOCATION: (11)..(11)
<223> OTHER INFORMATION: Nle

<400> SEQUENCE: 79

Glu Arg Pro Arg Leu Lys Phe Lys Gly Pro Leu Phe
1               5                   10

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln(Trt)
<220> FEATURE:
<221> NAME/KEY: MOD_RES
<222> LOCATION: (2)..(2)
<223> OTHER INFORMATION: Arg(Pbf)
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (6)..(6)
<223> OTHER INFORMATION: Cys(Trt)
<220> FEATURE:
<221> NAME/KEY: MOD_RES
<222> LOCATION: (8)..(8)
<223> OTHER INFORMATION: Lys(Boc)
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: Cys(Trt)

<400> SEQUENCE: 80

Gln Arg Pro Arg Leu Cys Phe Lys Gly Pro Leu Cys Phe Gly Gly
1               5                   10                  15

<210> SEQ ID NO 81
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (2)..(2)
<223> OTHER INFORMATION: Arg(Pbf)
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (6)..(6)
<223> OTHER INFORMATION: Cys(Trt)
<220> FEATURE:
<221> NAME/KEY: MOD_RES
<222> LOCATION: (7)..(7)
<223> OTHER INFORMATION: His(Trt)
<220> FEATURE:
<221> NAME/KEY: MOD_RES
<222> LOCATION: (8)..(8)
<223> OTHER INFORMATION: Lys(Boc)
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: Cys(Trt)

<400> SEQUENCE: 81

Glu Arg Pro Arg Leu Cys His Lys Gly Pro Leu Cys Phe
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (2)..(2)
<223> OTHER INFORMATION: Arg(Pbf)
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (6)..(6)
<223> OTHER INFORMATION: Cys(Trt)
<220> FEATURE:
<221> NAME/KEY: MOD_RES
<222> LOCATION: (7)..(7)
<223> OTHER INFORMATION: Aib
<220> FEATURE:
<221> NAME/KEY: MOD_RES
<222> LOCATION: (8)..(8)
<223> OTHER INFORMATION: Lys(Boc)
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
```

<222> LOCATION: (12)..(12)
<223> OTHER INFORMATION: Cys(Trt)

<400> SEQUENCE: 82

Glu Arg Pro Arg Leu Cys Xaa Lys Gly Pro Leu Cys Phe
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (2)..(2)
<223> OTHER INFORMATION: Arg(Pbf)
<220> FEATURE:
<221> NAME/KEY: MOD_RES
<222> LOCATION: (4)..(4)
<223> OTHER INFORMATION: Cys(Acm)
<220> FEATURE:
<221> NAME/KEY: MOD_RES
<222> LOCATION: (6)..(6)
<223> OTHER INFORMATION: Cys(Trt)
<220> FEATURE:
<221> NAME/KEY: MOD_RES
<222> LOCATION: (7)..(7)
<223> OTHER INFORMATION: Cys(Acm)
<220> FEATURE:
<221> NAME/KEY: MOD_RES
<222> LOCATION: (8)..(8)
<223> OTHER INFORMATION: Lys(Boc)
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: Cys(Trt)

<400> SEQUENCE: 83

Glu Arg Pro Cys Leu Cys Cys Lys Gly Pro Leu Cys Phe
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (4)..(4)
<223> OTHER INFORMATION: Cys(Acm)
<220> FEATURE:
<221> NAME/KEY: MOD_RES
<222> LOCATION: (7)..(7)
<223> OTHER INFORMATION: Cys(Acm)
<220> FEATURE:
<221> NAME/KEY: MOD_RES
<222> LOCATION: (11)..(11)
<223> OTHER INFORMATION: Nle

```
<400> SEQUENCE: 84

Glu Arg Pro Cys Leu Cys Cys Lys Gly Pro Leu Cys Phe
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (2)..(2)
<223> OTHER INFORMATION: Arg(Pbf)
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (6)..(6)
<223> OTHER INFORMATION: Cys(Trt)
<220> FEATURE:
<221> NAME/KEY: MOD_RES
<222> LOCATION: (7)..(7)
<223> OTHER INFORMATION: His(Trt)
<220> FEATURE:
<221> NAME/KEY: MOD_RES
<222> LOCATION: (8)..(8)
<223> OTHER INFORMATION: Lys(Boc)
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: Cys(Trt)

<400> SEQUENCE: 85

Glu Arg Pro Arg Leu Cys His Lys Gly Pro Leu Cys Phe
1               5                   10

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: O2Oc
<220> FEATURE:
<221> NAME/KEY: MOD_RES
<222> LOCATION: (2)..(2)
<223> OTHER INFORMATION: O2Oc
<220> FEATURE:
<221> NAME/KEY: MOD_RES
<222> LOCATION: (3)..(3)
<223> OTHER INFORMATION: O2Oc
<220> FEATURE:
<221> NAME/KEY: MOD_RES
<222> LOCATION: (4)..(4)
<223> OTHER INFORMATION: O2Oc
<220> FEATURE:
<221> NAME/KEY: MOD_RES
<222> LOCATION: (15)..(15)
<223> OTHER INFORMATION: Nle
```

```
<220> FEATURE:
<221> NAME/KEY: MOD_RES
<222> LOCATION: (17)..(17)
<223> OTHER INFORMATION: D-Phe

<400> SEQUENCE: 86

Xaa Xaa Xaa Xaa Gln Arg Pro Arg Leu Cys His Phe Gly Pro Leu Cys
1               5                   10                  15
Phe

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: O2Oc
<220> FEATURE:
<221> NAME/KEY: MOD_RES
<222> LOCATION: (2)..(2)
<223> OTHER INFORMATION: O2Oc
<220> FEATURE:
<221> NAME/KEY: MOD_RES
<222> LOCATION: (3)..(3)
<223> OTHER INFORMATION: O2Oc
<220> FEATURE:
<221> NAME/KEY: MOD_RES
<222> LOCATION: (4)..(4)
<223> OTHER INFORMATION: O2Oc
<220> FEATURE:
<221> NAME/KEY: MOD_RES
<222> LOCATION: (5)..(5)
<223> OTHER INFORMATION: Gln(Trt)
<220> FEATURE:
<221> NAME/KEY: MOD_RES
<222> LOCATION: (6)..(6)
<223> OTHER INFORMATION: Arg(Pbf)
<220> FEATURE:
<221> NAME/KEY: MOD_RES
<222> LOCATION: (8)..(8)
<223> OTHER INFORMATION: Arg(Pbf)
<220> FEATURE:
<221> NAME/KEY: MOD_RES
<222> LOCATION: (10)..(10)
<223> OTHER INFORMATION: Cys(Trt)
<220> FEATURE:
<221> NAME/KEY: MOD_RES
<222> LOCATION: (11)..(11)
<223> OTHER INFORMATION: His(Trt)
<220> FEATURE:
<221> NAME/KEY: MOD_RES
<222> LOCATION: (15)..(15)
<223> OTHER INFORMATION: Nle
<220> FEATURE:
<221> NAME/KEY: MOD_RES
<222> LOCATION: (16)..(16)
<223> OTHER INFORMATION: Cys(Trt)
<220> FEATURE:
<221> NAME/KEY: MOD_RES
<222> LOCATION: (17)..(17)
<223> OTHER INFORMATION: D-Phe

<400> SEQUENCE: 87

Xaa Xaa Xaa Xaa Gln Arg Pro Arg Leu Cys His Phe Gly Pro Leu Cys
1               5                   10                  15
Phe

<210> SEQ ID NO 88
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Nle

<400> SEQUENCE: 88

Ala Arg Pro Arg Leu Ser His Lys Gly Pro Leu Pro Phe
1               5                   10

<210> SEQ ID NO 89
<211> LENGTH: 829
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
gctagccacc atggaaactg acaccctgct gctgtgggtc ctgctgctgt gggtgcctgg     60
cagcactggc gataagacac acacttgccc cccttgtcca gcaccagagg cagctggagg    120
accaagcgtg ttcctgtttc acccaagcc taaagacaca ctgatgatct caaggacccc    180
agaagtcaca tgcgtggtcg tggacgtgtc tcacgaggac cccgaagtca agttcaactg    240
gtacgtggat ggcgtcgagg tgcataatgc taagaccaaa ccccgagagg aacagtacaa    300
cagcacctat cgggtcgtgt ccgtcctgac agtgctgcac caggattggc tgaacggcaa    360
agagtataag tgcaaagtga gtaataaggc tctgcctgca ccaatcgaga aaacaatttc    420
taaggctaaa gggcagccaa gagaaccccca ggtgtacact ctgcctccat ctagggagga    480
aatgacaaag aaccaggtca gtctgacttg tctggtgaaa ggcttctacc cctccgacat    540
cgcagtggag tgggaatcta atggccagcc tgaaaacaat tacaagacca cccccctgt    600 gctggactcc gatgggtctt tctttctgta ttctaagctg accgtggata aaagtcggtg    660
gcagcaggga aacgtcttct catgcagcgt gatgcacgag gccctgcaca atcattacac    720
acagaagtcc ctgtctctga gtccaggcaa aggtggcgga ggcagcggcg gtggaggcag    780
ccagcggccc cggctgagcc acaagggccc catgcccttc taagaattc               829

<210> SEQ ID NO 90
<211> LENGTH: 844
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
gctagccacc atggaaactg acaccctgct gctgtgggtc ctgctgctgt gggtgcctgg     60
cagcactggc gataagacac acacttgccc cccttgtcca gcaccagagg cagctggagg    120
accaagcgtg ttcctgtttc acccaagcc taaagacaca ctgatgatct caaggacccc    180
agaagtcaca tgcgtggtcg tggacgtgtc tcacgaggac cccgaagtca agttcaactg    240
gtacgtggat ggcgtcgagg tgcataatgc taagaccaaa ccccgagagg aacagtacaa    300
cagcacctat cgggtcgtgt ccgtcctgac agtgctgcac caggattggc tgaacggcaa    360
agagtataag tgcaaagtga gtaataaggc tctgcctgca ccaatcgaga aaacaatttc    420
```

```
taaggctaaa gggcagccaa gagaacccca ggtgtacact ctgcctccat ctagggagga    480
aatgacaaag aaccaggtca gtctgacttg tctggtgaaa ggcttctacc cctccgacat    540
cgcagtggag tgggaatcta atggccagcc tgaaaacaat tacaagacca caccccctgt    600
gctggactcc gatgggtctt tctttctgta ttctaagctg accgtggata aaagtcggtg    660
gcagcaggga aacgtcttct catgcagcgt gatgcacgag gccctgcaca atcattacac    720
acagaagtcc ctgtctctga gtccaggcaa aggtggcgga ggcagcggcg gtggaggcag    780
cggaggtggc ggaagccagc ggccccggct gagccacaag ggcccatgc ccttctaaga    840 attc                                                                844

<210> SEQ ID NO 91
<211> LENGTH: 829
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
gctagccacc atggaaactg acaccctgct gctgtgggtc ctgctgctgt gggtgcctgg     60
cagcactggc gataagacac acacttgccc cccttgtcca gcaccagagg cagctggagg    120
accaagcgtg ttcctgtttc acccaagcc taaagacaca ctgatgatct caaggacccc    180
agaagtcaca tgcgtggtcg tggacgtgtc tcacgaggac cccgaagtca agttcaactg    240
gtacgtggat ggcgtcgagg tgcataatgc taagaccaaa ccccgagagg aacagtacaa    300
cagcacctat cgggtcgtgt ccgtcctgac agtgctgcac caggattggc tgaacggcaa    360
agagtataag tgcaaagtga gtaataaggc tctgcctgca ccaatcgaga aaacaatttc    420
taaggctaaa gggcagccaa gagaacccca ggtgtacact ctgcctccat ctagggagga    480
aatgacaaag aaccaggtca gtctgacttg tctggtgaaa ggcttctacc cctccgacat    540
cgcagtggag tgggaatcta atggccagcc tgaaaacaat tacaagacca caccccctgt    600
gctggactcc gatgggtctt tctttctgta ttctaagctg accgtggata aaagtcggtg    660
gcagcaggga aacgtcttct catgcagcgt gatgcacgag gccctgcaca atcattacac    720
acagaagtcc ctgtctctga gtccaggcaa aggtggcgga ggcagcggcg gtggaggcag    780
ccagcggccc cggctgtgcc acaagggccc catgtgcttc taagaattc                829

<210> SEQ ID NO 92
<211> LENGTH: 844
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
gctagccacc atggaaactg acaccctgct gctgtgggtc ctgctgctgt gggtgcctgg     60
cagcactggc gataagacac acacttgccc cccttgtcca gcaccagagg cagctggagg    120
accaagcgtg ttcctgtttc acccaagcc taaagacaca ctgatgatct caaggacccc    180
agaagtcaca tgcgtggtcg tggacgtgtc tcacgaggac cccgaagtca agttcaactg    240
gtacgtggat ggcgtcgagg tgcataatgc taagaccaaa ccccgagagg aacagtacaa    300
cagcacctat cgggtcgtgt ccgtcctgac agtgctgcac caggattggc tgaacggcaa    360
agagtataag tgcaaagtga gtaataaggc tctgcctgca ccaatcgaga aaacaatttc    420
```

| | | |
|---|---|---|
| taaggctaaa gggcagccaa gagaacccca ggtgtacact ctgcctccat ctagggagga | 480 |
| aatgacaaag aaccaggtca gtctgacttg tctggtgaaa ggcttctacc cctccgacat | 540 |
| cgcagtggag tgggaatcta atggccagcc tgaaaacaat tacaagacca caccccctgt | 600 |
| gctggactcc gatgggtctt tctttctgta ttctaagctg accgtggata aaagtcggtg | 660 |
| gcagcaggga aacgtcttct catgcagcgt gatgcacgag gccctgcaca atcattacac | 720 |
| acagaagtcc ctgtctctga gtccaggcaa aggtggcgga ggcagcggcg gtggaggcag | 780 |
| cggaggtggc ggaagccagc ggccccggct gtgccacaag ggccccatgt gcttctaaga | 840 |
| attc | 844 |

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gcttgctagc caccatggaa actg                                           24

<210> SEQ ID NO 94
<211> LENGTH: 108
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gttgattgaa ttcttagaag ggcatggggc ccttgtggct cagccggggc cgctggctgc     60
ctccaccgcc gctgcctccg ccacctttgc ctggactcag agacaggg                 108

<210> SEQ ID NO 95
<211> LENGTH: 123
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gttgattgaa ttcttagaag ggcatggggc ccttgtggct cagccggggc cgctggcttc     60
cgccacctcc gctgcctcca ccgccgctgc ctccgccacc tttgcctgga ctcagagaca   120
ggg                                                                 123

<210> SEQ ID NO 96
<211> LENGTH: 108
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gttgattgaa ttcttagaag cacatggggc ccttgtggca cagccggggc cgctggctgc     60
ctccaccgcc gctgcctccg ccacctttgc ctggactcag agacaggg                 108

<210> SEQ ID NO 97

<211> LENGTH: 123
<212> TYPE: DNA
<213> ORGANISM: Artificial Sequence
<220> FEATURE:
<223> OTHER INFORMATION: Description of Artificial Sequence: Synthetic primer

<400> SEQUENCE: 97

```
gttgattgaa ttcttagaag cacatggggc ccttgtggca cagccggggc cgctggcttc    60
cgccacctcc gctgcctcca ccgccgctgc ctccgccacc tttgcctgga ctcagagaca   120
ggg                                                                 123
```

<210> SEQ ID NO 98
<211> LENGTH: 270
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

```
Met Glu Thr Asp Thr Leu Leu Leu Trp Val Leu Leu Leu Trp Val Pro
1               5                   10                  15
Gly Ser Thr Gly Asp Lys Thr His Thr Cys Pro Pro Cys Pro Ala Pro
                20                  25                  30
Glu Ala Ala Gly Gly Pro Ser Val Phe Leu Phe Pro Pro Lys Pro Lys
            35                  40                  45
Asp Thr Leu Met Ile Ser Arg Thr Pro Glu Val Thr Cys Val Val Val
        50                  55                  60
Asp Val Ser His Glu Asp Pro Glu Val Lys Phe Asn Trp Tyr Val Asp
65                  70                  75                  80
Gly Val Glu Val His Asn Ala Lys Thr Lys Pro Arg Glu Glu Gln Tyr
                85                  90                  95
Asn Ser Thr Tyr Arg Val Val Ser Val Leu Thr Val Leu His Gln Asp
            100                 105                 110
Trp Leu Asn Gly Lys Glu Tyr Lys Cys Lys Val Ser Asn Lys Ala Leu
        115                 120                 125
Pro Ala Pro Ile Glu Lys Thr Ile Ser Lys Ala Lys Gly Gln Pro Arg
130                 135                 140
Glu Pro Gln Val Tyr Thr Leu Pro Pro Ser Arg Glu Glu Met Thr Lys
145                 150                 155                 160
Asn Gln Val Ser Leu Thr Cys Leu Val Lys Gly Phe Tyr Pro Ser Asp
                165                 170                 175
Ile Ala Val Glu Trp Glu Ser Asn Gly Gln Pro Glu Asn Asn Tyr Lys
            180                 185                 190
Thr Thr Pro Pro Val Leu Asp Ser Asp Gly Ser Phe Phe Leu Tyr Ser
        195                 200                 205
Lys Leu Thr Val Asp Lys Ser Arg Trp Gln Gln Gly Asn Val Phe Ser
210                 215                 220
Cys Ser Val Met His Glu Ala Leu His Asn His Tyr Thr Gln Lys Ser
225                 230                 235                 240
Leu Ser Leu Ser Pro Gly Lys Gly Gly Gly Ser Gly Gly Gly Gly
                245                 250                 255
Ser Gln Arg Pro Arg Leu Ser His Lys Gly Pro Met Pro Phe
            260                 265                 270
```

<210> SEQ ID NO 99

<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Ala Ala Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
            85                  90                  95

Asn Ser Thr Tyr Arg Val Val Ser Val Leu Thr Val Leu His Gln Asp
        100                 105                 110

Trp Leu Asn Gly Lys Glu Tyr Lys Cys Lys Val Ser Asn Lys Ala Leu
    115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
            165                 170                 175

Ile Ala Val Glu Trp Glu Ser Asn Gly Gln Pro Glu Asn Asn Tyr Lys
        180                 185                 190

Thr Thr Pro Pro Val Leu Asp Ser Asp Gly Ser Phe Phe Leu Tyr Ser
    195                 200                 205

Lys Leu Thr Val Asp Lys Ser Arg Trp Gln Gln Gly Asn Val Phe Ser
210                 215                 220

Cys Ser Val Met His Glu Ala Leu His Asn His Tyr Thr Gln Lys Ser
225                 230                 235                 240

Leu Ser Leu Ser Pro Gly Lys Gly Gly Gly Ser Gly Gly Gly Gly
            245                 250                 255

Ser Gly Gly Gly Gly Ser Gln Arg Pro Arg Leu Ser His Lys Gly Pro
            260                 265                 270

Met Pro Phe
        275

<210> SEQ ID NO 100
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Ala Ala Gly Gly Pro Ser Val Phe Leu Phe Pro Pro Lys Pro Lys
                35                  40                  45

Asp Thr Leu Met Ile Ser Arg Thr Pro Glu Val Thr Cys Val Val Val
 50                  55                  60

Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
            195                 200                 205

Lys Leu Thr Val Asp Lys Ser Arg Trp Gln Gln Gly Asn Val Phe Ser
210                 215                 220

Cys Ser Val Met His Glu Ala Leu His Asn His Tyr Thr Gln Lys Ser
225                 230                 235                 240

Leu Ser Leu Ser Pro Gly Lys Gly Gly Gly Ser Gly Gly Gly Gly
                245                 250                 255

Ser Gln Arg Pro Arg Leu Cys His Lys Gly Pro Met Cys Phe
            260                 265                 270

<210> SEQ ID NO 101
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Glu Thr Asp Thr Leu Leu Leu Trp Val Leu Leu Leu Trp Val Pro
 1               5                  10                  15

Gly Ser Thr Gly Asp Lys Thr His Thr Cys Pro Pro Cys Pro Ala Pro
                20                  25                  30

Glu Ala Ala Gly Gly Pro Ser Val Phe Leu Phe Pro Pro Lys Pro Lys
                35                  40                  45

Asp Thr Leu Met Ile Ser Arg Thr Pro Glu Val Thr Cys Val Val Val
 50                  55                  60

Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu

```
            115                 120                 125
Pro Ala Pro Ile Glu Lys Thr Ile Ser Lys Ala Lys Gly Gln Pro Arg
        130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
210                 215                 220

Cys Ser Val Met His Glu Ala Leu His Asn His Tyr Thr Gln Lys Ser
225                 230                 235                 240

Leu Ser Leu Ser Pro Gly Lys Gly Gly Gly Gly Ser Gly Gly Gly Gly
                245                 250                 255

Ser Gly Gly Gly Gly Ser Gln Arg Pro Arg Leu Cys His Lys Gly Pro
            260                 265                 270

Met Cys Phe
        275

<210> SEQ ID NO 102
<211> LENGTH: 123
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gttgattgaa ttcttagaag cacatggggc ccttgtggca cagccggggc cgctggcttc      60
cgccacctcc gctgcctcca ccgccgctgc ctccgccacc tgcgcctgga ctcagagaca     120
ggg                                                                    123

<210> SEQ ID NO 103
<211> LENGTH: 841
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
gctagccacc atggaaaccg acaccctgct gctgtgggtg ctgctgctgt gggtgccagg      60
cagcacaggc gataagggca gccagaggcc tagactgtgc acaagggccc catgtgcttt     120
tggcggcgga ggatctggcg gaggcggcag cgataagacc cacacctgtc ctccatgccc     180
tgcccctgaa gctgctggcg ccctagcgtt gttcctgttc cccccaaagc caaggacac     240 cctgatgatc agccggaccc ccgaagtgac ctgcgtggtg gtggatgtgt cccacgagga     300
ccctgaagtg aagttcaatt ggtacgtgga cggcgtggaa gtgcacaacg ccaagaccaa     360 gccccagagag gaacagtaca acagcaccta ccgggtggtg tccgtgctga ccgtgctgca     420
ccaggactgg ctgaacggca agagtacaa gtgcaaggtg tccaacaagg ccctgcctgc     480
ccccatcgag aaaaccatca gcaaggccaa gggccagccc cgcgaacccc aggtgtacac     540
actgccccct agccgggaag agatgaccaa gaaccaggtg tccctgacct gtctcgtgaa     600
```

```
gggcttctac ccctccgata tcgccgtgga atgggagagc aacggccagc ccgagaacaa    660
ctacaagacc accccccctg tgctggacag cgacggctca ttcttcctgt acagcaagct    720
gacagtggac aagagccggt ggcagcaggg caacgtgttc agctgcagcg tgatgcacga    780
ggccctgcac aaccactaca cccagaagtc cctgagcctg agccccggca atgagaatt     840 c                                                                    841

<210> SEQ ID NO 104
<211> LENGTH: 841
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
gctagccacc atggaaactg acaccctgct gctgtgggtc ctgctgctgt gggtgcctgg     60
cagcactggc gataagacac acttgcccc ccttgtcca gcaccagagg cagctggagg     120
accaagcgtg ttcctgtttc acccaagcc taaagacaca ctgatgatct caaggacccc    180
agaagtcaca tgcgtggtcg tggacgtgtc tcacgaggac cccgaagtca agttcaactg    240
gtacgtggat ggcgtcgagg tgcataatgc taagaccaaa ccccgagagg aacagtacaa    300
cagcacctat cgggtcgtgt ccgtcctgac agtgctgcac caggattggc tgaacggcaa    360
agagtataag tgcaaagtga gtaataaggc tctgcctgca ccaatcgaga aaacaatttc    420
taaggctaaa gggcagccaa gagaaccccca ggtgtacact ctgcctccat ctagggagga    480
aatgacaaag aaccaggtca gtctgacttg tctggtgaaa ggcttctacc cctccgacat    540
cgcagtggag tgggaatcta atggccagcc tgaaaacaat tacaagacca ccccctgt    600 gctggactcc gatgggtctt tcttctgta ttctaagctg accgtggata aaagtcggtg    660
gcagcaggga aacgtcttct catgcagcgt gatgcacgag gccctgcaca atcattacac    720
acagaagtcc ctgtctctga gtccaggcgg tggcggaggc agcggcggtg gaggcagcgg    780
aggtggcgga agccagcggc cccggctgtg ccacaagggc cccatgtgct tctaagaatt    840
c                                                                    841

<210> SEQ ID NO 105
<211> LENGTH: 805
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
gctagccacc atggaaactg acaccctgct gctgtgggtc ctgctgctgt gggtgcctgg     60
cagcactggc gataagacac acttgcccc ccttgtcca gcaccagagg cagctggagg     120
accaagcgtg ttcctgtttc acccaagcc taaagacaca ctgatgatct caaggacccc    180
agaagtcaca tgcgtggtcg tggacgtgtc tcacgaggac cccgaagtca agttcaactg    240
gtacgtggat ggcgtcgagg tgcataatgc taagaccaaa ccccgagagg aacagtacaa    300
cagcacctat cgggtcgtgt ccgtcctgac agtgctgcac caggattggc tgaacggcaa    360
agagtataag tgcaaagtga gtaataaggc tctgcctgca ccaatcgaga aaacaatttc    420
taaggctaaa gggcagccaa gagaaccccca ggtgtacact ctgcctccat ctagggagga    480
```

| aatgacaaag aaccaggtca gtctgacttg tctggtgaaa ggcttctacc cctccgacat | 540 |
| cgcagtggag tgggaatcta atggccagcc tgaaaacaat tacaagacca ccccctgt | 600 |
| gctggactcc gatgggtctt tctttctgta ttctaagctg accgtggata aaagtcggtg | 660 |
| gcagcaggga aacgtcttct catgcagcgt gatgcacgag gccctgcaca atcattacac | 720 |
| acagaagtcc ctgtctctga gtccaggcaa aggtagccag cggccccggc tgtgccacaa | 780 |
| gggccccatg tgcttctaag aattc | 805 |

<210> SEQ ID NO 106
<211> LENGTH: 805
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 106

| gctagccacc atggaaactg acaccctgct gctgtgggtc ctgctgctgt gggtgcctgg | 60 |
| cagcactggc gataagacac acacttgccc cccttgtcca gcaccagagg cagctggagg | 120 |
| accaagcgtg ttcctgtttc cacccaagcc taaagacaca ctgatgatct caaggacccc | 180 |
| agaagtcaca tgcgtggtcg tggacgtgtc tcacgaggac cccgaagtca agttcaactg | 240 |
| gtacgtggat ggcgtcgagg tgcataatgc taagaccaaa cccgagagg aacagtacaa | 300 |
| cagcacctat cgggtcgtgt ccgtcctgac agtgctgcac caggattggc tgaacggcaa | 360 |
| agagtataag tgcaaagtga gtaataaggc tctgcctgca ccaatcgaga aaacaatttc | 420 |
| taaggctaaa gggcagccaa gagaaccca ggtgtacact ctgcctccat ctagggagga | 480 |
| aatgacaaag aaccaggtca gtctgacttg tctggtgaaa ggcttctacc cctccgacat | 540 |
| cgcagtggag tgggaatcta atggccagcc tgaaaacaat tacaagacca ccccctgt | 600 |
| gctggactcc gatgggtctt tctttctgta ttctaagctg accgtggata aaagtcggtg | 660 |
| gcagcaggga aacgtcttct catgcagcgt gatgcacgag gccctgcaca atcattacac | 720 |
| acagaagtcc ctgtctctga gtccaggcaa aggtggccag cggccccggc tgtgccacaa | 780 |
| gggccccatg tgcttctaag aattc | 805 |

<210> SEQ ID NO 107
<211> LENGTH: 814
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107

| gctagccacc atggaaactg acaccctgct gctgtgggtc ctgctgctgt gggtgcctgg | 60 |
| cagcactggc gataagacac acacttgccc cccttgtcca gcaccagagg cagctggagg | 120 |
| accaagcgtg ttcctgtttc cacccaagcc taaagacaca ctgatgatct caaggacccc | 180 |
| agaagtcaca tgcgtggtcg tggacgtgtc tcacgaggac cccgaagtca agttcaactg | 240 |
| gtacgtggat ggcgtcgagg tgcataatgc taagaccaaa cccgagagg aacagtacaa | 300 |
| cagcacctat cgggtcgtgt ccgtcctgac agtgctgcac caggattggc tgaacggcaa | 360 |
| agagtataag tgcaaagtga gtaataaggc tctgcctgca ccaatcgaga aaacaatttc | 420 |
| taaggctaaa gggcagccaa gagaaccca ggtgtacact ctgcctccat ctagggagga | 480 |
| aatgacaaag aaccaggtca gtctgacttg tctggtgaaa ggcttctacc cctccgacat | 540 |

```
cgcagtggag tgggaatcta atggccagcc tgaaaacaat tacaagacca cacccctgt      600 gctggactcc gatgggtctt tctttctgta ttctaagctg accgtggata aaagtcggtg     660
gcagcaggga acgtcttct catgcagcgt gatgcacgag ccctgcaca atcattacac      720 acagaagtcc ctgtctctga gtccaggcaa aggtggcgga ggcagccagc ggccccggct    780
gtgccacaag ggccccatgt gcttctaaga attc                                 814

<210> SEQ ID NO 108
<211> LENGTH: 844
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
gctagccacc atggaaactg acaccctgct gctgtgggtc ctgctgctgt gggtgcctgg      60
cagcactggc gataagacac acacttgccc cccttgtcca gcaccagagg cagctggagg    120
accaagcgtg ttcctgtttc cacccaagcc taaagacaca ctgatgatct caaggacccc    180
agaagtcaca tgcgtggtcg tggacgtgtc tcacgaggac cccgaagtca agttcaactg    240
gtacgtggat ggcgtcgagg tgcataatgc taagaccaaa ccccgagagg aacagtacaa    300
cagcacctat cgggtcgtgt ccgtcctgac agtgctgcac caggattggc tgaacggcaa    360
agagtataag tgcaaagtga gtaataaggc tctgcctgca ccaatcgaga aaacaatttc    420
taaggctaaa gggcagccaa gagaaccccca ggtgtacact ctgcctccat ctagggagga    480
aatgacaaag aaccaggtca gtctgacttg tctggtgaaa ggcttctacc cctccgacat    540
cgcagtggag tgggaatcta atggccagcc tgaaaacaat tacaagacca cccccctgt    600 gctggactcc gatgggtctt tctttctgta ttctaagctg accgtggata aaagtcggtg    660
gcagcaggga acgtcttct catgcagcgt gatgcacgag ccctgcaca atcattacac     720 acagaagtcc ctgtctctga gtccaggcaa aggtggcgga ggcagcggcg tggaggcag    780 cggaggtggc ggaagccagc ggccccggct gtgccacaag ggccccatgt gctagtaaga    840
attc                                                                 844

<210> SEQ ID NO 109
<211> LENGTH: 841
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
gctagccacc atggaaactg acaccctgct gctgtgggtc ctgctgctgt gggtgcctgg     60
cagcactggc gataagacac acacttgccc cccttgtcca gcaccagagg cagctggagg   120
accaagcgtg ttcctgtttc cacccaagcc taaagacaca ctgatgatct caaggacccc   180
agaagtcaca tgcgtggtcg tggacgtgtc tcacgaggac cccgaagtca agttcaactg   240
gtacgtggat ggcgtcgagg tgcataatgc taagaccaaa ccccgagagg aacagtacaa   300
cagcacctat cgggtcgtgt ccgtcctgac agtgctgcac caggattggc tgaacggcaa   360
agagtataag tgcaaagtga gtaataaggc tctgcctgca ccaatcgaga aaacaatttc   420
taaggctaaa gggcagccaa gagaacccca ggtgtacact ctgcctccat ctagggagga   480
```

```
aatgacaaag aaccaggtca gtctgacttg tctggtgaaa ggcttctacc cctcygacat    540
cgcagtggag tgggaatcta atggccagcc tgaaaacaat tacaagacca cacccctgt    600 gctggactcc gatgggtctt tctttctgta ttctaagctg accgtggata aagtcggtg    660 gcagcaggga acgtcttct catgcagcgt gatgcacgag gccctgcaca atcattacac    720
acagaagtcc ctgtctctga gtccaggcgc aggtggcgga ggcagcggcg gtggaggcag    780
cggaggtggc ggaagccagc ggccccggct gtgccacaag gccccatgt gctaagaatt    840 c                                                                    841
```

<210> SEQ ID NO 110
<211> LENGTH: 838
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

```
gctagccacc atggaaactg acaccctgct gctgtgggtc ctgctgctgt gggtgcctgg     60
cagcactggc gataagacac acacttgccc cccttgtcca gcaccagagg cagctggagg    120
accaagcgtg ttcctgtttc cacccaagcc taaagacaca ctgatgatct caaggacccc    180
agaagtcaca tgcgtggtcg tggacgtgtc tcacgaggac cccgaagtca agttcaactg    240
gtacgtggat ggcgtcgagg tgcataatgc taagaccaaa cccgagagg aacagtacaa    300 cagcacctat cgggtcgtgt ccgtcctgac agtgctgcac caggattggc tgaacggcaa    360
agagtataag tgcaaagtga gtaataaggc tctgcctgca ccaatcgaga aacaatttc    420 taaggctaaa gggcagccaa gagaaccccca ggtgtacact ctgcctccat ctagggagga    480
aatgacaaag aaccaggtca gtctgacttg tctggtgaaa ggcttctacc cctccgacat    540
cgcagtggag tgggaatcta atggccagcc tgaaaacaat tacaagacca cacccctgt    600 gctggactcc gatgggtctt tctttctgta ttctaagctg accgtggata aagtcggtg    660 gcagcaggga acgtcttct catgcagcgt gatgcacgag gccctgcaca atcattacac    720
acagaagtcc ctgtctctga gtccaggcgg tggcggaggc agcggcggtg gaggcagcgg    780
aggtggcgga agccagcggc cccggctgtg ccacaagggc cccatgtgct aagaattc      838
```

<210> SEQ ID NO 111
<211> LENGTH: 802
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111

```
gctagccacc atggaaactg acaccctgct gctgtgggtc ctgctgctgt gggtgcctgg     60
cagcactggc gataagacac acacttgccc cccttgtcca gcaccagagg cagctggagg    120
accaagcgtg ttcctgtttc cacccaagcc taaagacaca ctgatgatct caaggacccc    180
agaagtcaca tgcgtggtcg tggacgtgtc tcacgaggac cccgaagtca agttcaactg    240
gtacgtggat ggcgtcgagg tgcataatgc taagaccaaa cccgagagg aacagtacaa    300 cagcacctat cgggtcgtgt ccgtcctgac agtgctgcac caggattggc tgaacggcaa    360
agagtataag tgcaaagtga gtaataaggc tctgcctgca ccaatcgaga aacaatttc    420 taaggctaaa gggcagccaa gagaaccccca ggtgtacact ctgcctccat ctagggagga    480
```

```
aatgacaaag aaccaggtca gtctgacttg tctggtgaaa ggcttctacc cctccgacat    540
cgcagtggag tgggaatcta atggccagcc tgaaaacaat tacaagacca cacccctgt     600 gctggactcc gatgggtctt tctttctgta ttctaagctg accgtggata aaagtcggtg    660
gcagcaggga aacgtcttct catgcagcgt gatgcacgag gccctgcaca atcattacac    720
acagaagtcc ctgtctctga gtccaggcaa aggtagccag cggccccggc tgtgccacaa    780
gggccccatg tgctaagaat tc                                             802
```

<210> SEQ ID NO 112
<211> LENGTH: 802
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112

```
gctagccacc atggaaactg acaccctgct gctgtgggtc ctgctgctgt gggtgcctgg     60
cagcactggc gataagacac acacttgccc cccttgtcca gcaccagagg cagctggagg    120
accaagcgtg ttcctgtttc cacccaagcc taaagacaca ctgatgatct caaggacccc    180
agaagtcaca tgcgtggtcg tggacgtgtc tcacgaggac cccgaagtca agttcaactg    240
gtacgtggat ggcgtcgagg tgcataatgc taagaccaaa ccccgagagg aacagtacaa    300
cagcacctat cgggtcgtgt ccgtcctgac agtgctgcac caggattggc tgaacggcaa    360
agagtataag tgcaaagtga gtaataaggc tctgcctgca ccaatcgaga aaacaatttc    420
taaggctaaa gggcagccaa gagaaccccca ggtgtacact ctgcctccat ctagggagga    480
aatgacaaag aaccaggtca gtctgacttg tctggtgaaa ggcttctacc cctccgacat    540
cgcagtggag tgggaatcta atggccagcc tgaaaacaat tacaagacca cacccctgt     600 gctggactcc gatgggtctt tctttctgta ttctaagctg accgtggata aaagtcggtg    660
gcagcaggga aacgtcttct catgcagcgt gatgcacgag gccctgcaca atcattacac    720
acagaagtcc ctgtctctga gtccaggcaa aggtggccag cggccccggc tgtgccacaa    780
gggccccatg tgctaagaat tc                                             802
```

<210> SEQ ID NO 113
<211> LENGTH: 811
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 113

```
gctagccacc atggaaactg acaccctgct gctgtgggtc ctgctgctgt gggtgcctgg     60
cagcactggc gataagacac acacttgccc cccttgtcca gcaccagagg cagctggagg    120
accaagcgtg ttcctgtttc cacccaagcc taaagacaca ctgatgatct caaggacccc    180
agaagtcaca tgcgtggtcg tggacgtgtc tcacgaggac cccgaagtca agttcaactg    240
gtacgtggat ggcgtcgagg tgcataatgc taagaccaaa ccccgagagg aacagtacaa    300
cagcacctat cgggtcgtgt ccgtcctgac agtgctgcac caggattggc tgaacggcaa    360
agagtataag tgcaaagtga gtaataaggc tctgcctgca ccaatcgaga aaacaatttc    420
taaggctaaa gggcagccaa gagaaccccca ggtgtacact ctgcctccat ctagggagga    480
```

```
aatgacaaag aaccaggtca gtctgacttg tctggtgaaa ggcttctacc cctccgacat    540
cgcagtggag tgggaatcta atggccagcc tgaaaacaat tacaagacca cccccctgt     600 gctggactcc gatgggtctt tctttctgta ttctaagctg accgtggata aaagtcggtg    660
gcagcaggga aacgtcttct catgcagcgt gatgcacgag gccctgcaca atcattacac    720
acagaagtcc ctgtctctga gtccaggcaa aggtggcgga ggcagccagc ggccccggct    780
gtgccacaag ggccccatgt gctaagaatt c                                   811

<210> SEQ ID NO 114
<211> LENGTH: 811
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
gctagccacc atggaaactg acaccctgct gctgtgggtc ctgctgctgt gggtgcctgg     60
cagcactggc gataagacac acacttgccc cccttgtcca gcaccagagg cagctggagg    120
accaagcgtg ttcctgtttc cacccaagcc taaagacaca ctgatgatct caaggacccc    180
agaagtcaca tgcgtggtcg tggacgtgtc tcacgaggac cccgaagtca agttcaactg    240
gtacgtggat ggcgtcgagg tgcataatgc taagaccaaa ccccgagagg aacagtacaa    300
cagcacctat cgggtcgtgt ccgtcctgac agtgctgcac caggattggc tgaacggcaa    360
agagtataag tgcaaagtga gtaataaggc tctgcctgca ccaatcgaga aaacaatttc    420
taaggctaaa gggcagccaa gagaaccccc ggtgtacact ctgcctccat ctagggagga    480
aatgacaaag aaccaggtca gtctgacttg tctggtgaaa ggcttctacc cctccgacat    540
cgcagtggag tgggaatcta atggccagcc tgaaaacaat tacaagacca cccccctgt     600 gctggactcc gatgggtctt tctttctgta ttctaagctg accgtggata aaagtcggtg    660
gcagcaggga aacgtcttct catgcagcgt gatgcacgag gccctgcaca atcattacac    720
acagaagtcc ctgtctctga gtccaggcaa aggtggcgga ggcagccagc ggccccggct    780
gtgccacaag ggccccatgt gctaagaatt c                                   811

<210> SEQ ID NO 115
<211> LENGTH: 766
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
gctagccacc atggaaactg acaccctgct gctgtgggtc ctgctgctgt gggtgcctgg     60
cagcactggc gctcatgata agacacacac atgccccccct tgtccagcac cagaggcagc    120
tggaggacca agcgtgttcc tgtttccacc caagcctaaa gacacactga tgatctcaag    180
gaccccagaa gtcacatgcg tggtcgtgga cgtgtctcac gaggacccccg aagtcaagtt    240 caactggtac gtggatggcg tcgaggtgca taatgctaag accaaacccc gagaggaaca    300
gtacaacagc acctatcggg tcgtgtccgt cctgacagtg ctgcaccagg attggctgaa    360
cggcaaagag tataagtgca aagtgagtaa taaggctctg cctgcaccaa tcgagaaaac    420
aatttctaag gctaaagggc agccaagaga accccaggtg tacactctgc ctccatctag    480
ggaggaaatg acaaagaacc aggtcagtct gacttgtctg gtgaaaggct tctacccctc    540
```

```
cgacatcgca gtggagtggg aatctaatgg ccagcctgaa acaattaca agaccacacc      600 ccctgtgctg gactccgatg ggtctttctt tctgtattct aagctgaccg tggataaaag      660
tcggtggcag cagggaaacg tcttctcatg cagcgtgatg cacgaggccc tgcacaatca      720
ttacacacag aagtccctgt ctctgagtcc aggcaaatga gaattc                     766
```

<210> SEQ ID NO 116
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Ala Ala Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Ala Gly Gly Gly Ser Gly Gly Gly Gly
                245                 250                 255

Ser Gly Gly Gly Gly Ser Gln Arg Pro Arg Leu Cys His Lys Gly Pro
            260                 265                 270

Met Cys Phe
        275
```

<210> SEQ ID NO 117
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Met Glu Thr Asp Thr Leu Leu Leu Trp Val Leu Leu Trp Val Pro
1               5                   10                  15

Gly Ser Thr Gly Asp Lys Thr His Thr Cys Pro Pro Cys Pro Ala Pro
            20                  25                  30

Glu Ala Ala Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Gly Gly Gly Ser Gly Gly Gly Gly Ser
                245                 250                 255

Gly Gly Gly Gly Ser Gln Arg Pro Arg Leu Cys His Lys Gly Pro Met
            260                 265                 270

Cys Phe

<210> SEQ ID NO 118
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Glu Thr Asp Thr Leu Leu Leu Trp Val Leu Leu Trp Val Pro
1               5                   10                  15

Gly Ser Thr Gly Asp Lys Thr His Thr Cys Pro Pro Cys Pro Ala Pro
            20                  25                  30

Glu Ala Ala Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
            50                  55                  60

Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
210                 215                 220

Cys Ser Val Met His Glu Ala Leu His Asn His Tyr Thr Gln Lys Ser
225                 230                 235                 240

Leu Ser Leu Ser Pro Gly Lys Gly Ser Gln Arg Pro Arg Leu Cys His
                245                 250                 255

Lys Gly Pro Met Cys Phe
            260

<210> SEQ ID NO 119
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Glu Thr Asp Thr Leu Leu Leu Trp Val Leu Leu Leu Trp Val Pro
 1               5                  10                  15

Gly Ser Thr Gly Asp Lys Thr His Thr Cys Pro Pro Cys Pro Ala Pro
                20                  25                  30

Glu Ala Ala Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
        50                  55                  60

Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
            165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
            195                 200                 205

Lys Leu Thr Val Asp Lys Ser Arg Trp Gln Gln Gly Asn Val Phe Ser
            210                 215                 220

Cys Ser Val Met His Glu Ala Leu His Asn His Tyr Thr Gln Lys Ser
225                 230                 235                 240

Leu Ser Leu Ser Pro Gly Lys Gly Gly Gln Arg Pro Arg Leu Cys His
            245                 250                 255

Lys Gly Pro Met Cys Phe
            260

<210> SEQ ID NO 120
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Ala Ala Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
            85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
            165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
            195                 200                 205

Lys Leu Thr Val Asp Lys Ser Arg Trp Gln Gln Gly Asn Val Phe Ser
            210                 215                 220

Cys Ser Val Met His Glu Ala Leu His Asn His Tyr Thr Gln Lys Ser

```
225                 230                 235                 240

Leu Ser Leu Ser Pro Gly Lys Gly Gly Gly Ser Gln Arg Pro Arg
            245                 250                 255

Leu Cys His Lys Gly Pro Met Cys Phe
            260                 265

<210> SEQ ID NO 121
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
                20                  25                  30

Glu Ala Ala Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys Gly Gly Gly Ser Gly Gly Gly Gly
                245                 250                 255

Ser Gly Gly Gly Gly Ser Gln Arg Pro Arg Leu Cys His Lys Gly Pro
            260                 265                 270

Met Cys

<210> SEQ ID NO 122
<211> LENGTH: 274
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 122

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Ala Ala Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Ala Gly Gly Gly Ser Gly Gly Gly Gly
                245                 250                 255

Ser Gly Gly Gly Gly Ser Gln Arg Pro Arg Leu Cys His Lys Gly Pro
            260                 265                 270

Met Cys

<210> SEQ ID NO 123
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Ala Ala Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

```
Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
210                 215                 220

Cys Ser Val Met His Glu Ala Leu His Asn His Tyr Thr Gln Lys Ser
225                 230                 235                 240

Leu Ser Leu Ser Pro Gly Gly Gly Gly Ser Gly Gly Gly Gly Ser
                245                 250                 255

Gly Gly Gly Gly Ser Gln Arg Pro Arg Leu Cys His Lys Gly Pro Met
            260                 265                 270

Cys

<210> SEQ ID NO 124
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Glu Thr Asp Thr Leu Leu Leu Trp Val Leu Leu Leu Trp Val Pro
  1               5                  10                  15

Gly Ser Thr Gly Asp Lys Thr His Thr Cys Pro Pro Cys Pro Ala Pro
                 20                  25                  30

Glu Ala Ala Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
 50                  55                  60

Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
130                 135                 140
```

```
Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys Gly Ser Gln Arg Pro Arg Leu Cys His
                245                 250                 255

Lys Gly Pro Met Cys
            260

<210> SEQ ID NO 125
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
                20                  25                  30

Glu Ala Ala Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
        50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
                100                 105                 110

Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
        130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
```

```
225                 230                 235                 240
Leu Ser Leu Ser Pro Gly Lys Gly Gly Gln Arg Pro Arg Leu Cys His
            245                 250                 255
Lys Gly Pro Met Cys
            260
```

<210> SEQ ID NO 126
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Met Glu Thr Asp Thr Leu Leu Leu Trp Val Leu Leu Leu Trp Val Pro
1               5                   10                  15
Gly Ser Thr Gly Asp Lys Thr His Thr Cys Pro Pro Cys Pro Ala Pro
            20                  25                  30
Glu Ala Ala Gly Gly Pro Ser Val Phe Leu Phe Pro Pro Lys Pro Lys
        35                  40                  45
Asp Thr Leu Met Ile Ser Arg Thr Pro Glu Val Thr Cys Val Val Val
    50                  55                  60
Asp Val Ser His Glu Asp Pro Glu Val Lys Phe Asn Trp Tyr Val Asp
65                  70                  75                  80
Gly Val Glu Val His Asn Ala Lys Thr Lys Pro Arg Glu Glu Gln Tyr
                85                  90                  95
Asn Ser Thr Tyr Arg Val Val Ser Val Leu Thr Val Leu His Gln Asp
            100                 105                 110
Trp Leu Asn Gly Lys Glu Tyr Lys Cys Lys Val Ser Asn Lys Ala Leu
        115                 120                 125
Pro Ala Pro Ile Glu Lys Thr Ile Ser Lys Ala Lys Gly Gln Pro Arg
    130                 135                 140
Glu Pro Gln Val Tyr Thr Leu Pro Pro Ser Arg Glu Glu Met Thr Lys
145                 150                 155                 160
Asn Gln Val Ser Leu Thr Cys Leu Val Lys Gly Phe Tyr Pro Ser Asp
                165                 170                 175
Ile Ala Val Glu Trp Glu Ser Asn Gly Gln Pro Glu Asn Asn Tyr Lys
            180                 185                 190
Thr Thr Pro Pro Val Leu Asp Ser Asp Gly Ser Phe Phe Leu Tyr Ser
        195                 200                 205
Lys Leu Thr Val Asp Lys Ser Arg Trp Gln Gln Gly Asn Val Phe Ser
    210                 215                 220
Cys Ser Val Met His Glu Ala Leu His Asn His Tyr Thr Gln Lys Ser
225                 230                 235                 240
Leu Ser Leu Ser Pro Gly Lys Gly Gly Gly Ser Gln Arg Pro Arg
                245                 250                 255
Leu Cys His Lys Gly Pro Met Cys
            260
```

<210> SEQ ID NO 127
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (1)..(1)
<223> OTHER INFORMATION: PyroGlu
<220> FEATURE:
<221> NAME/KEY: MOD_RES
<222> LOCATION: (8)..(8)
<223> OTHER INFORMATION: N6-[[(1-alpha,8-alpha,9-alpha)-bicyclo[6.1.0]
      non-4-yn-9-ylmethoxy]carbonyl-Lys
<220> FEATURE:
<221> NAME/KEY: MOD_RES
<222> LOCATION: (11)..(11)
<223> OTHER INFORMATION: Nle

<400> SEQUENCE: 127

Glu Arg Pro Arg Leu Cys His Lys Gly Pro Leu Cys Phe
1               5                   10

<210> SEQ ID NO 128
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Gly Gly Gly Ser Leu Pro Glu Thr Gly Gly Leu Glu Val Leu Phe
1               5                   10                  15

Gln Gly Pro

<210> SEQ ID NO 129
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Nle

<400> SEQUENCE: 129

Gly Gly Gly Gly Gly Gln Arg Pro Arg Leu Cys His Lys Gly Pro Leu
1               5                   10                  15

Cys Phe

<210> SEQ ID NO 130
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Nle

<400> SEQUENCE: 130

Gly Gly Gly Gly Ser Leu Pro Glu Thr Gly Gly Gly Gly Gln Arg
1               5                   10                  15

Pro Arg Leu Cys His Lys Gly Pro Leu Cys Phe
            20                  25

<210> SEQ ID NO 131
<211> LENGTH: 5
<212> TYPE: PRT
```

<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Any amino acid

<400> SEQUENCE: 131

```
Leu Pro Xaa Thr Gly
1               5
```

<210> SEQ ID NO 132
<211> LENGTH: 817
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 132

```
gctagccacc atggaaaccg acaccctgct gctgtgggtg ctgctgctgt gggtgccagg    60
cagcaccggc gataagaccc acacctgtcc tccctgtcct gccccctgaag ctgctggcgg  120 ccctagcgtg ttcctgttcc ccccaaagcc caaggacacc ctgatgatca gccggacccc  180
cgaagtgacc tgcgtggtgg tggatgtgtc cacgaggac cctgaagtga agttcaattg   240
gtacgtggac ggcgtggaag tgcacaacgc caagaccaag cccagagagg aacagtacaa  300
cagcacctac cgggtggtgt ccgtgctgac cgtgctgcac caggactggc tgaacggcaa  360
agagtacaag tgcaaggtgt ccaacaaggc cctgccagcc cccatcgaga aaccatcag   420 caaggccaag ggccagcccc gcgaacccca ggtgtacaca ctgccccta gccgggaaga   480 gatgaccaag aaccaggtgt ccctgacctg tctcgtgaag ggcttctacc cctccgatat   540
cgccgtggaa tgggagagca acggccagcc cgagaacaac tacaagacca ccccccctgt   600
gctggacagc gacggctcat tcttcctgta cagcaagctg acagtggaca gagccggtg   660 gcagcagggc aacgtgttca gctgcagcgt gatgcacgag ccctgcaca accactacac    720 ccagaagtcc ctgagcctga gccctggaaa aggcggcgga ggctctctgc ctgaaacagg   780
cggactggaa gtgctgttcc agggccccta agaattc                             817
```

<210> SEQ ID NO 133
<211> LENGTH: 266
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

```
Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Ala Ala Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80
```

```
Gly Val Glu Val His Asn Ala Lys Thr Lys Pro Arg Glu Glu Gln Tyr
            85                  90                  95

Asn Ser Thr Tyr Arg Val Val Ser Val Leu Thr Val Leu His Gln Asp
        100                 105                 110

Trp Leu Asn Gly Lys Glu Tyr Lys Cys Lys Val Ser Asn Lys Ala Leu
    115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys Gly Gly Gly Ser Leu Pro Glu Thr
                245                 250                 255

Gly Gly Leu Glu Val Leu Phe Gln Gly Pro
            260                 265

<210> SEQ ID NO 134
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Leu Pro Glu Thr Gly Gly Leu Glu Val Leu Phe Gln Gly Pro
1               5                   10

<210> SEQ ID NO 135
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Gln(Trt)
<220> FEATURE:
<221> NAME/KEY: MOD_RES
<222> LOCATION: (7)..(7)
<223> OTHER INFORMATION: Arg(Pbf)
<220> FEATURE:
<221> NAME/KEY: MOD_RES
<222> LOCATION: (9)..(9)
<223> OTHER INFORMATION: Arg(Pbf)
<220> FEATURE:
<221> NAME/KEY: MOD_RES
<222> LOCATION: (11)..(11)
<223> OTHER INFORMATION: Cys(Trt)
<220> FEATURE:
<221> NAME/KEY: MOD_RES
<222> LOCATION: (12)..(12)
<223> OTHER INFORMATION: His(Trt)
<220> FEATURE:
```

```
<221> NAME/KEY: MOD_RES
<222> LOCATION: (13)..(13)
<223> OTHER INFORMATION: Lys(Boc)
<220> FEATURE:
<221> NAME/KEY: MOD_RES
<222> LOCATION: (16)..(16)
<223> OTHER INFORMATION: Nle
<220> FEATURE:
<221> NAME/KEY: MOD_RES
<222> LOCATION: (17)..(17)
<223> OTHER INFORMATION: Cys(Trt)

<400> SEQUENCE: 135

Gly Gly Gly Gly Gly Gln Arg Pro Arg Leu Cys His Lys Gly Pro Leu
1               5                   10                  15

Cys Phe

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Leu Pro Glu Thr Gly Gly
1               5

<210> SEQ ID NO 137
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
            20                  25                  30

Pro Ala Thr Arg Glu Gln Leu Asn Arg Gly Val Ser Phe Ala Lys Glu
        35                  40                  45

Asn Gln Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Ala Val Glu Val Leu Asp
            100                 105                 110

Glu Gln Lys Gly Lys Asp Lys Gln Leu Thr Leu Ile Thr Cys Asp Asp
        115                 120                 125

Tyr Asn Glu Glu Thr Gly Val Trp Glu Thr Arg Lys Ile Phe Val Ala
    130                 135                 140

Thr Glu Val Lys Leu Glu His His His His His
145                 150                 155

<210> SEQ ID NO 138
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Nle

<400> SEQUENCE: 138

Gln Arg Pro Arg Leu Cys His Lys Gly Pro Leu Cys Phe
1               5                   10

<210> SEQ ID NO 139
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PyroGlu, Arg, Gln, Isn or absent
<220> FEATURE:
<221> NAME/KEY: MOD_RES
<222> LOCATION: (5)..(5)
<223> OTHER INFORMATION: Leu or Cha
<220> FEATURE:
<221> NAME/KEY: MOD_RES
<222> LOCATION: (6)..(6)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (7)..(7)
<223> OTHER INFORMATION: His, Aib, Phe or Lys
<220> FEATURE:
<221> NAME/KEY: MOD_RES
<222> LOCATION: (8)..(8)
<223> OTHER INFORMATION: Lys, Phe or 4-amino-Isn
<220> FEATURE:
<221> NAME/KEY: MOD_RES
<222> LOCATION: (9)..(9)
<223> OTHER INFORMATION: Gly or Aib
<220> FEATURE:
<221> NAME/KEY: MOD_RES
<222> LOCATION: (11)..(11)
<223> OTHER INFORMATION: Nle or Cha
<220> FEATURE:
<221> NAME/KEY: MOD_RES
<222> LOCATION: (12)..(12)
<223> OTHER INFORMATION: Cys, D-Cys, homoCys, D-homoCys, Lys, Asp, Orn,
      Dab or Glu
<220> FEATURE:
<221> NAME/KEY: MOD_RES
<222> LOCATION: (13)..(13)
<223> OTHER INFORMATION: Phe, D-Phe, Lys or absent
<220> FEATURE:
<223> OTHER INFORMATION: See specification as filed for detailed
      description of substitutions and preferred embodiments

<400> SEQUENCE: 139

Xaa Arg Pro Arg Xaa Xaa Xaa Xaa Xaa Pro Xaa Xaa Xaa
1               5                   10
```